United States Patent [19]

Tessier-Lavigne et al.

[11] Patent Number: 6,054,293
[45] Date of Patent: Apr. 25, 2000

[54] SEMAPHORIN RECEPTORS

[75] Inventors: Marc Tessier-Lavigne; Zhigang He; Hang Chen, all of San Francisco, Calif.

[73] Assignee: The Regents of the University of California, Oakland, Calif.

[21] Appl. No.: 08/936,135

[22] Filed: Sep. 24, 1997

Related U.S. Application Data

[63] Continuation-in-part of application No. 08/889,458, Jul. 8, 1997, abandoned.
[51] Int. Cl.$^7$ .......................... C07H 21/04; C12N 15/12; C12N 15/63
[52] U.S. Cl. .................... 435/69.1; 536/23.1; 536/24.31; 435/320.1; 435/325; 435/252.3; 435/172.3; 530/300; 530/350
[58] Field of Search ................................. 435/69.1, 70.1, 435/7.2, 325, 320.1, 252.3, 172.3; 530/300, 350; 536/23.1, 24.31

[56] References Cited

FOREIGN PATENT DOCUMENTS

WO 94/03599   8/1993   WIPO .

OTHER PUBLICATIONS

Watson J.D. et al., Molecular Biology of the Gene, Fourth Edition, The Benjamin/Cummings Publishing Company, Inc., p. 313, 1987.

Kawakami A. et al., Developmentally regulated Expression of a Cell Surface Protein, Neuropilin, in Mouse Nervous System, Journal of Neurobiology, vol. 29, No. 1, pp. 1–17, Jan. 1, 1996.

He. Z. et al., Neuropilin is a Receptor for the Axonal Chemorepellent Semaphorin II. Cell, vol. 90, pp. 739–751, 1997.

Kolodkin A. et al., Neuropilin is a Semaphorin III Receptor, Cell, vol. 90, pp. 753–762, 1997.

Takagi S. et al., Expression of a Cell Adhesion Molecule, Neuropilin, in the Developing Chick Nervous system, Developmental Biology, vol. 170, pp. 207–222, 1995.

Takagi S. et al., The A5 Antigen, a candidate for the Neuronal Recognition Molecole, has Homologies to Complement Components and Coagulation Factors, Neuron, vol. 7, pp. 295–307, 1991.

Chen, H. et al., Neuropilin–2, a Novel member of the Neuropilin family, Is a high affinity receptor for thr Semaphorins Sema E and Sema IV but not Sema III, Neuron, vol. 19, pp. 547–559, Sep., 1997.

*Primary Examiner*—Elizabeth Kemmerer
*Assistant Examiner*—Nirmal S. Basi
*Attorney, Agent, or Firm*—Richard Aron Osman

[57] ABSTRACT

The invention provides methods and compositions relating to two classes of semaphorin receptors, SR1 and SR2. The polypeptides may be produced recombinantly from transformed host cells from the disclosed SR encoding nucleic acids or purified from human cells. The invention provides isolated SR hybridization probes and primers capable of specifically hybridizing with the disclosed SR genes, SR-specific binding agents such as specific antibodies, and methods of making and using the subject compositions in diagnosis, therapy and in the biopharmaceutical industry.

45 Claims, 10 Drawing Sheets

SEMAPHORIN RECEPTORS

This Application is a continuation-in-part application under 35USC120 of U.S. Ser. No. 08/889,458 filed Jul. 8, 1997 by Marc Tessier-Lavigne, Zhigang He and Hang Chen and entitled Semaphorin Receptors now abandoned.

The research carried out in the subject application was supported in part by grants from the National Institutes of Health. The government may have rights in any patent issuing on this application.

FIELD OF THE INVENTION

The field of this invention is proteins involved in nerve cell guidance.

BACKGROUND

During nervous system development, axons migrate along prescribed pathways in the embryo to reach their appropriate synaptic targets (reviewed in Tessier-Lavigne and Goodman, 1996). One mechanism that contributes to accurate pathfinding is chemorepulsion, the guidance of axons away from non-target regions by diffusible chemorepellent factors secreted by non-target cells. Experiments in which axons are confronted with non-target tissues in tissue culture and are repelled by these tissues at a distance have demonstrated the existence of diffusible chemorepellent activities for numerous axonal classes (Pini, 1993; Fitzgerald et al., 1993; Colamarino and Tessier-Lavigne, 1995; Tamada et al., 1995; Guthrie and Pini, 1995; Shirasaki et al., 1996) as well as for migrating neuronal cells (Hu and Rutishauser, 1996). At the molecular level, two families of guidance cues, the netrin and semaphorin families, have been shown to comprise members that can function as chemorepellents. In Caenorhaditis elegans, the netrin UNC-6 is thought to repel axons that migrate away from the netrin source since these axons are misrouted at a certain frequency in UNC-6 mutants; this presumed repulsion appears to be mediated by the candidate receptors UNC-5 and UNC-40, which are members of the immunoglobulin superfamily (Hedgecock et al., 1990; Leung-Hagesteijn et al, 1992; Hamelin et al., 1993; Wadsworth et al., 1996; Chan et al., 1996). Similarly, in vertebrates netrin-1 can repel subsets of motor axons that migrate away from a source of netrin-1 (Colamarino and Tessier-Lavigne, 1994; Varela-Echavarria et al., 1997), a process which might involve vertebrate homologues of UNC-5 and UNC-40, which have been shown to be netrin-binding proteins (Leonardo et al., 1997; Ackermann et al., 1997; Keino-Masu et al., 1996).

The semaphorins are a large family of structurally diverse secreted and transmembrane proteins characterized by the presence of a conserved ~500 amino acid semaphorin domain at their amino termini (reviewed in Kolodkin, 1996). The family was first described and implicated in axon guidance through antibody perturbation studies in insects (Kolodkin et al., 1992; Kolodkin et al., 1993). The connection of this family to chemorepulsion was made with the purification of chicken collapsing as a factor that can cause collapse of sensory growth cones when added acutely in cell culture (Luo et al., 1993). Collapsin-1 and its mammalian homologues (Semaphorin III, also known as Semaphorin D) are secreted semaphorins that possess in addition to the semaphorin domain an immunoglobulin domain and a highly basic carboxy-terminal domain (Luo et al., 1993; Kolodkin et al., 1993; Messersmith et al., 1995; Püschel et al., 1995). When presented chronically from a point source, collapsin-1/SemaIII/D (hereafter referred to as SemaIII) can repel sensory and sympathetic axons and has been implicated in patterning sensory axon projections into the ventral spinal cord (Messersmith et al., 1995; Püschel et al., 1995, 1996; Behar et al., 1996; Shepherd et al., 1997). Sema E, which is structurally-related to SemaIII, has also been reported to repel sympathetic axons in culture (cited in Varela-Echavarria and Guthrie, 1997). In Drosophila, the secreted semaphorin SemaIII has been implicated as an inhibitor of axon terminal branch formation (Matthes et al., 1995). However, the mechanisms through which semaphorins produce their repellent or inhibitory actions have not been determined.

To elucidate the mechanisms through which semaphorin proteins produce their repulsive actions on axons, we have sought to identify binding proteins for semphorins on the surfaces of sensory axons. Here we identify two classes of semaphorin receptors, SR1 and SR2, expressed by axons whose function is required for the collapse-inducing and repulsive actions of semaphorins.

SUMMARY OF THE INVENTION

The invention provides methods and compositions relating to isolated semaphorin receptor class 1 and 2 (SR1 and SR2, collectively SR) polypeptides, related nucleic acids, polypeptide domains thereof having SR-specific structure and activity, and modulators of SR function, particularly semaphorin-binding activity. SR polypeptides can regulate cell, especially nerve cell, function and morphology. The polypeptides may be produced recombinantly from transformed host cells from the subject SR polypeptide encoding nucleic acids or purified from mammalian cells. The invention provides isolated SR hybridization probes and primers capable of specifically hybridizing with the disclosed SR genes, SR-specific binding agents such as specific antibodies, and methods of making and using the subject compositions in diagnosis (e.g. genetic hybridization screens for SR transcripts), therapy (e.g. SR inhibitors to promote nerve cell growth) and in the biopharmaceutical industry (e.g. as immunogens, reagents for isolating other Srs, reagents for screening chemical libraries for lead pharmacological agents, etc.).

BRIEF DESCRIPTION OF THE FIGURES

FIGS. 1A1–1B. Structure of rat and human SR1.
(A) Alignment of the amino acid sequences of mouse, rat and human SR1s (SEQ ID NO: 6, 4 and 2, respectively).
(B) Diagram displaying the modular structure of SR1s conserved among different species, and the five SR1 domains (a1, a2, b1, b2, c). S: signal peptide; C1r/s, complement C1r/s homology domain (CUB domain); FV/VIII, regions of homology to coagulation factors V and VIII, the DDR tyrosine kinase, and MFGPs; MAM, MAM domain; TM, transmembrane domain.

FIGS. 3A–3B. Alignment of the amino acid sequences of neuropilin-1 (SR1) and neuropilin-2 (SR2). Alignment of the mouse neuropilin-1 (m-npn-1, SEQ ID NO: 6) mouse neuropilin-2 (m-npn-2, SEQ ID NO: 10) and human neuropilin-2 (h-npn-2, SEQ ID NO: 18) sequences was performed using the Clustal V program. Different domains of the molecules, named according to Kawakami et al. (1996) (see FIG. 2A), are indicated. The a0 isoform of neuropilin-2 (see FIG. 2) was used to create the alignment.

(A) Diagram illustrating the domain structures of mouse neuropilin-1 (Kawakami, et al., 1996) and the full length mouse neuropilin-2(a0) and neuropilin-2(b0) isoforms. s: signal peptide; a1 and a2 domains are CUB domains (Busby and Ingham, 1990; Bork and Beckmann, 1993); b1 and b2 domains show homology to the C1 and C2 domains of coagulation factors V and VIII and of milk fat globular membrane protein; c domain contains a MAM domain, which is found in the metalloendopeptidase meprin and receptor tyrosine phosphatases $\mu$, $\lambda$, and $\kappa$; TM: transmembrane domain; Cy: cytoplasmic domain. The numbers with arrows indicate percent amino acid identity in the indicated domains. The dashed line and arrow indicate the site in neuropilin-2 where the neuropilin-2a and -2b isoforms diverge; this is also the site of the 5-, 17- and 22-amino acid insertions (see also FIG. 2B).

(B) Isoforms of neuropilin-2(a) with 0, 5, 17 and 22 amino acid insertions after amino acid 809 (isoforms 2(a0), 2(a5), 2(a17) and 2(a22), SEQ ID NO: 10,12,14 and 16 respectively), and of neuropilin-2(b) without and with the 5 amino acid insertion (isoforms 2(b0) and 2(b5), SEQ ID NO: 22 and 24 respectively). Shown are the sequences of the insertions, flanked by 3 amino acids N terminal to the insertion (AFA) and 4 amino acids C terminal to the insertions (DEYE in neuropilin-2a, GGTL in neuropilin-2b).

(C) Sequence of neuropilin-2(b0) SEQ ID NO: 22 and partial sequence of human neuropilin-2(b0) SEQ ID NO: 26 from EST (AA25804) in the region where the sequence of neuropilin-2(b0) diverges from that of neuropilin-2 (a0). Three amino acids N terminal to the site of divergence (AFA) are shown.

Figure 5A:
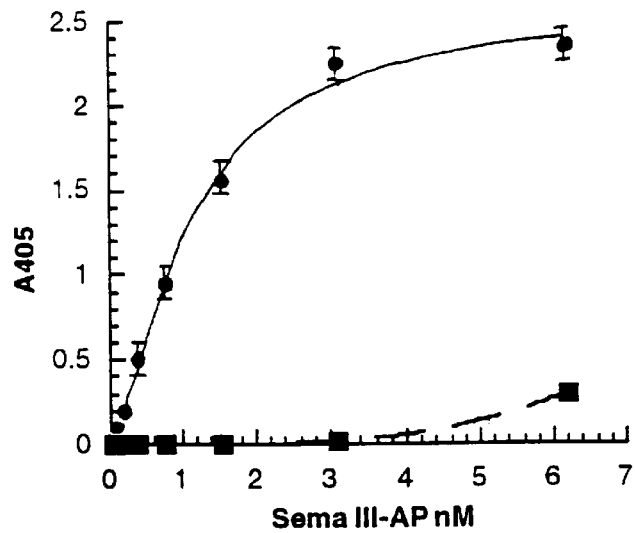
Figure 5B:
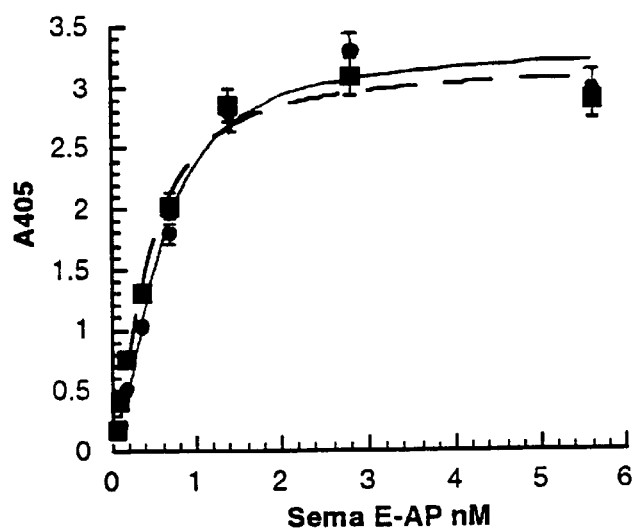

FIGS. 5A–5B. Equilibrium binding of semaphorin-AP fusion proteins to neuropilin-expressing cells. Transfected or control COS cells were incubated with concentrated media containing the indicated concentrations of semaphorin-AP fusion proteins. AP activity derived from bound fusion proteins was measured colorimetrically at 405 nm; specific binding was obtained after subtraction of background from control cells. Specific binding curves to cells expressing neuropilin-1 (closed circles) or neuropilin-1 (closed squares) are shown for Sema III-AP (A), Sema E-AP (B), and Sema IV-AP (C). Dissociation constants for interaction with neuropilin-2-expressing cells were 0.29 for Sema E-AP and 0.09 nM for Sema IV-AP.

DETAILED DESCRIPTION OF THE INVENTION

Figure 3A:
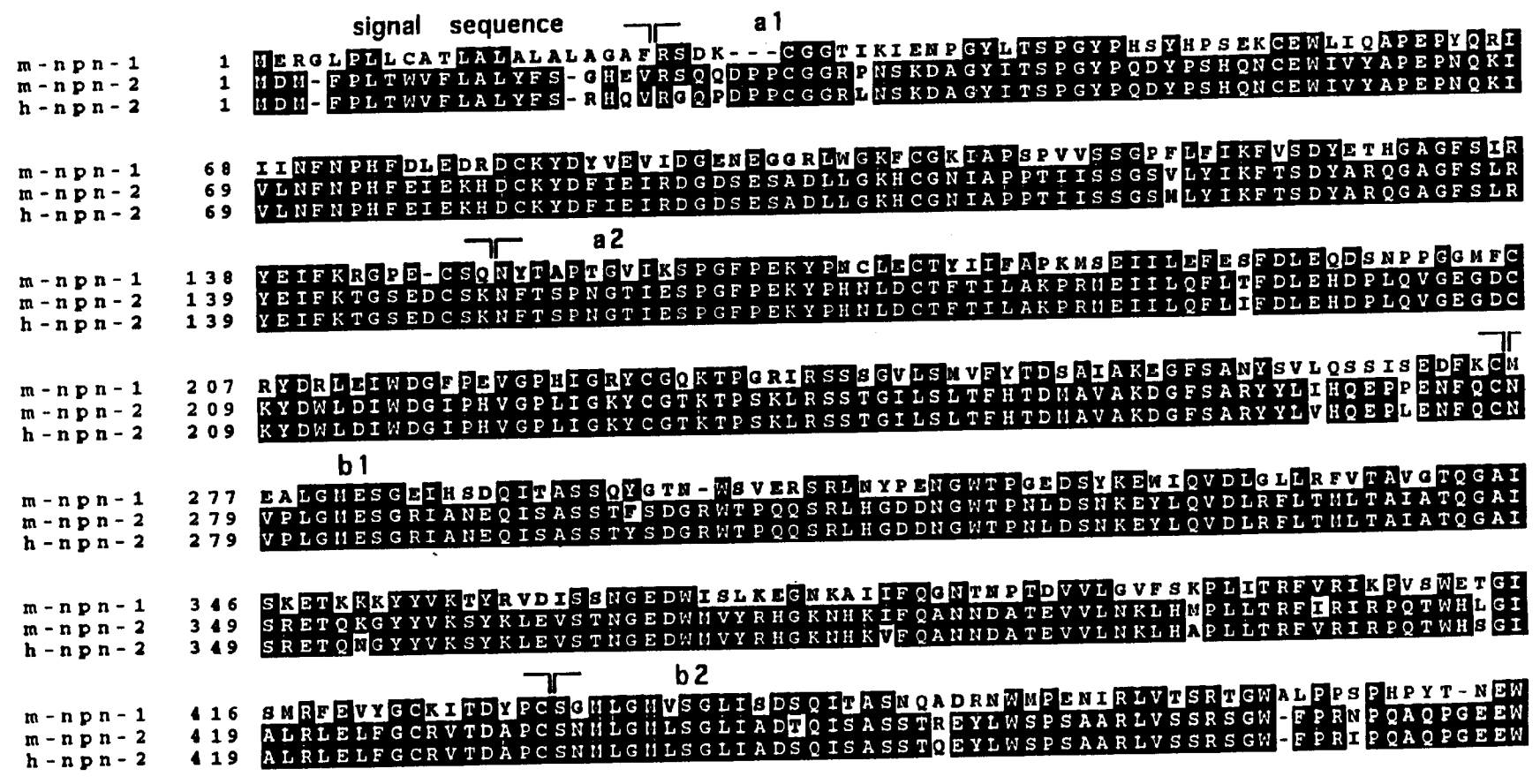
Figure 3B:
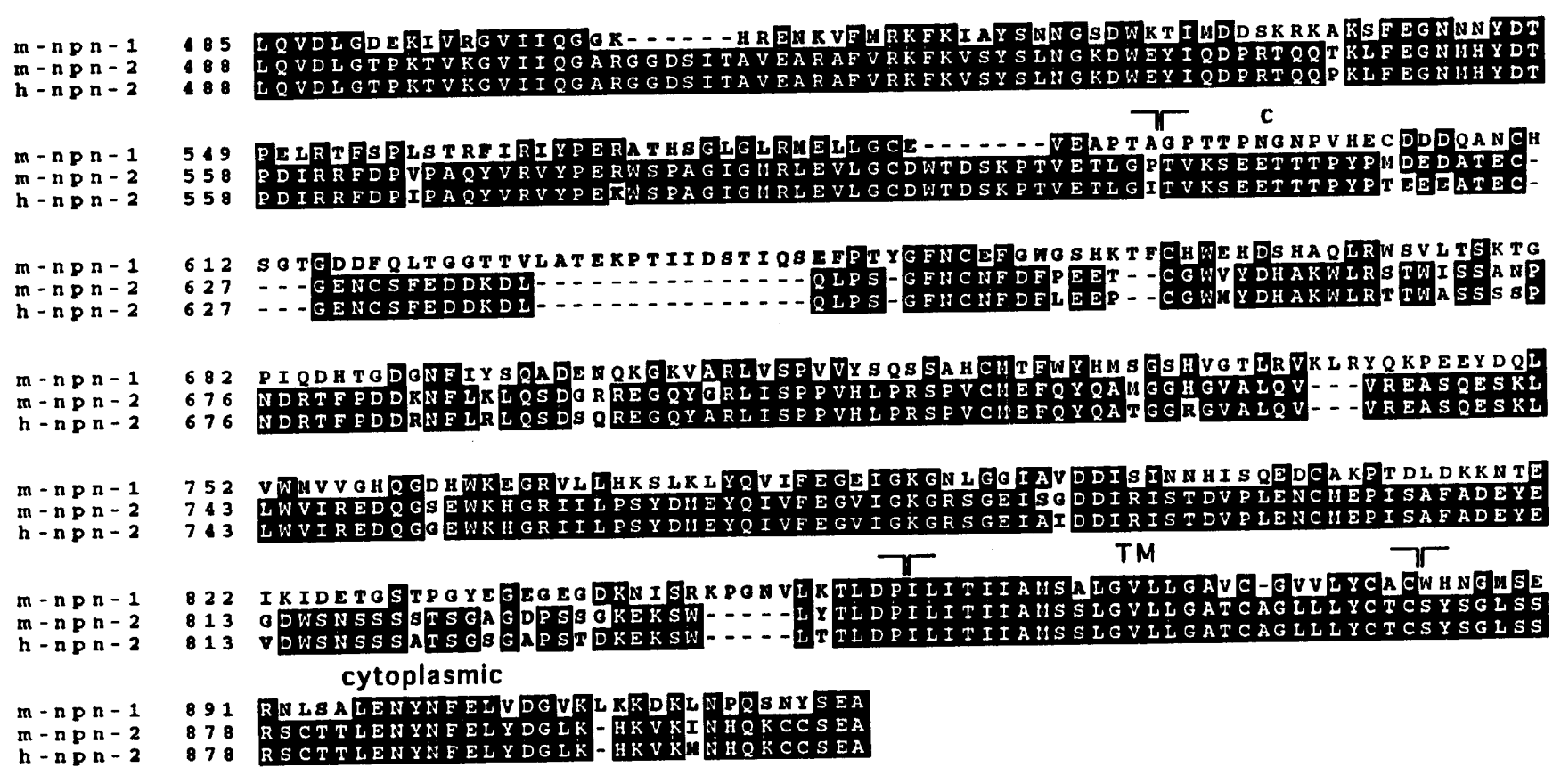

The nucleotide sequences of exemplary natural cDNAs encoding human, rat and mouse SR1 polypeptides are shown as SEQ ID NOS:1, 3 and 5, respectively, and the full conceptual translates are shown as SEQ ID NOS:2, 4 and 6. Natural SR2 cDNAs are found in (a) and (b) forms deriving from two distinct genes, with transcripts of each found in four alternatively spliced forms designated 0, 5, 17 and 22, depending on the size of an insert (below). For example, the nucleotide sequences of exemplary natural cDNAs encoding mouse SR2(a)0, 5, 17 and 22 polypeptides are shown as SEQ ID NOS:9, 11, 13 and 15, respectively, and the full conceptual translates are shown as SEQ ID NOS:10, 12, 14 and 16. Other sequences recited in the Sequence Listing include the nucleotide sequences of exemplary natural cDNAs encoding mouse SR2(b)0 and 5 polypeptides (SEQ ID NOS:21 and 23) and their full conceptual translates (SEQ ID NOS:22 and 24); rat SR2(a)0 polypeptide (SEQ ID NO:7) and its full conceptual translate (SEQ ID NO:8); human SR2(a)0 and 17 polypeptides (SEQ ID NOS:17 and 19) and their full conceptual translates (SEQ ID NOS:18 and 20); and human SR2(b)0 polypeptide (SEQ ID NO:25) and its full conceptual translate (SEQ ID NO:26). The SR polypeptides of the invention include incomplete translates of SEQ ID NOS:1, 3, 7, 9, 11, 13, 15, 17, 19, 21, 23 and 25 and deletion mutants of SEQ ID NOS:2, 4, 8, 10, 12, 14, 16, 18, 20, 22, 24 and 26, which translates and deletion mutants have SR-specific amino acid sequence, binding specificity or function. Preferred translates/deletion mutants comprise at least a 6, preferably at least an 8, more preferably at least a 10, most preferably at least a 12 residue domain of the translates not found in mouse, drosophila or chick neuropilin-1. Other preferred mutants comprise a domain comprising at least one SR2 and/or human specific residue. Such domains are readily discernable from alignments of the disclosed SR1 and SR2 polypeptides, e.g. FIGS. 1 and 3. For example, human SR1 specific residues include V11, V15, P18, A19, N24, E26, D29, S35, D62, M68, F90, N96, H98, F99, R100, T153, S155, S170, V177, P196, D219, I242, V269, S298, A303, R323, K360, 1361, V363, T372, 1373, P379, V380, L381, V393, A394, P399, A40, T411, S449, G453, S469, A476, S479, I481, I487, E491, I498, G518, M528, T553, P555, A556, G572, A587, L599, D601, V634, N667, V669, K672, S674, N717, R737, A755, 1756, S805, A813, P820, G835, E838, E855, T916, Q917 and T919.

The subject domains provide SR domain specific activity or function, such as SR-specific cell, especially neuron modulating or modulating inhibitory activity, semaphorin-binding or binding inhibitory activity. SR-specific activity or function may be determined by convenient in vitro, cell-based, or in vivo assays: e.g. in vitro binding assays, cell culture assays, in animals (e.g. gene therapy, transgenics, etc.), etc. Binding assays encompass any assay where the molecular interaction of an SR polypeptide with a binding target is evaluated. The binding target may be a natural intracellular binding target such as a semaphorin, a SR regulating protein or other regulator that directly modulates SR activity or its localization; or non-natural binding target such a specific immune protein such as an antibody, or an SR specific agent such as those identified in screening assays such as described below. SR-binding specificity may assayed by binding equilibrium constants (usually at least about $10^7 M^{-1}$, preferably at least about $10^8 M^{-1}$, more preferably at least about $10^9 M^{-1}$), by the ability of the subject polypeptide to function as negative mutants in SR-expressing cells, to elicit SR specific antibody in a heterologous host (e.g a rodent or rabbit), etc. In any event, the SR binding specificity of the subject SR polypeptides necessarily distinguishes mouse, chick and drosophila neuropilin-1.

Figures 4A, 4B, 4C:
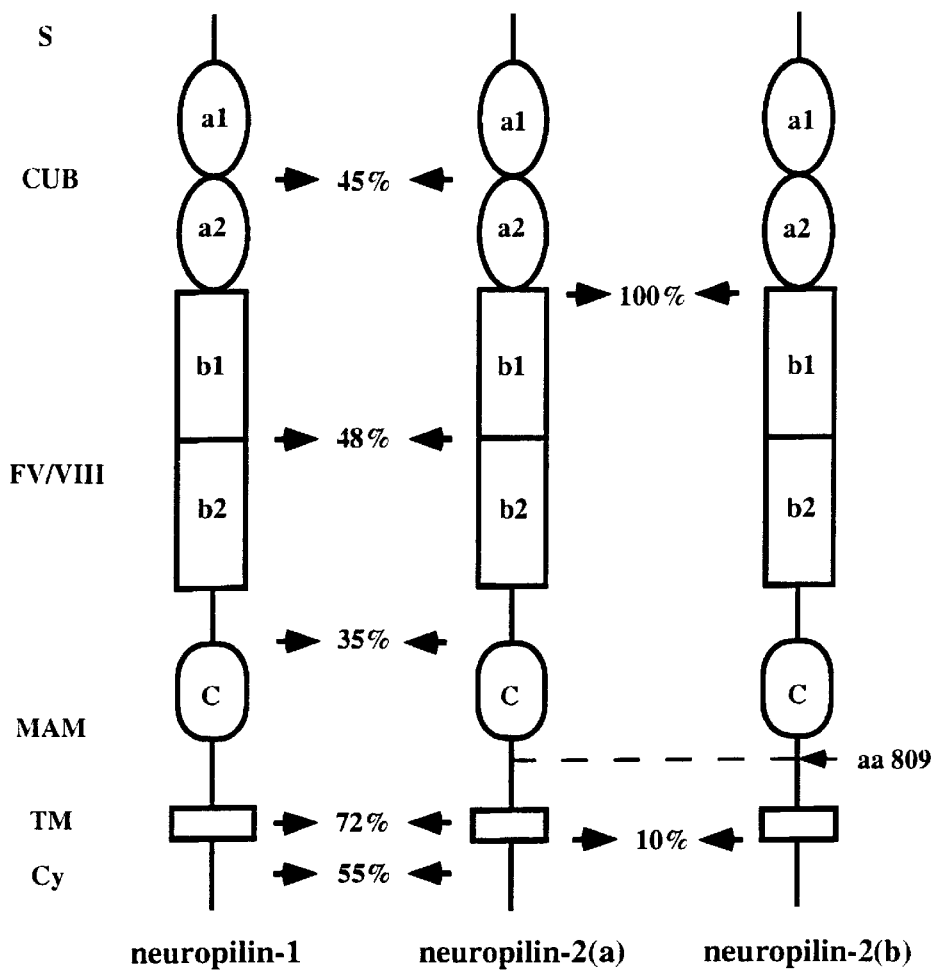
FIGS. 4A–4C. Domain structure and isoforms of neuropilin-2.

For example, the a1, a2, b1, b2, c, TM and Cy domains (FIG. 4A) and the polypeptides comprising the inserts shown in FIGS. 4B and 4C are all shown to exhibit SR specific binding. Similarly, high throughput screens (e.g. see below) using SR-specific binding agents such as SemaIII and anti-SR antibodies are used to readily demonstrate SR-specific binding agents in a wide variety of deletion mutants of the disclosed SR polypeptides. For example, human SR1 peptides with assay demonstrable SR-specific activity include: SEQ ID NO:2, residues 24–34; SEQ ID NO:2, residues 57–68; SEQ ID NO:2, residues 85–111; SEQ ID NO:2, residues 147–155; SEQ ID NO:2, residues 166–178; SEQ ID NO:2, residues 288–299 SEQ ID NO:2, residues 354–366; SEQ ID NO:2, residues 368–690; SEQ ID NO:2, residues 397–415; SEQ ID NO:2, residues 595–615; SEQ ID NO:2, residues 671–689; SEQ ID NO:2, residues 911–919. Human SR2 peptides with assay demonstrable SR-specific activity include: SEQ ID NO:20, residues 14–35; SEQ ID NO:20, residues 261– 278; SEQ ID NO:20, residues 285–301; SEQ ID NO:20, residues 471–485; SEQ ID NO.20, residues 616–628; SEQ ID NO:20, residues 651–685; SEQ ID NO:20, residues 682–696; SEQ ID NO:20, residues 719–745; SEQ ID NO:20, residues 802–825; SEQ ID NO:20, residues 815–830; SEQ ID NO:20, residues 827–839; and SEQ ID NO:20, residues 898–929.

The claimed SR polypeptides are isolated or pure: an "isolated" polypeptide is unaccompanied by at least some of the material with which it is associated in its natural state, preferably constituting at least about 0.5%, and more preferably at least about 5% by weight of the total polypeptide in a given sample and a pure polypeptide constitutes at least about 90%, and preferably at least about 99% by weight of the total polypeptide in a given sample. A polypeptide, as used herein, is an polymer of amino acids, generally at least 6 residues, preferably at least about 10 residues, more preferably at least about 25 residues, most preferably at least about 50 residues in length. The SR polypeptides and polypeptide domains may be synthesized, produced by recombinant technology, or purified from mammalian, preferably human cells. A wide variety of molecular and biochemical methods are available for biochemical synthesis, molecular expression and purification of the subject compositions, see e.g. Molecular Cloning, A Laboratory Manual (Sambrook, el al. Cold Spring Harbor Laboratory), Current Protocols in Molecular Biology (Eds. Ausubel, et al., Greene Publ. Assoc., Wiley-Interscience, NY) or that are otherwise known in the art.

The invention provides binding agents specific to the claimed SR polypeptides, including natural intracellular binding targets, etc., methods of identifying and making such agents, and their use in diagnosis, therapy and pharmaceutical development. For example, specific binding agents are useful in a variety of diagnostic and therapeutic applications, especially where disease or disease prognosis is associated with improper or undesirable axon outgrowth or orientation. Novel SR-specific binding agents include SR-specific receptors, such as somatically recombined polypeptide receptors like specific antibodies or T-cell antigen receptors (see, e.g Harlow and Lane (1988) Antibodies, A Laboratory Manual, Cold Spring Harbor Laboratory), semaphorins and other natural intracellular binding agents identified with assays such as one-, two- and three-hybrid screens, non-natural intracellular binding agents identified in screens of chemical libraries such as described below, etc. Agents of particular interest modulate SR function, e.g. semaphorin-mediated cell modulation. For example, a wide variety of inhibitors of SR activity may be used to cell function involving SR, especially SR-semaphorin interations. Exemplary SR activity inhibitors include SR-derived peptide inhibitors, esp. dominant negative deletion mutants, etc., see Experimental, below.

Accordingly, the invention provides methods for modulating cell function comprising the step of modulating SR activity, e.g. by contacting the cell with an SR inhibitor. The cell may reside in culture or in situ, i.e. within the natural host. Preferred inhibitors are orally active in mammalian hosts. For diagnostic uses, the inhibitors or other SR binding agents are frequently labeled, such as with fluorescent, radioactive, chemiluminescent, or other easily detectable molecules, either conjugated directly to the binding agent or conjugated to a probe specific for the binding agent.

The amino acid sequences of the disclosed SR polypeptides are used to back-translate SR polypeptide-encoding nucleic acids optimized for selected expression systems (Holler et al. (1993) Gene 136, 323–328; Martin et al. (1995) Gene 154, 150–166) or used to generate degenerate oligonucleotide primers and probes for use in the isolation of natural SR-encoding nucleic acid sequences ("GCG" software, Genetics Computer Group, Inc, Madison Wis.). SR-encoding nucleic acids used in SR-expression vectors and incorporated into recombinant host cells, e.g. for expression and screening, transgenic animals, e.g. for functional studies such as the efficacy of candidate drugs for disease associated with SR-modulated cell function, etc.

The invention also provides nucleic acid hybridization probes and replication/amplification primers having a SR cDNA specific sequence comprising SEQ ID NO:1, 3, 7, 9, 11, 13, 15, 17, 19, 21, 23, or 25, and sufficient to effect specific hybridization thereto (i.e. specifically hybridize with SEQ ID NO:1, 3, 7, 9, 11, 13, 15, 17, 19, 21, 23, or 25, respectively, in the presence of mouse, drosophila and chick neuropilin cDNA. Such primers or probes are at least 12, preferably at least 24, more preferably at least 36 and most preferably at least 96 bases in length. Demonstrating specific hybridization generally requires stringent conditions, for example, hybridizing in a buffer comprising 30% formamide in 5× SSPE (0.18 M NaCl, 0.01 M NaPO$_4$, pH7.7, 0.001 M EDTA) buffer at a temperature of 42° C. and remaining bound when subject to washing at 42° C. with 0.2× SSPE; preferably hybridizing in a buffer comprising 50% formamide in 5× SSPE buffer at a temperature of 42° C. and remaining bound when subject to washing at 42° C. with 0.2× SSPE buffer at 42° C. SR nucleic acids can also be distinguished using alignment algorithms, such as BLASTX (Altschul et al. (1990) Basic Local Alignment Search Tool, J Mol Biol 215, 403–410).

The subject nucleic acids are of synthetic/non-natural sequences and/or are isolated, i.e. unaccompanied by at least some of the material with which it is associated in its natural state, preferably constituting at least about 0.5%, preferably at least about 5% by weight of total nucleic acid present in a given fraction, and usually recombinant, meaning they comprise a non-natural sequence or a natural sequence joined to nucleotide(s) other than that which it is joined to on a natural chromosome. The subject recombinant nucleic acids comprising the nucleotide sequence of SEQ ID NO:1, 3, 7, 9, 11, 13, 15, 17, 19, 21, 23, or 25, or fragments thereof, contain such sequence or fragment at a terminus, immediately flanked by (i.e. contiguous with) a sequence other than that which it is joined to on a natural chromosome, or flanked by a native flanking region fewer than 10 kb, preferably fewer than 2 kb, which is at a terminus or is immediately flanked by a sequence other than that which it is joined to on a natural chromosome. While the nucleic acids are usually RNA or DNA, it is often advantageous to use nucleic acids comprising other bases or nucleotide analogs to provide modified stability, etc.

The subject nucleic acids find a wide variety of applications including use as translatable transcripts, hybridization probes, PCR primers, diagnostic nucleic acids, etc.; use in detecting the presence of SR genes and gene transcripts and in detecting or amplifying nucleic acids encoding additional SR homologs and structural analogs. In diagnosis, SR hybridization probes find use in identifying wild-type and mutant SR alleles in clinical and laboratory samples. Mutant alleles are used to generate allele-specific oligonucleotide (ASO) probes for high-throughput clinical diagnoses. In therapy, therapeutic SR nucleic acids are used to modulate cellular expression or intracellular concentration or availability of active SR.

The invention provides efficient methods of identifying agents, compounds or lead compounds for agents active at the level of a SR modulatable cellular function. Generally, these screening methods involve assaying for compounds which modulate SR interaction with a natural SR binding target such as a semaphorin. A wide variety of assays for binding agents are provided including labeled in vitro protein-protein binding assays, immunoassays, cell based assays, etc. The methods are amenable to automated, cost-effective high throughput screening of chemical libraries for lead compounds. Identified reagents find use in the pharmaceutical industries for animal and human trials; for example, the reagents may be derivatized and rescreened in in vitro and in vivo assays to optimize activity and minimize toxicity for pharmaceutical development.

In vitro binding assays employ a mixture of components including an SR polypeptide, which may be part of a fusion product with another peptide or polypeptide, e.g. a tag for detection or anchoring, etc. The assay mixtures comprise a natural intracellular SR binding target. In a particular embodiment, the binding target is a semaphorin polypeptide. While native full-length binding targets may be used, it is frequently preferred to use portions (e.g. peptides) thereof so long as the portion provides binding affinity and avidity to the subject SR polypeptide conveniently measurable in the assay. The assay mixture also comprises a candidate pharmacological agent. Candidate agents encompass numerous chemical classes, though typically they are organic compounds; preferably small organic compounds and are obtained from a wide variety of sources including libraries of synthetic or natural compounds. A variety of other reagents may also be included in the mixture. These include reagents like salts, buffers, neutral proteins, e.g. albumin, detergents, protease inhibitors, nuclease inhibitors, antimicrobial agents, etc. may be used.

The resultant mixture is incubated tinder conditions whereby, but for the presence of the candidate pharmacological agent, the SR polypeptide specifically binds the cellular binding target, portion or analog with a reference binding affinity. The mixture components can be added in any order that provides for the requisite bindings and incubations may be performed at any temperature which facilitates optimal binding. Incubation periods are likewise selected for optimal binding but also minimized to facilitate rapid, high-throughput screening.

After incubation, the agent-biased binding between the SR polypeptide and one or more binding targets is detected by any convenient way. Where at least one of the SR or binding target polypeptide comprises a label, the label may provide for direct detection as radioactivity, luminescence, optical or electron density, etc. or indirect detection such as an epitope tag, etc. A variety of methods may be used to detect the label depending on the nature of the label and other assay components, e.g. through optical or electron density, radiative emissions, nonradiative energy transfers, etc. or indirectly detected with antibody conjugates, etc.

A difference in the binding affinity of the SR polypeptide to the target in the absence of the agent as compared with the binding affinity in the presence of the agent indicates that the agent modulates the binding of the SR polypeptide to the SR binding target. For example, in the cell-based assay also described below, a difference in SR-dependent modulation of axon outgrowth or orientation in the presence and absence of an agent indicates the agent modulates SR function. A difference, as used herein, is statistically significant and preferably represents at least a 50%, more preferably at least a 90% difference.

The following experimental section and examples are offered by way of illustration and not by way of limitation.

EXPERIMENTAL

Expression cloning of a cDNA encoding a SemaIII-binding protein

To facilitate isolation of SemaIII-binding proteins through expression cloning, we fused the coding region of SemaIII to that of alkaline phosphatase (AP), a readily detectable histochemical reporter, and expressed the resulting chimeric protein in human embryonic kidney 293 cells. This protein could be detected by Western blotting in conditioned medium from these cells as a major band of ~180 kDa, consistent with the combined sizes of SemaIII and AP; a few smaller products, apparently degradation products, were also detected in this medium. When this medium was applied to dissociated sensory neurons from dorsal root ganglia (DRG), AP-reactivity could be detected on the axons and cell bodies of neurons from E14 DRG but not E18 DRG. AP alone, also expressed in 293 cells, did not bind cells at either age. The binding of Sema-AP to E14 but not E18 DRG cells is not unexpected since at E14 DRG axons are beginning to project into the spinal cord and can be repelled by a factor, likely Sema III, secreted by the ventral spinal cord (Fitzgerald et al., 1993; Messersmith et al., 1995; Shepherd et al., 1997), whereas by E18 they are no longer repelled by ventral spinal cord tissue (Fitzgerald et al., 1993), perhaps reflecting a downregulation of their responsiveness to SemaIII.

To identify SemaIII-binding proteins on E14 rat DRG neurons, a cDNA expression library was constructed in a COS cell expression vector using cDNA derived from E14 DRG tissue (see Experimental Procedures). Pools of ~1000–2000 cDNA clones from the library were transfected into COS cells and screened for the presence of cells that bound SemaIII-AP. A positive pool was identified after screening 70 pools. After three rounds of screening subpools from this pool, a single cDNA encoding a SemaIII-AP binding activity was identified. COS-7 cells transfected with this cDNA specifically bound SemaIII-AP but not AP or a netrin-Fc fusion protein (Keino-Masu et al., 1996).

Figure 1A1:
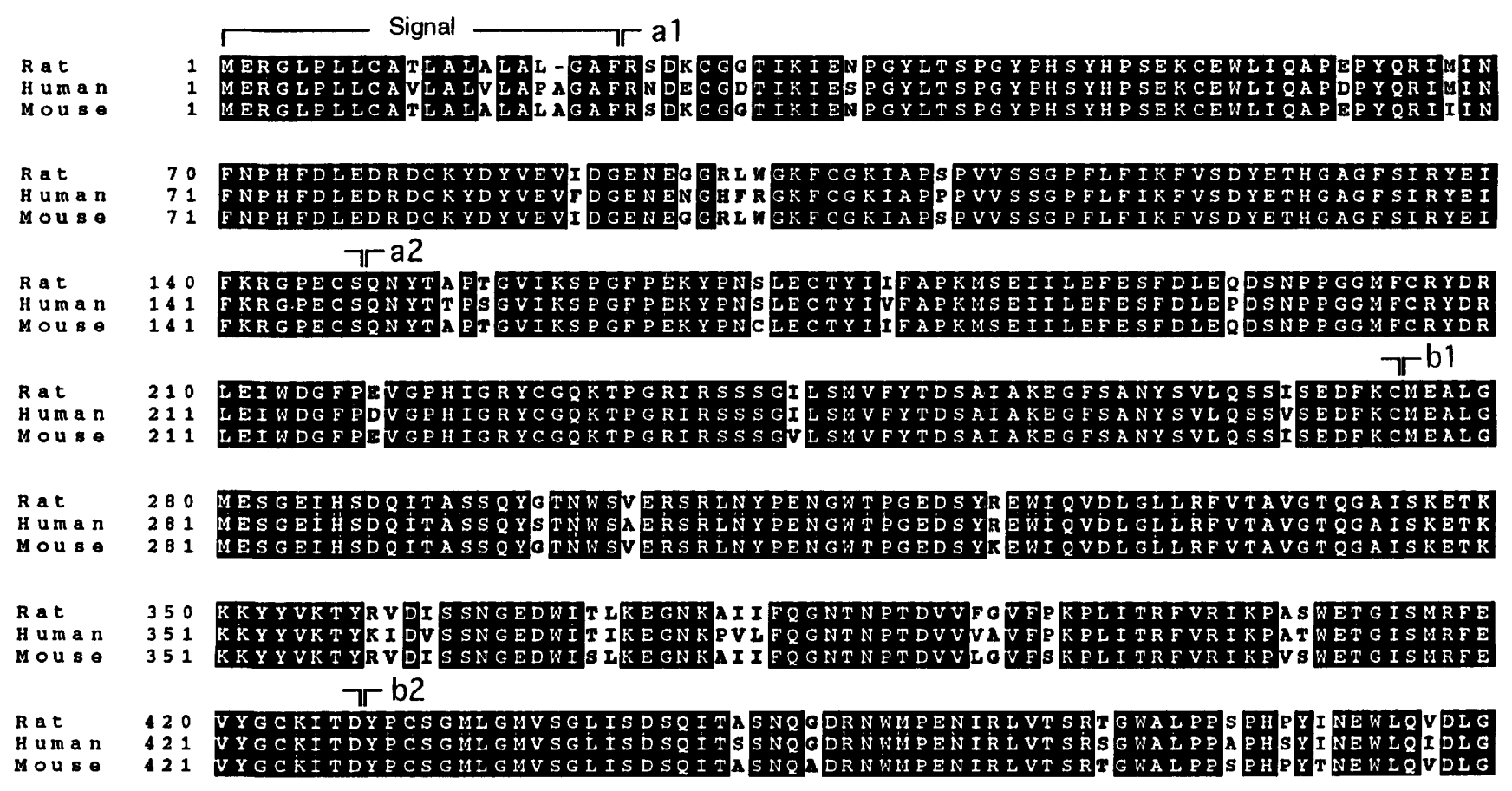
Figure 1A2:
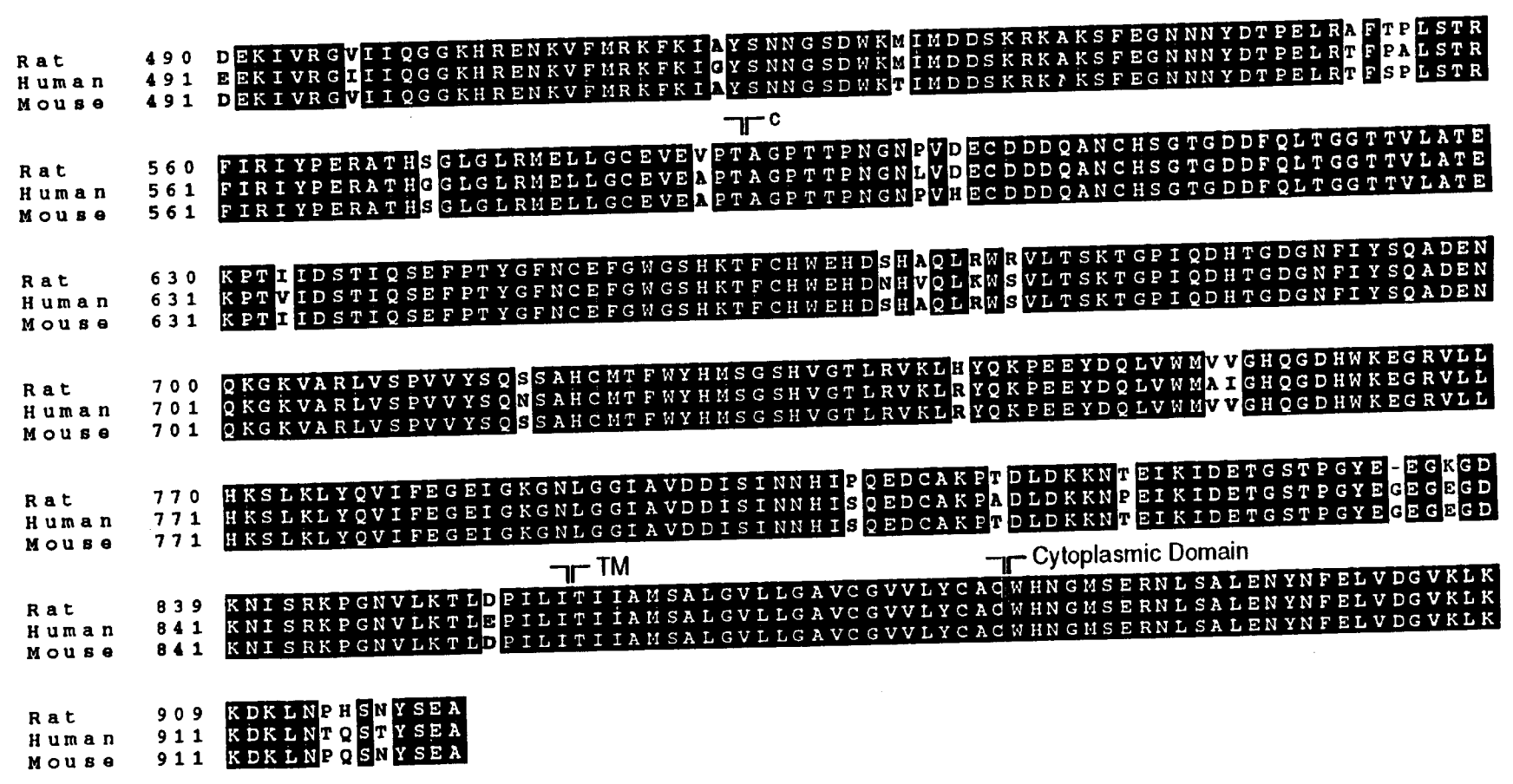
Figure 1B:
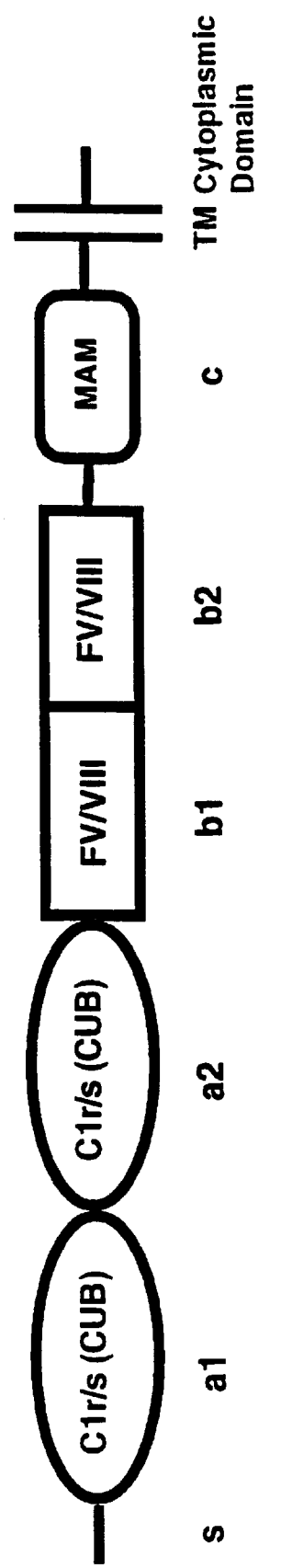

Nucleotide sequencing of the entire 5 kB cDNA insert revealed a single long open reading frame predicted to encode a protein (rat semaphorin receptor 1, rSR1) of 921 amino acids with sequence similarity with mouse, chicken and Xenopus neuropilin (Takagi et al., 1991, 1995; Kawakami et al., 1996). We further isolated a cDNA encoding a human homolog of our semphorin binding protein (hSR1) from a fetal human brain library (see Experimental Procedures), and FIG. 1A shows an alignment of the full conceptual translated amino acid sequences of our rat and human proteins with mouse neuropilin. The rat and human proteins share a high degree of sequence homology with the mouse protein (97% and 93% identity at the amino acid level, respectively), and are predicted to have the domain structure previously described for neuropilins from other species, including a short but highly conserved cytoplasmic domain (FIG. 1B).

We next performed coimmunoprecipitation experiments to test whether the binding of SemaIII-AP to COS-7 cells expressing rSR1 reflected a direct interaction between SemaIII and rSR1 or required cellular factors made by the COS-7 cells. For this purpose we constructed a soluble version of the ectodomain of rSR1 fused to AP. A myc-tagged SemaIII protein could be precipitated by beads conjugated with this SR-AP fusion, but not with beads conjugated with a control fusion protein, c-kit-AP (Flanagan and Leder, 1990), indicating a direct interaction between the SR1 ectodomain and SemaIII.

SR1 binds both the semaphorin and the C-terminal domains of SemaIII

SemaIII consists of a signature semaphorin domain, a single immunoglobulin (Ig) domain, and a carboxy terminal (C) domain that is rich in basic residues (Luo et al., 1993; Kolodkin et al., 1993; Messersmith et al., 1995; Püschel et al., 1995). The conservation of semaphorin domains among different semaphorin family members (reviewed in Tessi-Lavigne and Goodman, 1996; Kolokin, 1996) suggests the potential importance of this domain for function. The functions of the other two domains are unknown, although the basic nature of the C domain has suggested a role for this domain in mediating interactions with cell surfaces or the extracellular matrix (Luo et al., 1993). To determine which domain of SemaIII mediates the interaction between SemaIII and SR1, constructs encoding various fusions of AP to different portions of SemaIII were expressed in COS cells. Media conditioned by these cells were applied to COS-7 cells expressing SR1 to test for binding of AP fusion proteins; in positive control experiments, binding was observed with medium containing full length SemaIII-AP but not AP alone. Binding was also observed with an AP fusion protein comprising the semaphorin and Ig domains (AP-SI) and a fusion protein comprising just the semaphorin domain (AP-S), but not with a fusion protein comprising a truncated semaphorin domain, suggesting that the integrity of the semaphorin domain is required for binding. Surprisingly, binding was also observed with AP fusion proteins comprising only the C domain (AP-C) and a fusion protein comprising the Ig and C domains. These results provide evidence that both the semaphorin and the C domains of SemaIII can bind SR1. The binding of the C domain does not appear to reflect a non-specific interaction arising from the basic nature of the C domain since we found that the C terminal domain of netrin-1 (Serafini et al., 1994), which is also highly basic but does not share any sequence homology with the SemaIII C domain, did not bind SR1.

Figure 2A:
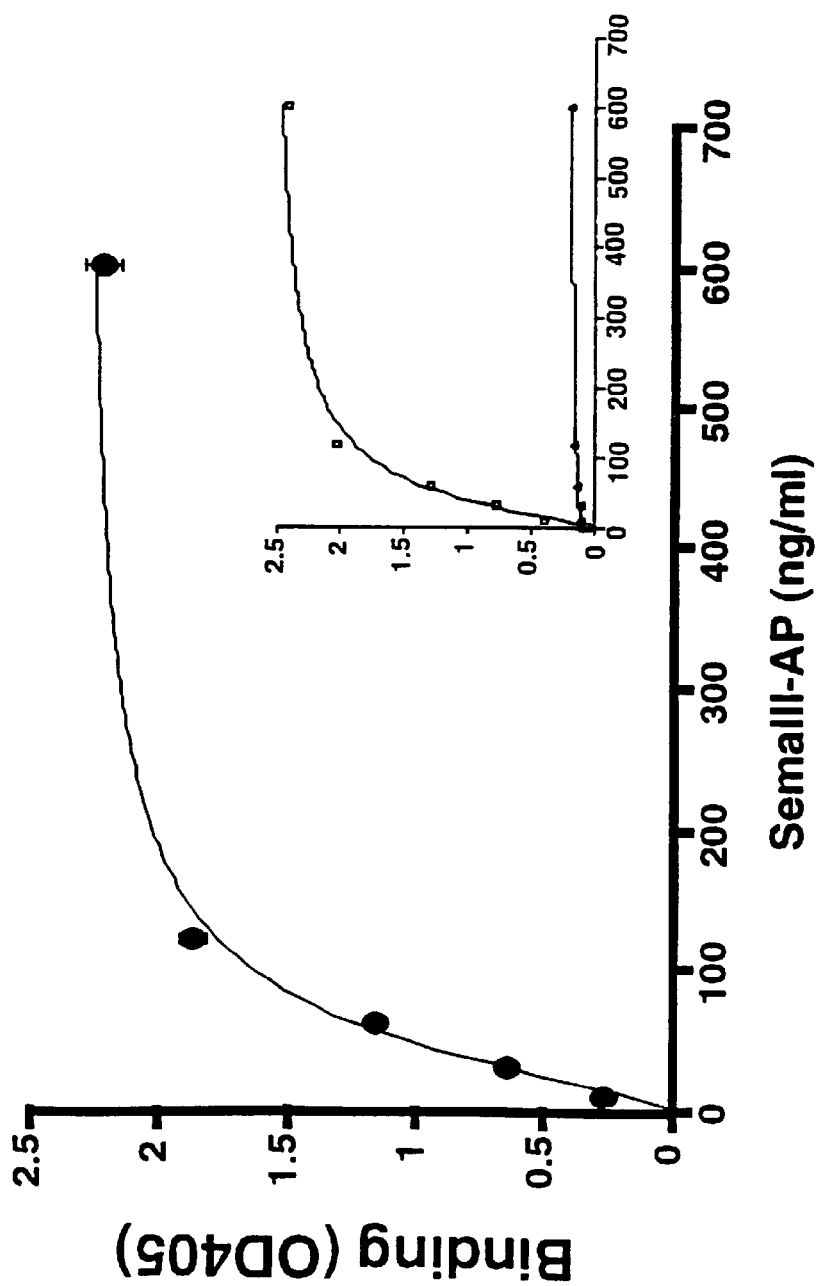
FIGS. 2A–2C. Equilibrium Binding of Fusion Proteins of AP and different portions of SemaIII to SR1-Expressing cells.
Figure 2B:
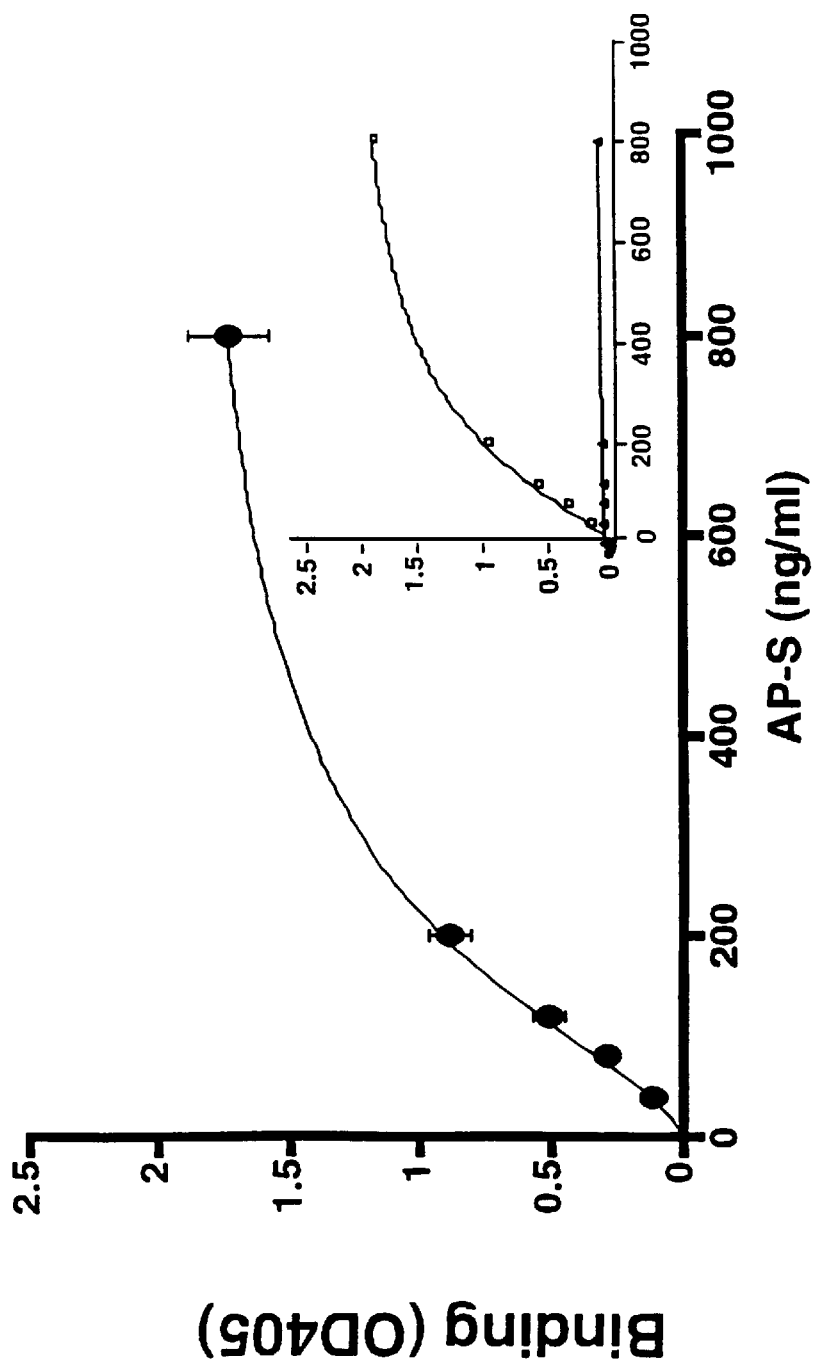
Figure 2C:
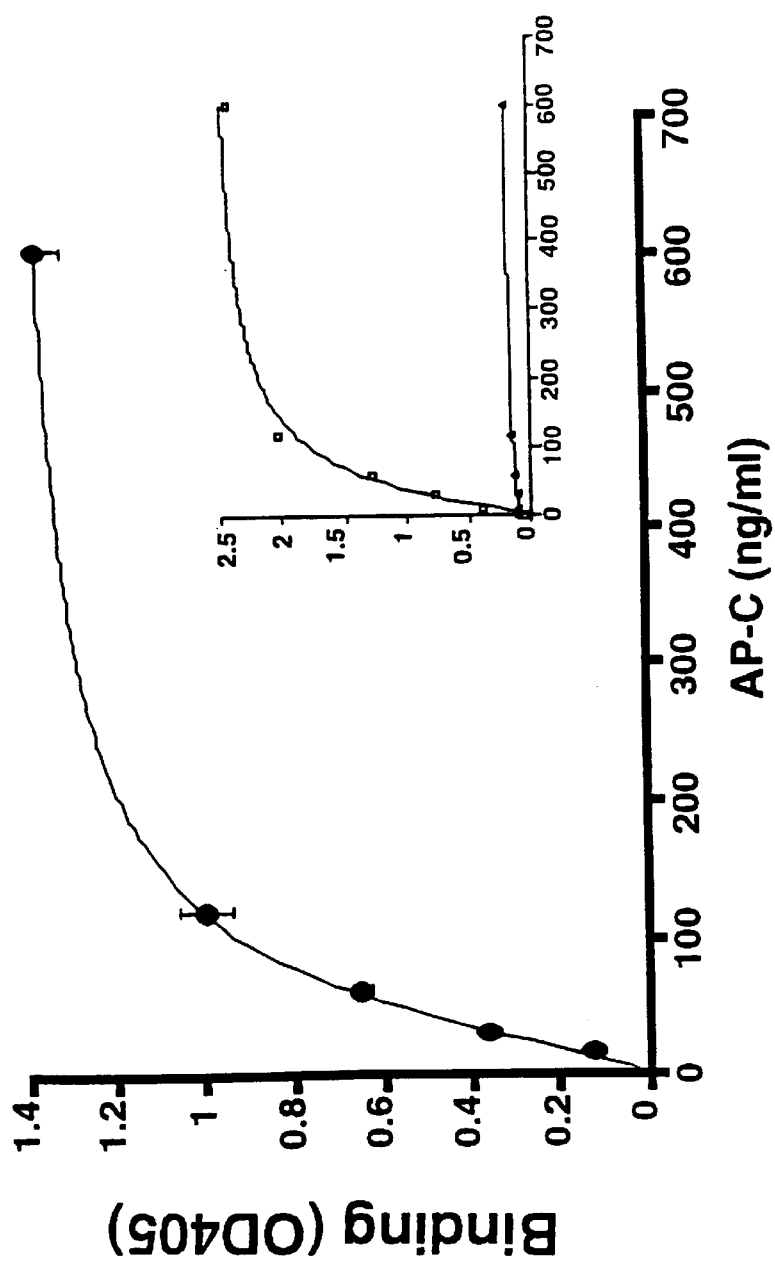

We next measured the binding affinity of the full-length and two of the truncated fusion ligands (AP-S and AP-C) to cells expressing SR1 in equilibrium binding experiments, based on the relative amounts of AP activity in the supernatant and bound to cells (FIG. 2). One limitation of these experiments is that we used partially purified conditioned media (see Experimental Procedures) which in the case of SemaIII-AP and AP-C contain both the full length fusion proteins as well as truncated forms that are presumed to arise by proteolysis. For each of these fusions, the estimated dissociation constant would be accurate only if all the degradation products that possess AP activity bind with the same affinity as the intact fusion protein; this is unlikely to be the case since the media contain protein species that appear to correspond to AP or fragments of AP, which do not bind SR1. This limitation does not apply to AP-S since in this case only the full length species is found in the supernatant; the estimated dissociation constant should therefore accurately reflect the affinity of AP-S for the SR1-expressing cells. With these caveats, we found that the specific binding curves of SemaIII-AP, AP-S and AP-C to cells expressing SR1 showed saturation and could be fitted with the Hill equation (FIGS. 2A–C). Predicted values for the dissociation constants (Kd) for SemaIII-AP, AP-S and AP-C binding to SR1-expressing cells were 0.325 nM, 1.45 nM, and 0.84 nM, respectively. For comparison, in the collapse assay, a half maximal collapse response is observed with conditioned medium containing 0.44 nM SemaIII-AP. This value is comparable to the estimated Kd for the interaction of SemaIII-AP with SR1. These results support the role of an interaction of SemaIII with SR1 on DRG axons in causally mediating collapse.

For these experiments, control 293-EBNA cells or 293-EBNA cells stably expressing rat SR1 were treated for 90 min with concentrated conditioned media containing the indicated concentrations of SemaIII-AP (A), AP-S (B), or AP-C (C). After washing six times in HBHA buffer, the cells were lysed and endogenous AP activity was heat-inactivated. AP activity derived from the bound recombinant AP fusion proteins was measured colorimetrically (optical density at 405 nm). Specific binding was determined by subtraction of values obtained from binding to SR1-expressing cells and to control cells; values obtained in this way were fitted to the Hill equation. Insets in FIG. 2 show raw data (circles, total binding to SR1-expressing cells; triangles, total binding to control cells). Kd values for the interactions of SemaIII-AP, AP-S and AP-C with SR1 were 55.3±6.5 ng/ml, 218.6±11.0 ng/ml, and 67.2±3.0 ng/ml, respectively (1 nM corresponds to 170 ng/ml, 150 ng/ml, and 80 ng/ml for SemaIII-AP, AP-S and AP-C, respectively). Bars indicated s.e.m. for triplicates. Hill coefficients for SemaIII-AP, AP-S and AP-C were 1.51±0.24, 1.70±0.10, and 1.44±0.07, respectively.

SR1 function is required for the repulsive action of SemaIII

We next raised antibodies to a portion of the SR1 ectodomain for use in tests of the functional role of SR1 in mediating responses to SemaIII (see Experimental Procedures). To verify the potential usefulness of the antiserum, we first examined whether it could detect SR1 protein on axons. The spatial and temporal pattern of expression of SR1 detected with this antiserum in transverse sections of rat embryos at spinal levels corresponded to the sites of SR1 gene expression detected by in situ hybridization, and matched the pattern previously observed in mouse and chick embryos (Kawakami et al., 1995; Takagi et al., 1995). At E14, when afferent fibers of DRG neurons start to penetrate the dorsal spinal cord (Windle and Baxter, 1936; Smith, 1983; Altman and Bayer, 1994; Snider et al., 1992; Zhang et al., 1994), SR1 transcripts were found in the DRG as well as in the ventral and dorsal spinal cord, and corresponding immunoreactivity for SR1 protein was detected on sensory and motor axons, as well as in the dorsal spinal cord. SR1 immunoreactivity could also be detected with this antiserum on the axons and growth cones of E14 rat DRG neurons in culture, as previously shown for neuropilin with chick DRG axons (Takagi et al., 1995). At E18, much lower levels of SR1 transcripts were detected in DRG and the ventral horn (see also Kawakami et al., 1995; Takagi et al., 1995 for similar results with neuropilin in mice and chickens). The timing of expression in DRG is consistent with the pattern of SemaIII-AP binding to E14 and E18 DRG cells in culture and with what might be expected of a SemaIII receptor (see Fitzgerald et al., 1993; Messersmith et al., 1995; and discussions therein)

Protein A-purified anti-SR1 antiserum was used to test the involvement of SR1 in mediating the function of SemaIII. Inclusion of the antiserum in the culture medium inhibited the repulsive effect of SemaIII-AP and SemaIII on E14 rat DRG axons in collagen gel cultures in a dose-dependent manner, whereas preimmune IgG, also purified on protein A, did not inhibit the repulsion. To verify that this neutralizing effect was due to antibodies directed against SR1 in the antiserum, aliquots of the antiserum were subjected to immunodepletion by incubation with beads conjugated with the portion of the SR1 ectodomain used to make the antiserum (depleted antiserum) or with control beads (mock-depleted antiserum). The mock-depleted antiserum still detected the SR1 ectodomain-AP fusion protein by Western blotting and was still capable of blocking the inhibitory effect of SemaIII-AP. In contrast, the depleted antiserum did not detect the SR1 ectodomain-AP fusion protein by Western blotting and did not block the inhibitory activity of SemaIII-AP, consistent with the hypothesis that the starting antiserum blocks SemaIII-AP activity by interfering with SR1 function. To rule out the possibility that the antiserum to SR1 affected a general mechanism required for axonal repulsion, the same protein A-purified antiserum was tested for its effect on netrin-mediated repulsion of trochlear motor axons (Colamarino and Tessier-Lavigne, 1995), a group of axons that can also be repelled by SemaIII (Serafini et al., 1996; Varela-Echavaria et al., 1997). The anti-SR1 antiserum stained these axons but did not block the repulsive effect of netrin-1 on these axons, consistent with a specific involvement of SR1 in SemaIII-mediated repulsion.

SR1 function is also required for the collapse-inducing effect of SemaIII

In addition to steering DRG axons away when presented chronically from a point source, SemaIII can also induce collapse of DRG growth cones when added acutely and uniformly to growth cones in culture (Luo et al., 1993). We therefore examined whether the anti-SR1 antiserum could affect the activity of SemaIII in the collapse assay. The anti-SR1 antiserum inhibited collapse of E14 rat DRG growth cones elicited by SemaIII-AP or SemaIII-myc; the blocking effect showed a dose-dependence that was similar to that observed for the block of repulsion (Table 1). As expected, the mock-depleted antiserum also blocked the collapse, whereas the depleted antiserum did not. To test the specificity of this blockade, we took advantage of the fact that lysophosphatidic acid (LPA) can also cause collapse of DRG growth cones (Jalink et al., 1994). Neither the preimmune serum nor the anti-SR1 antiserum inhibited the collapse of DRG growth cones induced by LPA, consistent with the hypothesis that the antiserum blocks SemaIII-induced collapse by specifically inhibiting SR1 function.

Cloning of a cDNA encoding SR2

To identify additional members of the SR family, we designed PCR primers which would selectively amplify rat cDNA molecules containing both the CUB the MAM motifs of SR1. A single cDNA (SEQ ID NO:7) encoding an 936 amino acid SR1 homolog, designated SR2 (SEQ ID NO:8) was identified. With these data, we were able to identify and composite ESTs in public databases to generate a cDNA sequence encoding hSR2. CDNA's comprising this clone are also isolated from a fetal human brain library (see Experimental Procedures). SR-specific function, including semaphorin binding and neuron axon outgrowth and/or orientation modulating activity are demonstrated as described herein for SR1 polypeptides.

SR1 is a SemaIII receptor

Neuropilin is a transmembrane protein initially identified by Fujisawa and colleagues as an epitope recognized by a monoclonal antibody (A5) that labels specific subsets of axons in the developing Xenopus nervous system (Takagi et al., 1987; Fujisawa et al., 1989; Takagi et al., 1991). Neuropilin comprises in its extracellular domain two so-called CUB motifs, which are found in the noncatalytic regions of the complement components C1r and C1s and several metalloproteinases (for review see Bork and Beckmann, 1993). These domains are followed in neuropilin by two domains ) with significant similarity to many proteins, including the C1 and C2 domains of coagulation factors V and VIII (Toole et al., 1984; Jenny et al., 1987), the milk fat globule membrane proteins (MFGPs) (Stubbs et al., 1990), and the discoidin domain receptor (DDR) (Johnson et al., 1993; Sanchez et al., 1994). More proximal to the transmembrane region is a MAM domain, a type of motif implicated in protein-protein interactions (Beckmann and Bork, 1993). The cytoplasmic domain of neuropilin is short (40 amino acids) and does not possess obvious motifs, but is highly conserved among Xenopus, mouse and chick (Takagi et al., 1995; Kawakami et al., 1996). In the developing nervous systems of these three species, neuropilin is expressed in dynamic fashion by a variety of different classes of axons (including motor and sensory axons) as they project to their targets (e.g., Takagi et al., 1987, 1991, 1995; Kawakami et al., 1996). Neuropilin can promote neurite outgrowth in vitro (Hirata et al., 1993) and forced expression of neuropilin under control of the β-actin promoter in transgenic mice results in axonal defasciculation (Kitsukawa et al., 1995). The forced ectopic expression of neuropilin also leads to abnormalities in development of the heart and limbs, two of the non-neural regions where neuropilin is expressed, which has suggested a role for neuropilin in organogenesis outside the nervous system (Kitsukawa et al., 1995).

We have identified SR1 and SR2 semaphorin receptors with sequence similarity to the neuropilin proteins. The spatiotemporal expression pattern of SR1 is consistant with SR1's role as a SemaIII receptor. In the region of the developing spinal cord, SR1 is most prominently expressed by sensory neurons in the DRG, particularly on their axons in the spinal nerves, the dorsal roots, and the dorsal funiculus and SR1 can also be detected on the growth cones of axons derived from dissociated DRG neurons in culture. The period during which SR1 and neuropilin is expressed by DRG neurons (between E9 and E15.5 in the mouse, decreasing sharply thereafter (Kawakami et al., 1995)) correponds to the timing of projection of SemaIII-responsive DRG axon projections into the spinal cord. During this period, Sema III is expressed at a high level in the ventral spinal cord and has been implicated as a diffusible chemorepellent that prevents inappropriate targeting of NGF-responsive axons that normally terminate in the dorsal spinal cord (Messersmith et al., 1995, Püschel et al., 1995, 1996; Shepherd et al., 1997). Our in situ hybridization studies suggest that SR1 may be expressed in only some populations of rat DRG cells at E14—possibly the NGF-responsive neurons, which are SemaIII responsive. In addition to developing DRG axons, several other classes of developing axons are repelled by or collapse in response to SemaIII, including sympathetic axons (Püschel et al., 1996), spinal motor axons (Shepherd et al., 1996; Varela-Echavarria et al., 1997), and many cranial motor axons such as trochlear, trigeminal motor, glossopharyngeal and vagal axons (Serafini et al., 1996; Varela-Echavarria et al., 1997). All of these axons express SR1.

SR1 also plays a role in mediating actions of SemaIII outside the nervous system. SR1, the neuropilins and SemaIII are expressed in a variety of non-neural tissues, including the developing cardiovascular system and limbs (Takagi et al., 1987, 1991, 1995; Kitsukawa et al., 1995; Püschel et al., 1995; Behar et al., 1996). Ectopic expression of m-neuropilin under control of the β-actin promoter in transgenic mice, in addition to causing sprouting and defasciculation of axons, leads to a variety of morphological abnormalities in non-neural tissues including the presence of excess capillaries and blood vessels, dilation of blood vessels, malformed hearts, and extra digits (Kitsukawa et al., 1995; see also, the defects in axonal, heart and skeletal development seen in SemaIII knock-out mice, Behar et al., 1996).

Our experiments have provided evidence that both the C domain and the semaphorin domain of SemaIII can independently bind SR1. The ability of both poles of the full length SemaIII molecule to bind SR1 could provide an explanation for the data suggesting that full length SemaIII has a higher affinity for SR1 than do either of the individual domains alone, since sequential binding of the two domains of each SemaIII molecule to neighboring SR1 molecules in the cell membrane would result in a higher apparent affinity. This observation indicates that signaling in response to SemaIII might be triggered by dimerization of SR1 molecules brought together by single SemaIII molecules; which is also supported by the observation that AP-S and AP-C, the fusions of AP to the semaphorin domain or the C domain, failed to induce repulsion or to cause collapse of DRG axons in vitro.

SR1 contains at its amino terminus two CUB domains, motifs implicated in protein-protein interactions whose structure is predicted to be an antiparallel β-barrel similar to those in two adhesive domains, immunoglobulin-like domains and fibronectin type III repeats (Bork et al., 1993; Bork and Beckmann, 1993). CUB domains in complement C1r/s appear to mediate calcium-dependent tetrameric complex formation between C1r/s dimers, as well as their association with C1q to form the mature C1 complex (Busby and Ingham, 1988, 1990), whereas a CUB domain in the metalloproteinase Tolloid (a relative of BMP-1) is suggested from genetic evidence to mediate an interaction with the BMP family member decapentaplegic (Childs and O'Connor, 1994; Finelli et al., 1995). In the central portion of the SR1 molecule, the b1 and b2 domains show homology to protein binding domains of coagulation factors V and VIII (Toole et al., 1984; Jenny et al., 1987), MFGF (Larocca et al., 1991) and two receptor protein-tyrosine kinases, DDR (Johnson et al., 1993) and Ptk-3 (Sanchez et al., 1994). Finally, SR1 also possesses a MAM domain, a ~170 amino acid module found in diverse transmembrane proteins (Beckmann and Bork, 1993), which has been suggested to mediate homophilic interactions (Zondag et al., 1995). We found that a truncated form of SR1 which lacks the amino terminal-most 264 amino acids retains the ability to bind SemaIII-AP, indicating that at least one of the semaphorin and C domains of SemaIII may interact with domains b1 or b2 or the MAM domain of SR1. SemaIII may also modulate the interactions of SR1 with other SR1 binding partner. In the repulsion assay the most obvious effect of Sema III is the steering away of DRG axons from a local source of SemaIII, rather than a change in fasciculation patterns (Messersmith et al, 1995). Furthermore, individual growth cones can be induced to collapse in vitro in response to SemaIII (Luo et al., 1993) in a SR1-dependent fashion, indicating a distinct signaling pathway involving SR1 that can be triggered by SemaIII.

The semaphorin family comprises over 20 proteins, secreted and transmembrane, which have been divided into five subfamilies based on sequence and structural similarity (reviewed by Tessier-Lavigne and Goodman, 1996; Kolodkin, 1996). We have found that the secreted semaphorins SemaA, SemaE and SemaIV, which belong to the same subfamily as SemaIII, can all bind SR1, suggesting promiscuity in interactions between SR1 and members of this subfamily of the semaphorin family. The bewildering diversity of semaphorin proteins may mask an underlying simplicity in interactions of these proteins and their receptors, much as the diversity of Eph receptors and ephrin ligands masks simpler binding relations, in which GPI-anchored ligands of the ephrin-A subclass interact primarily and promiscuously with EphA class receptors, and ligands of the ephrin-B subclass interact primarily and promiscuously with EphB class receptors (Gale et al.; 1996; Eph Nomenclature Committee, 1997).

Experimental procedures: Construction and expression of AP fusion proteins

To produce a Sema III-AP fusion protein, the cDNA encoding full-length Sema III was amplified by PCR and subcloned into APTag-1 (Flanagan and Leder, 1990). From the resulting plasmid, the fragment encoding both Sema III and AP was then transferred to the expression vector pCEP4 (Invitrogen), and used to transfect 293-EBNA cells (Invitrogen). A cell line stably expressing Sema-AP was established after selection with geneticin and hygromycin. Cells were grown to confluence and then cultured in Optimen medium (BRL) for 3 days. The conditioned medium was collected and partially purified using a Centriprep-100 device (Amicon). A construct encoding the ectodomain of SR1 (amino acids 1 to 857) fused to AP was similarly made in pCEP4 and used to derived a stable cell line. Conditioned medium from this line was prepared in the same way.

For other AP fusion proteins, sequences encoding the Sema domain and Ig domain (amino acids 25 to 654), the Sema domain alone (amino acids 25 to 585), a truncated Sema domain (amino acids 25 to 526), the Ig domain and C-domain together (amino acids 586 to 755), or the C-domain alone (amino acids 655 to 755) were amplified by PCR, fused to the sequence encoding AP, and subcloned into cloning sites after the Ig_κ-chain signal sequence of the expression vector pSecTag B (Invitrogen). These resulting constructs were transiently transfected into Cos-1 or Cos-7 cells with Lipofectamine (GIBCO BPL). Conditioned media were collected as described above.

Expression library construction and screening 80 mg of DRG tissue was dissected from two litters of E14 rat embryos (with kind help of K. Wang) and frozen on dry ice. mRNA was isolated from these rat DRGs using a QuickPrep mRNA purification kit (Pharmicia), and used to generate cDNA using a Stratagene cDNA synthesis kit according to manufacturer's instructions, except that the cDNA was size-fractionated using a DNA Size Fractionation Column (GIBCO BRL). Fractions containing cDNA larger than 500 bp were collected and ligated to the EcoRI-XhoI sites of the COS cell expression vector pMT21 (Genetics Institute). Ligated DNA was ethanol precipitated, resuspended in water at 10 ng/μl, electroporated into SURE 2 supercompetent cells (Stratagene) (1 μl DNA to 40 μl bacteria), and the resulting transformants were divided into pools of ~1000 to 2000 colonies.

To screen the library, DNA was extracted from the bacteria in each pool using the SNAP miniprep kit (Invitrogen) and transiently transfected into COS-1 cells in six wells plates with lipofectamine (GIBCO BRL). After 48 hr, the cells were washed once with Hank's balanced salt solution (HBHA, Cheng and Flanagan, 1994), and then incubated in HBHA containing 50–100 ng/ml SemaIII-AP fusion protein for 75 min at room temperature. Plates were washed in HBHA six times, fixed with acetone-formaldehyde, then washed twice in HBS as described by Cheng and Flanagen (1994). Plates were kept in a 65° C. incubator for 2 hr to inactivate the endogenous alkaline phosphatase activity in COS cells. The cells in the plates were stained for 2–6 hr in AP buffer containing the AP substrate BCIP and NBT (GIBCO BRL) as described previously by Cheng and Flanagan (1994). Staining of the cells was monitored using a dissecting microscope.

After identification of a positive pool, 10 ng of DNA from the pool was transfected into DH5α competent cells and the transformants were subdivided into subpools of 200–300 colonies. These subpools were rescreened as described above, and a positive subpool subdivided further through two more rounds until a single positive plasmid (p28) was isolated. The insert DNA in the p28 plasmid was sequenced from both strands using a Licor (L4000) automated sequencer as well as by $^{33}$P cycle sequencing.

Human cDNA library screening

A search of the human expressed sequence tag (EST) databases with the sequence of rat SR1 (p28) revealed many short sequences with homology to its middle portion. An EST clone (Genbank accession number R61632) was obtained from Genome System Inc. and used as a probe to screen a human fetal brain cDNA library (Stratagene) at high stingency, leading to the isolation of four overlapping cDNAs covering the full-length coding region of human SR1.

In situ hybridization

Cryosat sections (10 μm) were made from the brachial region of E14 rat embryos prefixed with 4% paraformaldehyde (PFA). In situ hybridization of these sections was performed as described by Schaeren-Wiemers and Gerfin-Moser (1993) and Kennedy et al (1994). A 1285 bp fragment including 490 bp of 5'-untranslated region and 795 bp of 5' SR1 coding region was released by Pst I digestion of the p28 plasmid and subcloned into pBluescript (Stratagene). Antisense and sense RNA probes were transcribed in the presence of digoxygenin-UTP (Boehringer Mannheim) using T7 and T3 polymerases as recommended by the manufacturer.

Cell surface binding and kinetic analysis

To examine the binding of SemaIII-AP to dissociated DRG cells, DRGs dissected from E14 or E18 rat embryos were digested with 0.25% of trypsin for 10 min at 37° C. and further dissociated by trituration with a fire-polished pipette. After removing the undissociated tissue clumps by precipitation, dissociated cells were collected by spinning at 430×g for 5 min, then cultured in eight-well chamber slides at 37° C. in 5% $CO_2$ for 20 hr in F12/N3 medium (Tessier-Lavigne et al., 1988) containing 0.5% fetal calf serum (FCS) and 25 ng/ml 2.5S NGF ((Bioproducts for Science Inc.). To examine binding activity, cells were incubated with HBHA buffer containing the indicated recombinant protein for 90 min, followed by washing, fixing, heating, and staining as described above. 293-EBNA cells stably expressing the full-length rat SR1 protein were established by transfection of a pCEP4-SR1 plasmid and selection with geneticin and hygromycin. The equilibrium-binding experiments were performed essentially as described (Flanagan and Leder, 1990; Cheng and Flanagan, 1994) using control 293-EBNA cells or SR1-expressing 293-EBNA cells cultured on six-well plates precoated with poly-D-lysine.

Generation of antibodies to SemaIII and SR1

For Western blotting studies on SemaIII, purified AP-S, a fusion of AP to the Sema domain of SemaIII, was used to raise a rabbit anti-serum. For function-blocking studies on SR1, a 1775 bp DNA fragment encoding amino acids 265 to 857 of SR1 was PCR amplified and subcloned into a bacterial expression vector pQE-9 (Qiagen) for the generation in *E. Coli* of a fusion protein comprising six histidine residues at its amino terminus. The His-tagged SR1 was expressed in XL1-Blue cells and purified according to manufacturer's instructions, and used to raise a rabbit anti-SR1 antiserum. Immunoglobulins in the anti-SR1 or preimmune sera were purified on protein A-Agarose (GIBCO BRL) columns. After application of the sera to the columns, the columns were washed first with 15 bed-volumns of 100 mM Tris (pH 8.0) and then with another 20 bed-volumns of 10 mM Tris (pH 8.0), then eluted with 5 bed volumns of 50 mM glycine (pH 3.0). The eluates from the columns were immediately neutralized by addition of ⅒ volume of 1 M Tris (pH 8.0), followed by concentration on a Centricon-10 device (Amicon). To deplete anti-SR1 antibodies from the antiserum, an equal volume of nickle-agarose beads was incubated with (or, for control, without) purified His-SR1 protein (1 mg/ml) at 4° C. for 4 hr. After washing three times with F12 medium, the beads were incubated at 4° C. for 3 hr with an equal volume of anti-SR1 serum. The supernatants were collected and then subjected to protein A-agarose affinity purification as described above.

Immunoprecipitation and Western analysis

To detect AP or AP fusion proteins by Western blotting, aliquots of the concentrated conditioned media were resolved by SDS-PAGE (8% gel). After transfer to nitrocellulose (Amersham), the proteins were probed with rabbit anti-AP antibody (DAKO). The blot was developed with BCIP and NBT as the substrate.

To detect an interaction between SR1 and SemaIII, 100 μl protein A-agarose beads (GIBCO BRL) were first incubated with 5 μg of anti-AP monoclonal antibody (Medix Biotech) in IP buffer (20 mM Hepes, pH 7.0, 100 mM NaCl, 1 mM EDTA, 1 mM DTT, and 0.02% NP-40) at 4° C. for 2 hr. After washing three times with 1 ml of IP buffer, half of the beads (50 μl) were incubated with 2 μg of Kit-AP (Flanagan and Leder, 1990) or SR1-AP protein (containing the entire SR1 ectodomain) at 4° C. for another 2 hr. Beads conjugated with recombinant proteins were then washed three times with IP buffer, and resuspended into 40 μl IP buffer containing 2 μg of myc-tagged Sema III protein. After the mixtures were incubated at 4° C. for 3 hr, the beads were washed six times with 1 ml IP buffer. The bound proteins were released by boiling the beads in 50 μl SDS-containing sample buffer and analyzed by SDS-PAGE (8% gel) and Western blotting with a monoclonal antibody (9E10) against a C-terminal Myc-epitope tag.

Immunohistochemistry

For immunostaining to detect the expression of SR1 in E14 rat spinal cord, cryostat sections (10 μm) from unfixed frozen embryos were collected and fixed with acetone for 5 min. The staining was performed with preimmune serum (1:500), or anti-SR1 serum (1:500) as the primary antibody and biotinylated goat anti-rabbit Ig (5 ng/ml, Biorad) as the secondary antibody. Diaminobenzidine (Sigma) was used as a chromogen, with signal enhancement by a Vectastain Elite ABC kit (Vector). For staining of cultured cells, E14 rat DRG were cultured as above for 20 hr, incubated with the anti-SR1 antiserum or preimmune serum (¹⁄₅₀₀ dilution) for 1 hr at room temperature, washed 3 times, fixed with methanol, and the bound antibody was visualized using a Cy3-conjugated secondary antibody (Jackson Immunological Laboratories).

Collapse assay

The collapse assay was performed essentially as described by Raper and Kapfhammer (1990) and Luo et al. (1993), with minor modifications. In brief, DRG explants were dissected from E14 rat embryos, and cultured at 37° C. in 5% $CO_2$ for 16– 20 hr on six-well plates precoated with poly-D-lysine (Sigma) and laminin (Becton Dickinson Labware) in F12/N3 medium containing 0.5% FCS and 25 ng/ml 2.5 S NGF. Small volumes of concentrated conditioned medium containing AP, SemaIII-AP, or SemaIII-myc were gently added into the culture medium, and the cultures were kept at 37° C. for 1 hr. The explants were fixed with 4% PFA in PBS containing 10% sucrose for min, then incubated with PHTX (PBS/1% heat-inactivated goat serum/1% Triton X-100) for 15 min. The explants were then stained with 2 µg/ml Rhodamine-Phalloidin (Molecular Probes) for 30 min, washed, and mounted with Fluoromount G (Fisher). As a control, aliquots of L-a-lysophosphatidic acid (LPA, Sigma) were added into the cultures at a final concentration of 1 µM (Jalink et al., 1994) and the cultures were incubated at 37° C. for 3 min prior to fixation and staining. To examine the effect of preimmune or anti-SR1 antisera, aliquots of each antiserum were added into the explant cultures, which were kept at 37° C. for 30 min prior to the addition of SemaIII protein or LPA.

Repulsion assay

The repulsion assay was essentially as previously described (Messersmith et al., 1995). In brief, E14 rat DRG explants were dissected and embedded in collagen gels with control 293 EBNA cells or 293 EBNA cells expressing SemaIII-AP. The indicated amount of antibodies were included into the culture medium (F12/N3 medium containing 0.5% FCS and 25 ng/ml 2.5 S NGF). After incubation at 37° C. for 40 hr, the explants were fixed with 4% PFA in PBS for 2 hr, and followed by immunostaining with a neurofilament-specific antibody (NF-M, 1:1500; Lee et al., 1987) and a horseradish peroxidase-conjugated secondary antibody (Boehringer-Mannheim; 1:250) as described (Kennedy et al., 1994; Messersmith et al., 1995). The quantification of neurite outgrowth was performed as described (Messersmith et al., 1995).

Identification of Neuropilin-2

The extracellular domain of neuropilin-1 is comprised of several predicted structural domains: two CUB motifs (domains a1 and a2), two domains of homology to coagulation factors V and VIII (domains b1 and b2) and a MAM domain (domain c) (Takagi et al., 1991; Kawakami et al., 1996) (FIGS. 1 and 2a). To determine whether neuropilin-1 is a member of a family of related molecules, we searched for relatives by reverse transcription-PCR (RT-PCR) using three sets of degenerate forward primers (5.1, 5.2 and 5.3) and three sets of degenerate reverse primers (3.1, 3.2, and 3.3). The primers were designed based on the sequences conserved among domain a2 and other CUB domain proteins (primer set 5.1), domains b1 and/or b2 and coagulation factors V and VIII (primer sets 5.2, 5.3 and 3. 1), domain c and other MAM domain proteins (primer set 3.2), or a sequence in the cytoplasmic domain that is highly conserved among neuropilin homologues from different species (primer set 3.3) (see Experimental Procedures). Sequences were amplified from whole E11 mouse embryo mRNA and adult mouse brain mRNA using all pairwise combinations of 5' and 3' primer sets (except 5.3 and 3.1). In all cases, products of the size expected for neuropilin-1 were amplified and subcloned. More than a dozen cDNAs for each pair of primer sets were sequenced, and in all cases mouse neuropilin-1 sequences were recovered. In addition, several of the cDNAs obtained by RT-PCR using primer sets 5.2 (b1 domain, KEWIQVD) and 3.3 (cytoplasmic domain, ENYNFE) encoded overlapping sequences that were related but not identical to a portion of the neuropilin-1 sequence. These sequences were extended in both the 5' and 3' directions using a combination of cDNA library screening and RACE (rapid amplification of cDNA ends) (see Experimental Procedures).

From these experiments, the full length sequence of a new neuropilin-1-related molecule was assembled (FIG. 3), which has been named neuropilin-2. By screening the expressed sequence tag (EST) data bases, we were also able to assemble the sequences of several human ESTs to predict the sequence of human neuropilin-2, which shares high homology (90% identity) with that of mouse neuropilin-2. The overall structure predicted for neuropilin-2 is identical to that of neuropilin-1, with all the same functional domains (FIG. 4A). At the amino acid level, the sequence of neuropilin-2 is 44% identical to that of neuropilin-1, in both mouse and human. The homology is distributed over the entire length of the proteins, with highest homology in the transmembrane domain.

In the course of these experiments (see Experimental Procedures), we also discovered evidence for the existence of alternative forms of neuropilin-2 which may arise by alternative splicing. First, an alternate form with a divergent carboxy terminus was identified, which we have named neuropilin-2(b0) (we will use the names neuropilin-2 and neuropilin-2(a0) interchangeably to refer to the original isoform). The sequence of neuropilin-2(b0) diverges from that of neuropilin-2(a0) at amino acid 809, between the MAM domain and the transmembrane domain of neuropilin-2(a0) (FIG. 4C). Neuropilin-2(b0) is predicted from hydrophobicity analysis to have a transmembrane domain, followed by a cytoplasmic domain of similar length to that in neuropilin-2(a0), but these two domains are highly divergent from those of neuropilin-2(a0), sharing only 10% identity. An expressed sequence tag (EST) encoding human sequences (346 bp fragment) corresponding to a portion of this diverged sequence was also found in the dbEST database (AA25840) (FIG. 4C). To test the prediction that neuropilin-2(b0) is a transmembrane protein, we tagged this protein at its carboxyl terminus with a myc-epitope, expressed the tagged construct by transient transfection into COS 7 cells, and examined expression of the tagged protein using monoclonal antibody 9E 10 directed against the epitope tag (Evan et al., 1985). Detection of the myc-tag at the carboxyl terminus of neuropilin-2(b0) by immunostaining required detergent permeabilization of the transfected cells, indicating that neuropilin-2 is indeed a transmembrane protein.

In addition, we found other isoforms of neuropilin-2(a0), including isoforms with insertions of 5, 17, or 22 (5+17) amino acids at amino acid 809 in neuropilin-2(a0), i.e. at the site of divergence of the a and b isoforms of neuropilin-2 (FIG. 4B). The 22 amino acid insertion is the sum of the 5 and the 17 amino acid insertions (FIG. 4B). We term these isoforms neuropilin-2(a5), neuropilin-2(a17) and neuropilin-2(a22). The isoform reported by Kolodkin et al. (1997) appears to be the rat neuropilin-2(a17) isoform. Similarly, we have found an isoform of neuropilin-2(b0) with the very same 5 amino acid insertion at amino acid 809, and which we name neuropilin-2(b5) (FIG. 4B). The pattern of combinations of the 5 and 17 amino acid inserts that we have observed in different neuropilin-2 isoforms indicates that these different isoforms arise from splicing in of separate exons encoding the 5 and 17 amino acid stretches.

To determine whether the a and b isoforms of neuropilin-2 show different temporal patterns of expression, we performed RT-PCR using a 5' primer designed to a sequence shared between all neuropilin-2 isoforms, and two 3' primers unique to the sequences in the cytoplasmic domains of neuropilin-2(a) and of neuropilin-2(b) (see Experimental Procedures). Using E11 whole mouse embryo mRNA as a template we found that at E11 only an amplification product corresponding to neuropilin-2(a) could be detected. However, using adult mouse brain mRNA as a template, we detected amplification products corresponding to both neuropilin-2(a) and neuropilin-2(b). Taken together, these results indicate that different isoforms of neuropilin-2 might arise by alternative splicing and that this splicing are regulated in a time-dependent or a cell type-dependent fashion.

Neuropilin-2 is expressed by specific classes of developing neurons. To determine whether neuropilin-2, like neuropilin, is a candidate for a receptor involved in axonal growth or guidance, we examined by in situ hybridization whether neuropilin-2 mRNA is expressed by embyronic neurons during the period of axonal extension. Given the large number of isoforms of neuropilin-2 that appear to exist, we decided in this first survey to use a probe corresponding to sequences that extend from domain b2 through the cytoplasmic domain of neuropilin-2(a0) (see Experimental Procedures). Most of this probe corresponds to sequences that are shared between all isoforms.

Spinal cord. We first examined the pattern of expression of neuropilin-2 in the region of the developing mouse spinal cord during the period of initial extension of axons of motor and sensory neurons (from E9.5), at the level of the forelimbs. This pattern was highly dynamic. Neuropilin-2 mRNA was detected in the ventral spinal cord of E9.5 embryos, including the region of developing motorneurons. Expression was also strong in the floor plate and in tissue adjacent to the neural tube, including the somites and prospective dorsal root ganglia (DRGs) but not the notochord. Between E10.5 and E13.5 we compared the expression of neuropilin-2 to that of neuropilin-1, which has already been described (Kawakami et al., 1996). By E10.5, the level of neuropilin-2 expression had increased in the spinal cord. The whole ventral half of the spinal cord including the floor plate was heavily labeled, but expression was also strong in cells localized in the lateral margin of the dorsal aspect of the spinal cord, which may include commissural neuron cell bodies. Neuropilin-1 expression was also detected in the ventral spinal cord but only in motorneurons, and was very weak or absent from the floor and roof plates. Neuropilin-2 and neuropilin-1 mRNAs were also coexpressed in prospective DRGS, although neuropilin-2 expression was in addition high in non-neural tissues surrounding the spinal cord. A similar pattern of neuropilin-2 expression was observed at E11.5. At E13.5, neuropilin-2 expression had decreased and was now restricted to the ventral portion of the spinal cord. Both neuropilins were still expressed in motorneurons, but neuropilin-2-expressing cells were found througout in the entire ventral spinal cord whereas the expression pattern of neuropilin-1 was more restricted. In addition, neuropilin-1 was now strongly expressed in the dorsal spinal cord and in the DRGs, whereas neuropilin-2 expression in the DRGs was very weak, and only just above background level. Weak expression of neuropilin-1 was also detected in the floor plate at this stage, but contrary to neuropilin-2, it was absent form the roof plate. Expression of neuropilin-2 at E15.5 was unchanged in the spinal cord, though no expression was detectable in DRGs at this stage.

Sympathetic ganglia. As early as E11.5, neuropilin-2 was detected in the ganglia of the sympathetic chain. This expression was more intense by E13.5, and had slightly decreased by E15.5). At this stage neuropilin-2 mRNA could also be detected in neurons of the superior cervical ganglion. Expression was also observed in the region of the enteric nervous system.

Olfactory system. High level neuropilin-2 expression was detected in all components of the olfactory system. Intense staining was observed at E13.5 and E15.5 in the vomeronasal organ, as well as in the accessory olfactory bulb, its target territory in the forebrain. Neuropilin-1 is not expressed in the accessory olfactory system (Kawakami et al., 1996).

By E15.5, the olfactory epithelium strongly expressed neuropilin-2, but this expression was not homogenous, being higher rostrally. A high level of neuropilin-2 mRNA was observed in the anterior olfactory nucleus and in the telencephalic regions interconnected to the olfactory bulb, such as the amygdala, the piriform cortex and the entorhinal cortex.

Neocortex. Neuropilin-2 expression in the cortex was first detected around E13.5, and was restricted to the intermediate zone of the ventral and lateral regions of the cortex. The mesenchymal cells covering the cortex also showed high level expression of neuropilin-2. By E15.5 the staining was still confined to the intermediate zone, and was stronger in its lower portion. At birth, neuropilin-2 expression was no longer detected in the cortex, with the exception of the cingulate cortex.

Hippocampal formation. The pattern of expression of neuropilin-2 was particularly interesting in the components of the hippocampal formation. Neuropilin-2 could be detected as early as E13.5 in the hippocampus, and by E15.5 expression was evident in both the dentate gyrus and in cells of CA3 and CA1 fields. The hybridization signal was uninterrupted and formed a continuum with neuropilin-2 expressing cells in the intermediate zone of the neocortex. By P0, expression of neuropilin-2 was still very high in granule cells of the dentate gyrus, the hilus, and in the pyramidal cell layer, intermediate zone, and in the interneurons of the CA3–CA1 fields. Expression was also observed in the subiculum but not the presubiculum or the parasubiculum. At this stage, neuropilin-2 expression was also very intense in most of the brain regions that project to the hippocampus. The neurons of the entorhinal cortex which project massively through the so-called perforant pathway to the dentate gyrus, the hippocampus and the subiculum, expressed neuropilin-2. Cells in the septal region (medial septum, diagonal band of Broca), another major source of afferent fibers to the hippocampal formation, also strongly expressed neuropilin-2 at E15.5 and at birth.

Visual system. At E11.5, neuropilin-2 was very highly expressed in the mesenchyme surrounding the eye-cup and the optic nerve, but was absent from the retina. At E15.5, low expression of neuropilin-2 mRNA was detected in the ganglion cell layer, and diffuse expression was observed in the superior colliculus, one of the targets of retinal axons. By P0, neuropilin-2 was very highly expressed in the most superficial layers of the superior colliculus, and at a lower level in the other layers. Expression stopped abruptly at the boundary between superior and inferior colliculus. Expression was not observed in the lateral geniculate nucleus of the thalamus at birth.

Thalamus. Neuropilin-2 was also expressed at birth in several thalamic nuclei such as the medial habenula.

Cerebellum. Neuropilin-2 expression was detected as early as E13.5 in the cerebellar primordium, and increased in level by E15.5. At P0, neuropilin-2 was expressed in subsets of deep nuclei neurons as well as in stripes of Purkinje cells. Neuropilin-1 in contrast, is not expressed in the cerebellum (Kawakami et al., 1996).

Hindbrain nuclei. Neuropilin-2 was detected at E15.5 and at birth (P0), in several branchiomotor nuclei, such as the trigeminal, facial and hypoglossal motor nuclei, but not in the dorsal motor nucleus of the vagus. We have not determined when expression in these nuclei starts. Lower levels of expression were observed in the regions of the inferior olive and vestibular nuclei. Expression was not detected in the pons, a region known to express neuropilin-1 at high level (Kawakami et al., 1996).

Expression of neuropilin-2 in non-neural tissues. In addition to its expression in the CNS, neuropilin-2 was also detected in many non-neural tissues. At E10.5 it was expressed in the limb bud in restricted areas in the regions of the dorsal and ventral muscle masses. Later on, expression was also observed in the developing bones, in particular in the vertebrae, ribs and digits. Expression of neuropilin-2 was also observed in several muscles such as the back muscles and the tongue, and the strongest expression was observed in the region of the smooth muscles of the gut. Expression was also observed in the intestinal epithelium, as well as in cells in the kidney, the submandibular gland, the lung, the whisker follicles of the snout, and in the inner ear. In contrast to neuropilin-1 (Kawakami et al., 1996), neuropilin-2 expression was not detected in the heart or in capillaries, but was found in the dorsal aorta.

Different binding patterns of neuropilin-1 and neuropilin-2 to different semaphorin family members. To test whether neuropilin-2, like neuropilin-1, is also a receptor for Sema III, we transiently expressed neuropilin-1, neuropilin-2(a0), -2(a5), -2(a22) and -2(b5) in COS-7 cells, for use in binding experiments. We were able to detect expression of neuropilin-1 and the different isoforms of neuropilin-2 in COS cells by immunostaining using either a polyclonal antibody against neuropilin-1 (He and Tessier-Lavigne, 1997) or monoclonal antibody 9E10 against the myc-tag at the carboxy terminus of all the neuropilin-2 isoforms. Western blot analysis showed that neuropilin-2 isoforms expressed in COS cells had the expected size of ~120kDa. To test for interactions with Sema III, we used a chimeric molecule in which Sema III was fused at its carboxy terminus to the histochemical reporter alkaline phosphatase (Sema III-AP: He and Tessier-Lavigne, 1997). Partially purified conditioned medium containing Sema III-AP was incubated with COS cells expressing neuropilins, and bound protein was detected by alkaline phosphatase histochemistry. As expected, Sema III-AP bound cells expressing neuropilin-1 (He and Tessier-Lavigne, 1997), and the alkaline phosphatase protein (AP) itself did not bind mock-transfected cells, cells expressing neuropilin-1, or any of the neuropilin-2 isoforms. Surprisingly, none of the isoforms of neuropilin-2 tested showed any detectable binding of Sema II-AP. We considered the possibility that neuropilin-2 binds the C terminal domain of Sema III and that the absence of binding was an artifact resulting from fusion of AP to the carboxy terminal portion of Sema III, masking the binding site. To address this possibility, we made use of a chimeric molecule in which AP is fused to the amino terminus of C domain of Sema III (AP-C: He and Tessier-Lavigne, 1997). The AP-C protein bound cells expressing neuropilin-1 but not cells expressing any of the neuropilin-2 isoforms. Thus, the absence of binding of full length Sema III-AP to cells expressing the different neuropilin-2 isoforms reflects a bona fide absence of binding of Sema III to neuropilin-2.

Since Sema III itself does not appear to bind neuropilin-2, we wondered whether neuropilin-2 might be a receptor for other members of the semaphorin family. Sema III is a member of a subfamily of structurally-related molecules within the semaphorin family that includes the members Sema E/Collapsin-3 (Luo et al., 1995; Püschel et al., 1995), Sema IV/Sema 3F (Sekido et al., 1996; Roche et al., 1996; Xiang et al., 1996), Sema A/Sema V (Sekido et al., 1996), and Sema H. Like Sema III, all of these proteins are secreted proteins possessing a semaphorin domain, an immunoglubulin domain and a basic carboxy terminal domain (Püshel et al., 1995; Luo et al., 1995). We therefore examined whether two of these molecules, Sema E and Sema IV, are ligands for neuropilin-1 and/or neuropilin-2. In addition, we tested another secreted semaphorin, Drosophila Sema II (Kolodkin et al., 1993), which is more distantly related in sequence, as well as a more divergent semaphorin, the transmembrane Sema VIa (Zhou, et al 1997). As for Sema III, we tested the ability of COS cells expressing neuropilin-1 or neuropilin-2 to bind chimeric molecules in which alkaline phosphatase was fused to Sema E, Sema IV, Drosophila D-Sema II or the ectodomain of Sema VIa (see Experimental Procedures). These AP fusion proteins were presented to the cells in the form of partially purified conditioned media from cells expressing each of the proteins; media were matched for AP activity. We found that both neuropilin and different isoforms of neuropilin-2 expressing cells bound Sema E-AP and Sema IV-AP. In contrast, neither neuropilin-1 nor any of the neuropilin-2 isoforms expressed in COS cells showed detectable binding to the AP fusions with D-Sema II or the Sema VIa ectodomain. In control experiments, we found that Sema E-AP and Sema IV-AP did not bind mock-transfected COS cells or COS cells expressing the netrin-1 receptor DCC.

Figure 5C:
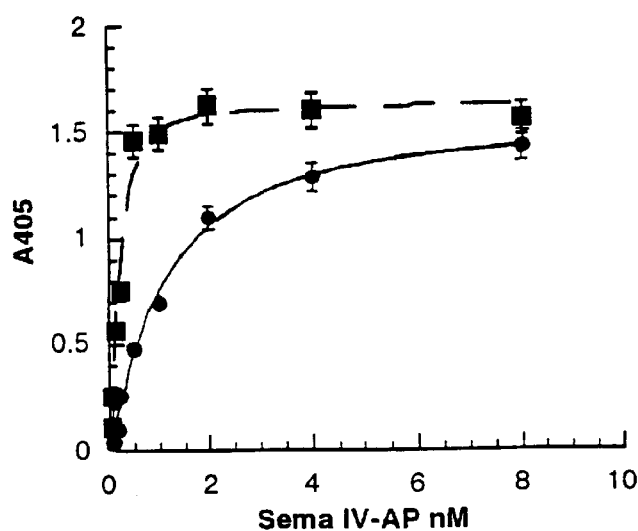

We estimated the binding affinity of the AP fusions of Sema III, Sema E and Sema IV to cells expressing neuropilin-1 or neuropilin-2 in equilibrium binding experiments. For these experiments, we used the a5 isoform of neuropilin-2. Specific binding curves of these molecules showed saturation and could be fitted with the Hill equation (FIGS. 5A–5C). The estimated dissociation constants (Kd) for Sema E binding to neuropilin-1 and neuropilin-2 were 5 nM and 18 nM, respectively. Those for Sema IV binding to neuropilin-1 and neuropilin-2 were 30 nM and 5 nM, respectively. No detectable binding of Sema III to neuropilin-2 expressing cells was detected, while the estimated Kd for Sema III binding to neuropilin-1 was 0.325 nM (sec also He and Tessier-Lavigne, 1997). Similar Kd values were obtained using the b5 isoform of neuropilin-2 and the degree of binding of different semaphorins to cells all isoforms tested appeared similar.

Dynamic expression of neuropilin-2 complementary to that of neuropilin-1. The specific pattern of expression of neuropilin-2 indicates the involvement of members of the Sema III subfamily other than Sema III itself in the guidance of a variety of different axonal classes, in particular in the spinal cord, olfactory system, and hippocampus.

In the spinal cord, commissural axons are guided along a dorso-ventral trajectory at least partly in response to the diffusible chemoattractant netrin-1 (Serafini et al., 1996). Neuropilin-2 transcripts are detected in the region of commissural neuron cell bodies, indicating that commissural neurons express neuropilin-2. Since Sema E is expressed in the ventral spinal cord (Püschel et al., 1995), this semaphorin might contribute to the guidance of commissural axons. Our in situ hybridization studies also indicate that different motorneuron populations express different complements of neuropilins, and therefore might respond differentially to different secreted semaphorins expressed in the periphery (Püschel et al., 1995; Wright et al., 1995; Giger et al., 1996). Thus, different semaphorins can contribute to patterning the projections of motor axons to distinct peripheral targets (Tsushida et al., 1994). The olfactory system is another site of significant neuropilin-2 expression, suggesting a role for secreted semaphorins distinct from Sema III in guidance in this system. Axons from the olfactory bulb are known to be repelled by an unidentified septum-derived chemorepellent (Pini, 1993). Neuropilin-2 transcripts are expressed in the region of the cell bodies of origin of these axons in the bulb, indicating that a secreted semaphorin can function as a septal-derived chemorepellent. Another interesting finding is that neuropilin-2 expression in the olfactory epithelium (presumably by primary olfactory neurons) is not uniform, indicating that secreted semaphorins can play a role in differential guidance of different complements of primary olfactory axons, contributing to the creation of an olfactory map.

Neuropilins are also expressed in the sites of origin of afferent projections to the hippocampus. Afferents to the hippocampus are known to be topographically organized, with septal, hippocampal, and entorhinal axons projecting to distinct dendritic locations on granule and pyramidal neurons (Paxinos 1995). Neuropilin-1 and-2 are expressed by the septal and hippocampal neurons, whereas only neuropilin-2 is expressed by entorhinal neurons. Sema E and Sema IV are highly expressed in the hippocampus (Püschel et al., 1995; Sekido et al., 1996), and these semaphorins can therefore contribute to the patterning of hippocampal afferent projections as well.

Finally, the observation that neuropilin-2 is expressed in many non-neuronal tissues also indicates the involvement of semaphorins other than Sema III in organogenesis outside the nervous system. A role for secreted semaphorins in tumor suppression is indicated by the fact that neuropilin-2 is expressed in the lung, since Sema IV and Sema A/V map to a region of chromosome 3p that is frequently deleted in small cell lung cancer, and which is thought to contain a tumor suppressor gene for lung cancer (Roche et al., 1996; Sekido et al., 1996; Xiang et al., 1996).

Experimental Procedures: Isolation of neuropilin-2 and its splice variants

Six sets of fully degenerate oligonucleotides were used to perform RT-PCR using pfu polymerase (Stratagene) on mRNA isolated from E11 whole mouse embryo and adult mouse brain. Primers were designed to conserved amino acid sequences in the a2 domain of neuropilin, the b1 domain, the b2 domain, the MAM domain and the cytoplasmic domain. For each of the reactions, DNA bands of the size expected for neuropilin-1 were excised, and the gel purified DNA was subjected to secondary PCR amplification using the same primers but with an EcoR I site at the 5' terminus of forward primers and an Xba I site in the reverse primers. The PCR products were cloned into pBluescript KS(−) and sequenced. From one of these reactions, a novel sequence corresponding to neuropilin-2 was isolated (see Results). A 1.2 kb fragment of neuropilin-2 was used as a probe to screen an adult mouse brain gt11 lambda phage library (Clontech). Partial cDNA fragments isolated in this way corresponded to two presumptive differential splicing isoforms, the a and b forms, with or without the 5, 17 and 22 amino acid insertions (FIG. 4). In order to obtain a full length cDNA, 5' RACE was performed on cDNA isolated from E11 mouse whole embryo and adult mouse brain. The 5'-RACE products were cloned into pBluescript KS(−) with 5' Not I and 3' Xho I sites, and sequenced. cDNAs containing the entire coding regions of the a and b isoforms of neuropilin-2 were assembled, with and without various combinations of the 5, 17 and 22 amino acid insertions (see Results).

In situ hybridization. A 1200 nucleotide fragment of neuropilin-2 was used to generate digoxigenin (DIG)-labeled and $^{35}$S-labeled antisense and sense RNA probes. In situ hybridization was performed on vibratome sections of P0 mouse brain with the DIG-labeled probe, and using the radioactive probe on cryosections taken at various stages between E9.5 and P0. The in situ hybridization procedures using digoxygenin-labeled probes were as described previously (Chedotal et al., 1996), and procedure using radioactive probes was as described by Messersmith et al. (1995).

Plasmid construction. The coding regions of neuropilin-2 of alternative splicing forms, deleted of their signal sequences, were subcloned into the expression vector pSecTag-A (Invitrogen) in the Hind III (5'-end) and Xba I (3'-end) sites and transiently transfected into COS 7 cells using Lipofectamine (GIBCO BRL). Expression of neuropilin-2 isoforms was detected by immunocytochemistry and Western analysis using monoclonal antibody 9E10 (to the myc tag at the C terminus of the neuropilin-2 isoforms).

The semaphorin III-AP fusion protein was described previously (He and Tessier-Lavigne, 1997). The mouse Sema E clone was obtained by PCR from P0 mouse brain cDNAs, using the PCR primers. The amplified band was subcloned into the expression vector, APtag-4 vector which a sequence coding for secreted alkaline phosphatase. The human Sema IV clone was subcloned in pSecTag-A (Invitrogen), which also contains the secreted alkaline phosphatase.

Semaphorin-AP fusion protein binding assay. The semaphorin-AP fusion protein binding experiments was as described by Cheng and Flanagan (1994), with the exception that in order to reduce background binding, 2 µg/ml of heparin was included in the binding mixture. Briefly, neuropilin-1 and neuropilin-2 expression constructs were transiently expressed in COS 7 cells as described above. After 48 hours of transfection, expressing cells were rinsed with HBHA buffer (Hank's balanced salt solution with 20 mM HEPES pH 7.0, 0.05% sodium azide) (Cheng and Flanagan, 1994). Concentrated supernatant containing semaphorin-AP fusion proteins in the presence of 20 mM HEPES and 0.05% of sodium azide was incubated with expressing COS cells at room temperature for 75 minutes, followed by heat inactivation of endogenous alkaline phosphatase, washing, and color development as described by Cheng and Flanagan (1994).

Protocol for high throughput SR-SemaIII binding assay.

A. Reagents:

Neutralite Avidin: 20 µg/ml in PBS.

Blocking buffer: 5% BSA, 0.5% Tween 20 in PBS; 1 hour at room temperature.

Assay Buffer: 100 mM KCl, 20 mM HEPES pH 7.6, 1 mM MgCl$_2$, 1% glycerol, 0.5% NP-40, 50 mM β-mercaptoethanol, 1 mg/ml BSA, cocktail of protease inhibitors.

$^{33}$P SR polypeptide 10× stock: $10^{-8}$–$10^{-6}$M "cold" SR polypeptide specific SR domain supplemented with 200,000–250,000 cpm of labeled SR (Beckman counter). Place in the 4° C. microfridge during screening.

Protease inhibitor cocktail (1000×): 10 mg Trypsin Inhibitor (BMB # 109894), 10 mg Aprotinin (BMB # 236624), 25 mg Benzamidine (Sigma # B-6506), 25 mg Leupeptin (BMB # 1017128), 10 mg APMSF (BMB # 917575), and 2 mM NaVO$_3$(Sigma # S-6508) in 10 ml of PBS.

SemaIII: $10^{-7}$–$10^{-5}$M biotinylated SemaIII in PBS.

B. Preparation of assay plates:
   Coat with 120 μl of stock N-Avidin per well overnight at 4° C.
   Wash 2 times with 200 μl PBS.
   Block with 150 μl of blocking buffer.
   Wash 2 times with 200 μl PBS.
C. Assay:
   Add 40 μl assay buffer/well.
   Add 10 μl compound or extract.
   Add 10 μl $^{33}$P-SR (20–25,000 cpm/0.1–10 pmoles/well= $10^{-9}$–$10^{-7}$ M final conc).
   Shake at 25° C. for 15 minutes.
   Incubate additional 45 minutes at 25° C.
   Add 40 μM biotinylated SemaIII (0.1–10 pmoles/40 ul in assay buffer)
   Incubate 1 hour at room temperature.
   Stop the reaction by washing 4 times with 200 μM PBS.
   Add 150 μM scintillation cocktail.
   Count in Topcount.
D. Controls for all assays (located on each plate):
   a. Non-specific binding
   b. Soluble (non-biotinylated SemaIII) at 80% inhibition.

REFERENCES

Ackerman, S. L., et al. (1997). Nature 386, 838–42.
Adams, R. H., et al. (1996). Mech. Dev. 57, 33–45.
Altman, J. and Bayer, S. A. (1984). Adv Anat Embryol Cell Biol 85, 1–164.
Arlaud, G. L., Colomb, M. G. and Gagnon, G. (1987). Immunology Today 8, 106–111.
Beckmann, G. and Bork, P. (1993). Trends Biochem Sci 18, 40–1.
Behar, O., et al. (1996). Nature 383, 525–8.
Bork, P. and Beckmann, G. (1993). J Mol Biol 231, 539–45.
Busby, T. F. and Ingham, K. C. (1988). Biochemistry 27, 6127–35.
Busby, T. F. and Ingham, K. C. (1990). Biochemistry 29, 4613–8.
Chan, S. S., et al. (1996). Cell 87, 187–95.
Chedotal, A., et al. (1996). J. Neurosci. 16, 3296–3310.
Cheng, H. J. and Flanagan, J. G. (1994). Cell 79, 157–68.
Childs, S. R. and O'Connor, M. B. (1994). Dev Biol 162, 209–20.
Colamarino, S. A. and Tessier-Lavigne, M. (1995). Cell 81, 621–9.
Culotti, J. G., et al. (1996). Curr. Opin. Neurobiol. 6, 81–88.
Evan, G. I., et al. (1985) Mol. Cell. Biol. 5, 3610–3616.
Finelli, A. L., Bossie, C. A., Xie, T. and Padgett, R. W. (1994). Development 120, 861–70.
Fitzgerald, M., Kwiat, G. C., Middleton, J. and Pini, A. (1993). Development 117, 1377–84.
Flanagan, J. G. and Leder, P. (1990). Cell 63, 185–94.
Fujisawa, H., Ohtsuki, T., Takagi, S. and Tsuji, T. (1989). Dev Biol 135, 231–40.
Fujisawa, H., Takagi, S. and Hirata, T. (1995). Dev Neurosci 17, 343–9.
Furuyama, T., et al. (1996). J. Biol. Chem. 271, 33376–33381.
Gale, N. W., et al. (1996). Neuron 1 7, 9–19.
Giger, R. J., et al. (1996). J. Comp. Neurol. 375, 378–392.
Goshima, Y., et al. (1995). Nature 376, 509–14.
Guthrie, S. and Pini, A. (1995). Neuron 14, 1117–30.
Hamelin, M., et al. (1993). Nature 364, 327–30.
He, Z. -H., et al. (1997). Cell in press.
Hedgecock, E. M., Culotti, J. G. and Hall, D. H. (1990). Neuron 4, 61–85.
Hirata, T., Takagi, S. and Fujisawa, H. (1993). Neurosci Res 17, 159–69.
Hu, H. and Rutishauser, U. (1996). Neuron 16, 933–40.
Igarashi, M., et al. (1993). Science 259, 77–9.
Inagaki, S., et al. (1995). FEBS Lett. 370, 269–272.
Jalink, K., et al. (1994). J Cell Biol 126, 801–10.
Jenny, R. J., et al. (1987). Proc Natl Acad Sci U S A 84, 4846–50.
Johnson, J. D., et al. (1993). Proc Natl Acad Sci U S A 90, 10891.
Kawakami, A., Kitsukawa, T., Takagi, S. and Fujisawa, H. (1996). J Neurobiol 29, 1–17.
Keino-Masu, K., et al. (1996). Cell 87, 175–85.
Kennedy, T. E., et al. (1994). Cell 78, 425–35.
Kindt, R. M. and Lander, A. D. (1995). Neuron 15, 79–88.
Kitsukawa, T., et al. (1995). Development 121, 4309–18.
Kolodkin, A. L. (1996). Trends in Cell Biology 6, 15–22.
Kolodkin, A. L., Matthes, D. J. and Goodman, C. S. (1993). Cell 75, 1389–99.
Kolodkin, A. L., et al. (1992). Neuron 9, 831–45.
Kolodziej, P. A., et al. (1996). Cell 87,197–204
Larocca, D., et al. (1991). Cancer Res 51, 4994–8.
Leonardo, E. D., et al. (1997). Nature 386, 833–8.
Leung-Hagesteijn, C., et al. (1992). Cell 71, 289–99.
Li, W., Herman, R. K. and Shaw, J. E. (1992). Genetics 132, 675–89.
Luo, Y., Raible, D. and Raper, J. A. (1993). Cell 75, 217–27.
Matthes, D. J., Sink, H., Kolodkin, A. L. and Goodman, C. S. (1995). Cell 81, 631–9.
Messersmith, E. K., et al. (1995). Neuron 14, 949–59.
Pini, A. (1993). Science 261, 95–8.
Püschel, A. W., Adams, R. H. and Betz, H. (1995). Neuron 14, 941–8.
Püschel, A. W., Adams, R. H. and Betz, H. (1996). Mol Cell Neurosci 7, 419–31.
Sanchez, M. P., et al. (1994). Proc Natl Acad Sci U S A 91, 1819–23.
Schaeren-Wiemers, N. and Gerfin-Moser, A. (1993). Histochemistry 100, 431–40.
Sekido, Y., et al. (1996). Proc. Natl. Acad. Sci. USA 93, 4120–4125.
Serafini, T., et al. (1994).-6. Cell 78, 409–24.
Serafini, T., et al. (1996). Cell 87, 1001–1014.
Shepherd, I., Luo, Y., Raper, J. A. and Chang, S. (1996). Dev Biol 173, 185–99.
Shepherd, I. T., et al. (1997). Development 124, 1377–85.
Shirasaki, R., et al. (1996). Neuron 17, 1079–1088.
Smith, C. L. (1983). J Comp Neurol 220, 29–43.
Snider, W. D., et al. (1992). J Neurosci 12, 3494–508.
Stubbs, J. D., et al. (1990). Proc. Natl. Acad. Sci. USA 87,8417–8421.
Takagi, S., et al. (1991). Neuron 7, 295–307.
Takagi, S., et al. (1995). Dev Biol 170, 207–22.
Takagi, S., et al. (1987). Dev Biol 122, 90–100.
Tamada, A., Shirasaki, R. and Murakami, F. (1995). Neuron 14, 1083–93.
Tessier-Lavigne, M. and Goodman, C. S. (1996). Science 274, 1123–33.
Tessier-Lavigne, M., et al. (1988). Nature 336, 775–8.
Toole, J. J., et al. (1984). Nature 312, 342–7.
Varela-Echavarria, A. and Guthrie, S. (1997). Genes Dev 11, 545–57.
Varela-Echavarria, A., et al. (1997). Neuron 18, 193–207.
Wadsworth, W. G., Bhatt, H. and Hedgecock, E. M. (1996). Neuron 16, 35–46.

Windle, W. F., and Baxter, R. E. (1936). J. Comp. Neuro. 63, 189–209.
Wright, D. E., et al. (1995). J Comp Neurol 361, 321–33.
Xiang, R. H., et al. (1996). Genomics 32, 39–48.
Zhang, L., et al. (1994). J Neurosci 14, 5187–201.
Zhou, L., et al. (1997). Mol. Cell. Neurosci. 9, 26–41.
Zondag, G. C., et al. (1995). J Biol Chem 270, 14247–50.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

SEQUENCE LISTING (1) GENERAL INFORMATION:

(iii) NUMBER OF SEQUENCES: 26

(2) INFORMATION FOR SEQ ID NO:1:

(i) SEQUENCE CHARACTERISTICS:
        (A) LENGTH: 2772 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:1:

```
ATGGAGAGGG GGCTGCCGCT CCTCTGCGCC GTGCTCGCCC TCGTCCTCGC CCCGGCCGGC      60

GCTTTTCGCA ACGATGAATG TGGCGATACT ATAAAAATTG AAAGCCCCGG GTACCTTACA     120

TCTCCTGGTT ATCCTCATTC TTATCACCCA AGTGAAAAAT GCGAATGGCT GATTCAGGCT     180

CCGGACCCAT ACCAGAGAAT TATGATCAAC TTCAACCCTC ACTTCGATTT GGAGGACAGA     240

GACTGCAAGT ATGACTACGT GGAAGTCTTC GATGGAGAAA ATGAAAATGG ACATTTTAGG     300

GGAAAGTTCT GTGGAAAGAT AGCCCCTCCT CCTGTTGTGT CTTCAGGGCC ATTTCTTTTT     360

ATCAAATTTG TCTCTGACTA CGAAACACAT GGTGCAGGAT TTTCCATACG TTATGAAATT     420

TTCAAGAGAG GTCCTGAATG TTCCCAGAAC TACACAACAC CTAGTGGAGT GATAAAGTCC     480

CCCGGATTCC CTGAAAAATA TCCCAACAGC CTTGAATGCA CTTATATTGT CTTTGCGCCA     540

AAGATGTCAG AGATTATCCT GGAATTTGAA AGCTTTGACC TGGAGCCTGA CTCAAATCCT     600

CCAGGGGGGA TGTTCTGTCG CTACGACCGG CTAGAAATCT GGGATGGATT CCCTGATGTT     660

GGCCCTCACA TTGGGCGTTA CTGTGGACAG AAAACACCAG GTCGAATCCG ATCCTCATCG     720

GGCATTCTCT CCATGGTTTT TTACACCGAC AGCGCGATAG CAAAAGAAGG TTTCTCAGCA     780

AACTACAGTG TCTTGCAGAG CAGTGTCTCA GAAGATTTCA AATGTATGGA AGCTCTGGGC     840

ATGGAATCAG GAGAAATTCA TTCTGACCAG ATCACAGCTT CTTCCCAGTA TAGCACCAAC     900

TGGTCTGCAG AGCGCTCCCG CCTGAACTAC CCTGAGAATG GGTGGACTCC CGGAGAGGAT     960

TCCTACCGAG AGTGGATACA GGTAGACTTG GGCCTTCTGC GCTTTGTCAC GGCTGTCGGG    1020

ACACAGGGCG CCATTTCAAA AGAAACCAAG AAGAAATATT ATGTCAAGAC TTACAAGATC    1080

GACGTTAGCT CCAACGGGGA AGACTGGATC ACCATAAAAG AAGGAAACAA ACCTGTTCTC    1140

TTTCAGGGAA ACACCAACCC CACAGATGTT GTGGTTGCAG TATTCCCCAA ACCACTGATA    1200

ACTCGATTTG TCCGAATCAA GCCTGCAACT TGGGAAACTG GCATATCTAT GAGATTTGAA    1260

GTATACGGTT GCAAGATAAC AGATTATCCT TGCTCTGGAA TGTTGGGTAT GGTGTCTGGA    1320

CTTATTTCTG ACTCCCAGAT CACATCATCC AACCAAGGAG ACAGAAACTG GATGCCTGAA    1380
```

-continued

```
AACATCCGCC TGGTAACCAG TCGCTCTGGC TGGGCACTTC CACCCGCACC TCATTCCTAC    1440

ATCAATGAGT GGCTCCAAAT AGACCTGGGG GAGGAGAAGA TCGTGAGGGG CATCATCATT    1500

CAGGGTGGGA AGCACCGAGA GAACAAGGTG TTCATGAGGA AGTTCAAGAT CGGGTACAGC    1560

AACAACGGCT CGGACTGGAA GATGATCATG GATGACAGCA AACGCAAGGC GAAGTCTTTT    1620

GAGGGCAACA CAACTATGA TACACCTGAG CTGCGGACTT TTCCAGCTCT CTCCACGCGA     1680

TTCATCAGGA TCTACCCCGA GAGAGCCACT CATGGCGGAC TGGGGCTCAG AATGGAGCTG    1740

CTGGGCTGTG AAGTGGAAGC CCCTACAGCT GGACCGACCA CTCCCAACGG GAACTTGGTG    1800

GATGAATGTG ATGACGACCA GGCCAACTGC CACAGTGGAA CAGGTGATGA CTTCCAGCTC    1860

ACAGGTGGCA CCACTGTGCT GGCCACAGAA AAGCCCACGG TCATAGACAG CACCATACAA    1920

TCAGAGTTTC CAACATATGG TTTTAACTGT GAATTTGGCT GGGGCTCTCA CAAGACCTTC    1980

TGCCACTGGG AACATGACAA TCACGTGCAG CTCAAGTGGA GTGTGTTGAC CAGCAAGACG    2040

GGACCCATTC AGGATCACAC AGGAGATGGC AACTTCATCT ATTCCCAAGC TGACGAAAAT    2100

CAGAAGGGCA AAGTGGCTCG CCTGGTGAGC CCTGTGGTTT ATTCCCAGAA CTCTGCCCAC    2160

TGCATGACCT TCTGGTATCA CATGTCTGGG TCCCACGTCG GCACACTCAG GGTCAAACTG    2220

CGCTACCAGA AGCCAGAGGA GTACGATCAG CTGGTCTGGA TGGCCATTGG ACACCAAGGT    2280

GACCACTGGA AGGAAGGGCG TGTCTTGCTC CACAAGTCTC TGAAACTTTA TCAGGTGATT    2340

TTCGAGGGCG AAATCGGAAA AGGAAACCTT GGTGGGATTG CTGTGGATGA CATTAGTATT    2400

AATAACCACA TTTCACAAGA AGATTGTGCA AAACCAGCAG ACCTGGATAA AAAGAACCCA    2460

GAAATTAAAA TTGATGAAAC AGGGAGCACG CCAGGATACG AAGGTGAAGG AGAAGGTGAC    2520

AAGAACATCT CCAGGAAGCC AGGCAATGTG TTGAAGACCT TAGAACCCAT CCTCATCACC    2580

ATCATAGCCA TGAGCGCCCT GGGGGTCCTC CTGGGGGCTG TCTGTGGGGT CGTGCTGTAC    2640

TGTGCCTGTT GGCATAATGG GATGTCAGAA AGAAACTTGT CTGCCCTGGA GAACTATAAC    2700

TTTGAACTTG TGGATGGTGT GAAGTTGAAA AAAGACAAAC TGAATACACA GAGTACTTAT    2760

TCGGAGGCAT GA                                                        2772
```

(2) INFORMATION FOR SEQ ID NO:2:

(i) SEQUENCE CHARACTERISTICS:
        (A) LENGTH: 2588 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:2:

```
Met Glu Thr Gly Leu Ala Arg Gly Gly Leu Tyr Leu Glu Pro Arg Leu
1               5                   10                  15

Glu Leu Glu Cys Tyr Ser Ala Leu Ala Val Ala Leu Leu Glu Ala Leu
            20                  25                  30

Ala Leu Glu Val Ala Leu Leu Glu Ala Leu Ala Pro Arg Ala Leu Ala
        35                  40                  45

Gly Leu Tyr Ala Leu Ala Pro His Glu Ala Arg Gly Ala Ser Asn Ala
    50                  55                  60

Ser Pro Gly Leu Cys Tyr Ser Gly Leu Tyr Ala Ser Pro Thr His Arg
65                  70                  75                  80

Ile Leu Glu Leu Tyr Ser Ile Leu Glu Gly Leu Ser Glu Arg Pro Arg
                85                  90                  95
```

-continued

```
Gly Leu Tyr Thr Tyr Arg Leu Glu Thr His Arg Ser Glu Arg Pro Arg
                100                 105                 110
Gly Leu Tyr Thr Tyr Arg Pro Arg His Ile Ser Ser Glu Arg Thr Tyr
                115                 120                 125
Arg His Ile Ser Pro Arg Ser Glu Arg Gly Leu Leu Tyr Ser Cys Tyr
            130                 135                 140
Ser Gly Leu Thr Arg Pro Leu Glu Ile Leu Glu Gly Leu Asn Ala Leu
145                 150                 155                 160
Ala Pro Arg Ala Ser Pro Pro Arg Thr Tyr Arg Gly Leu Asn Ala Arg
                165                 170                 175
Gly Ile Leu Glu Met Glu Thr Ile Leu Glu Ala Ser Asn Pro His Glu
                180                 185                 190
Ala Ser Asn Pro Arg His Ile Ser Pro His Glu Ala Ser Pro Leu Glu
            195                 200                 205
Gly Leu Ala Ser Pro Ala Arg Gly Ala Ser Pro Cys Tyr Ser Leu Tyr
            210                 215                 220
Ser Thr Tyr Arg Ala Ser Pro Thr Tyr Arg Val Ala Leu Gly Leu Val
225                 230                 235                 240
Ala Leu Pro His Glu Ala Ser Pro Gly Leu Tyr Gly Leu Ala Ser Asn
                245                 250                 255
Gly Leu Ala Ser Asn Gly Leu Tyr His Ile Ser Pro His Glu Ala Arg
            260                 265                 270
Gly Gly Leu Tyr Leu Tyr Ser Pro His Glu Cys Tyr Ser Gly Leu Tyr
            275                 280                 285
Leu Tyr Ser Ile Leu Glu Ala Leu Ala Pro Arg Pro Arg Pro Arg Val
        290                 295                 300
Ala Leu Val Ala Leu Ser Glu Arg Ser Glu Arg Gly Leu Tyr Pro Arg
305                 310                 315                 320
Pro His Glu Leu Glu Pro His Glu Ile Leu Glu Leu Tyr Ser Pro His
                325                 330                 335
Glu Val Ala Leu Ser Glu Arg Ala Ser Pro Thr Tyr Arg Gly Leu Thr
            340                 345                 350
His Arg His Ile Ser Gly Leu Tyr Ala Leu Ala Gly Leu Tyr Pro His
        355                 360                 365
Glu Ser Glu Arg Ile Leu Glu Ala Arg Gly Thr Tyr Arg Gly Leu Ile
    370                 375                 380
Leu Glu Pro His Glu Leu Tyr Ser Ala Arg Gly Gly Leu Tyr Pro Arg
385                 390                 395                 400
Gly Leu Cys Tyr Ser Ser Glu Arg Gly Leu Asn Ala Ser Asn Thr Tyr
                405                 410                 415
Arg Thr His Arg Thr His Arg Pro Arg Ser Glu Arg Gly Leu Tyr Val
            420                 425                 430
Ala Leu Ile Leu Glu Leu Tyr Ser Ser Glu Arg Pro Arg Gly Leu Tyr
        435                 440                 445
Pro His Glu Pro Arg Gly Leu Leu Tyr Ser Thr Tyr Arg Pro Arg Ala
    450                 455                 460
Ser Asn Ser Glu Arg Leu Glu Gly Leu Cys Tyr Ser Thr His Arg Thr
465                 470                 475                 480
Tyr Arg Ile Leu Glu Val Ala Leu Pro His Glu Ala Leu Ala Pro Arg
                485                 490                 495
Leu Tyr Ser Met Glu Thr Ser Glu Arg Gly Leu Ile Leu Glu Ile Leu
                500                 505                 510
```

-continued

```
Glu Leu Glu Gly Leu Pro His Glu Gly Leu Ser Glu Arg Pro His Glu
        515                 520                 525

Ala Ser Pro Leu Glu Gly Leu Pro Arg Ala Ser Pro Ser Glu Arg Ala
        530                 535                 540

Ser Asn Pro Arg Pro Arg Gly Leu Tyr Gly Leu Tyr Met Glu Thr Pro
545                 550                 555                 560

His Glu Cys Tyr Ser Ala Arg Gly Thr Tyr Arg Ala Ser Pro Ala Arg
                565                 570                 575

Gly Leu Glu Gly Leu Ile Leu Glu Thr Arg Pro Ala Ser Pro Gly Leu
                580                 585                 590

Tyr Pro His Glu Pro Arg Ala Ser Pro Val Ala Leu Gly Leu Tyr Pro
        595                 600                 605

Arg His Ile Ser Ile Leu Glu Gly Leu Tyr Ala Arg Gly Thr Tyr Arg
        610                 615                 620

Cys Tyr Ser Gly Leu Tyr Gly Leu Asn Leu Tyr Ser Thr His Arg Pro
625                 630                 635                 640

Arg Gly Leu Tyr Ala Arg Gly Ile Leu Glu Ala Arg Gly Ser Glu Arg
                645                 650                 655

Ser Glu Arg Ser Glu Arg Gly Leu Tyr Ile Leu Glu Leu Glu Ser Glu
                660                 665                 670

Arg Met Glu Thr Val Ala Leu Pro His Glu Thr Tyr Arg Thr His Arg
        675                 680                 685

Ala Ser Pro Ser Glu Arg Ala Leu Ala Ile Leu Glu Ala Leu Ala Leu
        690                 695                 700

Tyr Ser Gly Leu Gly Leu Tyr Pro His Glu Ser Glu Arg Ala Leu Ala
705                 710                 715                 720

Ala Ser Asn Thr Tyr Arg Ser Glu Arg Val Ala Leu Leu Glu Gly Leu
                725                 730                 735

Asn Ser Glu Arg Ser Glu Arg Val Ala Leu Ser Glu Arg Gly Leu Ala
                740                 745                 750

Ser Pro Pro His Glu Leu Tyr Ser Cys Tyr Ser Met Glu Thr Gly Leu
        755                 760                 765

Ala Leu Ala Leu Glu Gly Leu Tyr Met Glu Thr Gly Leu Ser Glu Arg
        770                 775                 780

Gly Leu Tyr Gly Leu Ile Leu Glu His Ile Ser Ser Glu Arg Ala Ser
785                 790                 795                 800

Pro Gly Leu Asn Ile Leu Glu Thr His Arg Ala Leu Ala Ser Glu Arg
                805                 810                 815

Ser Glu Arg Gly Leu Asn Thr Tyr Arg Ser Glu Arg Thr His Arg Ala
                820                 825                 830

Ser Asn Thr Arg Pro Ser Glu Arg Ala Leu Ala Gly Leu Ala Arg Gly
        835                 840                 845

Ser Glu Arg Ala Arg Gly Leu Glu Ala Ser Asn Thr Tyr Arg Pro Arg
        850                 855                 860

Gly Leu Ala Ser Asn Gly Leu Tyr Thr Arg Pro Thr His Arg Pro Arg
865                 870                 875                 880

Gly Leu Tyr Gly Leu Ala Ser Pro Ser Glu Arg Thr Tyr Arg Ala Arg
                885                 890                 895

Gly Gly Leu Thr Arg Pro Ile Leu Glu Gly Leu Asn Val Ala Leu Ala
                900                 905                 910

Ser Pro Leu Glu Gly Leu Tyr Leu Glu Leu Glu Ala Arg Gly Pro His
        915                 920                 925
```

```
Glu Val Ala Leu Thr His Arg Ala Leu Ala Val Ala Leu Gly Leu Tyr
    930                 935                 940

Thr His Arg Gly Leu Asn Gly Leu Tyr Ala Leu Ala Ile Leu Glu Ser
945                 950                 955                 960

Glu Arg Leu Tyr Ser Gly Leu Thr His Arg Leu Tyr Ser Leu Tyr Ser
                965                 970                 975

Leu Tyr Ser Thr Tyr Arg Thr Tyr Arg Val Ala Leu Leu Tyr Ser Thr
            980                 985                 990

His Arg Thr Tyr Arg Leu Tyr Ser Ile Leu Glu Ala Ser Pro Val Ala
            995                 1000                1005

Leu Ser Glu Arg Ser Glu Arg Ala Ser Asn Gly Leu Tyr Gly Leu Ala
            1010                1015                1020

Ser Pro Thr Arg Pro Ile Leu Glu Thr His Arg Ile Leu Glu Leu Tyr
1025                1030                1035                1040

Ser Gly Leu Gly Leu Tyr Ala Ser Asn Leu Tyr Ser Pro Arg Val Ala
                1045                1050                1055

Leu Leu Glu Pro His Glu Gly Leu Asn Gly Leu Tyr Ala Ser Asn Thr
                1060                1065                1070

His Arg Ala Ser Asn Pro Arg Thr His Arg Ala Ser Pro Val Ala Leu
            1075                1080                1085

Val Ala Leu Val Ala Leu Ala Leu Ala Val Ala Leu Pro His Glu Pro
            1090                1095                1100

Arg Leu Tyr Ser Pro Arg Leu Glu Ile Leu Glu Thr His Arg Ala Arg
1105                1110                1115                1120

Gly Pro His Glu Val Ala Leu Ala Arg Gly Ile Leu Glu Leu Tyr Ser
                1125                1130                1135

Pro Arg Ala Leu Ala Thr His Arg Thr Arg Pro Gly Leu Thr His Arg
                1140                1145                1150

Gly Leu Tyr Ile Leu Glu Ser Glu Arg Met Glu Thr Ala Arg Gly Pro
                1155                1160                1165

His Glu Gly Leu Val Ala Leu Thr Tyr Arg Gly Leu Tyr Cys Tyr Ser
            1170                1175                1180

Leu Tyr Ser Ile Leu Glu Thr His Arg Ala Ser Pro Thr Tyr Arg Pro
1185                1190                1195                1200

Arg Cys Tyr Ser Ser Glu Arg Gly Leu Tyr Met Glu Thr Leu Glu Gly
                1205                1210                1215

Leu Tyr Met Glu Thr Val Ala Leu Ser Glu Arg Gly Leu Tyr Leu Glu
                1220                1225                1230

Ile Leu Glu Ser Glu Arg Ala Ser Pro Ser Glu Arg Gly Leu Asn Ile
                1235                1240                1245

Leu Glu Thr His Arg Ser Glu Arg Ser Glu Arg Ala Ser Asn Gly Leu
                1250                1255                1260

Asn Gly Leu Tyr Ala Ser Pro Ala Arg Gly Ala Ser Asn Thr Arg Pro
1265                1270                1275                1280

Met Glu Thr Pro Arg Gly Leu Ala Ser Asn Ile Leu Glu Ala Arg Gly
                1285                1290                1295

Leu Glu Val Ala Leu Thr His Arg Ser Glu Arg Ala Arg Gly Ser Glu
                1300                1305                1310

Arg Gly Leu Tyr Thr Arg Pro Ala Leu Ala Leu Glu Pro Arg Pro Arg
                1315                1320                1325

Ala Leu Ala Pro Arg His Ile Ser Ser Glu Arg Thr Tyr Arg Ile Leu
                1330                1335                1340
```

-continued

```
Glu Ala Ser Asn Gly Leu Thr Arg Pro Leu Glu Gly Leu Asn Ile Leu
1345                1350                1355                1360

Glu Ala Ser Pro Leu Glu Gly Leu Tyr Gly Leu Gly Leu Leu Tyr Ser
            1365                1370                1375

Ile Leu Glu Val Ala Leu Ala Arg Gly Gly Leu Tyr Ile Leu Glu Ile
            1380                1385                1390

Leu Glu Ile Leu Glu Gly Leu Asn Gly Leu Tyr Gly Leu Tyr Leu Tyr
        1395                1400                1405

Ser His Ile Ser Ala Arg Gly Gly Leu Ala Ser Asn Leu Tyr Ser Val
        1410                1415                1420

Ala Leu Pro His Glu Met Glu Thr Ala Arg Gly Leu Tyr Ser Pro His
1425                1430                1435                1440

Glu Leu Tyr Ser Ile Leu Glu Gly Leu Tyr Thr Tyr Arg Ser Glu Arg
            1445                1450                1455

Ala Ser Asn Ala Ser Asn Gly Leu Tyr Ser Glu Arg Ala Ser Pro Thr
            1460                1465                1470

Arg Pro Leu Tyr Ser Met Glu Thr Ile Leu Glu Met Glu Thr Ala Ser
            1475                1480                1485

Pro Ala Ser Pro Ser Glu Arg Leu Tyr Ser Ala Arg Gly Leu Tyr Ser
        1490                1495                1500

Ala Leu Ala Leu Tyr Ser Ser Glu Arg Pro His Glu Gly Leu Gly Leu
1505                1510                1515                1520

Tyr Ala Ser Asn Ala Ser Asn Ala Ser Asn Thr Tyr Arg Ala Ser Pro
            1525                1530                1535

Thr His Arg Pro Arg Gly Leu Leu Glu Ala Arg Gly Thr His Arg Pro
            1540                1545                1550

His Glu Pro Arg Ala Leu Ala Leu Glu Ser Glu Arg Thr His Arg Ala
        1555                1560                1565

Arg Gly Pro His Glu Ile Leu Glu Ala Arg Gly Ile Leu Glu Thr Tyr
        1570                1575                1580

Arg Pro Arg Gly Leu Ala Arg Gly Ala Leu Ala Thr His Arg His Ile
1585                1590                1595                1600

Ser Gly Leu Tyr Gly Leu Tyr Leu Glu Gly Leu Tyr Leu Glu Ala Arg
            1605                1610                1615

Gly Met Glu Thr Gly Leu Leu Glu Leu Glu Gly Leu Tyr Cys Tyr Ser
            1620                1625                1630

Gly Leu Val Ala Leu Gly Leu Ala Leu Ala Pro Arg Thr His Arg Ala
        1635                1640                1645

Leu Ala Gly Leu Tyr Pro Arg Thr His Arg Thr His Arg Pro Arg Ala
        1650                1655                1660

Ser Asn Gly Leu Tyr Ala Ser Asn Leu Glu Val Ala Leu Ala Ser Pro
1665                1670                1675                1680

Gly Leu Cys Tyr Ser Ala Ser Pro Ala Ser Pro Ala Ser Pro Gly Leu
            1685                1690                1695

Asn Ala Leu Ala Ala Ser Asn Cys Tyr Ser His Ile Ser Ser Glu Arg
            1700                1705                1710

Gly Leu Tyr Thr His Arg Gly Leu Tyr Ala Ser Pro Ala Ser Pro Pro
            1715                1720                1725

His Glu Gly Leu Asn Leu Glu Thr His Arg Gly Leu Tyr Gly Leu Tyr
        1730                1735                1740

Thr His Arg Thr His Arg Val Ala Leu Leu Glu Ala Leu Ala Thr His
1745                1750                1755                1760
```

-continued

Arg Gly Leu Leu Tyr Ser Pro Arg Thr His Arg Val Ala Leu Ile Leu
            1765               1770              1775

Glu Ala Ser Pro Ser Glu Arg Thr His Arg Ile Leu Glu Gly Leu Asn
        1780               1785              1790

Ser Glu Arg Gly Leu Pro His Glu Pro Arg Thr His Arg Thr Tyr Arg
        1795               1800              1805

Gly Leu Tyr Pro His Glu Ala Ser Asn Cys Tyr Ser Gly Leu Pro His
        1810               1815              1820

Glu Gly Leu Tyr Thr Arg Pro Gly Leu Tyr Ser Glu Arg His Ile Ser
1825            1830              1835              1840

Leu Tyr Ser Thr His Arg Pro His Glu Cys Tyr Ser His Ile Ser Thr
            1845              1850              1855

Arg Pro Gly Leu His Ile Ser Ala Ser Pro Ala Ser Asn His Ile Ser
            1860              1865              1870

Val Ala Leu Gly Leu Asn Leu Glu Leu Tyr Ser Thr Arg Pro Ser Glu
            1875              1880              1885

Arg Val Ala Leu Leu Glu Thr His Arg Ser Glu Arg Leu Tyr Ser Thr
        1890              1895              1900

His Arg Gly Leu Tyr Pro Arg Ile Leu Glu Gly Leu Asn Ala Ser Pro
1905            1910              1915              1920

His Ile Ser Thr His Arg Gly Leu Tyr Ala Ser Pro Gly Leu Tyr Ala
            1925              1930              1935

Ser Asn Pro His Glu Ile Leu Glu Thr Tyr Arg Ser Glu Arg Gly Leu
        1940              1945              1950

Asn Ala Leu Ala Ala Ser Pro Gly Leu Ala Ser Asn Gly Leu Asn Leu
        1955              1960              1965

Tyr Ser Gly Leu Tyr Leu Tyr Ser Val Ala Leu Ala Leu Ala Ala Arg
        1970              1975              1980

Gly Leu Glu Val Ala Leu Ser Glu Arg Pro Arg Val Ala Leu Val Ala
1985            1990              1995              2000

Leu Thr Tyr Arg Ser Glu Arg Gly Leu Asn Ala Ser Asn Ser Glu Arg
            2005              2010              2015

Ala Leu Ala His Ile Ser Cys Tyr Ser Met Glu Thr Thr His Arg Pro
            2020              2025              2030

His Glu Thr Arg Pro Thr Tyr Arg His Ile Ser Met Glu Thr Ser Glu
        2035              2040              2045

Arg Gly Leu Tyr Ser Glu Arg His Ile Ser Val Ala Leu Gly Leu Tyr
        2050              2055              2060

Thr His Arg Leu Glu Ala Arg Gly Val Ala Leu Leu Tyr Ser Leu Glu
2065            2070              2075              2080

Ala Arg Gly Thr Tyr Arg Gly Leu Asn Leu Tyr Ser Pro Arg Gly Leu
            2085              2090              2095

Gly Leu Thr Tyr Arg Ala Ser Pro Gly Leu Asn Leu Glu Val Ala Leu
            2100              2105              2110

Thr Arg Pro Met Glu Thr Ala Leu Ala Ile Leu Glu Gly Leu Tyr His
        2115              2120              2125

Ile Ser Gly Leu Asn Gly Leu Tyr Ala Ser Pro His Ile Ser Thr Arg
        2130              2135              2140

Pro Leu Tyr Ser Gly Leu Gly Leu Tyr Ala Arg Gly Val Ala Leu Leu
2145            2150              2155              2160

Glu Leu Glu His Ile Ser Leu Tyr Ser Ser Glu Arg Leu Glu Leu Tyr
            2165              2170              2175

```
Ser Leu Glu Thr Tyr Arg Gly Leu Asn Val Ala Leu Ile Leu Glu Pro
            2180                2185                2190

His Glu Gly Leu Gly Leu Tyr Gly Leu Ile Leu Glu Gly Leu Tyr Leu
            2195                2200                2205

Tyr Ser Gly Leu Tyr Ala Ser Asn Leu Glu Gly Leu Tyr Gly Leu Tyr
            2210                2215                2220

Ile Leu Glu Ala Leu Ala Val Ala Leu Ala Ser Pro Ala Ser Pro Ile
2225                2230                2235                2240

Leu Glu Ser Glu Arg Ile Leu Glu Ala Ser Asn Ala Ser Asn His Ile
            2245                2250                2255

Ser Ile Leu Glu Ser Glu Arg Gly Leu Asn Gly Leu Ala Ser Pro Cys
            2260                2265                2270

Tyr Ser Ala Leu Ala Leu Tyr Ser Pro Arg Ala Leu Ala Ala Ser Pro
            2275                2280                2285

Leu Glu Ala Ser Pro Leu Tyr Ser Leu Tyr Ser Ala Ser Asn Pro Arg
            2290                2295                2300

Gly Leu Ile Leu Glu Leu Tyr Ser Ile Leu Glu Ala Ser Pro Gly Leu
2305                2310                2315                2320

Thr His Arg Gly Leu Tyr Ser Glu Arg Thr His Arg Pro Arg Gly Leu
            2325                2330                2335

Tyr Thr Tyr Arg Gly Leu Gly Leu Tyr Gly Leu Gly Leu Tyr Gly Leu
            2340                2345                2350

Gly Leu Tyr Ala Ser Pro Leu Tyr Ser Ala Ser Asn Ile Leu Glu Ser
            2355                2360                2365

Glu Arg Ala Arg Gly Leu Tyr Ser Pro Arg Gly Leu Tyr Ala Ser Asn
            2370                2375                2380

Val Ala Leu Leu Glu Leu Tyr Ser Thr His Arg Leu Glu Gly Leu Pro
2385                2390                2395                2400

Arg Ile Leu Glu Leu Glu Ile Leu Glu Thr His Arg Ile Leu Glu Ile
            2405                2410                2415

Leu Glu Ala Leu Ala Met Glu Thr Ser Glu Arg Ala Leu Ala Leu Glu
            2420                2425                2430

Gly Leu Tyr Val Ala Leu Leu Glu Leu Glu Gly Leu Tyr Ala Leu Ala
            2435                2440                2445

Val Ala Leu Cys Tyr Ser Gly Leu Tyr Val Ala Leu Val Ala Leu Leu
            2450                2455                2460

Glu Thr Tyr Arg Cys Tyr Ser Ala Leu Ala Cys Tyr Ser Thr Arg Pro
2465                2470                2475                2480

His Ile Ser Ala Ser Asn Gly Leu Tyr Met Glu Thr Ser Glu Arg Gly
            2485                2490                2495

Leu Ala Arg Gly Ala Ser Asn Leu Glu Ser Glu Arg Ala Leu Ala Leu
            2500                2505                2510

Glu Gly Leu Ala Ser Asn Thr Tyr Arg Ala Ser Asn Pro His Glu Gly
            2515                2520                2525

Leu Leu Glu Val Ala Leu Ala Ser Pro Gly Leu Tyr Val Ala Leu Leu
            2530                2535                2540

Tyr Ser Leu Glu Leu Tyr Ser Leu Tyr Ser Ala Ser Pro Leu Tyr Ser
2545                2550                2555                2560

Leu Glu Ala Ser Asn Thr His Arg Gly Leu Asn Ser Glu Arg Thr His
            2565                2570                2575

Arg Thr Tyr Arg Ser Glu Arg Gly Leu Ala Leu Ala
            2580                2585
```

(2) INFORMATION FOR SEQ ID NO:3:

(i) SEQUENCE CHARACTERISTICS:
        (A) LENGTH: 2766 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:3:

```
ATGGAGAGGG GGCTGCCGTT GCTGTGCGCC ACGCTCGCCC TTGCCCTCGC CCTGGGGGCT     60

TTCCGCAGCG ATAAATGTGG CGGGACTATA AAAATTGAAA ACCCGGGGTA CCTTACATCT    120

CCCGGCTACC CTCATTCTTA CCATCCAAGT GAGAAATGTG AATGGCTAAT CCAAGCTCCG    180

GAGCCCTACC AGAGAATCAT GATCAACTTC AACCCACATT TCGATTTGGA GGACAGAGAC    240

TGCAAGTATG ACTATGTGGA AGTGATCGAT GGAGAGAATG AAGGTGGCCG CCTGTGGGGG    300

AAGTTCTGTG GAAGATCGC ACCTTCACCT GTGGTGTCTT CAGGGCCATT TCTCTTCATC    360

AAATTTGTCT CTGACTATGA GACCCACGGG GCAGGATTTT CCATCCGCTA TGAAATCTTC    420

AAGAGAGGGC CCGAATGTTC TCAGAACTAT ACAGCACCTA CTGGAGTGAT AAAGTCCCCT    480

GGGTTCCCTG AAAAATACCC CAACAGCTTG GAGTGCACCT ACATCATCTT TGCACCAAAG    540

ATGTCTGAGA TAATCCTAGA GTTTGAAAGT TTTGACCTGG AGCAAGACTC AAATCCTCCC    600

GGAGGAATGT TCTGTCGCTA TGACCGGCTG GAGATCTGGG ATGGATTCCC TGAAGTTGGC    660

CCTCACATTG GGCGTTACTG TGGGCAGAAA ACTCCTGGCC GGATCCGCTC CTCTTCAGGC    720

ATTCTATCCA TGGTCTTCTA CACTGACAGC GCAATAGCAA AGGAAGGTTT CTCAGCCAAC    780

TACAGCGTGC TGCAGAGCAG CATCTCTGAA GATTTCAAGT GTATGGAGGC TCTGGGCATG    840

GAATCTGGAG AGATCCATTC TGACCAGATC ACTGCATCTT CCCAGTATGG TACCAACTGG    900

TCTGTTGAGC GCTCCCGCCT GAACTACCCT GAAAACGGGT GGACACCAGG AGAGGACTCC    960

TACAGGGAGT GGATCCAGGT GGACTTGGGC CTCCTGCGAT TCGTTACTGC TGTGGGGACA   1020

CAGGGTGCCA TTTCCAAGGA AACCAAGAAG AAATATTATG TCAAGACTTA CAGAGTAGAC   1080

ATCAGCTCCA ACGGAGAGGA CTGGATCACC CTGAAGGAGG GAAATAAAGC CATTATCTTT   1140

CAGGGAAACA CCAATCCCAC GGATGTTGTC TTTGGAGTTT TCCCCAAACC ACTGATAACT   1200

CGATTTGTCC GAATCAAACC TGCATCCTGG GAAACTGGAA TATCTATGAG ATTTGAAGTT   1260

TATGGCTGCA AGATAACAGA TTACCCTTGC TCTGGAATGT TGGGCATGGT GTCTGGACTT   1320

ATTTCAGACT CCCAGATTAC AGCATCCAAC CAAGGAGACA GGAACTGGAT GCCAGAAAAC   1380

ATCCGCCTGG TGACCAGTCG AACCGGCTGG GCCCTGCCAC CCTCACCCCA CCCATACATC   1440

AATGAATGGC TCCAAGTGGA CCTGGGAGAT GAGAAGATAG TAAGAGGTGT CATCATTCAA   1500

GGTGGGAAGC ACCGAGAAAA CAAAGTGTTC ATGAGGAAGT TCAAGATCGC CTACAGTAAC   1560

AATGGTTCTG ACTGGAAAAT GATCATGGAT GACAGCAAGC GCAAGGCTAA GTCTTTTGAA   1620

GGCAACAACA ACTATGACAC ACCTGAGCTC CGGGCCTTTA CACCTCTCTC CACAAGATTC   1680

ATCAGGATCT ACCCCGAGAG AGCCACACAT AGTGGGCTCG GACTGAGGAT GGAGCTACTG   1740

GGCTGTGAAG TAGAAGTGCC TACAGCTGGA CCCACGACAC CAATGGGAA CCCCGTGGAC   1800

GAGTGTGACG ATGACCAGGC CAACTGCCAC AGTGGCACAG TGATGACTT CCAGCTCACA   1860

GGAGGCACCA CTGTCCTGGC CACAGAGAAG CCCACCATTA TAGACAGCAC CATCCAATCA   1920

GAGTTCCCGA CATACGGTTT TAACTGCGAG TTTGGCTGGG GCTCTCACAA GACATTCTGC   1980
```

-continued

```
CACTGGGAAC ATGACAGCCA CGCGCAGCTC AGGTGGAGGG TGCTGACCAG CAAGACGGGG    2040

CCCATTCAGG ACCACACAGG AGATGGCAAC TTCATCTATT CCCAAGCTGA TGAAAATCAG    2100

AAAGGCAAAG TAGCCCGCCT GGTGAGCCCT GTGGTCTATT CCCAGAGTTC TGCCCACTGC    2160

ATGACCTTCT GGTATCACAT GTCCGGCTCT CATGTGGGTA CACTGAGGGT CAAACTGCAC    2220

TACCAGAAGC CAGAGGAATA TGATCAACTG GTCTGGATGG TGGTCGGGCA CCAAGGAGAC    2280

CACTGGAAGG AAGGGCGTGT CTTGCTGCAC AAATCTCTGA AACTGTATCA GGTTATTTTT    2340

GAAGGTGAAA TCGGAAAAGG AAACCTCGGT GGGATTGCTG TGGATGATAT CAGTATTAAC    2400

AACCACATTC CTCAGGAGGA CTGTGCAAAA CCAACAGACC TAGATAAAAA GAACACAGAA    2460

ATTAAAATAG ATGAAACAGG GAGCACCCCA GGATATGAAG AAGGGAAAGG CGACAAGAAC    2520

ATCTCCAGGA AGCCAGGCAA TGTGCTTAAG ACCCTGGACC CCATCCTGAT CACCATCATA    2580

GCCATGAGTG CCCTGGGGGT GCTCCTGGGT GCAGTCTGTG GAGTTGTGCT GTACTGTGCC    2640

TGTTGGCACA ATGGGATGTC GGAAAGGAAC CTATCTGCCC TGGAGAACTA TAACTTTGAA    2700

CTTGTGGATG GTGTAAAGTT GAAAAAAGAT AAACTGAACC CACACAGTAA TTACTCAGAG    2760

GCGTGA                                                             2766
```

(2) INFORMATION FOR SEQ ID NO:4:

(i) SEQUENCE CHARACTERISTICS:
        (A) LENGTH: 2584 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:4:

```
Met Glu Thr Gly Leu Ala Arg Gly Gly Leu Tyr Leu Glu Pro Arg Leu
 1               5                  10                  15

Glu Leu Glu Cys Tyr Ser Ala Leu Ala Thr His Arg Leu Glu Ala Leu
            20                  25                  30

Ala Leu Glu Ala Leu Ala Leu Glu Ala Leu Ala Leu Glu Gly Leu Tyr
        35                  40                  45

Ala Leu Ala Pro His Glu Ala Arg Gly Ser Glu Arg Ala Ser Pro Leu
    50                  55                  60

Tyr Ser Cys Tyr Ser Gly Leu Tyr Gly Leu Tyr Thr His Arg Ile Leu
65                  70                  75                  80

Glu Leu Tyr Ser Ile Leu Glu Gly Leu Ala Ser Asn Pro Arg Gly Leu
                85                  90                  95

Tyr Thr Tyr Arg Leu Glu Thr His Arg Ser Glu Arg Pro Arg Gly Leu
            100                 105                 110

Tyr Thr Tyr Arg Pro Arg His Ile Ser Ser Glu Arg Thr Tyr Arg His
        115                 120                 125

Ile Ser Pro Arg Ser Glu Arg Gly Leu Leu Tyr Ser Cys Tyr Ser Gly
    130                 135                 140

Leu Thr Arg Pro Leu Glu Ile Leu Glu Gly Leu Asn Ala Leu Ala Pro
145                 150                 155                 160

Arg Gly Leu Pro Arg Thr Tyr Arg Gly Leu Asn Ala Arg Gly Ile Leu
                165                 170                 175

Glu Met Glu Thr Ile Leu Glu Ala Ser Asn Pro His Glu Ala Ser Asn
            180                 185                 190
```

-continued

```
Pro Arg His Ile Ser Pro His Glu Ala Ser Pro Leu Glu Gly Leu Ala
        195                 200                 205

Ser Pro Ala Arg Gly Ala Ser Pro Cys Tyr Ser Leu Tyr Ser Thr Tyr
        210                 215                 220

Arg Ala Ser Pro Thr Tyr Arg Val Ala Leu Gly Leu Val Ala Leu Ile
225                 230                 235                 240

Leu Glu Ala Ser Pro Gly Leu Tyr Gly Leu Ala Ser Asn Gly Leu Gly
                245                 250                 255

Leu Tyr Gly Leu Tyr Ala Arg Gly Leu Glu Thr Arg Pro Gly Leu Tyr
            260                 265                 270

Leu Tyr Ser Pro His Glu Cys Tyr Ser Gly Leu Tyr Leu Tyr Ser Ile
        275                 280                 285

Leu Glu Ala Leu Ala Pro Arg Ser Glu Arg Pro Arg Val Ala Leu Val
        290                 295                 300

Ala Leu Ser Glu Arg Ser Glu Arg Gly Leu Tyr Pro Arg Pro His Glu
305                 310                 315                 320

Leu Glu Pro His Glu Ile Leu Glu Leu Tyr Ser Pro His Glu Val Ala
                325                 330                 335

Leu Ser Glu Arg Ala Ser Pro Thr Tyr Arg Gly Leu Thr His Arg His
            340                 345                 350

Ile Ser Gly Leu Tyr Ala Leu Ala Gly Leu Tyr Pro His Glu Ser Glu
        355                 360                 365

Arg Ile Leu Glu Ala Arg Gly Thr Tyr Arg Gly Leu Ile Leu Glu Pro
370                 375                 380

His Glu Leu Tyr Ser Ala Arg Gly Gly Leu Tyr Pro Arg Gly Leu Cys
385                 390                 395                 400

Tyr Ser Ser Glu Arg Gly Leu Asn Ala Ser Asn Thr Tyr Arg Thr His
                405                 410                 415

Arg Ala Leu Ala Pro Arg Thr His Arg Gly Leu Tyr Val Ala Leu Ile
            420                 425                 430

Leu Glu Leu Tyr Ser Ser Glu Arg Pro Arg Gly Leu Tyr Pro His Glu
        435                 440                 445

Pro Arg Gly Leu Leu Tyr Ser Thr Tyr Arg Pro Arg Ala Ser Asn Ser
        450                 455                 460

Glu Arg Leu Glu Gly Leu Cys Tyr Ser Thr His Arg Thr Tyr Arg Ile
465                 470                 475                 480

Leu Glu Ile Leu Glu Pro His Glu Ala Leu Ala Pro Arg Leu Tyr Ser
                485                 490                 495

Met Glu Thr Ser Glu Arg Gly Leu Ile Leu Glu Ile Leu Glu Leu Glu
            500                 505                 510

Gly Leu Pro His Glu Gly Leu Ser Glu Arg Pro His Glu Ala Ser Pro
        515                 520                 525

Leu Glu Gly Leu Gly Leu Asn Ala Ser Pro Ser Glu Arg Ala Ser Asn
530                 535                 540

Pro Arg Pro Arg Gly Leu Tyr Gly Leu Tyr Met Glu Thr Pro His Glu
545                 550                 555                 560

Cys Tyr Ser Ala Arg Gly Thr Tyr Arg Ala Ser Pro Ala Arg Gly Leu
                565                 570                 575

Glu Gly Leu Ile Leu Glu Thr Arg Pro Ala Ser Pro Gly Leu Tyr Pro
            580                 585                 590

His Glu Pro Arg Gly Leu Val Ala Leu Gly Leu Tyr Pro Arg His Ile
        595                 600                 605
```

-continued

```
Ser Ile Leu Glu Gly Leu Tyr Ala Arg Gly Thr Tyr Arg Cys Tyr Ser
    610                 615                 620

Gly Leu Tyr Gly Leu Asn Leu Tyr Ser Thr His Arg Pro Arg Gly Leu
625                 630                 635                 640

Tyr Ala Arg Gly Ile Leu Glu Ala Arg Gly Ser Glu Arg Ser Glu Arg
                645                 650                 655

Ser Glu Arg Gly Leu Tyr Ile Leu Glu Leu Ser Glu Arg Met Glu
            660                 665                 670

Thr Val Ala Leu Pro His Glu Thr Tyr Arg Thr His Arg Ala Ser Pro
            675                 680                 685

Ser Glu Arg Ala Leu Ala Ile Leu Glu Ala Leu Ala Leu Tyr Ser Gly
            690                 695                 700

Leu Gly Leu Tyr Pro His Glu Ser Glu Arg Ala Leu Ala Ala Ser Asn
705                 710                 715                 720

Thr Tyr Arg Ser Glu Arg Val Ala Leu Leu Glu Gly Leu Asn Ser Glu
                725                 730                 735

Arg Ser Glu Arg Ile Leu Glu Ser Glu Arg Gly Leu Ala Ser Pro Pro
            740                 745                 750

His Glu Leu Tyr Ser Cys Tyr Ser Met Glu Thr Gly Leu Ala Leu Ala
            755                 760                 765

Leu Glu Gly Leu Tyr Met Glu Thr Gly Leu Ser Glu Arg Gly Leu Tyr
770                 775                 780

Gly Leu Ile Leu Glu His Ile Ser Ser Glu Arg Ala Ser Pro Gly Leu
785                 790                 795                 800

Asn Ile Leu Glu Thr His Arg Ala Leu Ala Ser Glu Arg Ser Glu Arg
                805                 810                 815

Gly Leu Asn Thr Tyr Arg Gly Leu Tyr Thr His Arg Ala Ser Asn Thr
            820                 825                 830

Arg Pro Ser Glu Arg Val Ala Leu Gly Leu Ala Arg Gly Ser Glu Arg
            835                 840                 845

Ala Arg Gly Leu Glu Ala Ser Asn Thr Tyr Arg Pro Arg Gly Leu Ala
            850                 855                 860

Ser Asn Gly Leu Tyr Thr Arg Pro Thr His Arg Pro Arg Gly Leu Tyr
865                 870                 875                 880

Gly Leu Ala Ser Pro Ser Glu Arg Thr Tyr Arg Ala Arg Gly Gly Leu
                885                 890                 895

Thr Arg Pro Ile Leu Glu Gly Leu Asn Val Ala Leu Ala Ser Pro Leu
            900                 905                 910

Glu Gly Leu Tyr Leu Glu Leu Glu Ala Arg Gly Pro His Glu Val Ala
            915                 920                 925

Leu Thr His Arg Ala Leu Ala Val Ala Leu Gly Leu Tyr Thr His Arg
            930                 935                 940

Gly Leu Asn Gly Leu Tyr Ala Leu Ala Ile Leu Glu Ser Glu Arg Leu
945                 950                 955                 960

Tyr Ser Gly Leu Thr His Arg Leu Tyr Ser Leu Tyr Ser Leu Tyr Ser
                965                 970                 975

Thr Tyr Arg Thr Tyr Arg Val Ala Leu Leu Tyr Ser Thr His Arg Thr
            980                 985                 990

Tyr Arg Ala Arg Gly Val Ala Leu Ala Ser Pro Ile Leu Glu Ser Glu
            995                 1000                1005

Arg Ser Glu Arg Ala Ser Asn Gly Leu Tyr Gly Leu Ala Ser Pro Thr
            1010                1015                1020
```

-continued

```
Arg Pro Ile Leu Glu Thr His Arg Leu Glu Leu Tyr Ser Gly Leu Gly
1025                1030                1035                1040

Leu Tyr Ala Ser Asn Leu Tyr Ser Ala Leu Ala Ile Leu Glu Ile Leu
                1045                1050                1055

Glu Pro His Glu Gly Leu Asn Gly Leu Tyr Ala Ser Asn Thr His Arg
                1060                1065                1070

Ala Ser Asn Pro Arg Thr His Arg Ala Ser Pro Val Ala Leu Val Ala
            1075                1080                1085

Leu Pro His Glu Gly Leu Tyr Val Ala Leu Pro His Glu Pro Arg Leu
            1090                1095                1100

Tyr Ser Pro Arg Leu Glu Ile Leu Glu Thr His Arg Ala Arg Gly Pro
1105                1110                1115                1120

His Glu Val Ala Leu Ala Arg Gly Ile Leu Glu Leu Tyr Ser Pro Arg
                1125                1130                1135

Ala Leu Ala Ser Glu Arg Thr Arg Pro Gly Leu Thr His Arg Gly Leu
                1140                1145                1150

Tyr Ile Leu Glu Ser Glu Arg Met Glu Thr Ala Arg Gly Pro His Glu
                1155                1160                1165

Gly Leu Val Ala Leu Thr Tyr Arg Gly Leu Tyr Cys Tyr Ser Leu Tyr
            1170                1175                1180

Ser Ile Leu Glu Thr His Arg Ala Ser Pro Thr Tyr Arg Pro Arg Cys
1185                1190                1195                1200

Tyr Ser Ser Glu Arg Gly Leu Tyr Met Glu Thr Leu Glu Gly Leu Tyr
                1205                1210                1215

Met Glu Thr Val Ala Leu Ser Glu Arg Gly Leu Tyr Leu Glu Ile Leu
            1220                1225                1230

Glu Ser Glu Arg Ala Ser Pro Ser Glu Arg Gly Leu Asn Ile Leu Glu
            1235                1240                1245

Thr His Arg Ala Leu Ala Ser Glu Arg Ala Ser Asn Gly Leu Asn Gly
            1250                1255                1260

Leu Tyr Ala Ser Pro Ala Arg Gly Ala Ser Asn Thr Arg Pro Met Glu
1265                1270                1275                1280

Thr Pro Arg Gly Leu Ala Ser Asn Ile Leu Glu Ala Arg Gly Leu Glu
                1285                1290                1295

Val Ala Leu Thr His Arg Ser Glu Arg Ala Arg Gly Thr His Arg Gly
            1300                1305                1310

Leu Tyr Thr Arg Pro Ala Leu Ala Leu Glu Pro Arg Pro Arg Ser Glu
            1315                1320                1325

Arg Pro Arg His Ile Ser Pro Arg Thr Tyr Arg Ile Leu Glu Ala Ser
            1330                1335                1340

Asn Gly Leu Thr Arg Pro Leu Glu Gly Leu Asn Val Ala Leu Ala Ser
1345                1350                1355                1360

Pro Leu Glu Gly Leu Tyr Ala Ser Pro Gly Leu Leu Tyr Ser Ile Leu
                1365                1370                1375

Glu Val Ala Leu Ala Arg Gly Gly Leu Tyr Val Ala Leu Ile Leu Glu
            1380                1385                1390

Ile Leu Glu Gly Leu Asn Gly Leu Tyr Gly Leu Tyr Leu Tyr Ser His
            1395                1400                1405

Ile Ser Ala Arg Gly Gly Leu Ala Ser Asn Leu Tyr Ser Val Ala Leu
            1410                1415                1420

Pro His Glu Met Glu Thr Ala Arg Gly Leu Tyr Ser Pro His Glu Leu
1425                1430                1435                1440
```

-continued

```
Tyr Ser Ile Leu Glu Ala Leu Ala Thr Tyr Arg Ser Glu Arg Ala Ser
            1445                1450                1455

Asn Ala Ser Asn Gly Leu Tyr Ser Glu Arg Ala Ser Pro Thr Arg Pro
            1460                1465                1470

Leu Tyr Ser Met Glu Thr Ile Leu Glu Met Glu Thr Ala Ser Pro Ala
            1475                1480                1485

Ser Pro Ser Glu Arg Leu Tyr Ser Ala Arg Gly Leu Tyr Ser Ala Leu
            1490                1495                1500

Ala Leu Tyr Ser Ser Glu Arg Pro His Glu Gly Leu Gly Leu Tyr Ala
1505                1510                1515                1520

Ser Asn Ala Ser Asn Ala Ser Asn Thr Tyr Arg Ala Ser Pro Thr His
            1525                1530                1535

Arg Pro Arg Gly Leu Leu Glu Ala Arg Gly Ala Leu Ala Pro His Glu
            1540                1545                1550

Thr His Arg Pro Arg Leu Glu Ser Glu Arg Thr His Arg Ala Arg Gly
            1555                1560                1565

Pro His Glu Ile Leu Glu Ala Arg Gly Ile Leu Glu Thr Tyr Arg Pro
            1570                1575                1580

Arg Gly Leu Ala Arg Gly Ala Leu Ala Thr His Arg His Ile Ser Ser
1585                1590                1595                1600

Glu Arg Gly Leu Tyr Leu Glu Gly Leu Tyr Leu Glu Ala Arg Gly Met
            1605                1610                1615

Glu Thr Gly Leu Leu Glu Leu Glu Gly Leu Tyr Cys Tyr Ser Gly Leu
            1620                1625                1630

Val Ala Leu Gly Leu Val Ala Leu Pro Arg Thr His Arg Ala Leu Ala
            1635                1640                1645

Gly Leu Tyr Pro Arg Thr His Arg Thr His Arg Pro Arg Ala Ser Asn
            1650                1655                1660

Gly Leu Tyr Ala Ser Asn Pro Arg Val Ala Leu Ala Ser Pro Gly Leu
1665                1670                1675                1680

Cys Tyr Ser Ala Ser Pro Ala Ser Pro Ala Ser Pro Gly Leu Asn Ala
            1685                1690                1695

Leu Ala Ala Ser Asn Cys Tyr Ser His Ile Ser Ser Glu Arg Gly Leu
            1700                1705                1710

Tyr Thr His Arg Gly Leu Tyr Ala Ser Pro Ala Ser Pro Pro His Glu
            1715                1720                1725

Gly Leu Asn Leu Glu Thr His Arg Gly Leu Tyr Gly Leu Tyr Thr His
            1730                1735                1740

Arg Thr His Arg Val Ala Leu Leu Glu Ala Leu Ala Thr His Arg Gly
1745                1750                1755                1760

Leu Leu Tyr Ser Pro Arg Thr His Arg Ile Leu Glu Ile Leu Glu Ala
            1765                1770                1775

Ser Pro Ser Glu Arg Thr His Arg Ile Leu Glu Gly Leu Asn Ser Glu
            1780                1785                1790

Arg Gly Leu Pro His Glu Pro Arg Thr His Arg Thr Tyr Arg Gly Leu
            1795                1800                1805

Tyr Pro His Glu Ala Ser Asn Cys Tyr Ser Gly Leu Pro His Glu Gly
            1810                1815                1820

Leu Tyr Thr Arg Pro Gly Leu Tyr Ser Glu Arg His Ile Ser Leu Tyr
1825                1830                1835                1840

Ser Thr His Arg Pro His Glu Cys Tyr Ser His Ile Ser Thr Arg Pro
            1845                1850                1855
```

-continued

```
Gly Leu His Ile Ser Ala Ser Pro Ser Glu Arg His Ile Ser Ala Leu
            1860                1865                1870

Ala Gly Leu Asn Leu Glu Ala Arg Gly Thr Arg Pro Ala Arg Gly Val
        1875                1880                1885

Ala Leu Leu Glu Thr His Arg Ser Glu Arg Leu Tyr Ser Thr His Arg
    1890                1895                1900

Gly Leu Tyr Pro Arg Ile Leu Glu Gly Leu Asn Ala Ser Pro His Ile
1905                1910                1915                1920

Ser Thr His Arg Gly Leu Tyr Ala Ser Pro Gly Leu Tyr Ala Ser Asn
                1925                1930                1935

Pro His Glu Ile Leu Glu Thr Tyr Arg Ser Glu Arg Gly Leu Asn Ala
            1940                1945                1950

Leu Ala Ala Ser Pro Gly Leu Ala Ser Asn Gly Leu Asn Leu Tyr Ser
        1955                1960                1965

Gly Leu Tyr Leu Tyr Ser Val Ala Leu Ala Leu Ala Ala Arg Gly Leu
    1970                1975                1980

Glu Val Ala Leu Ser Glu Arg Pro Arg Val Ala Leu Val Ala Leu Thr
1985                1990                1995                2000

Tyr Arg Ser Glu Arg Gly Leu Asn Ser Glu Arg Ser Glu Arg Ala Leu
                2005                2010                2015

Ala His Ile Ser Cys Tyr Ser Met Glu Thr Thr His Arg Pro His Glu
            2020                2025                2030

Thr Arg Pro Thr Tyr Arg His Ile Ser Met Glu Thr Ser Glu Arg Gly
        2035                2040                2045

Leu Tyr Ser Glu Arg His Ile Ser Val Ala Leu Gly Leu Tyr Thr His
    2050                2055                2060

Arg Leu Glu Ala Arg Gly Val Ala Leu Leu Tyr Ser Leu Glu His Ile
2065                2070                2075                2080

Ser Thr Tyr Arg Gly Leu Asn Leu Tyr Ser Pro Arg Gly Leu Gly Leu
                2085                2090                2095

Thr Tyr Arg Ala Ser Pro Gly Leu Asn Leu Glu Val Ala Leu Thr Arg
            2100                2105                2110

Pro Met Glu Thr Val Ala Leu Val Ala Leu Gly Leu Tyr His Ile Ser
        2115                2120                2125

Gly Leu Asn Gly Leu Tyr Ala Ser Pro His Ile Ser Thr Arg Pro Leu
    2130                2135                2140

Tyr Ser Gly Leu Gly Leu Tyr Ala Arg Gly Val Ala Leu Leu Glu Leu
2145                2150                2155                2160

Glu His Ile Ser Leu Tyr Ser Ser Glu Arg Leu Glu Leu Tyr Ser Leu
                2165                2170                2175

Glu Thr Tyr Arg Gly Leu Asn Val Ala Leu Ile Leu Glu Pro His Glu
            2180                2185                2190

Gly Leu Gly Leu Tyr Gly Leu Ile Leu Glu Gly Leu Tyr Leu Tyr Ser
        2195                2200                2205

Gly Leu Tyr Ala Ser Asn Leu Glu Gly Leu Tyr Gly Leu Tyr Ile Leu
    2210                2215                2220

Glu Ala Leu Ala Val Ala Leu Ala Ser Pro Ala Ser Pro Ile Leu Glu
2225                2230                2235                2240

Ser Glu Arg Ile Leu Glu Ala Ser Asn Ala Ser Asn His Ile Ser Ile
                2245                2250                2255

Leu Glu Pro Arg Gly Leu Asn Gly Leu Ala Ser Pro Cys Tyr Ser Ala
            2260                2265                2270
```

```
Leu Ala Leu Tyr Ser Pro Arg Thr His Arg Ala Ser Pro Leu Glu Ala
        2275                2280                2285

Ser Pro Leu Tyr Ser Leu Tyr Ser Ala Ser Asn Thr His Arg Gly Leu
        2290                2295                2300

Ile Leu Glu Leu Tyr Ser Ile Leu Glu Ala Ser Pro Gly Leu Thr His
2305                2310                2315                2320

Arg Gly Leu Tyr Ser Glu Arg Thr His Arg Pro Arg Gly Leu Tyr Thr
            2325                2330                2335

Tyr Arg Gly Leu Gly Leu Gly Leu Tyr Leu Tyr Ser Gly Leu Tyr Ala
            2340                2345                2350

Ser Pro Leu Tyr Ser Ala Ser Asn Ile Leu Glu Ser Glu Arg Ala Arg
        2355                2360                2365

Gly Leu Tyr Ser Pro Arg Gly Leu Tyr Ala Ser Asn Val Ala Leu Leu
        2370                2375                2380

Glu Leu Tyr Ser Thr His Arg Leu Glu Ala Ser Pro Pro Arg Ile Leu
2385                2390                2395                2400

Glu Leu Glu Ile Leu Glu Thr His Arg Ile Leu Glu Ile Leu Glu Ala
            2405                2410                2415

Leu Ala Met Glu Thr Ser Glu Arg Ala Leu Ala Leu Glu Gly Leu Tyr
            2420                2425                2430

Val Ala Leu Leu Glu Leu Glu Gly Leu Tyr Ala Leu Ala Val Ala Leu
        2435                2440                2445

Cys Tyr Ser Gly Leu Tyr Val Ala Leu Val Ala Leu Leu Glu Thr Tyr
        2450                2455                2460

Arg Cys Tyr Ser Ala Leu Ala Cys Tyr Ser Thr Arg Pro His Ile Ser
2465                2470                2475                2480

Ala Ser Asn Gly Leu Tyr Met Glu Thr Ser Glu Arg Gly Leu Ala Arg
            2485                2490                2495

Gly Ala Ser Asn Leu Glu Ser Glu Arg Ala Leu Ala Leu Glu Gly Leu
            2500                2505                2510

Ala Ser Asn Thr Tyr Arg Ala Ser Asn Pro His Glu Gly Leu Leu Glu
            2515                2520                2525

Val Ala Leu Ala Ser Pro Gly Leu Tyr Val Ala Leu Leu Tyr Ser Leu
        2530                2535                2540

Glu Leu Tyr Ser Leu Tyr Ser Ala Ser Pro Leu Tyr Ser Leu Glu Ala
2545                2550                2555                2560

Ser Asn Pro Arg His Ile Ser Ser Glu Arg Ala Ser Asn Thr Tyr Arg
            2565                2570                2575

Ser Glu Arg Gly Leu Ala Leu Ala
            2580

(2) INFORMATION FOR SEQ ID NO:5:

(i) SEQUENCE CHARACTERISTICS:
        (A) LENGTH: 3652 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:5:

TTTTTTTTTT TTTTTTTTTT TTTTTTTTTT TTTTTCCTCC TTCTTCTTCT TCCTGAGACA      60

TGGCCCGGGC AGTGGCTCCT GGAAGAGGAA CAAGTGTGGG AAAAGGGAGA GGAAATCGGA     120

GCTAAATGAC AGGATGCAGG CGACTTGAGA CACAAAAAGA GAAGCGCTTC TCGCGAATTC     180
```

-continued

```
AGGCATTGCC TCGCCGCTAG CCTTCCCCGC CAAGACCCGC TGAGGATTTT ATGGTTCTTA      240
GGCGGACTTA AGAGCGTTTC GGATTGTTAA GATTATCGTT TGCTGGTTTT TCGTCCGCGC      300
AATCGTGTTC TCCTGCGGCT GCCTGGGGAC TGGCTTGGCG AAGGAGGATG GAGAGGGGGC      360
TGCCGTTGCT GTGCGCCACG CTCGCCCTTG CCCTCGCCCT GGCGGCGCT TTCCGCAGCG       420
ACAAATGTGG CGGGACCATA AAAATCGAAA ACCCAGGGTA CCTCACATCT CCCGGTTACC      480
CTCATTCTTA CCATCCAAGT GAGAAGTGTG AATGGCTAAT CCAAGCTCCG GAACCCTACC     540
AGAGAATCAT AATCAACTTC AACCCACATT TCGATTTGGA GGACAGAGAC TGCAAGTATG      600
ACTACGTGGA AGTAATTGAT GGGGAGAATG AAGGCGGCCG CCTGTGGGGG AAGTTCTGTG      660
GGAAGATTGC ACCTTCTCCT GTGGTGTCTT CAGGGCCCTT TCTCTTCATC AAATTTGTCT      720
CTGACTATGA GACACATGGG GCAGGGTTTT CCATCCGCTA TGAAATCTTC AAGAGAGGGC      780
CCGAATGTTC TCAGAACTAT ACAGCACCTA CTGGAGTGAT AAAGTCCCCT GGGTTCCCTG      840
AAAAATACCC CAACTGCTTG GAGTGCACCT ACATCATCTT TGCACCAAAG ATGTCTGAGA      900
TAATCCTGGA GTTTGAAAGT TTTGACCTGG AGCAAGACTC GAATCCTCCC GGAGGAATGT      960
TCTGTCGCTA TGACCGGCTG GAGATCTGGG ATGGATTCCC TGAAGTTGGC CCTCACATTG     1020
GGCGTTATTG TGGGCAGAAA ACTCCTGGCC GGATCCGCTC CTCTTCAGGC GTTCTATCCA     1080
TGGTCTTTTA CACTGACAGC GCAATAGCAA AAGAAGGTTT CTCAGCCAAC TACAGTGTGC     1140
TACAGAGCAG CATCTCTGAA GATTTTAAGT GTATGGAGGC TCTGGGCATG GAATCTGGAG     1200
AGATCCATTC TGATCAGATC ACTGCATCTT CACAGTATGG TACCAACTGG TCTGTAGAGC     1260
GCTCCCGCCT GAACTACCCT GAAAATGGGT GGACTCCAGG AGAAGACTCC TACAAGGAGT     1320
GGATCCAGGT GGACTTGGGC CTCCTGCGAT TCGTTACTGC TGTAGGGACA CAGGGTGCCA     1380
TTTCCAAGGA AACCAAGAAG AAATATTATG TCAAGACTTA CAGAGTAGAC ATCAGCTCCA     1440
ACGGAGAGGA CTGGATCTCC CTGAAAGAGG GAAATAAAGC CATTATCTTT CAGGGAAACA     1500
CCAACCCCAC AGATGTTGTC TTAGGAGTTT TCTCCAAACC ACTGATAACT CGATTTGTCC     1560
GAATCAAACC TGTATCCTGG GAAACTGGTA TATCTATGAG ATTTGAAGTT TATGGCTGCA     1620
AGATAACAGA TTATCCTTGC TCTGGAATGT TGGGCATGGT GTCTGGACTT ATTTCAGACT     1680
CCCAGATTAC AGCATCCAAT CAAGCCGACA GGAATTGGAT GCCAGAAAAC ATCCGTCTGG     1740
TGACCAGTCG TACCGGCTGG GCACTGCCAC CCTCACCCCA CCCATACACC AATGAATGGC     1800
TCCAAGTGGA CCTGGGAGAT GAGAAGATAG TAAGAGGTGT CATCATTCAG GGTGGGAAGC     1860
ACCGAGAAAA CAAGGTGTTC ATGAGGAAGT TCAAGATCGC CTATAGTAAC AATGGCTCTG     1920
ACTGGAAAAC TATCATGGAT GACAGCAAGC GCAAGGCTAA GTCGTTCGAA GGCAACAACA     1980
ACTATGACAC ACCTGAGCTT CGGACGTTTT CACCTCTCTC CACAAGGTTC ATCAGGATCT     2040
ACCCTGAGAG AGCCACACAC AGTGGGCTTG GCTGAGGAT GGAGCTACTG GCTGTGAAG       2100
TGGAAGCACC TACAGCTGGA CCAACCACAC CCAATGGGAA CCCAGTGCAT GAGTGTGACG     2160
ACGACCAGGC CAACTGCCAC AGTGGCACAG GTGATGACTT CCAGCTCACA GGAGGCACCA     2220
CTGTCCTGGC CACAGAGAAG CCAACCATTA TAGACAGCAC CATCCAATCA GAGTTCCCGA     2280
CATACGGTTT TAACTGCGAG TTTGGCTGGG GCTCTCACAA GACATTCTGC CACTGGGAGC     2340
ATGACAGCCA TGCACAGCTC AGGTGGAGTG TGCTGACCAG CAAGCAGGG CCGATTCAGG      2400
ACCATACAGG AGATGGCAAC TTCATCTATT CCCAAGCTGA TGAAAATCAG AAAGGCAAAG     2460
TAGCCCGCCT GGTGAGCCCT GTGGTCTATT CCCAGAGCTC TGCCCACTGT ATGACCTTCT     2520
```

-continued

```
GGTATCACAT GTCCGGCTCT CATGTGGGTA CACTGAGGGT CAAACTACGC TACCAGAAGC    2580

CAGAGGAATA TGATCAACTG GTCTGGATGG TGGTTGGGCA CCAAGGAGAC CACTGGAAAG    2640

AAGGACGTGT CTTGCTGCAC AAATCTCTGA ACTATATCA GGTTATTTTT GAAGGTGAAA    2700

TCGGAAAAGG AAACCTTGGT GGAATTGCTG TGGATGATAT CAGTATTAAC AACCATATTT    2760

CTCAGGAAGA CTGTGCAAAA CCAACAGACC TAGATAAAAA GAACACAGAA ATTAAAATTG    2820

ATGAAACAGG GAGCACTCCA GGATATGAAG GAGAAGGGGA AGGTGACAAG AACATCTCCA    2880

GGAAGCCAGG CAATGTGCTT AAGACCCTGG ATCCCATCCT GATCACCATC ATAGCCATGA    2940

GTGCCCTGGG AGTACTCCTG GGTGCAGTCT GTGGAGTTGT GCTGTACTGT GCCTGTTGGC    3000

ACAATGGGAT GTCAGAAAGG AACCTATCTG CCCTGGAGAA CTATAACTTT GAACTTGTGG    3060

ATGGTGTAAA GTTGAAAAAA GATAAACTGA ACCCACAGAG TAATTACTCA GAGGCGTGAA    3120

GGCACGGAGC TGGAGGGAAC AAGGGAGGAG CACGGCAGGA GAACAGGTGG AGGCATGGGG    3180

ACTCTGTTAC TCTGCTTTCA CTGTAAGCTG GGAAGGGCGG GGACTCTGTT ACTCCGCTTT    3240

CACTGTAAGC TCGGAAGGGC ATCCACGATG CCATGCCAGG CTTTTCTCAG GAGCTTCAAT    3300

GAGCGTCACC TACAGACACA AGCAGGTGAC TGCGGTAACA ACAGGAATCA TGTACAAGCC    3360

TGCTTTCTTC TCTTGGTTTC ATTTGGGTAA TCAGAAGCCA TTTGAGACCA AGTGTGACTG    3420

ACTTCATGGT TCATCCTACT AGCCCCCTTT TTTCCTCTCT TTCTCCTTAC CCTGTGGTGG    3480

ATTCTTCTCG GAAACTGCAA AATCCAAGAT GCTGGCACTA GCCGTTATTC AGTGGGCCCT    3540

TTTGATGGAC ATGTGACCTG TAGCCCAGTG CCCAGAGCAT ATTATCATAA CCACATTTCA    3600

GGGGACGCCA ACGTCCATCC ACCTTTGCAT CGCTACCTGC AGCGAGCACA GG            3652
```

(2) INFORMATION FOR SEQ ID NO:6:

(i) SEQUENCE CHARACTERISTICS:
        (A) LENGTH: 923 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:6:

```
Met Glu Arg Gly Leu Pro Leu Leu Cys Ala Thr Leu Ala Leu Ala Leu
 1               5                  10                  15

Ala Leu Ala Gly Ala Phe Arg Ser Asp Lys Cys Gly Gly Thr Ile Lys
            20                  25                  30

Ile Glu Asn Pro Gly Tyr Leu Thr Ser Pro Gly Tyr Pro His Ser Tyr
        35                  40                  45

His Pro Ser Glu Lys Cys Glu Trp Leu Ile Gln Ala Pro Glu Pro Tyr
    50                  55                  60

Gln Arg Ile Ile Ile Asn Phe Asn Pro His Phe Asp Leu Glu Asp Arg
65                  70                  75                  80

Asp Cys Lys Tyr Asp Tyr Val Glu Val Ile Asp Gly Glu Asn Glu Gly
                85                  90                  95

Gly Arg Leu Trp Gly Lys Phe Cys Gly Lys Ile Ala Pro Ser Pro Val
            100                 105                 110

Val Ser Ser Gly Pro Phe Leu Phe Ile Lys Phe Val Ser Asp Tyr Glu
        115                 120                 125

Thr His Gly Ala Gly Phe Ser Ile Arg Tyr Glu Ile Phe Lys Arg Gly
    130                 135                 140
```

-continued

```
Pro Glu Cys Ser Gln Asn Tyr Thr Ala Pro Thr Gly Val Ile Lys Ser
145                 150                 155                 160

Pro Gly Phe Pro Glu Lys Tyr Pro Asn Cys Leu Glu Cys Thr Tyr Ile
            165                 170                 175

Ile Phe Ala Pro Lys Met Ser Glu Ile Ile Leu Glu Phe Glu Ser Phe
            180                 185                 190

Asp Leu Glu Gln Asp Ser Asn Pro Pro Gly Gly Met Phe Cys Arg Tyr
            195                 200                 205

Asp Arg Leu Glu Ile Trp Asp Gly Phe Pro Glu Val Gly Pro His Ile
210                 215                 220

Gly Arg Tyr Cys Gly Gln Lys Thr Pro Gly Arg Ile Arg Ser Ser Ser
225                 230                 235                 240

Gly Val Leu Ser Met Val Phe Tyr Thr Asp Ser Ala Ile Ala Lys Glu
                245                 250                 255

Gly Phe Ser Ala Asn Tyr Ser Val Leu Gln Ser Ser Ile Ser Glu Asp
                260                 265                 270

Phe Lys Cys Met Glu Ala Leu Gly Met Glu Ser Gly Glu Ile His Ser
            275                 280                 285

Asp Gln Ile Thr Ala Ser Ser Gln Tyr Gly Thr Asn Trp Ser Val Glu
290                 295                 300

Arg Ser Arg Leu Asn Tyr Pro Glu Asn Gly Trp Thr Pro Gly Glu Asp
305                 310                 315                 320

Ser Tyr Lys Glu Trp Ile Gln Val Asp Leu Gly Leu Leu Arg Phe Val
                325                 330                 335

Thr Ala Val Gly Thr Gln Gly Ala Ile Ser Lys Glu Thr Lys Lys Lys
                340                 345                 350

Tyr Tyr Val Lys Thr Tyr Arg Val Asp Ile Ser Ser Asn Gly Glu Asp
                355                 360                 365

Trp Ile Ser Leu Lys Glu Gly Asn Lys Ala Ile Ile Phe Gln Gly Asn
370                 375                 380

Thr Asn Pro Thr Asp Val Val Leu Gly Val Phe Ser Lys Pro Leu Ile
385                 390                 395                 400

Thr Arg Phe Val Arg Ile Lys Pro Val Ser Trp Glu Thr Gly Ile Ser
                405                 410                 415

Met Arg Phe Glu Val Tyr Gly Cys Lys Ile Thr Asp Tyr Pro Cys Ser
            420                 425                 430

Gly Met Leu Gly Met Val Ser Gly Leu Ile Ser Asp Ser Gln Ile Thr
            435                 440                 445

Ala Ser Asn Gln Ala Asp Arg Asn Trp Met Pro Glu Asn Ile Arg Leu
450                 455                 460

Val Thr Ser Arg Thr Gly Trp Ala Leu Pro Pro Ser Pro His Pro Tyr
465                 470                 475                 480

Thr Asn Glu Trp Leu Gln Val Asp Leu Gly Asp Glu Lys Ile Val Arg
                485                 490                 495

Gly Val Ile Ile Gln Gly Gly Lys His Arg Glu Asn Lys Val Phe Met
                500                 505                 510

Arg Lys Phe Lys Ile Ala Tyr Ser Asn Asn Gly Ser Asp Trp Lys Thr
            515                 520                 525

Ile Met Asp Asp Ser Lys Arg Lys Ala Lys Ser Phe Glu Gly Asn Asn
            530                 535                 540

Asn Tyr Asp Thr Pro Glu Leu Arg Thr Phe Ser Pro Leu Ser Thr Arg
545                 550                 555                 560
```

```
Phe Ile Arg Ile Tyr Pro Glu Arg Ala Thr His Ser Gly Leu Gly Leu
                565                 570                 575

Arg Met Glu Leu Leu Gly Cys Glu Val Glu Ala Pro Thr Ala Gly Pro
            580                 585                 590

Thr Thr Pro Asn Gly Asn Pro Val His Glu Cys Asp Asp Gln Ala
        595                 600                 605

Asn Cys His Ser Gly Thr Gly Asp Asp Phe Gln Leu Thr Gly Gly Thr
    610                 615                 620

Thr Val Leu Ala Thr Glu Lys Pro Thr Ile Ile Asp Ser Thr Ile Gln
625                 630                 635                 640

Ser Glu Phe Pro Thr Tyr Gly Phe Asn Cys Glu Phe Gly Trp Gly Ser
                645                 650                 655

His Lys Thr Phe Cys His Trp Glu His Asp Ser His Ala Gln Leu Arg
                660                 665                 670

Trp Ser Val Leu Thr Ser Lys Thr Gly Pro Ile Gln Asp His Thr Gly
            675                 680                 685

Asp Gly Asn Phe Ile Tyr Ser Gln Ala Asp Glu Asn Gln Lys Gly Lys
        690                 695                 700

Val Ala Arg Leu Val Ser Pro Val Val Tyr Ser Gln Ser Ser Ala His
705                 710                 715                 720

Cys Met Thr Phe Trp Tyr His Met Ser Gly Ser His Val Gly Thr Leu
                725                 730                 735

Arg Val Lys Leu Arg Tyr Gln Lys Pro Glu Glu Tyr Asp Gln Leu Val
            740                 745                 750

Trp Met Val Val Gly His Gln Gly Asp His Trp Lys Glu Gly Arg Val
        755                 760                 765

Leu Leu His Lys Ser Leu Lys Leu Tyr Gln Val Ile Phe Glu Gly Glu
        770                 775                 780

Ile Gly Lys Gly Asn Leu Gly Gly Ile Ala Val Asp Asp Ile Ser Ile
785                 790                 795                 800

Asn Asn His Ile Ser Gln Glu Asp Cys Ala Lys Pro Thr Asp Leu Asp
                805                 810                 815

Lys Lys Asn Thr Glu Ile Lys Ile Asp Glu Thr Gly Ser Thr Pro Gly
            820                 825                 830

Tyr Glu Gly Glu Gly Glu Asp Lys Asn Ile Ser Arg Lys Pro Gly
        835                 840                 845

Asn Val Leu Lys Thr Leu Asp Pro Ile Leu Ile Thr Ile Ala Met
850                 855                 860

Ser Ala Leu Gly Val Leu Leu Gly Ala Val Cys Gly Val Val Leu Tyr
865                 870                 875                 880

Cys Ala Cys Trp His Asn Gly Met Ser Glu Arg Asn Leu Ser Ala Leu
                885                 890                 895

Glu Asn Tyr Asn Phe Glu Leu Val Asp Gly Val Lys Leu Lys Lys Asp
            900                 905                 910

Lys Leu Asn Pro Gln Ser Asn Tyr Ser Glu Ala
        915                 920

(2) INFORMATION FOR SEQ ID NO:7:

(i) SEQUENCE CHARACTERISTICS:
        (A) LENGTH: 3539 base pairs
        (B) TYPE: nucleic acid
        (C) STRANDEDNESS: single
        (D) TOPOLOGY: linear
```

(ii) MOLECULE TYPE: cDNA (xi) SEQUENCE DESCRIPTION: SEQ ID NO:7:

```
AAACTGGAGC TCCACCGCGG TGGCGGCCGC CCGGGCAGGT CTAGAATTCA GCGGCCGCTG      60
AATTCTATCC AGCGGTCGGT GCCTCTGCCC GCGTGTGTGT CCCGGGTGCC GGGGGACCTG     120
TGTCAGTTAG CGCTTCTGAG ATCACACAGC TGCCTAGGGG CCGTGTGATG CCCAGGGCAA     180
TTCTTGGCTT TGATTTTTAT TATTATTACT ATTATTTTGC GTTCAGCTTT CGGGAAACCC     240
TCGTGATGTT GTAGGATAAA GGAAATGACA CTTTGAGGAA CTGGAGAGAA CATACACGCG     300
TTTGGGTTTG AAGAGGAAAC CGGTCTCCGC TTCCTTAGCT TGCTCCCTCT TTGCTGATTT     360
CAAGAGCTAT CTCCTATGAG GTGGAGATAT CCAGCAAGA  ATAAAGGTGA AGACAGACTG     420
ACTGCCAGGA CCCAGGAGGA AAACGTTGAT CGTTAGAGAC CTTTGCAGAA GACACCACCA     480
GGAGGAAAAT TAGAGAGGAA AAACACAAAG ACATAATTAT ATGGAGATCC CACAAACTTA     540
GCCCGGGAGA GAGCTTCTCT GTCAAAAATG GATATGTTTC CTCTTACCTG GGTTTTCTTA     600
GCTCTGTACT TTTCAGGACA CGAAGTGAGA AGCCAGCAAG ATCCACCTTG CGGAGGTCGG     660
CCGAATTCCA AGGATGCTGG CTACATCACT TCCCCAGGCT ACCCCAGGA  CTATCCCTCC     720
CACCAGAACT GTGAGTGGAT TGTCTACGCC CCCGAACCCA ACCAGAAGAT TGTTCTCAAC     780
TTCAACCCTC ACTTTGAAAT CGAGAAACAC GACTGCAAGT ATGACTTCAT TGAGATTCGG     840
GATGGGGACA GTGAGTCAGC TGACCTCCTG GGCAAGCACT GTGGGAACAT CGCCCCGCCC     900
ACCATCATCT CCTCAGGCTC CGTGTTATAC ATCAAGTTCA CCTCAGACTA CGCCCGGCAG     960
GGGGCAGGTT TCTCTCTACG CTATGAGATC TTCAAAACAG GCTCTGAAGA TTGTTCCAAG    1020
AACTTTACAA GCCCCAATGG GACCATTGAA TCTCCAGGGT TTCAGAGAA  GTATCCACAC    1080
AATCTGGACT GTACCTTCAC CATCCTGGCC AAACCCAGGA TGGAGATCAT CCTACAGTTC    1140
CTGACCTTTG ACCTGGAGCA TGACCCTCTA CAAGTGGGGG AAGGAGACTG TAAATATGAC    1200
TGGCTGGACA TCTGGGATGG CATTCCACAT GTTGGACCTC TGATTGGCAA GTACTGTGGG    1260
ACGAAAACAC CCTCCAAACT CCGCTCGTCC ACGGGGATCC TCTCCTTGAC CTTTCACACG    1320
GACATGGCAG TGGCCAAGGA TGGCTTCTCC GCACGTTACT ATTTGATCCA CCAGGAGCCA    1380
CCTGAGAATT TCAGTGCAA  TGTCCCTTTG GGAATGGAGT CTGGCCGGAT TGCTAATGAA    1440
CAGATCAGTG CCTCCTCCAC CTTCTCTGAT GGGAGGTGGA CTCCTCAACA GAGCCGGCTC    1500
CATGGTGATG ACAATGGCTG GACACCCAAT TTGGATTCCA ACAAGGAGTA TCTCCAGGTG    1560
GACCTGCGCT TCCTAACCAT GCTCACAGCC ATTGCAACAC AGGGAGCCAT TCCAGGGAA     1620
ACCCAGAAAG GCTACTACGT CAAATCGTAC AAGCTGGAAG TCAGCACAAA TGGTGAAGAT    1680
TGGATGGTCT ACCGGCATGG CAAAAACCAC AAGATATTCC AAGCGAACAA TGATGCGACC    1740
GAGGTGGTGC TAAACAAGCT CCACATGCCA CTGCTGACTC GGTTCATCAG GATCCGCCCG    1800
CAGACGTGGC ATTTGGGCAT TGCCCTTCGC CTGGAGCTCT TTGGCTGCCG GGTCACAGAT    1860
GCACCCTGCT CCAACATGCT GGGGATGCTC TCGGGCCTCA TTGCTGATAC CCAGATCTCT    1920
GCCTCCTCCA CCCGAGAGTA CCTCTGGAGC CCCAGTGCTG CCCGCCTGGT TAGTAGCCGC    1980
TCTGGCTGGT TTCCTCGGAA CCCTCAAGCC CAGCCAGGTG AAGAATGGCT TCAGGTTGAC    2040
CTGGGGACAC CCAAGACAGT GAAAGGGGTC ATCATCCAGG GAGCCCGAGG AGGAGACAGC    2100
ATCACTGCCG TGGAAGCCAG GGCGTTTGTA CGCAAGTTCA AAGTCTCCTA CAGCCTAAAT    2160
GGCAAGGACT GGGAATATAT CCAGGACCCC AGGACTCAGC AGACAAAGCT GTTTGAAGGG    2220
```

-continued

```
AACATGCACT ATGACACCCC TGACATCCGA AGGTTCGATC CTGTTCCAGC GCAGTATGTG    2280

CGGGTGTACC CAGAGAGGTG GTCGCCAGCA GGCATCGGGA TGAGGCTGGA GGTGCTGGGC    2340

TGTGACTGGA CAGACTCAAA GCCCACAGTG GAGACGCTGG GACCCACCGT GAAGAGTGAA    2400

GAGACTACCA CCCCATATCC CATGGATGAG GATGCCACCG AGTGTGGGGA AAACTGCAGC    2460

TTTGAGGATG ACAAAGATTT GCAACTTCCT TCAGGATTCA ACTGCAACTT TGATTTTCCG    2520

GAAGAGACCT GTGGTTGGGT GTACGACCAT GCCAAGTGGC TCCGGAGCAC GTGGATCAGC    2580

AGCGCTAACC CCAATGACAG AACATTTCCA GATGACAAGA ACTTCTTGAA ACTGCAGAGT    2640

GATGGCCGAC GAGAGGGCCA GTACGGGCGG CTCATCAGCC CACCGGTGCA CCTGCCCCGA    2700

AGCCCTGTGT GCATGGAGTT CCAGTACCAA GCCATGGGCG GCCACGGGGT GGCACTGCAG    2760

GTGGTTCGGG AAGCCAGCCA GGAAAGCAAA CTCCTTTGGG TCATCCGTGA GGACCAGGGC    2820

AGCGAGTGGA AGCACGGGCG CATTATCCTG CCCAGCTATG ACATGGAGTA TCAGATCGTG    2880

TTCGAGGGAG TGATAGGGAA GGGACGATCG GGAGAGATTT CCATCGATGA CATTCGGATA    2940

AGCACTGATG TCCCACTGGA GAACTGCATG GAACCCATAT CAGCTTTTGC AGATGAATAT    3000

GAAGGAGATT GGAGCAACTC TTCTTCCTCT ACCTCAGGGG CTGGTGACCC CTCATCTGGC    3060

AAAGAAAAGA GCTGGCTGTA CACCCTAGAT CCCATTCTGA TCACCATCAT CGCCATGAGC    3120

TCGCTGGGGG TCCTGCTGGG GGCCACCTGT GCGGGCCTCC TCCTTTACTG CACCTGCTCC    3180

TATTCGGGTC TGAGTTCGAG GAGCTGCACC ACACTGGAGA ACTACAACTT TGAGCTCTAC    3240

GATGGCCTCA AGCACAAGGT CAAGATCAAT CATCAGAAGT GCTGCTCGGA GGCATGACCG    3300

ATTGTGTCTG GATCGCTTCT GGCGTTTCAT TCCAGTGAGA GGGGCTAGCG AAGATTACAG    3360

TTTTGTTTTG TTTTGTTTTG TTTTCCCTTT GGAAACTGAA TGCCATAATC TGGATCAAAG    3420

TGTTCCAGAA TACTGAAGGT ATGGACAGGA CAGACAGGCC AGTCTAGGGA GAAAGGGAGA    3480

TGCAGCTGTG AAGGGGATCG TTGCCCACCA GGACTGTGGT GGCCAAGTGA ATGCAGGAA     3539
```

(2) INFORMATION FOR SEQ ID NO:8:

(i) SEQUENCE CHARACTERISTICS:
        (A) LENGTH: 909 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:8:

```
Met Asp Met Phe Pro Leu Thr Trp Val Phe Leu Ala Leu Tyr Phe Ser
1               5                   10                  15

Gly His Glu Val Arg Ser Gln Gln Asp Pro Pro Cys Gly Gly Arg Pro
            20                  25                  30

Asn Ser Lys Asp Ala Gly Tyr Ile Thr Ser Pro Gly Tyr Pro Gln Asp
        35                  40                  45

Tyr Pro Ser His Gln Asn Cys Glu Trp Ile Val Tyr Ala Pro Glu Pro
    50                  55                  60

Asn Gln Lys Ile Val Leu Asn Phe Asn Pro His Phe Glu Ile Glu Lys
65                  70                  75                  80

His Asp Cys Lys Tyr Asp Phe Ile Glu Ile Arg Asp Gly Asp Ser Glu
                85                  90                  95

Ser Ala Asp Leu Leu Gly Lys His Cys Gly Asn Ile Ala Pro Pro Thr
            100                 105                 110
```

-continued

```
Ile Ile Ser Ser Gly Ser Val Leu Tyr Ile Lys Phe Thr Ser Asp Tyr
        115                 120                 125

Ala Arg Gln Gly Ala Gly Phe Ser Leu Arg Tyr Glu Ile Phe Lys Thr
130                 135                 140

Gly Ser Glu Asp Cys Ser Lys Asn Phe Thr Ser Pro Asn Gly Thr Ile
145                 150                 155                 160

Glu Ser Pro Gly Phe Pro Glu Lys Tyr Pro His Asn Leu Asp Cys Thr
                165                 170                 175

Phe Thr Ile Leu Ala Lys Pro Arg Met Glu Ile Ile Leu Gln Phe Leu
            180                 185                 190

Thr Phe Asp Leu Glu His Asp Pro Leu Gln Val Gly Glu Gly Asp Cys
        195                 200                 205

Lys Tyr Asp Trp Leu Asp Ile Trp Asp Gly Ile Pro His Val Gly Pro
210                 215                 220

Leu Ile Gly Lys Tyr Cys Gly Thr Lys Thr Pro Ser Lys Leu Arg Ser
225                 230                 235                 240

Ser Thr Gly Ile Leu Ser Leu Thr Phe His Thr Asp Met Ala Val Ala
                245                 250                 255

Lys Asp Gly Phe Ser Ala Arg Tyr Tyr Leu Ile His Gln Glu Pro Pro
            260                 265                 270

Glu Asn Phe Gln Cys Asn Val Pro Leu Gly Met Glu Ser Gly Arg Ile
        275                 280                 285

Ala Asn Glu Gln Ile Ser Ala Ser Ser Thr Phe Ser Asp Gly Arg Trp
290                 295                 300

Thr Pro Gln Gln Ser Arg Leu His Gly Asp Asp Asn Gly Trp Thr Pro
305                 310                 315                 320

Asn Leu Asp Ser Asn Lys Glu Tyr Leu Gln Val Asp Leu Arg Phe Leu
                325                 330                 335

Thr Met Leu Thr Ala Ile Ala Thr Gln Gly Ala Ile Ser Arg Glu Thr
            340                 345                 350

Gln Lys Gly Tyr Tyr Val Lys Ser Tyr Lys Leu Glu Val Ser Thr Asn
        355                 360                 365

Gly Glu Asp Trp Met Val Tyr Arg His Gly Lys Asn His Lys Ile Phe
370                 375                 380

Gln Ala Asn Asn Asp Ala Thr Glu Val Val Leu Asn Lys Leu His Met
385                 390                 395                 400

Pro Leu Leu Thr Arg Phe Ile Arg Ile Arg Pro Gln Thr Trp His Leu
                405                 410                 415

Gly Ile Ala Leu Arg Leu Glu Leu Phe Gly Cys Arg Val Thr Asp Ala
            420                 425                 430

Pro Cys Ser Asn Met Leu Gly Met Leu Ser Gly Leu Ile Ala Asp Thr
        435                 440                 445

Gln Ile Ser Ala Ser Ser Thr Arg Glu Tyr Leu Trp Ser Pro Ser Ala
450                 455                 460

Ala Arg Leu Val Ser Ser Arg Ser Gly Trp Phe Pro Arg Asn Pro Gln
465                 470                 475                 480

Ala Gln Pro Gly Glu Glu Trp Leu Gln Val Asp Leu Gly Thr Pro Lys
                485                 490                 495

Thr Val Lys Gly Val Ile Ile Gln Gly Ala Arg Gly Gly Asp Ser Ile
            500                 505                 510

Thr Ala Val Glu Ala Arg Ala Phe Val Arg Lys Phe Lys Val Ser Tyr
        515                 520                 525
```

```
Ser Leu Asn Gly Lys Asp Trp Glu Tyr Ile Gln Asp Pro Arg Thr Gln
        530                 535                 540
Gln Thr Lys Leu Phe Glu Gly Asn Met His Tyr Asp Thr Pro Asp Ile
545                 550                 555                 560
Arg Arg Phe Asp Pro Val Pro Ala Gln Tyr Val Arg Val Tyr Pro Glu
                565                 570                 575
Arg Trp Ser Pro Ala Gly Ile Gly Met Arg Leu Glu Val Leu Gly Cys
            580                 585                 590
Asp Trp Thr Asp Ser Lys Pro Thr Val Glu Thr Leu Gly Pro Thr Val
            595                 600                 605
Lys Ser Glu Glu Thr Thr Thr Pro Tyr Pro Met Asp Glu Asp Ala Thr
        610                 615                 620
Glu Cys Gly Glu Asn Cys Ser Phe Glu Asp Asp Lys Asp Leu Gln Leu
625                 630                 635                 640
Pro Ser Gly Phe Asn Cys Asn Phe Asp Phe Pro Glu Glu Thr Cys Gly
                645                 650                 655
Trp Val Tyr Asp His Ala Lys Trp Leu Arg Ser Thr Trp Ile Ser Ser
            660                 665                 670
Ala Asn Pro Asn Asp Arg Thr Phe Pro Asp Asp Lys Asn Phe Leu Lys
        675                 680                 685
Leu Gln Ser Asp Gly Arg Arg Glu Gly Gln Tyr Gly Arg Leu Ile Ser
        690                 695                 700
Pro Pro Val His Leu Pro Arg Ser Pro Val Cys Met Glu Phe Gln Tyr
705                 710                 715                 720
Gln Ala Met Gly Gly His Gly Val Ala Leu Gln Val Val Arg Glu Ala
                725                 730                 735
Ser Gln Glu Ser Lys Leu Leu Trp Val Ile Arg Glu Asp Gln Gly Ser
            740                 745                 750
Glu Trp Lys His Gly Arg Ile Ile Leu Pro Ser Tyr Asp Met Glu Tyr
            755                 760                 765
Gln Ile Val Phe Glu Gly Val Ile Gly Lys Gly Arg Ser Gly Glu Ile
770                 775                 780
Ser Ile Asp Asp Ile Arg Ile Ser Thr Asp Val Pro Leu Glu Asn Cys
785                 790                 795                 800
Met Glu Pro Ile Ser Ala Phe Ala Asp Glu Tyr Glu Gly Asp Trp Ser
                805                 810                 815
Asn Ser Ser Ser Ser Thr Ser Gly Ala Gly Asp Pro Ser Ser Gly Lys
                820                 825                 830
Glu Lys Ser Trp Leu Tyr Thr Leu Asp Pro Ile Leu Ile Thr Ile Ile
            835                 840                 845
Ala Met Ser Ser Leu Gly Val Leu Leu Gly Ala Thr Cys Ala Gly Leu
        850                 855                 860
Leu Leu Tyr Cys Thr Cys Ser Tyr Ser Gly Leu Ser Ser Arg Ser Cys
865                 870                 875                 880
Thr Thr Leu Glu Asn Tyr Asn Phe Glu Leu Tyr Asp Gly Leu Lys His
                885                 890                 895
Lys Val Lys Ile Asn His Gln Lys Cys Cys Ser Glu Ala
                900                 905
```

(2) INFORMATION FOR SEQ ID NO:9:

(i) SEQUENCE CHARACTERISTICS:
       (A) LENGTH: 4718 base pairs
       (B) TYPE: nucleic acid (C) STRANDEDNESS: double
    (D) TOPOLOGY: linear (ii) MOLECULE TYPE: cDNA (xi) SEQUENCE DESCRIPTION: SEQ ID NO:9:

```
AAACTGGAGC TCCACCGCGG TGGCGGCCGC CCGGGCAGGT CTAGAATTCA GCGGCCGCTG      60

AATTCTATCC AGCGGTCGGT GCCTCTGCCC GCGTGTGTGT CCCGGGTGCC GGGGGACCTG     120

TGTCAGTTAG CGCTTCTGAG ATCACACAGC TGCCTAGGGG CCGTGTGATG CCCAGGGCAA     180

TTCTTGGCTT TGATTTTTAT TATTATTACT ATTATTTTGC GTTCAGCTTT CGGGAAACCC     240

TCGTGATGTT GTAGGATAAA GGAAATGACA CTTTGAGGAA CTGGAGAGAA CATACACGCG     300

TTTGGGTTTG AAGAGGAAAC CGGTCTCCGC TTCCTTAGCT TGCTCCCTCT TTGCTGATTT     360

CAAGAGCTAT CTCCTATGAG GTGGAGATAT TCCAGCAAGA ATAAAGGTGA AGACAGACTG     420

ACTGCCAGGA CCCAGGAGGA AAACGTTGAT CGTTAGAGAC CTTTGCAGAA GACACCACCA     480

GGAGGAAAAT TAGAGAGGAA AAACACAAAG ACATAATTAT AGGAGATCCC ACAAACCTAG     540

CCCGGGAGAG AGCCTCTCTG TCAAAAATGG ATATGTTTCC TCTTACCTGG GTTTTCTTAG     600

CTCTGTACTT TTCAGGACAC GAAGTGAGAA GCCAGCAAGA TCCACCCTGC GGAGGTCGGC     660

CGAATTCCAA AGATGCTGGC TACATCACTT CCCCAGGCTA CCCCCAGGAC TATCCCTCCC     720

ACCAGAACTG TGAGTGGATT GTCTACGCCC CCGAACCCAA CCAGAAGATT GTTCTCAACT     780

TCAACCCTCA CTTTGAAATC GAGAAACACG ACTGCAAGTA TGACTTCATT GAGATTCGGG     840

ATGGGACAG TGAGTCAGCT GACCTCCTGG GCAAGCACTG TGGGAACATC GCCCCGCCCA     900

CCATCATCTC CTCAGGCTCC GTGTTATACA TCAAGTTCAC CTCAGACTAC GCCCGGCAGG     960

GGGCAGGTTT CTCTCTACGC TATGAGATCT TCAAAACAGG CTCTGAAGAT TGTTCCAAGA    1020

ACTTTACAAG CCCCAATGGG ACCATTGAAT CTCCAGGGTT TCCAGAGAAG TATCCACACA    1080

ATCTGGACTG TACCTTCACC ATCCTGGCCA AACCCAGGAT GGAGATCATC CTACAGTTCC    1140

TGACCTTTGA CCTGGAGCAT GACCCTCTAC AAGTGGGGGA AGGAGACTGT AAATATGACT    1200

GGCTGGACAT CTGGGATGGC ATTCCACATG TTGGACCTCT GATTGGCAAG TACTGTGGGA    1260

CGAAAACACC CTCCAAACTC CGCTCGTCCA CGGGGATCCT CTCCTTGACC TTTCACACGG    1320

ACATGGCAGT GGCCAAGGAT GGCTTCTCCG CACGTTACTA TTTGATCCAC CAGGAGCCAC    1380

CTGAGAATTT TCAGTGCAAT GTCCCTTTGG GAATGGAGTC TGGCCGGATT GCTAATGAAC    1440

AGATCAGTGC CTCCTCCACC TTCTCTGATG GGAGGTGGAC TCCTCAACAG AGCCGGCTCC    1500

ATGGTGATGA CAATGGCTGG ACACCCAATT TGGATTCCAA CAAGGAGTAT CTCCAGGTGG    1560

ACCTGCGCTT CCTAACCATG CTCACAGCCA TTGCAACACA GGGAGCCATT TCCAGGGAAA    1620

CCCAGAAAGG CTACTACGTC AAATCGTACA AGCTGGAAGT CAGCACAAAT GGTGAAGATT    1680

GGATGGTCTA CCGGCATGGC AAAAACCACA AGATATTCCA AGCGAACAAT GATGCGACCG    1740

AGGTGGTGCT AAACAAGCTC CACATGCCAC TGCTGACTCG GTTCATCAGG ATCCGCCCGC    1800

AGACGTGGCA TTTGGGCATT GCCCTTCGCC TGGAGCTCTT TGGCTGCCGG GTCACAGATG    1860

CACCCTGCTC CAACATGCTG GGGATGCTCT CGGGCCTCAT TGCTGATACC CAGATCTCTG    1920

CCTCCTCCAC CCGAGAGTAC CTCTGGAGCC CCAGTGCTGC CCGCCTGGTT AGTAGCCGCT    1980

CTGGCTGGTT TCCTCGGAAC CCTCAAGCCC AGCCAGGTGA AGAATGGCTT CAGGTAGACC    2040

TGGGGACACC CAAGACAGTG AAAGGGGTCA TCATCCAGGG AGCCCGAGGA GGAGACAGCA    2100

TCACTGCCGT GGAAGCCAGG GCGTTTGTAC GCAAGTTCAA AGTCTCCTAC AGCCTAAATG    2160
```

-continued

```
GCAAGGACTG GGAATATATC CAGGACCCCA GGACTCAGCA GACAAAGCTG TTTGAAGGGA    2220

ACATGCACTA TGACACCCCT GACATCCGAA GGTTCGATCC TGTTCCAGCG CAGTATGTGC    2280

GGGTGTACCC AGAGAGGTGG TCGCCAGCAG GCATCGGGAT GAGGCTGGAG GTGCTGGGCT    2340

GTGACTGGAC AGACTCAAAG CCCACAGTGG AGACGCTGGG ACCCACCGTG AAGAGTGAAG    2400

AGACTACCAC CCCATATCCC ATGGATGAGG ATGCCACCGA GTGTGGGAA AACTGCAGCT     2460

TTGAGGATGA CAAAGATTTG CAACTTCCTT CAGGATTCAA CTGCAACTTT GATTTTCCGG    2520

AAGAGACCTG TGGTTGGGTG TACGACCATG CCAAGTGGCT CCGGAGCACG TGGATCAGCA    2580

GCGCTAACCC CAATGACAGA ACATTTCCAG ATGACAAGAA CTTCTTGAAA CTGCAGAGTG    2640

ATGGCCGACG AGAGGGCCAG TACGGGCGGC TCATCAGCCC ACCGGTGCAC CTGCCCCGAA    2700

GCCCTGTGTG CATGGAGTTC CAGTACCAAG CCATGGGCGG CCACGGGGTG GCACTGCAGG    2760

TGGTTCGGGA AGCCAGCCAG GAAAGCAAAC TCCTTTGGGT CATCCGTGAG GACCAGGGCA    2820

GCGAGTGGAA GCACGGGCGC ATTATCCTGC CCAGCTATGA CATGGAGTAT CAGATCGTGT    2880

TCGAGGGAGT GATAGGGAAG GGACGATCGG GAGAGATTTC CGGCGATGAC ATTCGGATAA    2940

GCACTGATGT CCCACTGGAG AACTGCATGG AACCCATATC AGCTTTTGCA GATGAATATG    3000

AAGGAGATTG GAGCAACTCT TCTTCCTCTA CCTCAGGGGC TGGTGACCCC TCATCTGGCA    3060

AAGAAAAGAG CTGGCTGTAC ACCCTAGATC CCATTCTGAT CACCATCATC GCCATGAGCT    3120

CGCTGGGGGT CCTGCTGGGG GCCACCTGTG CGGGCCTCCT CCTTTACTGC ACCTGCTCCT    3180

ATTCGGGTCT GAGTTCGAGG AGCTGCACCA CACTGGAGAA CTACAACTTT GAGCTCTACG    3240

ATGGCCTCAA GCACAAGGTC AAGATCAATC ATCAGAAGTG CTGCTCGGAG GCATGACCGA    3300

TTGTGTCTGG ATCGCTTCTG GCGTTTCATT CCAGTGAGAG GGGCTAGCGA AGATTACAGT    3360

TTTGTTTTGT TTTGTTTTGT TTTCCCTTTG GAAACTGAAT GCCATAATCT GGATCAAAGT    3420

GTTCCAGAAT ACTGAAGGTA TGGACAGGAC AGACAGGCCA GTCTAGGGAG AAAGGGAGAT    3480

GCAGCTGTGA AGGGGATCGT TGCCCACCAG GACTGTGGTG GCCAAGTGAA TGCAGGAACC    3540

GGGCCCGGAA TTCCGGCTCT CGGCTAAAAT CTCAGCTGCC TCTGGAAAGG CTCAACCATA    3600

CTCAGTGCCA ACTCAGACTC TGTTGCTGTG GTGTCAACAT GGATGGATCA TCTGTACCTT    3660

GTATTTTTAG CAGAATTCAT GCTCAGATTT CTTTGTTCTG AATCCTTGCT TTGTGCTAGA    3720

CACAAAGCAT ACATGTCCTT CTAAAATTAA TATGATCACT ATAATCTCCT GTGTGCAGAA    3780

TTCAGAAATA GACCTTTGAA ACCATTTGCA TTGTGAGTGC AGATCCATGA CTGGGCTAG    3840

TGCAGCAATG AAACAGAATT CCAGAAACAG TGTGTTCTTT TTATTATGGG AAAATACAGA    3900

TAAAAATGGC CACTGATGAA CATGAAAGTT AGCACTTTCC CAACACAGTG TACACTTGCA    3960

ACCTTGTTTT GGATTTCTCA TACACCAAGA CTGTGAAACA CAAATTTCAA GAATGTGTTC    4020

AAATGTGTGT GTGTGTGTGT GTGTGTGTGT GTGTGTGTGT GTATGTGTGT GTGTGTGTGT    4080

GTGCTTGTGT GTTTCTGTCA GTGGTATGAG TGATATGTAT GCATGTGTGT ATGTATATGT    4140

ATGTATGTAT GTATGTATGT ACGTACATAT GTATGTATGT ATGTATGTAT GTATGTATGT    4200

ATATGTGTGT GTGTGTTTGT GTGTGTGTGT GTTTGTGTGT GTGTGTGTGG TAAGTGTGGT    4260

ATGTGTGTAT GCATTTGTCT ATATGTGTAT CTGTGTGTCT ATGTGTTTCT GTCAGTGGAA    4320

TGAGTGGCAT GTGTGCATGT GTATGTATGT GGATATGTGT GTTGTGTTTA TGTGCTTGTG    4380

TATAAGAGGT AAGTGTGGTG TGTGTGCATG TGTCTCTGTG TGTGTTTGTC TGTGTACCTC    4440

TTTGTATAAG TACCTGTGTT TGTATGTGGG AATATGTATA TTGAGGCATT GCTGTGTTAG    4500
```

```
TATGTTTATA GAAAAGAAGA CAGTCTGAGA TGTCTTCCTC AATACCTCTC CACTTATATC        4560

TTGGATAGAC AAAAGTAATG ACAAAAAATT GCTGGTGTGT ATATGGAAAA GGGGGACACA        4620

TATCCATGGA TGGTAGAAGT GTAAACTGTG CAGTCACTGT GGACATCAAT ATGCAGGTTC        4680

TTCACAAATG TAGATATAAA GCTACTATAG TTATACCC                                4718
```

(2) INFORMATION FOR SEQ ID NO:10:

(i) SEQUENCE CHARACTERISTICS:
        (A) LENGTH: 909 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:10:

```
Met Asp Met Phe Pro Leu Thr Trp Val Phe Leu Ala Leu Tyr Phe Ser
 1               5                  10                  15

Gly His Glu Val Arg Ser Gln Gln Asp Pro Pro Cys Gly Gly Arg Pro
                20                  25                  30

Asn Ser Lys Asp Ala Gly Tyr Ile Thr Ser Pro Gly Tyr Pro Gln Asp
            35                  40                  45

Tyr Pro Ser His Gln Asn Cys Glu Trp Ile Val Tyr Ala Pro Glu Pro
50                  55                  60

Asn Gln Lys Ile Val Leu Asn Phe Asn Pro His Phe Glu Ile Glu Lys
65                  70                  75                  80

His Asp Cys Lys Tyr Asp Phe Ile Glu Ile Arg Asp Gly Asp Ser Glu
                85                  90                  95

Ser Ala Asp Leu Leu Gly Lys His Cys Gly Asn Ile Ala Pro Pro Thr
                100                 105                 110

Ile Ile Ser Ser Gly Ser Val Leu Tyr Ile Lys Phe Thr Ser Asp Tyr
            115                 120                 125

Ala Arg Gln Gly Ala Gly Phe Ser Leu Arg Tyr Glu Ile Phe Lys Thr
        130                 135                 140

Gly Ser Glu Asp Cys Ser Lys Asn Phe Thr Ser Pro Asn Gly Thr Ile
145                 150                 155                 160

Glu Ser Pro Gly Phe Pro Glu Lys Tyr Pro His Asn Leu Asp Cys Thr
                165                 170                 175

Phe Thr Ile Leu Ala Lys Pro Arg Met Glu Ile Ile Leu Gln Phe Leu
                180                 185                 190

Thr Phe Asp Leu Glu His Asp Pro Leu Gln Val Gly Glu Gly Asp Cys
            195                 200                 205

Lys Tyr Asp Trp Leu Asp Ile Trp Asp Gly Ile Pro His Val Gly Pro
        210                 215                 220

Leu Ile Gly Lys Tyr Cys Gly Thr Lys Thr Pro Ser Lys Leu Arg Ser
225                 230                 235                 240

Ser Thr Gly Ile Leu Ser Leu Thr Phe His Thr Asp Met Ala Val Ala
                245                 250                 255

Lys Asp Gly Phe Ser Ala Arg Tyr Tyr Leu Ile His Gln Glu Pro Pro
                260                 265                 270

Glu Asn Phe Gln Cys Asn Val Pro Leu Gly Met Glu Ser Gly Arg Ile
            275                 280                 285

Ala Asn Glu Gln Ile Ser Ala Ser Ser Thr Phe Ser Asp Gly Arg Trp
        290                 295                 300
```

-continued

```
Thr Pro Gln Gln Ser Arg Leu His Gly Asp Asp Asn Gly Trp Thr Pro
305                 310                 315                 320

Asn Leu Asp Ser Asn Lys Glu Tyr Leu Gln Val Asp Leu Arg Phe Leu
            325                 330                 335

Thr Met Leu Thr Ala Ile Ala Thr Gln Gly Ala Ile Ser Arg Glu Thr
            340                 345                 350

Gln Lys Gly Tyr Tyr Val Lys Ser Tyr Lys Leu Glu Val Ser Thr Asn
            355                 360                 365

Gly Glu Asp Trp Met Val Tyr Arg His Gly Lys Asn His Lys Ile Phe
370                 375                 380

Gln Ala Asn Asn Asp Ala Thr Glu Val Val Leu Asn Lys Leu His Met
385                 390                 395                 400

Pro Leu Leu Thr Arg Phe Ile Arg Ile Arg Pro Gln Thr Trp His Leu
            405                 410                 415

Gly Ile Ala Leu Arg Leu Glu Leu Phe Gly Cys Arg Val Thr Asp Ala
            420                 425                 430

Pro Cys Ser Asn Met Leu Gly Met Leu Ser Gly Leu Ile Ala Asp Thr
            435                 440                 445

Gln Ile Ser Ala Ser Ser Thr Arg Glu Tyr Leu Trp Ser Pro Ser Ala
450                 455                 460

Ala Arg Leu Val Ser Ser Arg Ser Gly Trp Phe Pro Arg Asn Pro Gln
465                 470                 475                 480

Ala Gln Pro Gly Glu Glu Trp Leu Gln Val Asp Leu Gly Thr Pro Lys
            485                 490                 495

Thr Val Lys Gly Val Ile Ile Gln Gly Ala Arg Gly Gly Asp Ser Ile
            500                 505                 510

Thr Ala Val Glu Ala Arg Ala Phe Val Arg Lys Phe Lys Val Ser Tyr
            515                 520                 525

Ser Leu Asn Gly Lys Asp Trp Glu Tyr Ile Gln Asp Pro Arg Thr Gln
530                 535                 540

Gln Thr Lys Leu Phe Glu Gly Asn Met His Tyr Asp Thr Pro Asp Ile
545                 550                 555                 560

Arg Arg Phe Asp Pro Val Pro Ala Gln Tyr Val Arg Val Tyr Pro Glu
            565                 570                 575

Arg Trp Ser Pro Ala Gly Ile Gly Met Arg Leu Glu Val Leu Gly Cys
            580                 585                 590

Asp Trp Thr Asp Ser Lys Pro Thr Val Glu Thr Leu Gly Pro Thr Val
            595                 600                 605

Lys Ser Glu Glu Thr Thr Thr Pro Tyr Pro Met Asp Glu Asp Ala Thr
610                 615                 620

Glu Cys Gly Glu Asn Cys Ser Phe Glu Asp Asp Lys Asp Leu Gln Leu
625                 630                 635                 640

Pro Ser Gly Phe Asn Cys Asn Phe Asp Phe Pro Glu Glu Thr Cys Gly
            645                 650                 655

Trp Val Tyr Asp His Ala Lys Trp Leu Arg Ser Thr Trp Ile Ser Ser
            660                 665                 670

Ala Asn Pro Asn Asp Arg Thr Phe Pro Asp Asp Lys Asn Phe Leu Lys
            675                 680                 685

Leu Gln Ser Asp Gly Arg Arg Glu Gly Gln Tyr Gly Arg Leu Ile Ser
            690                 695                 700

Pro Pro Val His Leu Pro Arg Ser Pro Val Cys Met Glu Phe Gln Tyr
705                 710                 715                 720
```

```
Gln Ala Met Gly Gly His Gly Val Ala Leu Gln Val Val Arg Glu Ala
                725                 730                 735

Ser Gln Glu Ser Lys Leu Leu Trp Val Ile Arg Glu Asp Gln Gly Ser
            740                 745                 750

Glu Trp Lys His Gly Arg Ile Ile Leu Pro Ser Tyr Asp Met Glu Tyr
        755                 760                 765

Gln Ile Val Phe Glu Gly Val Ile Gly Lys Gly Arg Ser Gly Glu Ile
    770                 775                 780

Ser Gly Asp Asp Ile Arg Ile Ser Thr Asp Val Pro Leu Glu Asn Cys
785                 790                 795                 800

Met Glu Pro Ile Ser Ala Phe Ala Asp Glu Tyr Glu Gly Asp Trp Ser
                805                 810                 815

Asn Ser Ser Ser Ser Thr Ser Gly Ala Gly Asp Pro Ser Ser Gly Lys
            820                 825                 830

Glu Lys Ser Trp Leu Tyr Thr Leu Asp Pro Ile Leu Ile Thr Ile Ile
        835                 840                 845

Ala Met Ser Ser Leu Gly Val Leu Leu Gly Ala Thr Cys Ala Gly Leu
    850                 855                 860

Leu Leu Tyr Cys Thr Cys Ser Tyr Ser Gly Leu Ser Ser Arg Ser Cys
865                 870                 875                 880

Thr Thr Leu Glu Asn Tyr Asn Phe Glu Leu Tyr Asp Gly Leu Lys His
                885                 890                 895

Lys Val Lys Ile Asn His Gln Lys Cys Cys Ser Glu Ala
            900                 905

(2) INFORMATION FOR SEQ ID NO:11:

(i) SEQUENCE CHARACTERISTICS:
        (A) LENGTH: 4733 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:11:

AAACTGGAGC TCCACCGCGG TGGCGGCCGC CCGGGCAGGT CTAGAATTCA GCGGCCGCTG      60

AATTCTATCC AGCGGTCGGT GCCTCTGCCC GCGTGTGTGT CCCGGGTGCC GGGGGACCTG    120

TGTCAGTTAG CGCTTCTGAG ATCACACAGC TGCCTAGGGG CCGTGTGATG CCCAGGGCAA    180

TTCTTGGCTT TGATTTTTAT TATTATTACT ATTATTTTGC GTTCAGCTTT CGGGAAACCC    240

TCGTGATGTT GTAGGATAAA GGAAATGACA CTTTGAGGAA CTGGAGAGAA CATACACGCG    300

TTTGGGTTTG AAGAGGAAAC CGGTCTCCGC TTCCTTAGCT TGCTCCCTCT TTGCTGATTT    360

CAAGAGCTAT CTCCTATGAG GTGGAGATAT TCCAGCAAGA ATAAAGGTGA AGACAGACTG    420

ACTGCCAGGA CCCAGGAGGA AAACGTTGAT CGTTAGAGAC CTTTGCAGAA GACACCACCA    480

GGAGGAAAAT TAGAGAGGAA AAACACAAAG ACATAATTAT AGGAGATCCC ACAAACCTAG    540

CCCGGGAGAG AGCCTCTCTG TCAAAAATGG ATATGTTTCC TCTTACCTGG GTTTTCTTAG    600

CTCTGTACTT TTCAGGACAC GAAGTGAGAA GCCAGCAAGA TCCACCCTGC GGAGGTCGGC    660

CGAATTCCAA AGATGCTGGC TACATCACTT CCCCAGGCTA CCCCCAGGAC TATCCCTCCC    720

ACCAGAACTG TGAGTGGATT GTCTACGCCC CCGAACCCAA CCAGAAGATT GTTCTCAACT    780

TCAACCCTCA CTTTGAAATC GAGAAACACG ACTGCAAGTA TGACTTCATT GAGATTCGGG    840

ATGGGGACAG TGAGTCAGCT GACCTCCTGG GCAAGCACTG TGGGAACATC GCCCCGCCCA    900
```

-continued

```
CCATCATCTC CTCAGGCTCC GTGTTATACA TCAAGTTCAC CTCAGACTAC GCCCGGCAGG      960

GGGCAGGTTT CTCTCTACGC TATGAGATCT TCAAAACAGG CTCTGAAGAT TGTTCCAAGA     1020

ACTTTACAAG CCCCAATGGG ACCATTGAAT CTCCAGGGTT TCCAGAGAAG TATCCACACA     1080

ATCTGGACTG TACCTTCACC ATCCTGGCCA AACCCAGGAT GGAGATCATC CTACAGTTCC     1140

TGACCTTTGA CCTGGAGCAT GACCCTCTAC AAGTGGGGGA AGGAGACTGT AAATATGACT     1200

GGCTGGACAT CTGGGATGGC ATTCCACATG TTGGACCTCT GATTGGCAAG TACTGTGGGA     1260

CGAAAACACC CTCCAAACTC CGCTCGTCCA CGGGGATCCT CTCCTTGACC TTTCACACGG     1320

ACATGGCAGT GGCCAAGGAT GGCTTCTCCG CACGTTACTA TTTGATCCAC CAGGAGCCAC     1380

CTGAGAATTT TCAGTGCAAT GTCCCTTTGG GAATGGAGTC TGGCCGGATT GCTAATGAAC     1440

AGATCAGTGC CTCCTCCACC TTCTCTGATG GGAGGTGGAC TCCTCAACAG AGCCGGCTCC     1500

ATGGTGATGA CAATGGCTGG ACACCCAATT TGGATTCCAA CAAGGAGTAT CTCCAGGTGG     1560

ACCTGCGCTT CCTAACCATG CTCACAGCCA TTGCAACACA GGGAGCCATT TCCAGGGAAA     1620

CCCAGAAAGG CTACTACGTC AAATCGTACA AGCTGGAAGT CAGCACAAAT GGTGAAGATT     1680

GGATGGTCTA CCGGCATGGC AAAAACCACA AGATATTCCA AGCGAACAAT GATGCGACCG     1740

AGGTGGTGCT AAACAAGCTC CACATGCCAC TGCTGACTCG GTTCATCAGG ATCCGCCCGC     1800

AGACGTGGCA TTTGGGCATT GCCCTTCGCC TGGAGCTCTT TGGCTGCCGG GTCACAGATG     1860

CACCCTGCTC CAACATGCTG GGGATGCTCT CGGGCCTCAT TGCTGATACC CAGATCTCTG     1920

CCTCCTCCAC CCGAGAGTAC CTCTGGAGCC CCAGTGCTGC CCGCCTGGTT AGTAGCCGCT     1980

CTGGCTGGTT TCCTCGGAAC CCTCAAGCCC AGCCAGGTGA AGAATGGCTT CAGGTAGACC     2040

TGGGGACACC CAAGACAGTG AAAGGGGTCA TCATCCAGGG AGCCCGAGGA GGAGACAGCA     2100

TCACTGCCGT GGAAGCCAGG GCGTTTGTAC GCAAGTTCAA AGTCTCCTAC AGCCTAAATG     2160

GCAAGGACTG GGAATATATC CAGGACCCCA GGACTCAGCA GACAAAGCTG TTTGAAGGGA     2220

ACATGCACTA TGACACCCCT GACATCCGAA GGTTCGATCC TGTTCCAGCG CAGTATGTGC     2280

GGGTGTACCC AGAGAGGTGG TCGCCAGCAG GCATCGGGAT GAGGCTGGAG GTGCTGGGCT     2340

GTGACTGGAC AGACTCAAAG CCCACAGTGG AGACGCTGGG ACCCACCGTG AAGAGTGAAG     2400

AGACTACCAC CCCATATCCC ATGGATGAGG ATGCCACCGA GTGTGGGGAA AACTGCAGCT     2460

TTGAGGATGA CAAAGATTTG CAACTTCCTT CAGGATTCAA CTGCAACTTT GATTTTCCGG     2520

AAGAGACCTG TGGTTGGGTG TACGACCATG CCAAGTGGCT CCGGAGCACG TGGATCAGCA     2580

GCGCTAACCC CAATGACAGA ACATTTCCAG ATGACAAGAA CTTCTTGAAA CTGCAGAGTG     2640

ATGGCCGACG AGAGGGCCAG TACGGGCGGC TCATCAGCCC ACCGGTGCAC CTGCCCCGAA     2700

GCCCTGTGTG CATGGAGTTC CAGTACCAAG CCATGGGCGG CCACGGGGTG GCACTGCAGG     2760

TGGTTCGGGA AGCCAGCCAG GAAAGCAAAC TCCTTTGGGT CATCCGTGAG GACCAGGGCA     2820

GCGAGTGGAA GCACGGGCGC ATTATCCTGC CCAGCTATGA CATGGAGTAT CAGATCGTGT     2880

TCGAGGGAGT GATAGGGAAG GGACGATCGG GAGAGATTTC CGGCGATGAC ATTCGGATAA     2940

GCACTGATGT CCCACTGGAG AACTGCATGG AACCCATATC AGCTTTTGCA GGTGAGGATT     3000

TTAAAGATGA ATATGAAGGA GATTGGAGCA ACTCTTCTTC CTCTACCTCA GGGGCTGGTG     3060

ACCCCTCATC TGGCAAAGAA AAGAGCTGGC TGTACACCCT AGATCCCATT CTGATCACCA     3120

TCATCGCCAT GAGCTCGCTG GGGGTCCTGC TGGGGGCCAC CTGTGCGGGC CTCCTCCTTT     3180

ACTGCACCTG CTCCTATTCG GGTCTGAGTT CGAGGAGCTG CACCACACTG GAGAACTACA     3240
```

```
ACTTTGAGCT CTACGATGGC CTCAAGCACA AGGTCAAGAT CAATCATCAG AAGTGCTGCT        3300

CGGAGGCATG ACCGATTGTG TCTGGATCGC TTCTGGCGTT TCATTCCAGT GAGAGGGGCT        3360

AGCGAAGATT ACAGTTTTGT TTTGTTTTGT TTTGTTTTCC CTTTGGAAAC TGAATGCCAT        3420

AATCTGGATC AAAGTGTTCC AGAATACTGA AGGTATGGAC AGGACAGACA GGCCAGTCTA        3480

GGGAGAAAGG GAGATGCAGC TGTGAAGGGG ATCGTTGCCC ACCAGGACTG TGGTGGCCAA        3540

GTGAATGCAG GAACCGGGCC CGGAATTCCG GCTCTCGGCT AAAATCTCAG CTGCCTCTGG        3600

AAAGGCTCAA CCATACTCAG TGCCAACTCA GACTCTGTTG CTGTGGTGTC AACATGGATG        3660

GATCATCTGT ACCTTGTATT TTTAGCAGAA TTCATGCTCA GATTTCTTTG TTCTGAATCC        3720

TTGCTTTGTG CTAGACACAA AGCATACATG TCCTTCTAAA ATTAATATGA TCACTATAAT        3780

CTCCTGTGTG CAGAATTCAG AAATAGACCT TTGAAACCAT TTGCATTGTG AGTGCAGATC        3840

CATGACTGGG GCTAGTGCAG CAATGAAACA GAATTCCAGA AACAGTGTGT TCTTTTTATT        3900

ATGGGAAAAT ACAGATAAAA ATGGCCACTG ATGAACATGA AAGTTAGCAC TTTCCCAACA        3960

CAGTGTACAC TTGCAACCTT GTTTTGGATT TCTCATACAC CAAGACTGTG AAACACAAAT        4020

TTCAAGAATG TGTTCAAATG TGTGTGTGTG TGTGTGTGTG TGTGTGTGTG TGTGTGTATG        4080

TGTGTGTGTG TGTGTGTGCT TGTGTGTTTC TGTCAGTGGT ATGAGTGATA TGTATGCATG        4140

TGTGTATGTA TATGTATGTA TGTATGTATG TATGTACGTA CATATGTATG TATGTATGTA        4200

TGTATGTATG TATGTATATG TGTGTGTGTG TTTGTGTGTG TGTGTGTTTG TGTGTGTGTG        4260

TGTGGTAAGT GTGGTATGTG TGTATGCATT TGTCTATATG TGTATCTGTG TGTCTATGTG        4320

TTTCTGTCAG TGGAATGAGT GGCATGTGTG CATGTGTATG TATGTGGATA TGTGTGTTGT        4380

GTTTATGTGC TTGTGTATAA GAGGTAAGTG TGGTGTGTGT GCATGTGTCT CTGTGTGTGT        4440

TTGTCTGTGT ACCTCTTTGT ATAAGTACCT GTGTTTGTAT GTGGGAATAT GTATATTGAG        4500

GCATTGCTGT GTTAGTATGT TTATAGAAAA GAAGACAGTC TGAGATGTCT TCCTCAATAC        4560

CTCTCCACTT ATATCTTGGA TAGACAAAAG TAATGACAAA AAATTGCTGG TGTGTATATG        4620

GAAAAGGGGG ACACATATCC ATGGATGGTA GAAGTGTAAA CTGTGCAGTC ACTGTGGACA        4680

TCAATATGCA GGTTCTTCAC AAATGTAGAT ATAAAGCTAC TATAGTTATA CCC              4733

(2) INFORMATION FOR SEQ ID NO:12:

(i) SEQUENCE CHARACTERISTICS:
        (A) LENGTH: 914 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:12:

Met Asp Met Phe Pro Leu Thr Trp Val Phe Leu Ala Leu Tyr Phe Ser
1               5                   10                  15

Gly His Glu Val Arg Ser Gln Gln Asp Pro Cys Gly Gly Arg Pro
                20                  25                  30

Asn Ser Lys Asp Ala Gly Tyr Ile Thr Ser Pro Gly Tyr Pro Gln Asp
                35                  40                  45

Tyr Pro Ser His Gln Asn Cys Glu Trp Ile Val Tyr Ala Pro Glu Pro
            50                  55                  60

Asn Gln Lys Ile Val Leu Asn Phe Asn Pro His Phe Glu Ile Glu Lys
65                  70                  75                  80
```

```
His Asp Cys Lys Tyr Asp Phe Ile Glu Ile Arg Asp Gly Asp Ser Glu
                85                  90                  95

Ser Ala Asp Leu Leu Gly Lys His Cys Gly Asn Ile Ala Pro Pro Thr
            100                 105                 110

Ile Ile Ser Ser Gly Ser Val Leu Tyr Ile Lys Phe Thr Ser Asp Tyr
        115                 120                 125

Ala Arg Gln Gly Ala Gly Phe Ser Leu Arg Tyr Glu Ile Phe Lys Thr
    130                 135                 140

Gly Ser Glu Asp Cys Ser Lys Asn Phe Thr Ser Pro Asn Gly Thr Ile
145                 150                 155                 160

Glu Ser Pro Gly Phe Pro Glu Lys Tyr Pro His Asn Leu Asp Cys Thr
                165                 170                 175

Phe Thr Ile Leu Ala Lys Pro Arg Met Glu Ile Ile Leu Gln Phe Leu
            180                 185                 190

Thr Phe Asp Leu Glu His Asp Pro Leu Gln Val Gly Glu Gly Asp Cys
        195                 200                 205

Lys Tyr Asp Trp Leu Asp Ile Trp Asp Gly Ile Pro His Val Gly Pro
    210                 215                 220

Leu Ile Gly Lys Tyr Cys Gly Thr Lys Thr Pro Ser Lys Leu Arg Ser
225                 230                 235                 240

Ser Thr Gly Ile Leu Ser Leu Thr Phe His Thr Asp Met Ala Val Ala
                245                 250                 255

Lys Asp Gly Phe Ser Ala Arg Tyr Tyr Leu Ile His Gln Glu Pro Pro
            260                 265                 270

Glu Asn Phe Gln Cys Asn Val Pro Leu Gly Met Glu Ser Gly Arg Ile
        275                 280                 285

Ala Asn Glu Gln Ile Ser Ala Ser Ser Thr Phe Ser Asp Gly Arg Trp
    290                 295                 300

Thr Pro Gln Gln Ser Arg Leu His Gly Asp Asp Asn Gly Trp Thr Pro
305                 310                 315                 320

Asn Leu Asp Ser Asn Lys Glu Tyr Leu Gln Val Asp Leu Arg Phe Leu
                325                 330                 335

Thr Met Leu Thr Ala Ile Ala Thr Gln Gly Ala Ile Ser Arg Glu Thr
            340                 345                 350

Gln Lys Gly Tyr Tyr Val Lys Ser Tyr Lys Leu Glu Val Ser Thr Asn
        355                 360                 365

Gly Glu Asp Trp Met Val Tyr Arg His Gly Lys Asn His Lys Ile Phe
    370                 375                 380

Gln Ala Asn Asn Asp Ala Thr Glu Val Val Leu Asn Lys Leu His Met
385                 390                 395                 400

Pro Leu Leu Thr Arg Phe Ile Arg Ile Arg Pro Gln Thr Trp His Leu
                405                 410                 415

Gly Ile Ala Leu Arg Leu Glu Leu Phe Gly Cys Arg Val Thr Asp Ala
            420                 425                 430

Pro Cys Ser Asn Met Leu Gly Met Leu Ser Gly Leu Ile Ala Asp Thr
        435                 440                 445

Gln Ile Ser Ala Ser Ser Thr Arg Glu Tyr Leu Trp Ser Pro Ser Ala
    450                 455                 460

Ala Arg Leu Val Ser Ser Arg Ser Gly Trp Phe Pro Arg Asn Pro Gln
465                 470                 475                 480

Ala Gln Pro Gly Glu Glu Trp Leu Gln Val Asp Leu Gly Thr Pro Lys
                485                 490                 495
```

```
Thr Val Lys Gly Val Ile Ile Gln Gly Ala Arg Gly Gly Asp Ser Ile
        500                 505                 510

Thr Ala Val Glu Ala Arg Ala Phe Val Arg Lys Phe Lys Val Ser Tyr
        515                 520                 525

Ser Leu Asn Gly Lys Asp Trp Glu Tyr Ile Gln Asp Pro Arg Thr Gln
        530                 535                 540

Gln Thr Lys Leu Phe Glu Gly Asn Met His Tyr Asp Thr Pro Asp Ile
545                 550                 555                 560

Arg Arg Phe Asp Pro Val Pro Ala Gln Tyr Val Arg Val Tyr Pro Glu
                565                 570                 575

Arg Trp Ser Pro Ala Gly Ile Gly Met Arg Leu Glu Val Leu Gly Cys
                580                 585                 590

Asp Trp Thr Asp Ser Lys Pro Thr Val Glu Thr Leu Gly Pro Thr Val
                595                 600                 605

Lys Ser Glu Glu Thr Thr Pro Tyr Pro Met Asp Glu Asp Ala Thr
        610                 615                 620

Glu Cys Gly Glu Asn Cys Ser Phe Glu Asp Asp Lys Asp Leu Gln Leu
625                 630                 635                 640

Pro Ser Gly Phe Asn Cys Asn Phe Asp Phe Pro Glu Glu Thr Cys Gly
                645                 650                 655

Trp Val Tyr Asp His Ala Lys Trp Leu Arg Ser Thr Trp Ile Ser Ser
                660                 665                 670

Ala Asn Pro Asn Asp Arg Thr Phe Pro Asp Asp Lys Asn Phe Leu Lys
                675                 680                 685

Leu Gln Ser Asp Gly Arg Arg Glu Gly Gln Tyr Gly Arg Leu Ile Ser
                690                 695                 700

Pro Pro Val His Leu Pro Arg Ser Pro Val Cys Met Glu Phe Gln Tyr
705                 710                 715                 720

Gln Ala Met Gly Gly His Gly Val Ala Leu Gln Val Val Arg Glu Ala
                725                 730                 735

Ser Gln Glu Ser Lys Leu Leu Trp Val Ile Arg Glu Asp Gln Gly Ser
                740                 745                 750

Glu Trp Lys His Gly Arg Ile Ile Leu Pro Ser Tyr Asp Met Glu Tyr
                755                 760                 765

Gln Ile Val Phe Glu Gly Val Ile Gly Lys Gly Arg Ser Gly Glu Ile
                770                 775                 780

Ser Gly Asp Asp Ile Arg Ile Ser Thr Asp Val Pro Leu Glu Asn Cys
785                 790                 795                 800

Met Glu Pro Ile Ser Ala Phe Ala Gly Glu Asp Phe Lys Asp Glu Tyr
                805                 810                 815

Glu Gly Asp Trp Ser Asn Ser Ser Ser Thr Ser Gly Ala Gly Asp
                820                 825                 830

Pro Ser Ser Gly Lys Glu Lys Ser Trp Leu Tyr Thr Leu Asp Pro Ile
                835                 840                 845

Leu Ile Thr Ile Ile Ala Met Ser Ser Leu Gly Val Leu Leu Gly Ala
                850                 855                 860

Thr Cys Ala Gly Leu Leu Leu Tyr Cys Thr Cys Ser Tyr Ser Gly Leu
865                 870                 875                 880

Ser Ser Arg Ser Cys Thr Thr Leu Glu Asn Tyr Asn Phe Glu Leu Tyr
                885                 890                 895
```

```
Asp Gly Leu Lys His Lys Val Lys Ile Asn His Gln Lys Cys Cys Ser
        900                 905                 910

Glu Ala (2) INFORMATION FOR SEQ ID NO:13:

(i) SEQUENCE CHARACTERISTICS:
        (A) LENGTH: 4769 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:13:

AAACTGGAGC TCCACCGCGG TGGCGGCCGC CCGGGCAGGT CTAGAATTCA GCGGCCGCTG      60

AATTCTATCC AGCGGTCGGT GCCTCTGCCC GCGTGTGTGT CCCGGGTGCC GGGGGACCTG     120

TGTCAGTTAG CGCTTCTGAG ATCACACAGC TGCCTAGGGG CCGTGTGATG CCCAGGGCAA     180

TTCTTGGCTT TGATTTTTAT TATTATTACT ATTATTTTGC GTTCAGCTTT CGGGAAACCC     240

TCGTGATGTT GTAGGATAAA GGAAATGACA CTTTGAGGAA CTGGAGAGAA CATACACGCG     300

TTTGGGTTTG AAGAGGAAAC CGGTCTCCGC TTCCTTAGCT TGCTCCCTCT TTGCTGATTT     360

CAAGAGCTAT CTCCTATGAG GTGGAGATAT TCCAGCAAGA ATAAAGGTGA AGACAGACTG     420

ACTGCCAGGA CCCAGGAGGA AAACGTTGAT CGTTAGAGAC CTTTGCAGAA GACACCACCA     480

GGAGGAAAAT TAGAGAGGAA AAACACAAAG ACATAATTAT AGGAGATCCC ACAAACCTAG     540

CCCGGGAGAG AGCCTCTCTG TCAAAAATGG ATATGTTTCC TCTTACCTGG GTTTTCTTAG     600

CTCTGTACTT TTCAGGACAC GAAGTGAGAA GCCAGCAAGA TCCACCCTGC GGAGGTCGGC     660

CGAATTCCAA AGATGCTGGC TACATCACTT CCCCAGGCTA CCCCCAGGAC TATCCCTCCC     720

ACCAGAACTG TGAGTGGATT GTCTACGCCC CGAACCCAA CCAGAAGATT GTTCTCAACT      780

TCAACCCTCA CTTTGAAATC GAGAAACACG ACTGCAAGTA TGACTTCATT GAGATTCGGG     840

ATGGGACAG TGAGTCAGCT GACCTCCTGG GCAAGCACTG TGGGAACATC GCCCCGCCCA      900

CCATCATCTC CTCAGGCTCC GTGTTATACA TCAAGTTCAC CTCAGACTAC GCCCGGCAGG     960

GGGCAGGTTT CTCTCTACGC TATGAGATCT TCAAAACAGG CTCTGAAGAT TGTTCCAAGA    1020

ACTTTACAAG CCCCAATGGG ACCATTGAAT CTCCAGGGTT TCCAGAGAAG TATCCACACA    1080

ATCTGGACTG TACCTTCACC ATCCTGGCCA AACCCAGGAT GGAGATCATC CTACAGTTCC    1140

TGACCTTTGA CCTGGAGCAT GACCCTCTAC AAGTGGGGGA AGGAGACTGT AAATATGACT    1200

GGCTGGACAT CTGGGATGGC ATTCCACATG TTGGACCTCT GATTGGCAAG TACTGTGGGA    1260

CGAAAACACC CTCCAAACTC CGCTCGTCCA CGGGGATCCT CTCCTTGACC TTTCACACGG    1320

ACATGGCAGT GGCCAAGGAT GGCTTCTCCG CACGTTACTA TTTGATCCAC CAGGAGCCAC    1380

CTGAGAATTT TCAGTGCAAT GTCCCTTTGG GAATGGAGTC TGGCCGGATT GCTAATGAAC    1440

AGATCAGTGC CTCCTCCACC TTCTCTGATG GGAGGTGGAC TCCTCAACAG AGCCGGCTCC    1500

ATGGTGATGA CAATGGCTGG ACACCCAATT TGGATTCCAA CAAGGAGTAT CTCCAGGTGG    1560

ACCTGCGCTT CCTAACCATG CTCACAGCCA TTGCAACACA GGGAGCCATT TCCAGGGAAA    1620

CCCAGAAAGG CTACTACGTC AAATCGTACA AGCTGGAAGT CAGCACAAAT GGTGAAGATT    1680

GGATGGTCTA CCGGCATGGC AAAAACCACA AGATATTCCA AGCGAACAAT GATGCGACCG    1740

AGGTGGTGCT AAACAAGCTC CACATGCCAC TGCTGACTCG GTTCATCAGG ATCCGCCCGC    1800
```

-continued

```
AGACGTGGCA TTTGGGCATT GCCCTTCGCC TGGAGCTCTT TGGCTGCCGG GTCACAGATG      1860

CACCCTGCTC CAACATGCTG GGGATGCTCT CGGGCCTCAT TGCTGATACC CAGATCTCTG      1920

CCTCCTCCAC CCGAGAGTAC CTCTGGAGCC CCAGTGCTGC CCGCCTGGTT AGTAGCCGCT      1980

CTGGCTGGTT TCCTCGGAAC CCTCAAGCCC AGCCAGGTGA AGAATGGCTT CAGGTAGACC      2040

TGGGGACACC CAAGACAGTG AAAGGGGTCA TCATCCAGGG AGCCCGAGGA GGAGACAGCA      2100

TCACTGCCGT GGAAGCCAGG GCGTTTGTAC GCAAGTTCAA AGTCTCCTAC AGCCTAAATG      2160

GCAAGGACTG GGAATATATC CAGGACCCCA GGACTCAGCA GACAAAGCTG TTTGAAGGGA      2220

ACATGCACTA TGACACCCCT GACATCCGAA GGTTCGATCC TGTTCCAGCG CAGTATGTGC      2280

GGGTGTACCC AGAGAGGTGG TCGCCAGCAG GCATCGGGAT GAGGCTGGAG GTGCTGGGCT      2340

GTGACTGGAC AGACTCAAAG CCCACAGTGG AGACGCTGGG ACCCACCGTG AAGAGTGAAG      2400

AGACTACCAC CCCATATCCC ATGGATGAGG ATGCCACCGA GTGTGGGGAA AACTGCAGCT      2460

TTGAGGATGA CAAAGATTTG CAACTTCCTT CAGGATTCAA CTGCAACTTT GATTTTCCGG      2520

AAGAGACCTG TGGTTGGGTG TACGACCATG CCAAGTGGCT CCGGAGCACG TGGATCAGCA      2580

GCGCTAACCC CAATGACAGA ACATTTCCAG ATGACAAGAA CTTCTTGAAA CTGCAGAGTG      2640

ATGGCCGACG AGAGGGCCAG TACGGGCGGC TCATCAGCCC ACCGGTGCAC CTGCCCCGAA      2700

GCCCTGTGTG CATGGAGTTC CAGTACCAAG CCATGGGCGG CCACGGGGTG GCACTGCAGG      2760

TGGTTCGGGA AGCCAGCCAG GAAAGCAAAC TCCTTTGGGT CATCCGTGAG GACCAGGGCA      2820

GCGAGTGGAA GCACGGGCGC ATTATCCTGC CCAGCTATGA CATGGAGTAT CAGATCGTGT      2880

TCGAGGGAGT GATAGGGAAG GGACGATCGG GAGAGATTTC CGGCGATGAC ATTCGGATAA      2940

GCACTGATGT CCCCACTGGAG AACTGCATGG AACCCATATC AGCTTTTGCA GTGGACATCC      3000

CAGAAACCCA TGGGGAGAG GGCTATGAAG ATGAGATTGA TGATGAATAT GAAGGAGATT      3060

GGAGCAACTC TTCTTCCTCT ACCTCAGGGG CTGGTGACCC CTCATCTGGC AAAGAAAGA      3120

GCTGGCTGTA CACCCTAGAT CCCATTCTGA TCACCATCAT CGCCATGAGC TCGCTGGGGG      3180

TCCTGCTGGG GGCCACCTGT GCGGGCCTCC TCCTTTACTG CACCTGCTCC TATTCGGGTC      3240

TGAGTTCGAG GAGCTGCACC ACACTGGAGA ACTACAACTT TGAGCTCTAC GATGGCCTCA      3300

AGCACAAGGT CAAGATCAAT CATCAGAAGT GCTGCTCGGA GGCATGACCG ATTGTGTCTG      3360

GATCGCTTCT GGCGTTTCAT TCCAGTGAGA GGGGCTAGCG AAGATTACAG TTTTGTTTTG      3420

TTTTGTTTTG TTTTCCCTTT GGAAACTGAA TGCCATAATC TGGATCAAAG TGTTCCAGAA      3480

TACTGAAGGT ATGGACAGGA CAGACAGGCC AGTCTAGGGA GAAAGGGAGA TGCAGCTGTG      3540

AAGGGGATCG TTGCCCACCA GGACTGTGGT GGCCAAGTGA ATGCAGGAAC CGGGCCCGGA      3600

ATTCCGGCTC TCGGCTAAAA TCTCAGCTGC CTCTGGAAAG GCTCAACCAT ACTCAGTGCC      3660

AACTCAGACT CTGTTGCTGT GGTGTCAACA TGGATGGATC ATCTGTACCT TGTATTTTTA      3720

GCAGAATTCA TGCTCAGATT TCTTTGTTCT GAATCCTTGC TTTGTGCTAG ACACAAAGCA      3780

TACATGTCCT TCTAAAATTA ATATGATCAC TATAATCTCC TGTGTGCAGA ATTCAGAAAT      3840

AGACCTTTGA AACCATTTGC ATTGTGAGTG CAGATCCATG ACTGGGGCTA GTGCAGCAAT      3900

GAAACAGAAT TCCAGAAACA GTGTGTTCTT TTTATTATGG GAAAATACAG ATAAAAATGG      3960

CCACTGATGA ACATGAAAGT TAGCACTTTC CCAACACAGT GTACACTTGC AACCTTGTTT      4020

TGGATTTCTC ATACACCAAG ACTGTGAAAC ACAAATTTCA AGAATGTGTT CAAATGTGTG      4080

TGTGTGTGTG TGTGTGTGTG TGTGTGTGTG TGTATGTGTG TGTGTGTGTG TGTGCTTGTG      4140
```

```
TGTTTCTGTC AGTGGTATGA GTGATATGTA TGCATGTGTG TATGTATATG TATGTATGTA      4200

TGTATGTATG TACGTACATA TGTATGTATG TATGTATGTA TGTATGTATG TATATGTGTG      4260

TGTGTGTTTG TGTGTGTGTG TGTTTGTGTG TGTGTGTGTG GTAAGTGTGG TATGTGTGTA      4320

TGCATTTGTC TATATGTGTA TCTGTGTGTC TATGTGTTTC TGTCAGTGGA ATGAGTGGCA      4380

TGTGTGCATG TGTATGTATG TGGATATGTG TGTTGTGTTT ATGTGCTTGT GTATAAGAGG      4440

TAAGTGTGGT GTGTGTGCAT GTGTCTCTGT GTGTGTTTGT CTGTGTACCT CTTTGTATAA      4500

GTACCTGTGT TTGTATGTGG GAATATGTAT ATTGAGGCAT TGCTGTGTTA GTATGTTTAT      4560

AGAAAAGAAG ACAGTCTGAG ATGTCTTCCT CAATACCTCT CCACTTATAT CTTGGATAGA      4620

CAAAGTAAT  GACAAAAAAT  TGCTGGTGTG  TATATGGAAA  AGGGGACAC  ATATCCATGG      4680

ATGGTAGAAG TGTAAACTGT GCAGTCACTG TGGACATCAA TATGCAGGTT CTTCACAAAT      4740

GTAGATATAA AGCTACTATA GTTATACCC                                        4769
```

(2) INFORMATION FOR SEQ ID NO:14:

(i) SEQUENCE CHARACTERISTICS:
        (A) LENGTH: 926 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:14:

```
Met Asp Met Phe Pro Leu Thr Trp Val Phe Leu Ala Leu Tyr Phe Ser
1               5                   10                  15

Gly His Glu Val Arg Ser Gln Gln Asp Pro Pro Cys Gly Gly Arg Pro
            20                  25                  30

Asn Ser Lys Asp Ala Gly Tyr Ile Thr Ser Pro Gly Tyr Pro Gln Asp
        35                  40                  45

Tyr Pro Ser His Gln Asn Cys Glu Trp Ile Val Tyr Ala Pro Glu Pro
    50                  55                  60

Asn Gln Lys Ile Val Leu Asn Phe Asn Pro His Phe Glu Ile Glu Lys
65                  70                  75                  80

His Asp Cys Lys Tyr Asp Phe Ile Glu Ile Arg Asp Gly Asp Ser Glu
                85                  90                  95

Ser Ala Asp Leu Leu Gly Lys His Cys Gly Asn Ile Ala Pro Pro Thr
            100                 105                 110

Ile Ile Ser Ser Gly Ser Val Leu Tyr Ile Lys Phe Thr Ser Asp Tyr
        115                 120                 125

Ala Arg Gln Gly Ala Gly Phe Ser Leu Arg Tyr Glu Ile Phe Lys Thr
    130                 135                 140

Gly Ser Glu Asp Cys Ser Lys Asn Phe Thr Ser Pro Asn Gly Thr Ile
145                 150                 155                 160

Glu Ser Pro Gly Phe Pro Glu Lys Tyr Pro His Asn Leu Asp Cys Thr
                165                 170                 175

Phe Thr Ile Leu Ala Lys Pro Arg Met Glu Ile Leu Gln Phe Leu
            180                 185                 190

Thr Phe Asp Leu Glu His Asp Pro Leu Gln Val Gly Glu Gly Asp Cys
        195                 200                 205

Lys Tyr Asp Trp Leu Asp Ile Trp Asp Gly Ile Pro His Val Gly Pro
    210                 215                 220
```

-continued

```
Leu Ile Gly Lys Tyr Cys Gly Thr Lys Thr Pro Ser Lys Leu Arg Ser
225                 230                 235                 240

Ser Thr Gly Ile Leu Ser Leu Thr Phe His Thr Asp Met Ala Val Ala
            245                 250                 255

Lys Asp Gly Phe Ser Ala Arg Tyr Tyr Leu Ile His Gln Glu Pro Pro
                260                 265                 270

Glu Asn Phe Gln Cys Asn Val Pro Leu Gly Met Glu Ser Gly Arg Ile
            275                 280                 285

Ala Asn Glu Gln Ile Ser Ala Ser Ser Thr Phe Ser Asp Gly Arg Trp
290                 295                 300

Thr Pro Gln Gln Ser Arg Leu His Gly Asp Asp Asn Gly Trp Thr Pro
305                 310                 315                 320

Asn Leu Asp Ser Asn Lys Glu Tyr Leu Gln Val Asp Leu Arg Phe Leu
                325                 330                 335

Thr Met Leu Thr Ala Ile Ala Thr Gln Gly Ala Ile Ser Arg Glu Thr
                340                 345                 350

Gln Lys Gly Tyr Tyr Val Lys Ser Tyr Lys Leu Glu Val Ser Thr Asn
            355                 360                 365

Gly Glu Asp Trp Met Val Tyr Arg His Gly Lys Asn His Lys Ile Phe
            370                 375                 380

Gln Ala Asn Asn Asp Ala Thr Glu Val Val Leu Asn Lys Leu His Met
385                 390                 395                 400

Pro Leu Leu Thr Arg Phe Ile Arg Ile Arg Pro Gln Thr Trp His Leu
                405                 410                 415

Gly Ile Ala Leu Arg Leu Glu Leu Phe Gly Cys Arg Val Thr Asp Ala
                420                 425                 430

Pro Cys Ser Asn Met Leu Gly Met Leu Ser Gly Leu Ile Ala Asp Thr
            435                 440                 445

Gln Ile Ser Ala Ser Ser Thr Arg Glu Tyr Leu Trp Ser Pro Ser Ala
            450                 455                 460

Ala Arg Leu Val Ser Ser Arg Ser Gly Trp Phe Pro Arg Asn Pro Gln
465                 470                 475                 480

Ala Gln Pro Gly Glu Glu Trp Leu Gln Val Asp Leu Gly Thr Pro Lys
                485                 490                 495

Thr Val Lys Gly Val Ile Ile Gln Gly Ala Arg Gly Gly Asp Ser Ile
            500                 505                 510

Thr Ala Val Glu Ala Arg Ala Phe Val Arg Lys Phe Lys Val Ser Tyr
            515                 520                 525

Ser Leu Asn Gly Lys Asp Trp Glu Tyr Ile Gln Asp Pro Arg Thr Gln
530                 535                 540

Gln Thr Lys Leu Phe Glu Gly Asn Met His Tyr Asp Thr Pro Asp Ile
545                 550                 555                 560

Arg Arg Phe Asp Pro Val Pro Ala Gln Tyr Val Arg Val Tyr Pro Glu
                565                 570                 575

Arg Trp Ser Pro Ala Gly Ile Gly Met Arg Leu Glu Val Leu Gly Cys
            580                 585                 590

Asp Trp Thr Asp Ser Lys Pro Thr Val Glu Thr Leu Gly Pro Thr Val
            595                 600                 605

Lys Ser Glu Glu Thr Thr Thr Pro Tyr Pro Met Asp Glu Asp Ala Thr
            610                 615                 620

Glu Cys Gly Glu Asn Cys Ser Phe Glu Asp Lys Asp Leu Gln Leu
625                 630                 635                 640
```

```
Pro Ser Gly Phe Asn Cys Asn Phe Asp Phe Pro Glu Glu Thr Cys Gly
                645                 650                 655

Trp Val Tyr Asp His Ala Lys Trp Leu Arg Ser Thr Trp Ile Ser Ser
            660                 665                 670

Ala Asn Pro Asn Asp Arg Thr Phe Pro Asp Asp Lys Asn Phe Leu Lys
        675                 680                 685

Leu Gln Ser Asp Gly Arg Arg Glu Gly Gln Tyr Gly Arg Leu Ile Ser
    690                 695                 700

Pro Pro Val His Leu Pro Arg Ser Pro Val Cys Met Glu Phe Gln Tyr
705                 710                 715                 720

Gln Ala Met Gly Gly His Gly Val Ala Leu Gln Val Val Arg Glu Ala
                725                 730                 735

Ser Gln Glu Ser Lys Leu Leu Trp Val Ile Arg Glu Asp Gln Gly Ser
            740                 745                 750

Glu Trp Lys His Gly Arg Ile Ile Leu Pro Ser Tyr Asp Met Glu Tyr
        755                 760                 765

Gln Ile Val Phe Glu Gly Val Ile Gly Lys Gly Arg Ser Gly Glu Ile
    770                 775                 780

Ser Gly Asp Asp Ile Arg Ile Ser Thr Asp Val Pro Leu Glu Asn Cys
785                 790                 795                 800

Met Glu Pro Ile Ser Ala Phe Ala Val Asp Ile Pro Glu Thr His Gly
                805                 810                 815

Gly Glu Gly Tyr Glu Asp Glu Ile Asp Asp Glu Tyr Glu Gly Asp Trp
            820                 825                 830

Ser Asn Ser Ser Ser Thr Ser Gly Ala Gly Asp Pro Ser Ser Gly
            835                 840                 845

Lys Glu Lys Ser Trp Leu Tyr Thr Leu Asp Pro Ile Leu Ile Thr Ile
    850                 855                 860

Ile Ala Met Ser Ser Leu Gly Val Leu Leu Gly Ala Thr Cys Ala Gly
865                 870                 875                 880

Leu Leu Leu Tyr Cys Thr Cys Ser Tyr Ser Gly Leu Ser Ser Arg Ser
                885                 890                 895

Cys Thr Thr Leu Glu Asn Tyr Asn Phe Glu Leu Tyr Asp Gly Leu Lys
            900                 905                 910

His Lys Val Lys Ile Asn His Gln Lys Cys Cys Ser Glu Ala
    915                 920                 925

(2) INFORMATION FOR SEQ ID NO:15:

(i) SEQUENCE CHARACTERISTICS:
        (A) LENGTH: 4784 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:15:

AAACTGGAGC TCCACCGCGG TGGCGGCCGC CCGGGCAGGT CTAGAATTCA GCGGCCGCTG     60

AATTCTATCC AGCGGTCGGT GCCTCTGCCC GCGTGTGTGT CCCGGGTGCC GGGGGACCTG    120

TGTCAGTTAG CGCTTCTGAG ATCACACAGC TGCCTAGGGG CCGTGTGATG CCCAGGGCAA    180

TTCTTGGCTT TGATTTTTAT TATTATTACT ATTATTTTGC GTTCAGCTTT CGGGAAACCC    240

TCGTGATGTT GTAGGATAAA GGAAATGACA CTTTGAGGAA CTGAGAGAA CATACACGCG     300

TTTGGGTTTG AAGAGGAAAC CGGTCTCCGC TTCCTTAGCT TGCTCCCTCT TTGCTGATTT    360
```

-continued

```
CAAGAGCTAT CTCCTATGAG GTGGAGATAT TCCAGCAAGA ATAAAGGTGA AGACAGACTG      420

ACTGCCAGGA CCCAGGAGGA AAACGTTGAT CGTTAGAGAC CTTTGCAGAA GACACCACCA      480

GGAGGAAAAT TAGAGAGGAA AAACACAAAG ACATAATTAT AGGAGATCCC ACAAACCTAG      540

CCCGGGAGAG AGCCTCTCTG TCAAAAATGG ATATGTTTCC TCTTACCTGG GTTTTCTTAG      600

CTCTGTACTT TTCAGGACAC GAAGTGAGAA GCCAGCAAGA TCCACCCTGC GGAGGTCGGC      660

CGAATTCCAA AGATGCTGGC TACATCACTT CCCCAGGCTA CCCCCAGGAC TATCCCTCCC      720

ACCAGAACTG TGAGTGGATT GTCTACGCCC CCGAACCCAA CCAGAAGATT GTTCTCAACT      780

TCAACCCTCA CTTTGAAATC GAGAAACACG ACTGCAAGTA TGACTTCATT GAGATTCGGG      840

ATGGGGACAG TGAGTCAGCT GACCTCCTGG GCAAGCACTG TGGGAACATC GCCCCGCCCA      900

CCATCATCTC CTCAGGCTCC GTGTTATACA TCAAGTTCAC CTCAGACTAC GCCCGGCAGG      960

GGGCAGGTTT CTCTCTACGC TATGAGATCT TCAAAACAGG CTCTGAAGAT TGTTCCAAGA     1020

ACTTTACAAG CCCCAATGGG ACCATTGAAT CTCCAGGGTT TCCAGAGAAG TATCCACACA     1080

ATCTGGACTG TACCTTCACC ATCCTGGCCA AACCCAGGAT GGAGATCATC CTACAGTTCC     1140

TGACCTTTGA CCTGGAGCAT GACCCTCTAC AAGTGGGGGA AGGAGACTGT AAATATGACT     1200

GGCTGGACAT CTGGGATGGC ATTCCACATG TTGGACCTCT GATTGGCAAG TACTGTGGGA     1260

CGAAAACACC CTCCAAACTC CGCTCGTCCA CGGGGATCCT CTCCTTGACC TTTCACACGG     1320

ACATGGCAGT GGCCAAGGAT GGCTTCTCCG CACGTTACTA TTTGATCCAC CAGGAGCCAC     1380

CTGAGAATTT TCAGTGCAAT GTCCCTTTGG GAATGGAGTC TGGCCGGATT GCTAATGAAC     1440

AGATCAGTGC CTCCTCCACC TTCTCTGATG GGAGGTGGAC TCCTCAACAG AGCCGGCTCC     1500

ATGGTGATGA CAATGGCTGG ACACCCAATT TGGATTCCAA CAAGGAGTAT CTCCAGGTGG     1560

ACCTGCGCTT CCTAACCATG CTCACAGCCA TTGCAACACA GGGAGCCATT TCCAGGGAAA     1620

CCCAGAAAGG CTACTACGTC AAATCGTACA AGCTGGAAGT CAGCACAAAT GGTGAAGATT     1680

GGATGGTCTA CCGGCATGGC AAAAACCACA AGATATTCCA AGCGAACAAT GATGCGACCG     1740

AGGTGGTGCT AAACAAGCTC CACATGCCAC TGCTGACTCG GTTCATCAGG ATCCGCCCGC     1800

AGACGTGGCA TTTGGGCATT GCCCTTCGCC TGGAGCTCTT TGGCTGCCGG GTCACAGATG     1860

CACCCTGCTC CAACATGCTG GGGATGCTCT CGGGCCTCAT TGCTGATACC CAGATCTCTG     1920

CCTCCTCCAC CCGAGAGTAC CTCTGGAGCC CCAGTGCTGC CCGCCTGGTT AGTAGCCGCT     1980

CTGGCTGGTT TCCTCGGAAC CCTCAAGCCC AGCCAGGTGA AGAATGGCTT CAGGTAGACC     2040

TGGGGACACC CAAGACAGTG AAAGGGGTCA TCATCCAGGG AGCCCGAGGA GGAGACAGCA     2100

TCACTGCCGT GGAAGCCAGG GCGTTTGTAC GCAAGTTCAA AGTCTCCTAC AGCCTAAATG     2160

GCAAGGACTG GAATATATC CAGGACCCCA GGACTCAGCA GACAAAGCTG TTTGAAGGGA      2220

ACATGCACTA TGACACCCCT GACATCCGAA GGTTCGATCC TGTTCCAGCG CAGTATGTGC     2280

GGGTGTACCC AGAGAGGTGG TCGCCAGCAG GCATCGGGAT GAGGCTGGAG GTGCTGGGCT     2340

GTGACTGGAC AGACTCAAAG CCCACAGTGG AGACGCTGGG ACCCACCGTG AAGAGTGAAG     2400

AGACTACCAC CCCATATCCC ATGGATGAGG ATGCCACCGA GTGTGGGAA AACTGCAGCT      2460

TTGAGGATGA CAAAGATTTG CAACTTCCTT CAGGATTCAA CTGCAACTTT GATTTTCCGG     2520

AAGAGACCTG TGGTTGGGTG TACGACCATG CCAAGTGGCT CCGGAGCACG TGGATCAGCA     2580

GCGCTAACCC CAATGACAGA ACATTTCCAG ATGACAAGAA CTTCTTGAAA CTGCAGAGTG     2640

ATGGCCGACG AGAGGGCCAG TACGGGCGGC TCATCAGCCC ACCGGTGCAC CTGCCCCGAA     2700
```

```
GCCCTGTGTG CATGGAGTTC CAGTACCAAG CCATGGGCGG CCACGGGGTG GCACTGCAGG    2760

TGGTTCGGGA AGCCAGCCAG GAAAGCAAAC TCCTTTGGGT CATCCGTGAG GACCAGGGCA    2820

GCGAGTGGAA GCACGGGCGC ATTATCCTGC CCAGCTATGA CATGGAGTAT CAGATCGTGT    2880

TCGAGGGAGT GATAGGGAAG GGACGATCGG GAGAGATTTC CGGCGATGAC ATTCGGATAA    2940

GCACTGATGT CCCACTGGAG AACTGCATGG AACCCATATC AGCTTTTGCA GGTGAGGATT    3000

TTAAAGTGGA CATCCCAGAA ACCCATGGGG GAGAGGGCTA TGAAGATGAG ATTGATGATG    3060

AATATGAAGG AGATTGGAGC AACTCTTCTT CCTCTACCTC AGGGGCTGGT GACCCCTCAT    3120

CTGGCAAAGA AAAGAGCTGG CTGTACACCC TAGATCCCAT TCTGATCACC ATCATCGCCA    3180

TGAGCTCGCT GGGGGTCCTG CTGGGGGCCA CCTGTGCGGG CCTCCTCCTT TACTGCACCT    3240

GCTCCTATTC GGGTCTGAGT TCGAGGAGCT GCACCACACT GGAGAACTAC AACTTTGAGC    3300

TCTACGATGG CCTCAAGCAC AAGGTCAAGA TCAATCATCA GAAGTGCTGC TCGGAGGCAT    3360

GACCGATTGT GTCTGGATCG CTTCTGGCGT TTCATTCCAG TGAGAGGGGC TAGCGAAGAT    3420

TACAGTTTTG TTTTGTTTTG TTTTGTTTTC CCTTTGGAAA CTGAATGCCA TAATCTGGAT    3480

CAAAGTGTTC CAGAATACTG AAGGTATGGA CAGGACAGAC AGGCCAGTCT AGGGAGAAAG    3540

GGAGATGCAG CTGTGAAGGG GATCGTTGCC CACCAGGACT GTGGTGGCCA AGTGAATGCA    3600

GGAACCGGGC CCGGAATTCC GGCTCTCGGC TAAAATCTCA GCTGCCTCTG GAAAGGCTCA    3660

ACCATACTCA GTGCCAACTC AGACTCTGTT GCTGTGGTGT CAACATGGAT GGATCATCTG    3720

TACCTTGTAT TTTTAGCAGA ATTCATGCTC AGATTTCTTT GTTCTGAATC CTTGCTTTGT    3780

GCTAGACACA AAGCATACAT GTCCTTCTAA AATTAATATG ATCACTATAA TCTCCTGTGT    3840

GCAGAATTCA GAAATAGACC TTTGAAACCA TTTGCATTGT GAGTGCAGAT CCATGACTGG    3900

GGCTAGTGCA GCAATGAAAC AGAATTCCAG AAACAGTGTG TTCTTTTTAT TATGGGAAAA    3960

TACAGATAAA AATGGCCACT GATGAACATG AAAGTTAGCA CTTTCCCAAC ACAGTGTACA    4020

CTTGCAACCT TGTTTTGGAT TTCTCATACA CCAAGACTGT GAAACACAAA TTTCAAGAAT    4080

GTGTTCAAAT GTGTGTGTGT GTGTGTGTGT GTGTGTGTGT GTGTGTGTAT GTGTGTGTGT    4140

GTGTGTGTGC TTGTGTGTTT CTGTCAGTGG TATGAGTGAT ATGTATGCAT GTGTGTATGT    4200

ATATGTATGT ATGTATGTAT GTATGTACGT ACATATGTAT GTATGTATGT ATGTATGTAT    4260

GTATGTATAT GTGTGTGTGT GTTTGTGTGT GTGTGTGTTT GTGTGTGTGT GTGTGGTAAG    4320

TGTGGTATGT GTGTATGCAT TTGTCTATAT GTGTATCTGT GTGTCTATGT GTTTCTGTCA    4380

GTGGAATGAG TGGCATGTGT GCATGTGTAT GTATGTGGAT ATGTGTGTTG TGTTTATGTG    4440

CTTGTGTATA AGAGGTAAGT GTGGTGTGTG TGCATGTGTC TCTGTGTGTG TTTGTCTGTG    4500

TACCTCTTTG TATAAGTACC TGTGTTTGTA TGTGGGAATA TGTATATTGA GGCATTGCTG    4560

TGTTAGTATG TTTATAGAAA AGAAGACAGT CTGAGATGTC TTCCTCAATA CCTCTCCACT    4620

TATATCTTGG ATAGACAAAA GTAATGACAA AAAATTGCTG GTGTGTATAT GGAAAAGGGG    4680

GACACATATC CATGGATGGT AGAAGTGTAA ACTGTGCAGT CACTGTGGAC ATCAATATGC    4740

AGGTTCTTCA CAAATGTAGA TATAAAGCTA CTATAGTTAT ACCC                    4784
```

(2) INFORMATION FOR SEQ ID NO:16:

(i) SEQUENCE CHARACTERISTICS:
        (A) LENGTH: 931 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:16:

| | | | | | | | | | | | | | | |
|---|---|---|---|---|---|---|---|---|---|---|---|---|---|---|
|Met|Asp|Met|Phe|Pro|Leu|Thr|Trp|Val|Phe|Leu|Ala|Leu|Tyr|Phe Ser|
|1| | | |5| | | |10| | | | |15| |

Met Asp Met Phe Pro Leu Thr Trp Val Phe Leu Ala Leu Tyr Phe Ser
1               5                  10                 15

Gly His Glu Val Arg Ser Gln Gln Asp Pro Cys Gly Gly Arg Pro
            20                  25                  30

Asn Ser Lys Asp Ala Gly Tyr Ile Thr Ser Pro Gly Tyr Pro Gln Asp
        35                  40                  45

Tyr Pro Ser His Gln Asn Cys Glu Trp Ile Val Tyr Ala Pro Glu Pro
    50                  55                  60

Asn Gln Lys Ile Val Leu Asn Phe Asn Pro His Phe Glu Ile Glu Lys
65                  70                  75                  80

His Asp Cys Lys Tyr Asp Phe Ile Glu Ile Arg Asp Gly Asp Ser Glu
            85                  90                  95

Ser Ala Asp Leu Leu Gly Lys His Cys Gly Asn Ile Ala Pro Pro Thr
                100                 105                 110

Ile Ile Ser Ser Gly Ser Val Leu Tyr Ile Lys Phe Thr Ser Asp Tyr
            115                 120                 125

Ala Arg Gln Gly Ala Gly Phe Ser Leu Arg Tyr Glu Ile Phe Lys Thr
    130                 135                 140

Gly Ser Glu Asp Cys Ser Lys Asn Phe Thr Ser Pro Asn Gly Thr Ile
145                 150                 155                 160

Glu Ser Pro Gly Phe Pro Glu Lys Tyr Pro His Asn Leu Asp Cys Thr
                165                 170                 175

Phe Thr Ile Leu Ala Lys Pro Arg Met Glu Ile Ile Leu Gln Phe Leu
            180                 185                 190

Thr Phe Asp Leu Glu His Asp Pro Leu Gln Val Gly Glu Gly Asp Cys
    195                 200                 205

Lys Tyr Asp Trp Leu Asp Ile Trp Asp Gly Ile Pro His Val Gly Pro
210                 215                 220

Leu Ile Gly Lys Tyr Cys Gly Thr Lys Thr Pro Ser Lys Leu Arg Ser
225                 230                 235                 240

Ser Thr Gly Ile Leu Ser Leu Thr Phe His Thr Asp Met Ala Val Ala
                245                 250                 255

Lys Asp Gly Phe Ser Ala Arg Tyr Tyr Leu Ile His Gln Glu Pro Pro
            260                 265                 270

Glu Asn Phe Gln Cys Asn Val Pro Leu Gly Met Glu Ser Gly Arg Ile
    275                 280                 285

Ala Asn Glu Gln Ile Ser Ala Ser Ser Thr Phe Ser Asp Gly Arg Trp
290                 295                 300

Thr Pro Gln Gln Ser Arg Leu His Gly Asp Asp Asn Gly Trp Thr Pro
305                 310                 315                 320

Asn Leu Asp Ser Asn Lys Glu Tyr Leu Gln Val Asp Leu Arg Phe Leu
                325                 330                 335

Thr Met Leu Thr Ala Ile Ala Thr Gln Gly Ala Ile Ser Arg Glu Thr
            340                 345                 350

Gln Lys Gly Tyr Tyr Val Lys Ser Tyr Lys Leu Glu Val Ser Thr Asn
    355                 360                 365

Gly Glu Asp Trp Met Val Tyr Arg His Gly Lys Asn His Lys Ile Phe
370                 375                 380

Gln Ala Asn Asn Asp Ala Thr Glu Val Val Leu Asn Lys Leu His Met
385                 390                 395                 400

-continued

```
Pro Leu Leu Thr Arg Phe Ile Arg Ile Arg Pro Gln Thr Trp His Leu
            405                 410                 415
Gly Ile Ala Leu Arg Leu Glu Leu Phe Gly Cys Arg Val Thr Asp Ala
            420                 425                 430
Pro Cys Ser Asn Met Leu Gly Met Leu Ser Gly Leu Ile Ala Asp Thr
            435                 440                 445
Gln Ile Ser Ala Ser Ser Thr Arg Glu Tyr Leu Trp Ser Pro Ser Ala
450                 455                 460
Ala Arg Leu Val Ser Ser Arg Ser Gly Trp Phe Pro Arg Asn Pro Gln
465                 470                 475                 480
Ala Gln Pro Gly Glu Glu Trp Leu Gln Val Asp Leu Gly Thr Pro Lys
            485                 490                 495
Thr Val Lys Gly Val Ile Ile Gln Gly Ala Arg Gly Gly Asp Ser Ile
            500                 505                 510
Thr Ala Val Glu Ala Arg Ala Phe Val Arg Lys Phe Lys Val Ser Tyr
            515                 520                 525
Ser Leu Asn Gly Lys Asp Trp Glu Tyr Ile Gln Asp Pro Arg Thr Gln
530                 535                 540
Gln Thr Lys Leu Phe Glu Gly Asn Met His Tyr Asp Thr Pro Asp Ile
545                 550                 555                 560
Arg Arg Phe Asp Pro Val Pro Ala Gln Tyr Val Arg Val Tyr Pro Glu
            565                 570                 575
Arg Trp Ser Pro Ala Gly Ile Gly Met Arg Leu Glu Val Leu Gly Cys
            580                 585                 590
Asp Trp Thr Asp Ser Lys Pro Thr Val Glu Thr Leu Gly Pro Thr Val
            595                 600                 605
Lys Ser Glu Glu Thr Thr Thr Pro Tyr Pro Met Asp Glu Asp Ala Thr
610                 615                 620
Glu Cys Gly Glu Asn Cys Ser Phe Glu Asp Asp Lys Asp Leu Gln Leu
625                 630                 635                 640
Pro Ser Gly Phe Asn Cys Asn Phe Asp Phe Pro Glu Glu Thr Cys Gly
            645                 650                 655
Trp Val Tyr Asp His Ala Lys Trp Leu Arg Ser Thr Trp Ile Ser Ser
            660                 665                 670
Ala Asn Pro Asn Asp Arg Thr Phe Pro Asp Asp Lys Asn Phe Leu Lys
            675                 680                 685
Leu Gln Ser Asp Gly Arg Arg Glu Gly Gln Tyr Gly Arg Leu Ile Ser
690                 695                 700
Pro Pro Val His Leu Pro Arg Ser Pro Val Cys Met Glu Phe Gln Tyr
705                 710                 715                 720
Gln Ala Met Gly Gly His Gly Val Ala Leu Gln Val Arg Glu Ala
            725                 730                 735
Ser Gln Glu Ser Lys Leu Leu Trp Val Ile Arg Glu Asp Gln Gly Ser
            740                 745                 750
Glu Trp Lys His Gly Arg Ile Ile Leu Pro Ser Tyr Asp Met Glu Tyr
            755                 760                 765
Gln Ile Val Phe Glu Gly Val Ile Gly Lys Gly Arg Ser Gly Glu Ile
            770                 775                 780
Ser Gly Asp Asp Ile Arg Ile Ser Thr Asp Val Pro Leu Glu Asn Cys
785                 790                 795                 800
Met Glu Pro Ile Ser Ala Phe Ala Gly Glu Asp Phe Lys Val Asp Ile
            805                 810                 815
```

```
Pro Glu Thr His Gly Gly Glu Gly Tyr Glu Asp Glu Ile Asp Asp Glu
            820                 825                 830

Tyr Glu Gly Asp Trp Ser Asn Ser Ser Ser Thr Ser Gly Ala Gly
            835                 840                 845

Asp Pro Ser Ser Gly Lys Glu Lys Ser Trp Leu Tyr Thr Leu Asp Pro
        850                 855                 860

Ile Leu Ile Thr Ile Ala Met Ser Ser Leu Gly Val Leu Leu Gly
865                 870                 875                 880

Ala Thr Cys Ala Gly Leu Leu Tyr Cys Thr Cys Ser Tyr Ser Gly
                885                 890                 895

Leu Ser Ser Arg Ser Cys Thr Thr Leu Glu Asn Tyr Asn Phe Glu Leu
            900                 905                 910

Tyr Asp Gly Leu Lys His Lys Val Lys Ile Asn His Gln Lys Cys Cys
        915                 920                 925

Ser Glu Ala
    930

(2) INFORMATION FOR SEQ ID NO:17:

(i) SEQUENCE CHARACTERISTICS:
        (A) LENGTH: 2730 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:17:

ATGGATATGT TCCTCTCAC CTGGGTTTTC TTAGCCCTCT ACTTTTCAAG ACACCAAGTG      60

AGAGGCCAAC CAGACCCACC GTGCGGAGGT CGTTTGAATT CCAAAGATGC TGGCTATATC    120

ACCTCTCCCG GTTACCCCCA GGACTACCCC TCCCACCAGA ACTGCGAGTG GATTGTTTAC    180

GCCCCCGAAC CCAACCAGAA GATTGTCCTC AACTTCAACC CTCACTTTGA AATCGAGAAG    240

CACGACTGCA AGTATGACTT TATCGAGATT CGGGATGGGG ACAGTGAATC CGCAGACCTC    300

CTGGGCAAAC ACTGTGGGAA CATCGCCCCG CCCACCATCA TCTCCTCGGG CTCCATGCTC    360

TACATCAAGT TCACCTCCGA CTACGCCCGG CAGGGGGCAG GCTTCTCTCT GCGCTACGAG    420

ATCTTCAAGA CAGGCTCTGA AGATTGCTCA AAAAACTTCA CAAGCCCCAA CGGGACCATC    480

GAATCTCCTG GGTTTCCTGA AAGTATCCA CACAACTTGG ACTGCACCTT TACCATCCTG    540

GCCAAACCCA AGATGGAGAT CATCCTGCAG TTCCTGATCT TTGACCTGGA GCATGACCCT    600

TTGCAGGTGG AGAGGGGGA CTGCAAGTAC GATTGGCTGG ACATCTGGGA TGGCATTCCA    660

CATGTTGGCC CCCTGATTGG CAAGTACTGT GGGACCAAAA CACCCTCTGA ACTTCGTTCA    720

TCGACGGGGA TCCTCTCCCT GACCTTTCAC ACGGACATGG CGGTGGCCAA GGATGGCTTC    780

TCTGCGCGTT ACTACCTGGT CCACCAAGAG CCACTAGAGA ACTTTCAGTG CAATGTTCCT    840

CTGGGCATGG AGTCTGGCCG GATTGCTAAT GAACAGATCA GTGCCTCATC TACCTACTCT    900

GATGGGAGGT GGACCCCTCA ACAAAGCCGG CTCCATGGTG ATGACAATGG CTGGACCCCC    960

AACTTGGATT CCAACAAGGA GTATCTCCAG GTGGACCTGC GCTTTTTAAC CATGCTCACG   1020

GCCATCGCAA CACAGGGAGC GATTTCCAGG GAAACACAGA ATGGCTACTA CGTCAAATCC   1080

TACAAGCTGG AAGTCAGCAC TAATGGAGAG GACTGGATGG TGTACCGGCA TGGCAAAAAC   1140

CACAAGGTAT TCAAGCCAA CAACGATGCA ACTGAGGTGG TTCTGAACAA GCTCCACGCT   1200

CCACTGCTGA CAAGGTTTGT TAGAATCCGC CCTCAGACCT GGCACTCAGG TATCGCCCTC   1260
```

```
CGGCTGGAGC TCTTCGGCTG CCGGGTCACA GATGCTCCCT GCTCCAACAT GCTGGGGATG    1320

CTCTCAGGCC TCATTGCAGA CTCCCAGATC TCCGCCTCTT CCACCCAGGA ATACCTCTGG    1380

AGCCCCAGTG CAGCCCGCCT GGTCAGCAGC CGCTCGGGCT GGTTCCCTCG AATCCCTCAG    1440

GCCCAGCCCG GTGAGGAGTG GCTTCAGGTA GATCTGGGAA CACCCAAGAC AGTGAAAGGT    1500

GTCATCATCC AGGGAGCCCG CGGAGGAGAC AGTATCACTG CTGTGGAAGC CAGAGCATTT    1560

GTGCGCAAGT TCAAAGTCTC CTACAGCCTA AACGGCAAGG ACTGGGAATA CATTCAGGAC    1620

CCCAGGACCC AGCAGCCAAA GCTGTTCGAA GGGAACATGC ACTATGACAC CCCTGACATC    1680

CGAAGGTTTG ACCCCATTCC GGCACAGTAT GTGCGGGTAT ACCCGGAGAG GTGGTCGCCG    1740

GCGGGGATTG GGATGCGGCT GGAGGTGCTG GGCTGTGACT GGACAGACTC CAAGCCCACG    1800

GTAAAAACGC TGGGACCCAC TGTGAAGAGC GAAGAGACAA CCACCCCCTA CCCCACCGAA    1860

GAGGAGGCCA CAGAGTGTGG GGAGAACTGC AGCTTTGAGG ATGACAAAGA TTTGCAGCTC    1920

CCTTCGGGAT TCAATTGCAA CTTCGATTTC CTCGAGGAGC CCTGTGGTTG GATGTATGAC    1980

CATGCCAAGT GGCTCCGGAC CACCTGGGCC AGCAGCTCCA GCCCAAACGA CCGGACGTTT    2040

CCAGATGACA GGAATTTCTT GCGGCTGCAG AGTGACAGCC AGAGAGAGGG CCAGTATGCC    2100

CGGCTCATCA GCCCCCCTGT CCACCTGCCC CGAAGCCCGG TGTGCATGGA GTTCCAGTAC    2160

CAGGCCACGG GCGGCCGCGG GGTGGCGCTG CAGGTGGTGC GGGAAGCCAG CCAGGAGAGC    2220

AAGTTGCTGT GGGTCATCCG TGAGGACCAG GGCGGCGAGT GGAAGCACGG GCGGATCATC    2280

CTGCCCAGCT ACGACATGGA GTACCAGATT GTGTTCGAGG GAGTGATAGG GAAAGGACGT    2340

TCCGGAGAGA TTGCCATTGA TGACATTCGG ATAAGCACTG ATGTCCCACT GGAGAACTGC    2400

ATGGAACCCA TCTCGGCTTT TGCAGATGAA TACGAGGTGG ACTGGAGCAA TTCTTCTTCT    2460

GCAACCTCAG GGTCTGGCGC CCCCTCGACC GACAAAGAAA AGAGCTGGCT GTACACCCTG    2520

GATCCCATCC TCATCACCAT CATCGCCATG AGCTCACTGG GCGTCCTCCT GGGGGCCACC    2580

TGTGCAGGCC TCCTGCTCTA CTGCACCTGT TCCTACTCGG GCCTGAGCTC CCGAAGCTGC    2640

ACCACACTGG AGAACTACAA CTTCGAGCTC TACGATGGCC TTAAGCACAA GGTCAAGATG    2700

AACCACCAAA AGTGCTGCTC CGAGGCATGA                                   2730
```

(2) INFORMATION FOR SEQ ID NO:18:

(i) SEQUENCE CHARACTERISTICS:
        (A) LENGTH: 909 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:18:

```
Met Asp Met Phe Pro Leu Thr Trp Val Phe Leu Ala Leu Tyr Phe Ser
1               5                   10                  15

Arg His Gln Val Arg Gly Gln Pro Asp Pro Cys Gly Gly Arg Leu
            20                  25                  30

Asn Ser Lys Asp Ala Gly Tyr Ile Thr Ser Pro Gly Tyr Pro Gln Asp
            35                  40                  45

Tyr Pro Ser His Gln Asn Cys Glu Trp Ile Val Tyr Ala Pro Glu Pro
        50                  55                  60

Asn Gln Lys Ile Val Leu Asn Phe Asn Pro His Phe Glu Ile Glu Lys
65                  70                  75                  80
```

-continued

```
His Asp Cys Lys Tyr Asp Phe Ile Glu Ile Arg Asp Gly Asp Ser Glu
                85                  90                  95

Ser Ala Asp Leu Leu Gly Lys His Cys Gly Asn Ile Ala Pro Pro Thr
            100                 105                 110

Ile Ile Ser Ser Gly Ser Met Leu Tyr Ile Lys Phe Thr Ser Asp Tyr
        115                 120                 125

Ala Arg Gln Gly Ala Gly Phe Ser Leu Arg Tyr Glu Ile Phe Lys Thr
    130                 135                 140

Gly Ser Glu Asp Cys Ser Lys Asn Phe Thr Ser Pro Asn Gly Thr Ile
145                 150                 155                 160

Glu Ser Pro Gly Phe Pro Glu Lys Tyr Pro His Asn Leu Asp Cys Thr
                165                 170                 175

Phe Thr Ile Leu Ala Lys Pro Lys Met Glu Ile Ile Leu Gln Phe Leu
            180                 185                 190

Ile Phe Asp Leu Glu His Asp Pro Leu Gln Val Gly Glu Gly Asp Cys
        195                 200                 205

Lys Tyr Asp Trp Leu Asp Ile Trp Asp Gly Ile Pro His Val Gly Pro
    210                 215                 220

Leu Ile Gly Lys Tyr Cys Gly Thr Lys Thr Pro Ser Glu Leu Arg Ser
225                 230                 235                 240

Ser Thr Gly Ile Leu Ser Leu Thr Phe His Thr Asp Met Ala Val Ala
                245                 250                 255

Lys Asp Gly Phe Ser Ala Arg Tyr Tyr Leu Val His Gln Glu Pro Leu
            260                 265                 270

Glu Asn Phe Gln Cys Asn Val Pro Leu Gly Met Glu Ser Gly Arg Ile
        275                 280                 285

Ala Asn Glu Gln Ile Ser Ala Ser Ser Thr Tyr Ser Asp Gly Arg Trp
    290                 295                 300

Thr Pro Gln Gln Ser Arg Leu His Gly Asp Asp Asn Gly Trp Thr Pro
305                 310                 315                 320

Asn Leu Asp Ser Asn Lys Glu Tyr Leu Gln Val Asp Leu Arg Phe Leu
                325                 330                 335

Thr Met Leu Thr Ala Ile Ala Thr Gln Gly Ala Ile Ser Arg Glu Thr
            340                 345                 350

Gln Asn Gly Tyr Tyr Val Lys Ser Tyr Lys Leu Glu Val Ser Thr Asn
        355                 360                 365

Gly Glu Asp Trp Met Val Tyr Arg His Gly Lys Asn His Lys Val Phe
    370                 375                 380

Gln Ala Asn Asn Asp Ala Thr Glu Val Val Leu Asn Lys Leu His Ala
385                 390                 395                 400

Pro Leu Leu Thr Arg Phe Val Arg Ile Arg Pro Gln Thr Trp His Ser
                405                 410                 415

Gly Ile Ala Leu Arg Leu Glu Leu Phe Gly Cys Arg Val Thr Asp Ala
            420                 425                 430

Pro Cys Ser Asn Met Leu Gly Met Leu Ser Gly Leu Ile Ala Asp Ser
        435                 440                 445

Gln Ile Ser Ala Ser Ser Thr Gln Glu Tyr Leu Trp Ser Pro Ser Ala
    450                 455                 460

Ala Arg Leu Val Ser Ser Arg Ser Gly Trp Phe Pro Arg Ile Pro Gln
465                 470                 475                 480

Ala Gln Pro Gly Glu Glu Trp Leu Gln Val Asp Leu Gly Thr Pro Lys
                485                 490                 495
```

-continued

Thr Val Lys Gly Val Ile Ile Gln Gly Ala Arg Gly Gly Asp Ser Ile
            500                 505                 510

Thr Ala Val Glu Ala Arg Ala Phe Val Arg Lys Phe Lys Val Ser Tyr
            515                 520                 525

Ser Leu Asn Gly Lys Asp Trp Glu Tyr Ile Gln Asp Pro Arg Thr Gln
            530                 535                 540

Gln Pro Lys Leu Phe Glu Gly Asn Met His Tyr Asp Thr Pro Asp Ile
545                 550                 555                 560

Arg Arg Phe Asp Pro Ile Pro Ala Gln Tyr Val Arg Val Tyr Pro Glu
                565                 570                 575

Arg Trp Ser Pro Ala Gly Ile Gly Met Arg Leu Glu Val Leu Gly Cys
            580                 585                 590

Asp Trp Thr Asp Ser Lys Pro Thr Val Lys Thr Leu Gly Pro Thr Val
            595                 600                 605

Lys Ser Glu Glu Thr Thr Thr Pro Tyr Pro Thr Glu Glu Glu Ala Thr
            610                 615                 620

Glu Cys Gly Glu Asn Cys Ser Phe Glu Asp Asp Lys Asp Leu Gln Leu
625                 630                 635                 640

Pro Ser Gly Phe Asn Cys Asn Phe Asp Phe Leu Glu Glu Pro Cys Gly
                645                 650                 655

Trp Met Tyr Asp His Ala Lys Trp Leu Arg Thr Thr Trp Ala Ser Ser
            660                 665                 670

Ser Ser Pro Asn Asp Arg Thr Phe Pro Asp Asp Arg Asn Phe Leu Arg
            675                 680                 685

Leu Gln Ser Asp Ser Gln Arg Glu Gly Gln Tyr Ala Arg Leu Ile Ser
            690                 695                 700

Pro Pro Val His Leu Pro Arg Ser Pro Val Cys Met Glu Phe Gln Tyr
705                 710                 715                 720

Gln Ala Thr Gly Gly Arg Gly Val Ala Leu Gln Val Val Arg Glu Ala
                725                 730                 735

Ser Gln Glu Ser Lys Leu Leu Trp Val Ile Arg Glu Asp Gln Gly Gly
            740                 745                 750

Glu Trp Lys His Gly Arg Ile Ile Leu Pro Ser Tyr Asp Met Glu Tyr
            755                 760                 765

Gln Ile Val Phe Glu Gly Val Ile Gly Lys Gly Arg Ser Gly Glu Ile
            770                 775                 780

Ala Ile Asp Asp Ile Arg Ile Ser Thr Asp Val Pro Leu Glu Asn Cys
785                 790                 795                 800

Met Glu Pro Ile Ser Ala Phe Ala Asp Glu Tyr Glu Val Asp Trp Ser
                805                 810                 815

Asn Ser Ser Ser Ala Thr Ser Gly Ser Gly Ala Pro Ser Thr Asp Lys
            820                 825                 830

Glu Lys Ser Trp Leu Tyr Thr Leu Asp Pro Ile Leu Ile Thr Ile Ile
            835                 840                 845

Ala Met Ser Ser Leu Gly Val Leu Leu Gly Ala Thr Cys Ala Gly Leu
850                 855                 860

Leu Leu Tyr Cys Thr Cys Ser Tyr Ser Gly Leu Ser Ser Arg Ser Cys
865                 870                 875                 880

Thr Thr Leu Glu Asn Tyr Asn Phe Glu Leu Tyr Asp Gly Leu Lys His
                885                 890                 895

Lys Val Lys Met Asn His Gln Lys Cys Cys Ser Glu Ala
            900                 905

(2) INFORMATION FOR SEQ ID NO:19:

(i) SEQUENCE CHARACTERISTICS:
        (A) LENGTH: 2781 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:19:

```
ATGGATATGT TCCTCTCAC CTGGGTTTTC TTAGCCCTCT ACTTTTCAAG ACACCAAGTG      60

AGAGGCCAAC CAGACCCACC GTGCGGAGGT CGTTTGAATT CCAAAGATGC TGGCTATATC     120

ACCTCTCCCG GTTACCCCCA GGACTACCCC TCCCACCAGA ACTGCGAGTG GATTGTTTAC     180

GCCCCCGAAC CCAACCAGAA GATTGTCCTC AACTTCAACC CTCACTTTGA AATCGAGAAG     240

CACGACTGCA AGTATGACTT TATCGAGATT CGGGATGGGG ACAGTGAATC CGCAGACCTC     300

CTGGGCAAAC ACTGTGGGAA CATCGCCCCG CCCACCATCA TCTCCTCGGG CTCCATGCTC     360

TACATCAAGT TCACCTCCGA CTACGCCCGG CAGGGGCAG GCTTCTCTCT GCGCTACGAG      420

ATCTTCAAGA CAGGCTCTGA AGATTGCTCA AAAAACTTCA CAAGCCCCAA CGGGACCATC     480

GAATCTCCTG GGTTTCCTGA GAAGTATCCA CACAACTTGG ACTGCACCTT TACCATCCTG     540

GCCAAACCCA AGATGGAGAT CATCCTGCAG TTCCTGATCT TTGACCTGGA GCATGACCCT     600

TTGCAGGTGG GAGAGGGGA CTGCAAGTAC GATTGGCTGG ACATCTGGGA TGGCATTCCA      660

CATGTTGGCC CCCTGATTGG CAAGTACTGT GGGACCAAAA CACCCTCTGA ACTTCGTTCA     720

TCGACGGGGA TCCTCTCCCT GACCTTTCAC ACGGACATGG CGGTGGCCAA GGATGGCTTC     780

TCTGCGCGTT ACTACCTGGT CCACCAAGAG CCACTAGAGA ACTTTCAGTG CAATGTTCCT     840

CTGGGCATGG AGTCTGGCCG GATTGCTAAT GAACAGATCA GTGCCTCATC TACCTACTCT     900

GATGGGAGGT GGACCCCTCA ACAAAGCCGG CTCCATGGTG ATGACAATGG CTGGACCCCC     960

AACTTGGATT CCAACAAGGA GTATCTCCAG GTGGACCTGC GCTTTTTAAC CATGCTCACG     1020

GCCATCGCAA CACAGGGAGC GATTTCCAGG GAAACACAGA ATGGCTACTA CGTCAAATCC     1080

TACAAGCTGG AAGTCAGCAC TAATGGAGAG GACTGGATGG TGTACCGGCA TGGCAAAAAC     1140

CACAAGGTAT TCAAGCCAA CAACGATGCA ACTGAGGTGG TTCTGAACAA GCTCCACGCT      1200

CCACTGCTGA CAAGGTTTGT TAGAATCCGC CCTCAGACCT GGCACTCAGG TATCGCCCTC     1260

CGGCTGGAGC TCTTCGGCTG CCGGGTCACA GATGCTCCCT GCTCCAACAT GCTGGGGATG     1320

CTCTCAGGCC TCATTGCAGA CTCCCAGATC TCCGCCTCTT CCACCCAGGA ATACCTCTGG     1380

AGCCCCAGTG CAGCCCGCCT GGTCAGCAGC CGCTCGGGCT GGTTCCCTCG AATCCCTCAG     1440

GCCCAGCCCG GTGAGGAGTG GCTTCAGGTA GATCTGGGAA CACCCAAGAC AGTGAAAGGT     1500

GTCATCATCC AGGGAGCCCG CGGAGGAGAC AGTATCACTG CTGTGGAAGC CAGAGCATTT     1560

GTGCGCAAGT TCAAAGTCTC CTACAGCCTA AACGGCAAGG ACTGGGAATA CATTCAGGAC     1620

CCCAGGACCC AGCAGCCAAA GCTGTTCGAA GGGAACATGC ACTATGACAC CCCTGACATC     1680

CGAAGGTTTG ACCCCATTCC GGCACAGTAT GTGCGGGTAT ACCGGAGAG GTGGTCGCCG      1740

GCGGGGATTG GGATGCGGCT GGAGGTGCTG GGCTGTGACT GGACAGACTC CAAGCCCACG     1800

GTAAAAACGC TGGACCCCAC TGTGAAGAGC AAGAGACAA CCACCCCCTA CCCCACCGAA      1860

GAGGAGGCCA CAGAGTGTGG GGAGAACTGC AGCTTTGAGG ATGACAAAGA TTTGCAGCTC     1920

CCTTCGGGAT TCAATTGCAA CTTCGATTTC CTCGAGGAGC CCTGTGGTTG GATGTATGAC     1980
```

```
CATGCCAAGT GGCTCCGGAC CACCTGGGCC AGCAGCTCCA GCCCAAACGA CCGGACGTTT    2040

CCAGATGACA GGAATTTCTT GCGGCTGCAG AGTGACAGCC AGAGAGAGGG CCAGTATGCC    2100

CGGCTCATCA GCCCCCCTGT CCACCTGCCC CGAAGCCCGG TGTGCATGGA GTTCCAGTAC    2160

CAGGCCACGG GCGGCCGCGG GGTGGCGCTG CAGGTGGTGC GGGAAGCCAG CCAGGAGAGC    2220

AAGTTGCTGT GGGTCATCCG TGAGGACCAG GGCGGCGAGT GGAAGCACGG GCGGATCATC    2280

CTGCCCAGCT ACGACATGGA GTACCAGATT GTGTTCGAGG GAGTGATAGG GAAAGGACGT    2340

TCCGGAGAGA TTGCCATTGA TGACATTCGG ATAAGCACTG ATGTCCCACT GGAGAACTGC    2400

ATGGAACCCA TCTCGGCTTT TGCAGTGGAC ATCCCAGAAA TACATGAGAG GAAGGATAT    2460

GAAGATGAAA TTGATGATGA ATACGAGGTG GACTGGAGCA ATTCTTCTTC TGCAACCTCA    2520

GGGTCTGGCG CCCCCTCGAC CGACAAAGAA AAGAGCTGGC TGTACACCCT GGATCCCATC    2580

CTCATCACCA TCATCGCCAT GAGCTCACTG GGCGTCCTCC TGGGGGCCAC CTGTGCAGGC    2640

CTCCTGCTCT ACTGCACCTG TTCCTACTCG GGCCTGAGCT CCCGAAGCTG CACCACACTG    2700

GAGAACTACA ACTTCGAGCT CTACGATGGC CTTAAGCACA AGGTCAAGAT GAACCACCAA    2760

AAGTGCTGCT CCGAGGCATG A                                              2781
```

(2) INFORMATION FOR SEQ ID NO:20:

(i) SEQUENCE CHARACTERISTICS:
        (A) LENGTH: 926 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:20:

```
Met Asp Met Phe Pro Leu Thr Trp Val Phe Leu Ala Leu Tyr Phe Ser
1               5                   10                  15

Arg His Gln Val Arg Gly Gln Pro Asp Pro Cys Gly Gly Arg Leu
                20                  25                  30

Asn Ser Lys Asp Ala Gly Tyr Ile Thr Ser Pro Gly Tyr Pro Gln Asp
            35                  40                  45

Tyr Pro Ser His Gln Asn Cys Glu Trp Ile Val Tyr Ala Pro Glu Pro
        50                  55                  60

Asn Gln Lys Ile Val Leu Asn Phe Asn Pro His Phe Glu Ile Glu Lys
65                  70                  75                  80

His Asp Cys Lys Tyr Asp Phe Ile Glu Ile Arg Asp Gly Asp Ser Glu
                85                  90                  95

Ser Ala Asp Leu Leu Gly Lys His Cys Gly Asn Ile Ala Pro Pro Thr
                100                 105                 110

Ile Ile Ser Ser Gly Ser Met Leu Tyr Ile Lys Phe Thr Ser Asp Tyr
            115                 120                 125

Ala Arg Gln Gly Ala Gly Phe Ser Leu Arg Tyr Glu Ile Phe Lys Thr
        130                 135                 140

Gly Ser Glu Asp Cys Ser Lys Asn Phe Thr Ser Pro Asn Gly Thr Ile
145                 150                 155                 160

Glu Ser Pro Gly Phe Pro Glu Lys Tyr Pro His Asn Leu Asp Cys Thr
                165                 170                 175

Phe Thr Ile Leu Ala Lys Pro Lys Met Glu Ile Ile Leu Gln Phe Leu
                180                 185                 190
```

-continued

```
Ile Phe Asp Leu Glu His Asp Pro Leu Gln Val Gly Glu Gly Asp Cys
            195                 200                 205

Lys Tyr Asp Trp Leu Asp Ile Trp Asp Gly Ile Pro His Val Gly Pro
210                 215                 220

Leu Ile Gly Lys Tyr Cys Gly Thr Lys Thr Pro Ser Glu Leu Arg Ser
225                 230                 235                 240

Ser Thr Gly Ile Leu Ser Leu Thr Phe His Thr Asp Met Ala Val Ala
                245                 250                 255

Lys Asp Gly Phe Ser Ala Arg Tyr Tyr Leu Val His Gln Glu Pro Leu
            260                 265                 270

Glu Asn Phe Gln Cys Asn Val Pro Leu Gly Met Glu Ser Gly Arg Ile
        275                 280                 285

Ala Asn Glu Gln Ile Ser Ala Ser Ser Thr Tyr Ser Asp Gly Arg Trp
    290                 295                 300

Thr Pro Gln Gln Ser Arg Leu His Gly Asp Asp Asn Gly Trp Thr Pro
305                 310                 315                 320

Asn Leu Asp Ser Asn Lys Glu Tyr Leu Gln Val Asp Leu Arg Phe Leu
                325                 330                 335

Thr Met Leu Thr Ala Ile Ala Thr Gln Gly Ala Ile Ser Arg Glu Thr
            340                 345                 350

Gln Asn Gly Tyr Tyr Val Lys Ser Tyr Lys Leu Glu Val Ser Thr Asn
        355                 360                 365

Gly Glu Asp Trp Met Val Tyr Arg His Gly Lys Asn His Lys Val Phe
    370                 375                 380

Gln Ala Asn Asn Asp Ala Thr Glu Val Val Leu Asn Lys Leu His Ala
385                 390                 395                 400

Pro Leu Leu Thr Arg Phe Val Arg Ile Arg Pro Gln Thr Trp His Ser
                405                 410                 415

Gly Ile Ala Leu Arg Leu Glu Leu Phe Gly Cys Arg Val Thr Asp Ala
            420                 425                 430

Pro Cys Ser Asn Met Leu Gly Met Leu Ser Gly Leu Ile Ala Asp Ser
        435                 440                 445

Gln Ile Ser Ala Ser Ser Thr Gln Glu Tyr Leu Trp Ser Pro Ser Ala
    450                 455                 460

Ala Arg Leu Val Ser Ser Arg Ser Gly Trp Phe Pro Arg Ile Pro Gln
465                 470                 475                 480

Ala Gln Pro Gly Glu Glu Trp Leu Gln Val Asp Leu Gly Thr Pro Lys
                485                 490                 495

Thr Val Lys Gly Val Ile Ile Gln Gly Ala Arg Gly Gly Asp Ser Ile
            500                 505                 510

Thr Ala Val Glu Ala Arg Ala Phe Val Arg Lys Phe Lys Val Ser Tyr
        515                 520                 525

Ser Leu Asn Gly Lys Asp Trp Glu Tyr Ile Gln Asp Pro Arg Thr Gln
    530                 535                 540

Gln Pro Lys Leu Phe Glu Gly Asn Met His Tyr Asp Thr Pro Asp Ile
545                 550                 555                 560

Arg Arg Phe Asp Pro Ile Pro Ala Gln Tyr Val Arg Val Tyr Pro Glu
                565                 570                 575

Arg Trp Ser Pro Ala Gly Ile Gly Met Arg Leu Glu Val Leu Gly Cys
            580                 585                 590

Asp Trp Thr Asp Ser Lys Pro Thr Val Lys Thr Leu Gly Pro Thr Val
        595                 600                 605
```

-continued

```
Lys Ser Glu Glu Thr Thr Thr Pro Tyr Pro Thr Glu Glu Ala Thr
    610             615                 620
Glu Cys Gly Glu Asn Cys Ser Phe Glu Asp Asp Lys Asp Leu Gln Leu
625                 630                 635                 640
Pro Ser Gly Phe Asn Cys Asn Phe Asp Phe Leu Glu Glu Pro Cys Gly
                645                 650                 655
Trp Met Tyr Asp His Ala Lys Trp Leu Arg Thr Thr Trp Ala Ser Ser
            660                 665                 670
Ser Ser Pro Asn Asp Arg Thr Phe Pro Asp Asp Arg Asn Phe Leu Arg
            675                 680                 685
Leu Gln Ser Asp Ser Gln Arg Glu Gly Gln Tyr Ala Arg Leu Ile Ser
    690                 695                 700
Pro Pro Val His Leu Pro Arg Ser Pro Val Cys Met Glu Phe Gln Tyr
705                 710                 715                 720
Gln Ala Thr Gly Gly Arg Gly Val Ala Leu Gln Val Val Arg Glu Ala
                725                 730                 735
Ser Gln Glu Ser Lys Leu Leu Trp Val Ile Arg Glu Asp Gln Gly Gly
            740                 745                 750
Glu Trp Lys His Gly Arg Ile Ile Leu Pro Ser Tyr Asp Met Glu Tyr
        755                 760                 765
Gln Ile Val Phe Glu Gly Val Ile Gly Lys Gly Arg Ser Gly Glu Ile
    770                 775                 780
Ala Ile Asp Asp Ile Arg Ile Ser Thr Asp Val Pro Leu Glu Asn Cys
785                 790                 795                 800
Met Glu Pro Ile Ser Ala Phe Ala Val Asp Ile Pro Glu Ile His Glu
                805                 810                 815
Arg Glu Gly Tyr Glu Asp Glu Ile Asp Asp Glu Tyr Glu Val Asp Trp
            820                 825                 830
Ser Asn Ser Ser Ser Ala Thr Ser Gly Ser Gly Ala Pro Ser Thr Asp
            835                 840                 845
Lys Glu Lys Ser Trp Leu Tyr Thr Leu Asp Pro Ile Leu Ile Thr Ile
    850                 855                 860
Ile Ala Met Ser Ser Leu Gly Val Leu Leu Gly Ala Thr Cys Ala Gly
865                 870                 875                 880
Leu Leu Leu Tyr Cys Thr Cys Ser Tyr Ser Gly Leu Ser Ser Arg Ser
                885                 890                 895
Cys Thr Thr Leu Glu Asn Tyr Asn Phe Glu Leu Tyr Asp Gly Leu Lys
            900                 905                 910
His Lys Val Lys Met Asn His Gln Lys Cys Cys Ser Glu Ala
    915                 920                 925
```

(2) INFORMATION FOR SEQ ID NO:21:

(i) SEQUENCE CHARACTERISTICS:
        (A) LENGTH: 4765 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:21:

```
AAACTGGAGC TCCACCGCGG TGGCGGCCGC CCGGGCAGGT CTAGAATTCA GCGGCCGCTG      60
AATTCTATCC AGCGGTCGGT GCCTCTGCCC GCGTGTGTGT CCCGGGTGCC GGGGGACCTG     120
TGTCAGTTAG CGCTTCTGAG ATCACACAGC TGCCTAGGGG CCGTGTGATG CCCAGGGCAA     180
```

-continued

```
TTCTTGGCTT TGATTTTTAT TATTATTACT ATTATTTTGC GTTCAGCTTT CGGGAAACCC    240

TCGTGATGTT GTAGGATAAA GGAAATGACA CTTTGAGGAA CTGGAGAGAA CATACACGCG    300

TTTGGGTTTG AAGAGGAAAC CGGTCTCCGC TTCCTTAGCT TGCTCCCTCT TTGCTGATTT    360

CAAGAGCTAT CTCCTATGAG GTGGAGATAT TCCAGCAAGA ATAAAGGTGA AGACAGACTG    420

ACTGCCAGGA CCCAGGAGGA AAACGTTGAT CGTTAGAGAC CTTTGCAGAA GACACCACCA    480

GGAGGAAAAT TAGAGAGGAA AAACACAAAG ACATAATTAT AGGAGATCCC ACAAACCTAG    540

CCCGGGAGAG AGCCTCTCTG TCAAAAATGG ATATGTTTCC TCTTACCTGG GTTTTCTTAG    600

CTCTGTACTT TTCAGGACAC GAAGTGAGAA GCCAGCAAGA TCCACCCTGC GGAGGTCGGC    660

CGAATTCCAA AGATGCTGGC TACATCACTT CCCCAGGCTA CCCCCAGGAC TATCCCTCCC    720

ACCAGAACTG TGAGTGGATT GTCTACGCCC CCGAACCCAA CCAGAAGATT GTTCTCAACT    780

TCAACCCTCA CTTTGAAATC GAGAAACACG ACTGCAAGTA TGACTTCATT GAGATTCGGG    840

ATGGGGACAG TGAGTCAGCT GACCTCCTGG GCAAGCACTG TGGGAACATC GCCCCGCCCA    900

CCATCATCTC CTCAGGCTCC GTGTTATACA TCAAGTTCAC CTCAGACTAC GCCCGGCAGG    960

GGGCAGGTTT CTCTCTACGC TATGAGATCT TCAAAACAGG CTCTGAAGAT TGTTCCAAGA   1020

ACTTTACAAG CCCCAATGGG ACCATTGAAT CTCCAGGGTT TCCAGAGAAG TATCCACACA   1080

ATCTGGACTG TACCTTCACC ATCCTGGCCA AACCCAGGAT GGAGATCATC CTACAGTTCC   1140

TGACCTTTGA CCTGGAGCAT GACCCTCTAC AAGTGGGGGA AGGAGACTGT AAATATGACT   1200

GGCTGGACAT CTGGGATGGC ATTCCACATG TTGGACCTCT GATTGGCAAG TACTGTGGGA   1260

CGAAAACACC CTCCAAACTC CGCTCGTCCA CGGGGATCCT CTCCTTGACC TTTCACACGG   1320

ACATGGCAGT GGCCAAGGAT GGCTTCTCCG CACGTTACTA TTTGATCCAC CAGGAGCCAC   1380

CTGAGAATTT TCAGTGCAAT GTCCCTTTGG GAATGGAGTC TGGCCGGATT GCTAATGAAC   1440

AGATCAGTGC CTCCTCCACC TTCTCTGATG GGAGGTGGAC TCCTCAACAG AGCCGGCTCC   1500

ATGGTGATGA CAATGGCTGG ACACCCAATT TGGATTCCAA CAAGGAGTAT CTCCAGGTGG   1560

ACCTGCGCTT CCTAACCATG CTCACAGCCA TTGCAACACA GGGAGCCATT TCCAGGGAAA   1620

CCCAGAAAGG CTACTACGTC AAATCGTACA AGCTGGAAGT CAGCACAAAT GGTGAAGATT   1680

GGATGGTCTA CCGGCATGGC AAAAACCACA AGATATTCCA AGCGAACAAT GATGCGACCG   1740

AGGTGGTGCT AAACAAGCTC CACATGCCAC TGCTGACTCG GTTCATCAGG ATCCGCCCGC   1800

AGACGTGGCA TTTGGGCATT GCCCTTCGCC TGGAGCTCTT TGGCTGCCGG GTCACAGATG   1860

CACCCTGCTC CAACATGCTG GGGATGCTCT CGGGCCTCAT TGCTGATACC CAGATCTCTG   1920

CCTCCTCCAC CCGAGAGTAC CTCTGGAGCC CCAGTGCTGC CCGCCTGGTT AGTAGCCGCT   1980

CTGGCTGGTT TCCTCGGAAC CCTCAAGCCC AGCCAGGTGA AGAATGGCTT CAGGTAGACC   2040

TGGGACACC CAAGACAGTG AAAGGGGTCA TCATCCAGGG AGCCCGAGGA GGAGACAGCA    2100

TCACTGCCGT GGAAGCCAGG GCGTTTGTAC GCAAGTTCAA AGTCTCCTAC AGCCTAAATG   2160

GCAAGGACTG GGAATATATC CAGGACCCCA GGACTCAGCA GACAAAGCTG TTTGAAGGGA   2220

ACATGCACTA TGACACCCCT GACATCCGAA GGTTCGATCC TGTTCCAGCG CAGTATGTGC   2280

GGGTGTACCC AGAGAGGTGG TCGCCAGCAG GCATCGGGAT GAGGCTGGAG GTGCTGGGCT   2340

GTGACTGGAC AGACTCAAAG CCCACAGTGG AGACGCTGGG ACCCACCGTG AAGAGTGAAG   2400

AGACTACCAC CCCATATCCC ATGGATGAGG ATGCCACCGA GTGTGGGAA AACTGCAGCT    2460

TTGAGGATGA CAAAGATTTG CAACTTCCTT CAGGATTCAA CTGCAACTTT GATTTTCCGG   2520
```

```
AAGAGACCTG TGGTTGGGTG TACGACCATG CCAAGTGGCT CCGGAGCACG TGGATCAGCA    2580

GCGCTAACCC CAATGACAGA ACATTTCCAG ATGACAAGAA CTTCTTGAAA CTGCAGAGTG    2640

ATGGCCGACG AGAGGGCCAG TACGGGCGGC TCATCAGCCC ACCGGTGCAC CTGCCCCGAA    2700

GCCCTGTGTG CATGGAGTTC CAGTACCAAG CCATGGGCGG CCACGGGGTG GCACTGCAGG    2760

TGGTTCGGGA AGCCAGCCAG GAAAGCAAAC TCCTTTGGGT CATCCGTGAG GACCAGGGCA    2820

GCGAGTGGAA GCACGGGCGC ATTATCCTGC CCAGCTATGA CATGGAGTAT CAGATCGTGT    2880

TCGAGGGAGT GATAGGGAAG GGACGATCGG GAGAGATTTC CATCGATGAC ATTCGGATAA    2940

GCACTGATGT CCCACTGGAG AACTGCATGG AACCCATATC AGCTTTTGCA GGGGGCACCC    3000

TCCCGCCAGG GACCGAGCCC ACAGTGGACA CGGTGCCCGT GCAGCCCATC CCAGCCTACT    3060

GGTATTACGT TATGGCGGCC GGGGGCGCCG TGCTGGTGCT GGCCTCCGTC GTCCTGGCCC    3120

TGGTGCTCCA CTACCACCGG TTCCGCTATG CGGCCAAGAA GACCGATCAC TCCATCACCT    3180

ACAAAACCTC CCACTACACC AACGGGGCCC CTCTGGCGGT CGAGCCCACC CTAACCATTA    3240

AGCTAGAGCA AGAGCGGGGC TCGCACTGCT GAGGGCCGAA GCAGGAACAG CGCCCCCCCA    3300

AAAAAAACCC AAGAAAGACT GCAAACACGT TGCCTCGATT TTGCACTTTT TTTCTCCTCG    3360

CCTAGTCTCT GTGTGAACCC TCAGACATCT CTCTCCAGGG TCCCCAACCC TGAGCGCTCT    3420

CATGTACCCC ACACCATTCT CTGTGGTTCT TGGTTCCGGT TTCTCTTTGC TCTGATATTG    3480

TTTGTTTTTA ATCATTATTT TTTTTCCTTT TCTTCTTTCC TTTTAATCTT CTCTCTTTTA    3540

TTCCTTTCTC CCCTCCCCGC CCCGCCTTTT TCTAATGATT TTAAACCAAC TCTAATGCTG    3600

CATCTGGAAT CCCAGAAGAG ACCCGCCCCT AAGCACTTCA CAACCCAAGG CTCTGTTGGT    3660

TTTGTTCCAG AGACAGGCCC TGTTGTTTTC TCCCCTTGCC TTATCCCATC CCTCCTCTCC    3720

TGGGCAGGCT GCCAGGTGTC TTGAGGGGAG CCTGGTCCTG TATGTATGTA CACAGTACAC    3780

TCCCATGTGA AGAGGTGTGT GTGTGTGTGT GTGTGTGTGT GTATTTTCGA GGGAGAGACT    3840

GATTCACTGT GGAAGGGGGG GAGTGTGGGT GTGTGTAGAG AGGGGCCCCT TCCCTCTTAT    3900

GTTGCTTCTT CTGGGGTACT TTTCAAGAAA ATAATATACT GTACACATTT TGTTTACTTG    3960

GAGAAGAGAT TGGAGCTTTT TTGTTGCCTT ATCTAGCTCT GGCTGGGTTT CTGTTGGCTG    4020

TCATTGTCAT CTCCAGGTAC CTAGACAAAT AGAGACCATT GGGAATGCAA TGTGGCTTCA    4080

CCCATCCTTA TCCCCATCCC AAGCCACCCA AGACTATGGT TCCTCCAGTG CACTCAGACA    4140

TGACCCCTTT TGTTATGTTT CCTGGTGTCT TTGAAGTCAC AAGATAACAG CCATTGGGTG    4200

CATGGAGTCA TTTCTACTTC CAGCCCTGAA GCAAATGTGT CTCATGTTGC CTTATAAAAA    4260

AAACCGGAAT TCCTGTAGTT GAAGAGTAAG ATTTTGTACG GTACATTTTT AATGACAGCT    4320

TGGATATTGG AATACTCAAC TTTTGTTGTA GCCAATGAGA GGGATATGCC ACTAATGGTA    4380

TCTAAATCAT ACAGTACGTA CTTTAGGATG GGGACAAAAA TCACAACGAT TTATTTATTT    4440

ATTTACTTAG TGTATGTGAG TGCACTGTTG GTGTCTTCAG ACACACCAGA AGATGACTTC    4500

AGATCCGATT ACATATGGGT TGTGAGCCAC CATGTGGTTG CTGGGATTTG AACTCTGGAC    4560

CTCTGGAAGA GCAGTCAGTG CTTGTAACTC TGAGCCATCT TTCTAGCCCC CCCCCCCCCC    4620

CCGCTATCTT TTAGAAATGT AATTTGCCAT ACTTTGAGCA ATGTTCTTGA TGTCATTAGG    4680

ATATTTCACA GATAACTTCA CTTAAGATAA TTAGAGCAAA AAAAAAAAAA AAAAAAAAA    4740

AAAAAAAAAA AAAAAAAAAA AAAAA                                         4765
```

(2) INFORMATION FOR SEQ ID NO:22:

(i) SEQUENCE CHARACTERISTICS:
        (A) LENGTH: 901 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:22:

```
Met Asp Met Phe Pro Leu Thr Trp Val Phe Leu Ala Leu Tyr Phe Ser
1               5                   10                  15

Gly His Glu Val Arg Ser Gln Gln Asp Pro Pro Cys Gly Gly Arg Pro
            20                  25                  30

Asn Ser Lys Asp Ala Gly Tyr Ile Thr Ser Pro Gly Tyr Pro Gln Asp
        35                  40                  45

Tyr Pro Ser His Gln Asn Cys Glu Trp Ile Val Tyr Ala Pro Glu Pro
    50                  55                  60

Asn Gln Lys Ile Val Leu Asn Phe Asn Pro His Phe Glu Ile Glu Lys
65                  70                  75                  80

His Asp Cys Lys Tyr Asp Phe Ile Glu Ile Arg Asp Gly Asp Ser Glu
                85                  90                  95

Ser Ala Asp Leu Leu Gly Lys His Cys Gly Asn Ile Ala Pro Pro Thr
            100                 105                 110

Ile Ile Ser Ser Gly Ser Val Leu Tyr Ile Lys Phe Thr Ser Asp Tyr
        115                 120                 125

Ala Arg Gln Gly Ala Gly Phe Ser Leu Arg Tyr Glu Ile Phe Lys Thr
    130                 135                 140

Gly Ser Glu Asp Cys Ser Lys Asn Phe Thr Ser Pro Asn Gly Thr Ile
145                 150                 155                 160

Glu Ser Pro Gly Phe Pro Glu Lys Tyr Pro His Asn Leu Asp Cys Thr
                165                 170                 175

Phe Thr Ile Leu Ala Lys Pro Arg Met Glu Ile Ile Leu Gln Phe Leu
            180                 185                 190

Thr Phe Asp Leu Glu His Asp Pro Leu Gln Val Gly Glu Gly Asp Cys
        195                 200                 205

Lys Tyr Asp Trp Leu Asp Ile Trp Asp Gly Ile Pro His Val Gly Pro
    210                 215                 220

Leu Ile Gly Lys Tyr Cys Gly Thr Lys Thr Pro Ser Lys Leu Arg Ser
225                 230                 235                 240

Ser Thr Gly Ile Leu Ser Leu Thr Phe His Thr Asp Met Ala Val Ala
                245                 250                 255

Lys Asp Gly Phe Ser Ala Arg Tyr Tyr Leu Ile His Gln Glu Pro Pro
            260                 265                 270

Glu Asn Phe Gln Cys Asn Val Pro Leu Gly Met Glu Ser Gly Arg Ile
        275                 280                 285

Ala Asn Glu Gln Ile Ser Ala Ser Ser Thr Phe Ser Asp Gly Arg Trp
    290                 295                 300

Thr Pro Gln Gln Ser Arg Leu His Gly Asp Asn Gly Trp Thr Pro Asn
305                 310                 315                 320

Asn Leu Asp Ser Asn Lys Glu Tyr Leu Gln Val Asp Leu Arg Phe Leu
                325                 330                 335

Thr Met Leu Thr Ala Ile Ala Thr Gln Gly Ala Ile Ser Arg Glu Thr
            340                 345                 350
```

-continued

```
Gln Lys Gly Tyr Tyr Val Lys Ser Tyr Lys Leu Glu Val Ser Thr Asn
            355                 360                 365

Gly Glu Asp Trp Met Val Tyr Arg His Gly Lys Asn His Lys Ile Phe
        370                 375                 380

Gln Ala Asn Asn Asp Ala Thr Glu Val Val Leu Asn Lys Leu His Met
385                     390                 395                 400

Pro Leu Leu Thr Arg Phe Ile Arg Ile Arg Pro Gln Thr Trp His Leu
                405                 410                 415

Gly Ile Ala Leu Arg Leu Glu Leu Phe Gly Cys Arg Val Thr Asp Ala
            420                 425                 430

Pro Cys Ser Asn Met Leu Gly Met Leu Ser Gly Leu Ile Ala Asp Thr
            435                 440                 445

Gln Ile Ser Ala Ser Ser Thr Arg Glu Tyr Leu Trp Ser Pro Ser Ala
    450                 455                 460

Ala Arg Leu Val Ser Ser Arg Ser Gly Trp Phe Pro Arg Asn Pro Gln
465                 470                 475                 480

Ala Gln Pro Gly Glu Glu Trp Leu Gln Val Asp Leu Gly Thr Pro Lys
                485                 490                 495

Thr Val Lys Gly Val Ile Ile Gln Gly Ala Arg Gly Gly Asp Ser Ile
                500                 505                 510

Thr Ala Val Glu Ala Arg Ala Phe Val Arg Lys Phe Lys Val Ser Tyr
            515                 520                 525

Ser Leu Asn Gly Lys Asp Trp Glu Tyr Ile Gln Asp Pro Arg Thr Gln
    530                 535                 540

Gln Thr Lys Leu Phe Glu Gly Asn Met His Tyr Asp Thr Pro Asp Ile
545                 550                 555                 560

Arg Arg Phe Asp Pro Val Pro Ala Gln Tyr Val Arg Val Tyr Pro Glu
                565                 570                 575

Arg Trp Ser Pro Ala Gly Ile Gly Met Arg Leu Glu Val Leu Gly Cys
                580                 585                 590

Asp Trp Thr Asp Ser Lys Pro Thr Val Glu Thr Leu Gly Pro Thr Val
                595                 600                 605

Lys Ser Glu Glu Thr Thr Thr Pro Tyr Pro Met Asp Glu Asp Ala Thr
            610                 615                 620

Glu Cys Gly Glu Asn Cys Ser Phe Glu Asp Asp Lys Asp Leu Gln Leu
625                 630                 635                 640

Pro Ser Gly Phe Asn Cys Asn Phe Asp Phe Pro Glu Glu Thr Cys Gly
                645                 650                 655

Trp Val Tyr Asp His Ala Lys Trp Leu Arg Ser Thr Trp Ile Ser Ser
                660                 665                 670

Ala Asn Pro Asn Asp Arg Thr Phe Pro Asp Lys Asn Phe Leu Lys
            675                 680                 685

Leu Gln Ser Asp Gly Arg Arg Glu Gly Gln Tyr Gly Arg Leu Ile Ser
    690                 695                 700

Pro Pro Val His Leu Pro Arg Ser Pro Val Cys Met Glu Phe Gln Tyr
705                 710                 715                 720

Gln Ala Met Gly Gly His Gly Val Ala Leu Gln Val Val Arg Glu Ala
                725                 730                 735

Ser Gln Glu Ser Lys Leu Leu Trp Val Ile Arg Glu Asp Gln Gly Ser
                740                 745                 750

Glu Trp Lys His Gly Arg Ile Ile Leu Pro Ser Tyr Asp Met Glu Tyr
            755                 760                 765
```

```
Gln Ile Val Phe Glu Gly Val Ile Gly Lys Gly Arg Ser Gly Glu Ile
    770             775             780

Ser Ile Asp Asp Ile Arg Ile Ser Thr Asp Val Pro Leu Glu Asn Cys
785             790             795                 800

Met Glu Pro Ile Ser Ala Phe Ala Gly Gly Thr Leu Pro Pro Gly Thr
                805             810             815

Glu Pro Thr Val Asp Thr Val Pro Val Gln Pro Ile Pro Ala Tyr Trp
            820             825             830

Tyr Tyr Val Met Ala Ala Gly Gly Ala Val Leu Val Leu Ala Ser Val
            835             840             845

Val Leu Ala Leu Val Leu His Tyr His Arg Phe Arg Tyr Ala Ala Lys
    850             855             860

Lys Thr Asp His Ser Ile Thr Tyr Lys Thr Ser His Tyr Thr Asn Gly
865             870             875                 880

Ala Pro Leu Ala Val Glu Pro Thr Leu Thr Ile Lys Leu Glu Gln Glu
                885             890             895

Arg Gly Ser His Cys
            900
```

(2) INFORMATION FOR SEQ ID NO:23:

(i) SEQUENCE CHARACTERISTICS:
        (A) LENGTH: 4780 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:23:

```
AAACTGGAGC TCCACCGCGG TGGCGGCCGC CCGGGCAGGT CTAGAATTCA GCGGCCGCTG    60

AATTCTATCC AGCGGTCGGT GCCTCTGCCC GCGTGTGTGT CCCGGGTGCC GGGGGACCTG   120

TGTCAGTTAG CGCTTCTGAG ATCACACAGC TGCCTAGGGG CCGTGTGATG CCCAGGGCAA   180

TTCTTGGCTT TGATTTTTAT TATTATTACT ATTATTTTGC GTTCAGCTTT CGGGAAACCC   240

TCGTGATGTT GTAGGATAAA GGAAATGACA CTTTGAGGAA CTGGAGAGAA CATACACGCG   300

TTTGGGTTTG AAGAGGAAAC CGGTCTCCGC TTCCTTAGCT TGCTCCCTCT TTGCTGATTT   360

CAAGAGCTAT CTCCTATGAG GTGGAGATAT CCAGCAAGA  ATAAAGGTGA AGACAGACTG   420

ACTGCCAGGA CCCAGGAGGA AAACGTTGAT CGTTAGAGAC CTTTGCAGAA GACACCACCA   480

GGAGGAAAAT TAGAGAGGAA AAACACAAAG ACATAATTAT AGGAGATCCC ACAAACCTAG   540

CCCGGGAGAG AGCCTCTCTG TCAAAAATGG ATATGTTTCC TCTTACCTGG GTTTTCTTAG   600

CTCTGTACTT TTCAGGACAC GAAGTGAGAA GCCAGCAAGA TCCACCCTGC GGAGGTCGGC   660

CGAATTCCAA AGATGCTGGC TACATCACTT CCCCAGGCTA CCCCCAGGAC TATCCCTCCC   720

ACCAGAACTG TGAGTGGATT GTCTACGCCC CCGAACCCAA CCAGAAGATT GTTCTCAACT   780

TCAACCCTCA CTTTGAAATC GAGAAACACG ACTGCAAGTA TGACTTCATT GAGATTCGGG   840

ATGGGGACAG TGAGTCAGCT GACCTCCTGG GCAAGCACTG TGGGAACATC GCCCCGCCCA   900

CCATCATCTC CTCAGGCTCC GTGTTATACA TCAAGTTCAC CTCAGACTAC GCCCGGCAGG   960

GGGCAGGTTT CTCTCTACGC TATGAGATCT TCAAAACAGG CTCTGAAGAT TGTTCCAAGA  1020

ACTTTACAAG CCCCAATGGG ACCATTGAAT CTCCAGGGTT TCCAGAGAAG TATCCACACA  1080

ATCTGGACTG TACCTTCACC ATCCTGGCCA AACCCAGGAT GGAGATCATC CTACAGTTCC  1140
```

-continued

```
TGACCTTTGA CCTGGAGCAT GACCCTCTAC AAGTGGGGGA AGGAGACTGT AAATATGACT    1200

GGCTGGACAT CTGGGATGGC ATTCCACATG TTGGACCTCT GATTGGCAAG TACTGTGGGA    1260

CGAAAACACC CTCCAAACTC CGCTCGTCCA CGGGGATCCT CTCCTTGACC TTTCACACGG    1320

ACATGGCAGT GGCCAAGGAT GGCTTCTCCG CACGTTACTA TTTGATCCAC CAGGAGCCAC    1380

CTGAGAATTT TCAGTGCAAT GTCCCTTTGG GAATGGAGTC TGGCCGGATT GCTAATGAAC    1440

AGATCAGTGC CTCCTCCACC TTCTCTGATG GGAGGTGGAC TCCTCAACAG AGCCGGCTCC    1500

ATGGTGATGA CAATGGCTGG ACACCCAATT TGGATTCCAA CAAGGAGTAT CTCCAGGTGG    1560

ACCTGCGCTT CCTAACCATG CTCACAGCCA TTGCAACACA GGGAGCCATT TCCAGGGAAA    1620

CCCAGAAAGG CTACTACGTC AAATCGTACA AGCTGGAAGT CAGCACAAAT GGTGAAGATT    1680

GGATGGTCTA CCGGCATGGC AAAAACCACA AGATATTCCA AGCGAACAAT GATGCGACCG    1740

AGGTGGTGCT AAACAAGCTC CACATGCCAC TGCTGACTCG GTTCATCAGG ATCCGCCCGC    1800

AGACGTGGCA TTTGGGCATT GCCCTTCGCC TGGAGCTCTT TGGCTGCCGG GTCACAGATG    1860

CACCCTGCTC CAACATGCTG GGGATGCTCT CGGGCCTCAT TGCTGATACC CAGATCTCTG    1920

CCTCCTCCAC CCGAGAGTAC CTCTGGAGCC CCAGTGCTGC CCGCCTGGTT AGTAGCCGCT    1980

CTGGCTGGTT TCCTCGGAAC CCTCAAGCCC AGCCAGGTGA AGAATGGCTT CAGGTAGACC    2040

TGGGACACC  CAAGACAGTG AAAGGGGTCA TCATCCAGGG AGCCCGAGGA GGAGACAGCA    2100

TCACTGCCGT GGAAGCCAGG GCGTTTGTAC GCAAGTTCAA AGTCTCCTAC AGCCTAAATG    2160

GCAAGGACTG GGAATATATC CAGGACCCCA GGACTCAGCA GACAAAGCTG TTTGAAGGGA    2220

ACATGCACTA TGACACCCCT GACATCCGAA GGTTCGATCC TGTTCCAGCG CAGTATGTGC    2280

GGGTGTACCC AGAGAGGTGG TCGCCAGCAG GCATCGGGAT GAGGCTGGAG GTGCTGGGCT    2340

GTGACTGGAC AGACTCAAAG CCCACAGTGG AGACGCTGGG ACCCACCGTG AAGAGTGAAG    2400

AGACTACCAC CCCATATCCC ATGGATGAGG ATGCCACCGA GTGTGGGGAA AACTGCAGCT    2460

TTGAGGATGA CAAAGATTTG CAACTTCCTT CAGGATTCAA CTGCAACTTT GATTTTCCGG    2520

AAGAGACCTG TGGTTGGGTG TACGACCATG CCAAGTGGCT CCGGAGCACG TGGATCAGCA    2580

GCGCTAACCC CAATGACAGA ACATTTCCAG ATGACAAGAA CTTCTTGAAA CTGCAGAGTG    2640

ATGGCCGACG AGAGGGCCAG TACGGGCGGC TCATCAGCCC ACCGGTGCAC CTGCCCCGAA    2700

GCCCTGTGTG CATGGAGTTC CAGTACCAAG CCATGGGCGG CCACGGGGTG GCACTGCAGG    2760

TGGTTCGGGA AGCCAGCCAG GAAAGCAAAC TCCTTTGGGT CATCCGTGAG GACCAGGGCA    2820

GCGAGTGGAA GCACGGGCGC ATTATCCTGC CCAGCTATGA CATGGAGTAT CAGATCGTGT    2880

TCGAGGGAGT GATAGGGAAG GGACGATCGG GAGAGATTTC CATCGATGAC ATTCGGATAA    2940

GCACTGATGT CCCACTGGAG AACTGCATGG AACCCATATC AGCTTTTGCA GGTGAGGATT    3000

TTAAAGGGGG CACCCTCCCG CCAGGGACCG AGCCACAGT  GGACACGGTG CCCGTGCAGC    3060

CCATCCCAGC CTACTGGTAT TACGTTATGG CGGCCGGGGG CGCCGTGCTG GTGCTGGCCT    3120

CCGTCGTCCT GGCCCTGGTG CTCCACTACC ACCGGTTCCG CTATGCGGCC AAGAAGACCG    3180

ATCACTCCAT CACCTACAAA ACCTCCCACT ACACCAACGG GGCCCCTCTG GCGGTCGAGC    3240

CCACCCTAAC CATTAAGCTA GAGCAAGAGC GGGGCTCGCA CTGCTGAGGG CCGAAGCAGG    3300

AACAGCGCCC CCCCAAAAAA AACCCAAGAA AGACTGCAAA CACGTTGCCT CGATTTTGCA    3360

CTTTTTTTCT CCTCGCCTAG TCTCTGTGTG AACCCTCAGA CATCTCTCTC CAGGGTCCCC    3420

AACCCTGAGC GCTCTCATGT ACCCCACACC ATTCTCTGTG GTTCTTGGTT CCGGTTTCTC    3480
```

```
TTTGCTCTGA TATTGTTTGT TTTTAATCAT TATTTTTTTT CCTTTTCTTC TTTCCTTTTA    3540

ATCTTCTCTC TTTTATTCCT TTCTCCCCTC CCCGCCCCGC CTTTTTCTAA TGATTTTAAA    3600

CCAACTCTAA TGCTGCATCT GGAATCCCAG AAGAGACCCG CCCCTAAGCA CTTCACAACC    3660

CAAGGCTCTG TTGGTTTTGT TCCAGAGACA GGCCCTGTTG TTTTCTCCCC TTGCCTTATC    3720

CCATCCCTCC TCTCCTGGGC AGGCTGCCAG GTGTCTTGAG GGGAGCCTGG TCCTGTATGT    3780

ATGTACACAG TACACTCCCA TGTGAAGAGG TGTGTGTGTG TGTGTGTGTG TGTGTGTATT    3840

TTCGAGGGAG AGACTGATTC ACTGTGGAAG GGGGGGAGTG TGGGTGTGTG TAGAGAGGGG    3900

CCCCTTCCCT CTTATGTTGC TTCTTCTGGG GTACTTTTCA AGAAAATAAT ATACTGTACA    3960

CATTTTGTTT ACTTGGAGAA GAGATTGGAG CTTTTTTGTT GCCTTATCTA GCTCTGGCTG    4020

GGTTTCTGTT GGCTGTCATT GTCATCTCCA GGTACCTAGA CAAATAGAGA CCATTGGGAA    4080

TGCAATGTGG CTTCACCCAT CCTTATCCCC ATCCCAAGCC ACCCAAGACT ATGGTTCCTC    4140

CAGTGCACTC AGACATGACC CCTTTTGTTA TGTTTCCTGG TGTCTTTGAA GTCACAAGAT    4200

AACAGCCATT GGGTGCATGG AGTCATTTCT ACTTCCAGCC CTGAAGCAAA TGTGTCTCAT    4260

GTTGCCTTAT AAAAAAAACC GGAATTCCTG TAGTTGAAGA GTAAGATTTT GTACGGTACA    4320

TTTTTAATGA CAGCTTGGAT ATTGGAATAC TCAACTTTTG TTGTAGCCAA TGAGAGGGAT    4380

ATGCCACTAA TGGTATCTAA ATCATACAGT ACGTACTTTA GGATGGGGAC AAAAATCACA    4440

ACGATTTATT TATTTATTTA CTTAGTGTAT GTGAGTGCAC TGTTGGTGTC TTCAGACACA    4500

CCAGAAGATG ACTTCAGATC CGATTACATA TGGGTTGTGA GCCACCATGT GGTTGCTGGG    4560

ATTTGAACTC TGGACCTCTG GAAGAGCAGT CAGTGCTTGT AACTCTGAGC CATCTTTCTA    4620

GCCCCCCCCC CCCCCCCGCT ATCTTTTAGA AATGTAATTT GCCATACTTT GAGCAATGTT    4680

CTTGATGTCA TTAGGATATT TCACAGATAA CTTCACTTAA GATAATTAGA GCAAAAAAAA    4740

AAAAAAAAAA AAAAAAAAA AAAAAAAAA AAAAAAAAA                           4780
```

(2) INFORMATION FOR SEQ ID NO:24:

(i) SEQUENCE CHARACTERISTICS:
        (A) LENGTH: 906 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:24:

```
Met Asp Met Phe Pro Leu Thr Trp Val Phe Leu Ala Leu Tyr Phe Ser
1               5                   10                  15

Gly His Glu Val Arg Ser Gln Gln Asp Pro Pro Cys Gly Gly Arg Pro
                20                  25                  30

Asn Ser Lys Asp Ala Gly Tyr Ile Thr Ser Pro Gly Tyr Pro Gln Asp
            35                  40                  45

Tyr Pro Ser His Gln Asn Cys Glu Trp Ile Val Tyr Ala Pro Glu Pro
        50                  55                  60

Asn Gln Lys Ile Val Leu Asn Phe Asn Pro His Phe Glu Ile Glu Lys
65                  70                  75                  80

His Asp Cys Lys Tyr Asp Phe Ile Glu Ile Arg Asp Gly Asp Ser Glu
                85                  90                  95

Ser Ala Asp Leu Leu Gly Lys His Cys Gly Asn Ile Ala Pro Pro Thr
                100                 105                 110
```

-continued

Ile Ile Ser Ser Gly Ser Val Leu Tyr Ile Lys Phe Thr Ser Asp Tyr
        115                 120                 125

Ala Arg Gln Gly Ala Gly Phe Ser Leu Arg Tyr Glu Ile Phe Lys Thr
130                 135                 140

Gly Ser Glu Asp Cys Ser Lys Asn Phe Thr Ser Pro Asn Gly Thr Ile
145                 150                 155                 160

Glu Ser Pro Gly Phe Pro Glu Lys Tyr Pro His Asn Leu Asp Cys Thr
                165                 170                 175

Phe Thr Ile Leu Ala Lys Pro Arg Met Glu Ile Ile Leu Gln Phe Leu
            180                 185                 190

Thr Phe Asp Leu Glu His Asp Pro Leu Gln Val Gly Glu Gly Asp Cys
        195                 200                 205

Lys Tyr Asp Trp Leu Asp Ile Trp Asp Gly Ile Pro His Val Gly Pro
    210                 215                 220

Leu Ile Gly Lys Tyr Cys Gly Thr Lys Thr Pro Ser Lys Leu Arg Ser
225                 230                 235                 240

Ser Thr Gly Ile Leu Ser Leu Thr Phe His Thr Asp Met Ala Val Ala
                245                 250                 255

Lys Asp Gly Phe Ser Ala Arg Tyr Tyr Leu Ile His Gln Glu Pro Pro
            260                 265                 270

Glu Asn Phe Gln Cys Asn Val Pro Leu Gly Met Glu Ser Gly Arg Ile
        275                 280                 285

Ala Asn Glu Gln Ile Ser Ala Ser Ser Thr Phe Ser Asp Gly Arg Trp
    290                 295                 300

Thr Pro Gln Gln Ser Arg Leu His Gly Asp Asp Asn Gly Trp Thr Pro
305                 310                 315                 320

Asn Leu Asp Ser Asn Lys Glu Tyr Leu Gln Val Asp Leu Arg Phe Leu
                325                 330                 335

Thr Met Leu Thr Ala Ile Ala Thr Gln Gly Ala Ile Ser Arg Glu Thr
            340                 345                 350

Gln Lys Gly Tyr Tyr Val Lys Ser Tyr Lys Leu Glu Val Ser Thr Asn
        355                 360                 365

Gly Glu Asp Trp Met Val Tyr Arg His Gly Lys Asn His Lys Ile Phe
    370                 375                 380

Gln Ala Asn Asn Asp Ala Thr Glu Val Val Leu Asn Lys Leu His Met
385                 390                 395                 400

Pro Leu Leu Thr Arg Phe Ile Arg Ile Arg Pro Gln Thr Trp His Leu
                405                 410                 415

Gly Ile Ala Leu Arg Leu Glu Leu Phe Gly Cys Arg Val Thr Asp Ala
            420                 425                 430

Pro Cys Ser Asn Met Leu Gly Met Leu Ser Gly Leu Ile Ala Asp Thr
        435                 440                 445

Gln Ile Ser Ala Ser Ser Thr Arg Glu Tyr Leu Trp Ser Pro Ser Ala
    450                 455                 460

Ala Arg Leu Val Ser Ser Arg Ser Gly Trp Phe Pro Arg Asn Pro Gln
465                 470                 475                 480

Ala Gln Pro Gly Glu Glu Trp Leu Gln Val Asp Leu Gly Thr Pro Lys
                485                 490                 495

Thr Val Lys Gly Val Ile Ile Gln Gly Ala Arg Gly Gly Asp Ser Ile
            500                 505                 510

Thr Ala Val Glu Ala Arg Ala Phe Val Arg Lys Phe Lys Val Ser Tyr
        515                 520                 525

-continued

```
Ser Leu Asn Gly Lys Asp Trp Glu Tyr Ile Gln Asp Pro Arg Thr Gln
    530                 535                 540
Gln Thr Lys Leu Phe Glu Gly Asn Met His Tyr Asp Thr Pro Asp Ile
545                 550                 555                 560
Arg Arg Phe Asp Pro Val Pro Ala Gln Tyr Val Arg Val Tyr Pro Glu
                565                 570                 575
Arg Trp Ser Pro Ala Gly Ile Gly Met Arg Leu Glu Val Leu Gly Cys
            580                 585                 590
Asp Trp Thr Asp Ser Lys Pro Thr Val Glu Thr Leu Gly Pro Thr Val
        595                 600                 605
Lys Ser Glu Glu Thr Thr Thr Pro Tyr Pro Met Asp Glu Asp Ala Thr
    610                 615                 620
Glu Cys Gly Glu Asn Cys Ser Phe Glu Asp Asp Lys Asp Leu Gln Leu
625                 630                 635                 640
Pro Ser Gly Phe Asn Cys Asn Phe Asp Phe Pro Glu Glu Thr Cys Gly
                645                 650                 655
Trp Val Tyr Asp His Ala Lys Trp Leu Arg Ser Thr Trp Ile Ser Ser
            660                 665                 670
Ala Asn Pro Asn Asp Arg Thr Phe Pro Asp Asp Lys Asn Phe Leu Lys
        675                 680                 685
Leu Gln Ser Asp Gly Arg Arg Glu Gly Gln Tyr Gly Arg Leu Ile Ser
    690                 695                 700
Pro Pro Val His Leu Pro Arg Ser Pro Val Cys Met Glu Phe Gln Tyr
705                 710                 715                 720
Gln Ala Met Gly Gly His Gly Val Ala Leu Gln Val Val Arg Glu Ala
                725                 730                 735
Ser Gln Glu Ser Lys Leu Leu Trp Val Ile Arg Glu Asp Gln Gly Ser
            740                 745                 750
Glu Trp Lys His Gly Arg Ile Ile Leu Pro Ser Tyr Asp Met Glu Tyr
        755                 760                 765
Gln Ile Val Phe Glu Gly Val Ile Gly Lys Gly Arg Ser Gly Glu Ile
    770                 775                 780
Ser Ile Asp Asp Ile Arg Ile Ser Thr Asp Val Pro Leu Glu Asn Cys
785                 790                 795                 800
Met Glu Pro Ile Ser Ala Phe Ala Gly Glu Asp Phe Lys Gly Gly Thr
                805                 810                 815
Leu Pro Pro Gly Thr Glu Pro Thr Val Asp Thr Val Pro Val Gln Pro
            820                 825                 830
Ile Pro Ala Tyr Trp Tyr Tyr Val Met Ala Ala Gly Gly Ala Val Leu
        835                 840                 845
Val Leu Ala Ser Val Val Leu Ala Leu Val Leu His Tyr His Arg Phe
    850                 855                 860
Arg Tyr Ala Ala Lys Lys Thr Asp His Ser Ile Thr Tyr Lys Thr Ser
865                 870                 875                 880
His Tyr Thr Asn Gly Ala Pro Leu Ala Val Glu Pro Thr Leu Thr Ile
                885                 890                 895
Lys Leu Glu Gln Glu Arg Gly Ser His Cys
            900                 905
```

(2) INFORMATION FOR SEQ ID NO:25:

(i) SEQUENCE CHARACTERISTICS:
       (A) LENGTH: 195 base pairs
       (B) TYPE: nucleic acid -continued

```
            (C) STRANDEDNESS: single
            (D) TOPOLOGY: linear (ii) MOLECULE TYPE: cDNA (xi) SEQUENCE DESCRIPTION: SEQ ID NO:25:

TTCGAGGGAG TGATAGGGAA AGGACGTTCC GGAGAGATTG CCATTGATGA CATTCGGATA      60

AGCACTGATG TCCCACTGGA GAACTGCATG GAACCCATCT CGGCTTTTGC AGGGGGCACC     120

CTCCTGCCAG GGACCGAGCC CACAGTGGAC ACGGTGCCCA TGCAGCCCAT CCCAGCCTAC     180

TGGTATTACG TAATG                                                     195

(2) INFORMATION FOR SEQ ID NO:26:

(i) SEQUENCE CHARACTERISTICS:
        (A) LENGTH: 65 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:26:

Phe Glu Gly Val Ile Gly Lys Gly Arg Ser Gly Glu Ile Ala Ile Asp
1               5                  10                  15

Asp Ile Arg Ile Ser Thr Asp Val Pro Leu Glu Asn Cys Met Glu Pro
            20                  25                  30

Ile Ser Ala Phe Ala Gly Gly Thr Leu Leu Pro Gly Thr Glu Pro Thr
        35                  40                  45

Val Asp Thr Val Pro Met Gln Pro Ile Pro Ala Tyr Trp Tyr Tyr Val
    50                  55                  60

Met
65
```

What is claimed is:

1. An isolated polypeptide comprising:
  (a) at least 12 consecutive residues of an amino acid sequence selected from SEQ ID NO: 4, 8, 10, 12, 14, 16, 18, 20, 22, and 24; or
  (b) at least 12 consecutive residues of the amino acid sequence of SEQ ID NO:2 and including at least one sequence selected from the group consisting of residues 24–34, 147–155, 166–178, 288–299, 354–366, 368–390, 397–415, 595–615, 671–689 and 911–919 of SEQ ID NO:2;
  said consecutive residues found in neither mouse, chick nor drosophila neuropilin-1 cDNA nor SEQ ID NO:26, wherein said polypeptide has a semaphorin receptor specific antigenicity or immunogenicity.

2. The isolated polypeptide of claim 1, comprising the amino acid sequence of SEQ ID NO:2, 18 or 20 or at least 12 consecutive residues of SEQ ID NO:2, 18 or 20.

3. A recombinant nucleic acid comprising a strand of SEQ ID NO:1, 3, 7, 9, 11, 13, 15, 17, 19, 21 or 23, wherein said strand is flanked by fewer than 2 kb of native flanking sequence.

4. A recombinant nucleic acid comprising a coding region encoding a polypeptide according to claim 1, wherein said coding region is flanked by fewer than 2 kb of native flanking sequence.

5. A cell comprising a nucleic acid according to claim 4.

6. A method of making an SR polypeptide said method comprising steps: introducing a nucleic acid according to claim 4 into a host cell or cellular extract, incubating said host cell or extract under conditions whereby said nucleic acid is expressed as a transcript and said transcript is expressed as a translation product comprising said polypeptide, and isolating said translation product.

7. A method of screening for an agent which modulates the interaction of a SR polypeptide to a binding target, said method comprising the steps of:
  incubating a mixture comprising:
    an isolated polypeptide according to claim 1,
    a binding target of said polypeptide, and
    a candidate agent;
  under conditions whereby, but for the presence of said agent, said polypeptide specifically binds said binding target at a reference affinity;
  detecting the binding affinity of said polypeptide to said binding target to determine an agent-biased affinity,
  wherein a difference between the agent-biased affinity and the reference affinity indicates that said agent modulates the binding of said polypeptide to said binding target.

8. A method according to claim 7, wherein said binding target is a semaphorin polypeptide.

9. The isolated polypeptide of claim 1, comprising at least 25 consecutive residues of SEQ ID NO: 2, 4, 8, 10, 12, 14, 16, 18, 20, 22 or 24.

10. The isolated polypeptide of claim 1, comprising at least one of an amino acid sequence selected from residues 24–34, 147–155, 166–178, 288–299, 354–366, 368–390, 397–415, 595–615, 671–689 and 911–919 of SEQ ID NO:2 or at least one of an amino acid sequence selected from residues 14–35, 261–278, 285–301, 471–485, 616–628, 651–685, 682–696, 719–745, 802–825, 815–830, 827–839 and 898–929 of SEQ ID NO:20.

11. The isolated polypeptide of claim 1, comprising the amino acid sequence of SEQ ID NO:2,4,8, 10, 12, 14, 16, 18,20,22 or 24.

12. The isolated polypeptide of claim 1, comprising at least 25 consecutive residues of SEQ ID NO: 2.

13. The isolated polypeptide of claim 1, comprising at least 25 consecutive residues of SEQ ID NO: 4.

14. The isolated polypeptide of claim 1, comprising at least 25 consecutive residues of SEQ ID NO: 8.

15. The isolated polypeptide of claim 1, comprising at least 25 consecutive residues of SEQ ID NO: 10.

16. The isolated polypeptide of claim 1, comprising at least 25 consecutive residues of SEQ ID NO: 12.

17. The isolated polypeptide of claim 1, comprising at least 25 consecutive residues of SEQ ID NO: 14.

18. The isolated polypeptide of claim 1, comprising at least 25 consecutive residues of SEQ ID NO: 16.

19. The isolated polypeptide of claim 1, comprising at least 25 consecutive residues of SEQ ID NO: 18.

20. The isolated polypeptide of claim 1, comprising at least 25 consecutive residues of SEQ ID NO: 20.

21. The isolated polypeptide of claim 1, comprising at least 25 consecutive residues of SEQ ID NO: 22.

22. The isolated polypeptide of claim 1, comprising at least 25 consecutive residues of SEQ ID NO: 24.

23. The recombinant nucleic acid of claim 3, comprising a strand of SEQ ID NO:1.

24. The recombinant nucleic acid of claim 3, comprising a strand of SEQ ID NO:3.

25. The recombinant nucleic acid of claim 3, comprising a strand of SEQ ID NO:7.

26. The recombinant nucleic acid of claim 3, comprising a strand of SEQ ID NO 9.

27. The recombinant nucleic acid of claim 3, comprising a strand of SEQ ID NO: 11.

28. The recombinant nucleic acid of claim 3, comprising a strand of SEQ ID NO: 13.

29. The recombinant nucleic acid of claim 3, comprising a strand of SEQ ID NO: 15.

30. The recombinant nucleic acid of claim 3, comprising a strand of SEQ ID NO: 17.

31. The recombinant nucleic acid of claim 3, comprising a strand of SEQ ID NO: 19.

32. The recombinant nucleic acid of claim 3, comprising a strand of SEQ ID NO:21.

33. The recombinant nucleic acid of claim 3, comprising a strand of SEQ ID NO:23.

34. The recombinant nucleic acid of claim 4, wherein the coding region encodes at least 25 consecutive residues of SEQ ID NO: 2, 4, 8, 10, 12, 14, 16, 18, 20, 22 or 24.

35. The recombinant nucleic acid of claim 4, wherein the coding region encodes at least one of an amino acid sequence selected from residues 24–34, 147–155, 166–178, 288–299, 354–366, 368–390, 397–415, 595–615, 671–689 and 911–919 of SEQ ID NO:2 or at least one of an amino acid sequence selected from residues 14–35, 261–278, 285–301, 471–485, 616–628, 651–685, 682–696, 719–745, 802–825, 815–830, 827–839 and 898–929 of SEQ ID NO:20.

36. The recombinant nucleic acid of claim 4, wherein the coding region encodes the amino acid sequence of SEQ ID NO:2, 4, 8, 10, 12, 14, 16, 18, 20, 22 or 24.

37. The cell of claim 5, wherein the coding region encodes at least 25 consecutive residues of SEQ ID NO: 2, 4, 8, 10, 12, 14, 16, 18, 20, 22 or 24.

38. The cell of claim 5, wherein the coding region encodes at least one of residues 24–34, 147–155, 166–178, 288–299, 354–366, 368–390, 397–415, 595–615, 671–689 and 911–919 of SEQ ID NO:2 or at least one of residues 14–35, 261–278, 285–301, 471–485, 616–628, 651–685, 682–696, 719–745, 802–825, 815–830, 827–839 and 898–929 of SEQ ID NO:20.

39. The cell of claim 5, wherein the coding region encodes the amino acid sequence of SEQ ID NO:2, 4, 8, 10, 12, 14, 16, 18, 20,22 or 24.

40. The method of claim 7, wherein the coding region encodes at least 25 consecutive residues of SEQ ID NO: 2, 4, 8, 10, 12, 14, 16, 18, 20, 22 or 24.

41. The method of claim 7, wherein the coding region encodes at least one of an amino acid sequence selected from residues 24–34, 147–155, 166–178, 288–299, 354–366, 368–390, 397–415, 595–615, 671–689 and 911–919 of SEQ ID NO:2 or at least one of an amino acid sequence selected from residues 14–35, 261–278, 285–301, 471–485, 616–628, 651–685, 682–696, 719–745, 802–825, 815–830, 827–839 and 898–929 of SEQ ID NO:20.

42. The method of claim 7, wherein the coding region encodes the amino acid sequence of SEQ ID NO:2, 4, 8, 10, 12, 14, 16, 18, 20, 22 or 24.

43. The method of claim 7, wherein the polypeptide comprises at least 25 consecutive residues of SEQ ID NO: 2, 4, 8, 10, 12, 14, 16, 18, 20, 22 or 24.

44. The method of claim 7, wherein the polypeptide comprises at least one of an amino acid sequence selected from residues 24–34, 147–155, 166–178, 288–299, 354–366, 368–390, 397–415, 595–615, 671–689 and 911–919 of SEQ ID NO:2 or at least one of an amino acid sequence selected from residues 1435, 261–278, 285–301, 471–485, 616–628, 651–685, 682–696, 719–745, 802–825, 815–830, 827–839 and 898–929 of SEQ ID NO:20.

45. The method of claim 7, wherein the polypeptide comprises the amino acid sequence of SEQ ID NO:2, 4, 8, 10, 12, 14, 16, 18, 20, 22 or 24.

* * * * *

UNITED STATES PATENT AND TRADEMARK OFFICE
CERTIFICATE OF CORRECTION

PATENT NO.    : 6,054,293
DATED         : April 25, 2000
INVENTOR(S)   : Tessier-Lauigne et al.

It is certified that error appears in the above-identified patent and that said Letters Patent is hereby corrected as shown below:

Column 3,
Line 36, should read -- Figs. 5A-5C --

Signed and Sealed this

Twenty-fourth Day of December, 2002

JAMES E. ROGAN
*Director of the United States Patent and Trademark Office*

UNITED STATES PATENT AND TRADEMARK OFFICE
CERTIFICATE OF CORRECTION

PATENT NO.   : 6,054,293
DATED        : April 25, 2000
INVENTOR(S)  : Tessier-Lauigne et al.

It is certified that error appears in the above-identified patent and that said Letters Patent is hereby corrected as shown below:

<u>Column 3,</u>
Line 31, after "neuropilin-2(b0)" insert attached sequence listing Signed and Sealed this Eighteenth Day of November, 2003

JAMES E. ROGAN
*Director of the United States Patent and Trademark Office*

SEQUENCE LISTING

<110> Tessier-Lavigne, Marc
      Zhigang, He
      Chen, Hang

<120> Semaphorin Receptors

<130> UC97-288-2

<140>
<141>

<150> 08/889,458
<151> 1997-07-08

<160> 26

<170> PatentIn Ver. 2.0

<210> 1
<211> 2772
<212> DNA
<213> human

<220>
<221> CDS
<222> (1)..(2769)

<400> 1
```
atg gag agg ggg ctg ccg ctc ctc tgc gcc gtg ctc gcc ctc gtc ctc    48
Met Glu Arg Gly Leu Pro Leu Leu Cys Ala Val Leu Ala Leu Val Leu
 1               5                  10                  15 gcc ccg gcc ggc gct ttt cgc aac gat gaa tgt ggc gat act ata aaa    96
Ala Pro Ala Gly Ala Phe Arg Asn Asp Glu Cys Gly Asp Thr Ile Lys
            20                  25                  30 att gaa agc ccc ggg tac ctt aca tct cct ggt tat cct cat tct tat   144
Ile Glu Ser Pro Gly Tyr Leu Thr Ser Pro Gly Tyr Pro His Ser Tyr
        35                  40                  45 cac cca agt gaa aaa tgc gaa tgg ctg att cag gct ccg gac cca tac   192
His Pro Ser Glu Lys Cys Glu Trp Leu Ile Gln Ala Pro Asp Pro Tyr
    50                  55                  60 cag aga att atg atc aac ttc aac cct cac ttc gat ttg gag gac aga   240
Gln Arg Ile Met Ile Asn Phe Asn Pro His Phe Asp Leu Glu Asp Arg
65                  70                  75                  80 gac tgc aag tat gac tac gtg gaa gtc ttc gat gga gaa aat gaa aat   288
Asp Cys Lys Tyr Asp Tyr Val Glu Val Phe Asp Gly Glu Asn Glu Asn
                85                  90                  95
```

UNITED STATES PATENT AND TRADEMARK OFFICE
CERTIFICATE OF CORRECTION

PATENT NO. : 6,054,293
DATED : April 25, 2000
INVENTOR(S) : Tessier-Lavigne et al.

It is certified that error appears in the above-identified patent and that said Letters Patent is hereby corrected as shown below:

Column 3,
Line 31, after "neuopilin-2(b0)", insert attached sequence listing.

Columns 27 and 28 through Columns 145 and 146,
Before the claims, insert therefore the attached sequence listing.

Column 148,
Lines 27, 30 and 38, "The method of claim 7" should read -- The method of claim 6 --.

Signed and Sealed this

Twenty-eighth Day of September, 2004

JON W. DUDAS
*Director of the United States Patent and Trademark Office*

SEQUENCE LISTING

<110> Tessier-Lavigne, Marc
      Zhigang, He
      Chen, Hang

<120> Semaphorin Receptors

<130> UC97-288-2

<140>
<141>

<150> 08/889,458
<151> 1997-07-08

<160> 26

<170> PatentIn Ver. 2.0

<210> 1
<211> 2772
<212> DNA
<213> human

<220>
<221> CDS
<222> (1)..(2769)

<400> 1
| atg | gag | agg | ggg | ctg | ccg | ctc | ctc | tgc | gcc | gtg | ctc | gcc | ctc | gtc | ctc | 48 |
|-----|-----|-----|-----|-----|-----|-----|-----|-----|-----|-----|-----|-----|-----|-----|-----|----|
| Met | Glu | Arg | Gly | Leu | Pro | Leu | Leu | Cys | Ala | Val | Leu | Ala | Leu | Val | Leu |    |
| 1   |     |     |     | 5   |     |     |     |     | 10  |     |     |     |     | 15  |     |    |

| gcc | ccg | gcc | ggc | gct | ttt | cgc | aac | gat | gaa | tgt | ggc | gat | act | ata | aaa | 96 |
|-----|-----|-----|-----|-----|-----|-----|-----|-----|-----|-----|-----|-----|-----|-----|-----|----|
| Ala | Pro | Ala | Gly | Ala | Phe | Arg | Asn | Asp | Glu | Cys | Gly | Asp | Thr | Ile | Lys |    |
|     |     |     | 20  |     |     |     |     | 25  |     |     |     |     | 30  |     |     |    |

| att | gaa | agc | ccc | ggg | tac | ctt | aca | tct | cct | ggt | tat | cct | cat | tct | tat | 144 |
|-----|-----|-----|-----|-----|-----|-----|-----|-----|-----|-----|-----|-----|-----|-----|-----|-----|
| Ile | Glu | Ser | Pro | Gly | Tyr | Leu | Thr | Ser | Pro | Gly | Tyr | Pro | His | Ser | Tyr |     |
|     |     | 35  |     |     |     |     | 40  |     |     |     |     | 45  |     |     |     |     |

| cac | cca | agt | gaa | aaa | tgc | gaa | tgg | ctg | att | cag | gct | ccg | gac | cca | tac | 192 |
|-----|-----|-----|-----|-----|-----|-----|-----|-----|-----|-----|-----|-----|-----|-----|-----|-----|
| His | Pro | Ser | Glu | Lys | Cys | Glu | Trp | Leu | Ile | Gln | Ala | Pro | Asp | Pro | Tyr |     |
|     | 50  |     |     |     |     | 55  |     |     |     |     | 60  |     |     |     |     |     |

| cag | aga | att | atg | atc | aac | ttc | aac | cct | cac | ttc | gat | ttg | gag | gac | aga | 240 |
|-----|-----|-----|-----|-----|-----|-----|-----|-----|-----|-----|-----|-----|-----|-----|-----|-----|
| Gln | Arg | Ile | Met | Ile | Asn | Phe | Asn | Pro | His | Phe | Asp | Leu | Glu | Asp | Arg |     |
| 65  |     |     |     | 70  |     |     |     |     | 75  |     |     |     |     | 80  |     |     |

| gac | tgc | aag | tat | gac | tac | gtg | gaa | gtc | ttc | gat | gga | gaa | aat | gaa | aat | 288 |
|-----|-----|-----|-----|-----|-----|-----|-----|-----|-----|-----|-----|-----|-----|-----|-----|-----|
| Asp | Cys | Lys | Tyr | Asp | Tyr | Val | Glu | Val | Phe | Asp | Gly | Glu | Asn | Glu | Asn |     |
|     |     |     | 85  |     |     |     |     | 90  |     |     |     |     | 95  |     |     |     |

```
gga cat ttt agg gga aag ttc tgt gga aag ata gcc cct cct cct gtt      336
Gly His Phe Arg Gly Lys Phe Cys Gly Lys Ile Ala Pro Pro Pro Val
            100                 105                 110 gtg tct tca ggg cca ttt ctt ttt atc aaa ttt gtc tct gac tac gaa      384
Val Ser Ser Gly Pro Phe Leu Phe Ile Lys Phe Val Ser Asp Tyr Glu
            115                 120                 125 aca cat ggt gca gga ttt tcc ata cgt tat gaa att ttc aag aga ggt      432
Thr His Gly Ala Gly Phe Ser Ile Arg Tyr Glu Ile Phe Lys Arg Gly
            130                 135                 140 cct gaa tgt tcc cag aac tac aca aca cct agt gga gtg ata aag tcc      480
Pro Glu Cys Ser Gln Asn Tyr Thr Thr Pro Ser Gly Val Ile Lys Ser
145                 150                 155                 160 ccc gga ttc cct gaa aaa tat ccc aac agc ctt gaa tgc act tat att      528
Pro Gly Phe Pro Glu Lys Tyr Pro Asn Ser Leu Glu Cys Thr Tyr Ile
                165                 170                 175 gtc ttt gcg cca aag atg tca gag att atc ctg gaa ttt gaa agc ttt      576
Val Phe Ala Pro Lys Met Ser Glu Ile Ile Leu Glu Phe Glu Ser Phe
            180                 185                 190 gac ctg gag cct gac tca aat cct cca ggg ggg atg ttc tgt cgc tac      624
Asp Leu Glu Pro Asp Ser Asn Pro Pro Gly Gly Met Phe Cys Arg Tyr
            195                 200                 205 gac cgg cta gaa atc tgg gat gga ttc cct gat gtt ggc cct cac att      672
Asp Arg Leu Glu Ile Trp Asp Gly Phe Pro Asp Val Gly Pro His Ile
            210                 215                 220 ggg cgt tac tgt gga cag aaa aca cca ggt cga atc cga tcc tca tcg      720
Gly Arg Tyr Cys Gly Gln Lys Thr Pro Gly Arg Ile Arg Ser Ser Ser
225                 230                 235                 240 ggc att ctc tcc atg gtt ttt tac acc gac agc gcg ata gca aaa gaa      768
Gly Ile Leu Ser Met Val Phe Tyr Thr Asp Ser Ala Ile Ala Lys Glu
            245                 250                 255 ggt ttc tca gca aac tac agt gtc ttg cag agc agt gtc tca gaa gat      816
Gly Phe Ser Ala Asn Tyr Ser Val Leu Gln Ser Ser Val Ser Glu Asp
            260                 265                 270 ttc aaa tgt atg gaa gct ctg ggc atg gaa tca gga gaa att cat tct      864
Phe Lys Cys Met Glu Ala Leu Gly Met Glu Ser Gly Glu Ile His Ser
            275                 280                 285 gac cag atc aca gct tct tcc cag tat agc acc aac tgg tct gca gag      912
Asp Gln Ile Thr Ala Ser Ser Gln Tyr Ser Thr Asn Trp Ser Ala Glu
        290                 295                 300 cgc tcc cgc ctg aac tac cct gag aat ggg tgg act ccc gga gag gat      960
Arg Ser Arg Leu Asn Tyr Pro Glu Asn Gly Trp Thr Pro Gly Glu Asp
```

```
                305                    310                    315                    320
tcc tac cga gag tgg ata cag gta gac ttg ggc ctt ctg cgc ttt gtc    1008
Ser Tyr Arg Glu Trp Ile Gln Val Asp Leu Gly Leu Leu Arg Phe Val
                325                    330                    335 acg gct gtc ggg aca cag ggc gcc att tca aaa gaa acc aag aag aaa    1056
Thr Ala Val Gly Thr Gln Gly Ala Ile Ser Lys Glu Thr Lys Lys Lys
            340                    345                    350 tat tat gtc aag act tac aag atc gac gtt agc tcc aac ggg gaa gac    1104
Tyr Tyr Val Lys Thr Tyr Lys Ile Asp Val Ser Ser Asn Gly Glu Asp
        355                    360                    365 tgg atc acc ata aaa gaa gga aac aaa cct gtt ctc ttt cag gga aac    1152
Trp Ile Thr Ile Lys Glu Gly Asn Lys Pro Val Leu Phe Gln Gly Asn
        370                    375                    380 acc aac ccc aca gat gtt gtg gtt gca gta ttc ccc aaa cca ctg ata    1200
Thr Asn Pro Thr Asp Val Val Val Ala Val Phe Pro Lys Pro Leu Ile
385                    390                    395                    400 act cga ttt gtc cga atc aag cct gca act tgg gaa act ggc ata tct    1248
Thr Arg Phe Val Arg Ile Lys Pro Ala Thr Trp Glu Thr Gly Ile Ser
                405                    410                    415 atg aga ttt gaa gta tac ggt tgc aag ata aca gat tat cct tgc tct    1296
Met Arg Phe Glu Val Tyr Gly Cys Lys Ile Thr Asp Tyr Pro Cys Ser
                420                    425                    430 gga atg ttg ggt atg gtg tct gga ctt att tct gac tcc cag atc aca    1344
Gly Met Leu Gly Met Val Ser Gly Leu Ile Ser Asp Ser Gln Ile Thr
            435                    440                    445 tca tcc aac caa gga gac aga aac tgg atg cct gaa aac atc cgc ctg    1392
Ser Ser Asn Gln Gly Asp Arg Asn Trp Met Pro Glu Asn Ile Arg Leu
        450                    455                    460 gta acc agt cgc tct ggc tgg gca ctt cca ccc gca cct cat tcc tac    1440
Val Thr Ser Arg Ser Gly Trp Ala Leu Pro Pro Ala Pro His Ser Tyr
465                    470                    475                    480 atc aat gag tgg ctc caa ata gac ctg ggg gag gag aag atc gtg agg    1488
Ile Asn Glu Trp Leu Gln Ile Asp Leu Gly Glu Glu Lys Ile Val Arg
                485                    490                    495 ggc atc atc att cag ggt ggg aag cac cga gag aac aag gtg ttc atg    1536
Gly Ile Ile Ile Gln Gly Gly Lys His Arg Glu Asn Lys Val Phe Met
                500                    505                    510 agg aag ttc aag atc ggg tac agc aac aac ggc tcg gac tgg aag atg    1584
Arg Lys Phe Lys Ile Gly Tyr Ser Asn Asn Gly Ser Asp Trp Lys Met
            515                    520                    525
```

```
atc atg gat gac agc aaa cgc aag gcg aag tct ttt gag ggc aac aac    1632
Ile Met Asp Asp Ser Lys Arg Lys Ala Lys Ser Phe Glu Gly Asn Asn
    530             535             540 aac tat gat aca cct gag ctg cgg act ttt cca gct ctc tcc acg cga    1680
Asn Tyr Asp Thr Pro Glu Leu Arg Thr Phe Pro Ala Leu Ser Thr Arg
545             550             555             560 ttc atc agg atc tac ccc gag aga gcc act cat ggc gga ctg ggg ctc    1728
Phe Ile Arg Ile Tyr Pro Glu Arg Ala Thr His Gly Gly Leu Gly Leu
                565             570             575 aga atg gag ctg ctg ggc tgt gaa gtg gaa gcc cct aca gct gga ccg    1776
Arg Met Glu Leu Leu Gly Cys Glu Val Glu Ala Pro Thr Ala Gly Pro
            580             585             590 acc act ccc aac ggg aac ttg gtg gat gaa tgt gat gac gac cag gcc    1824
Thr Thr Pro Asn Gly Asn Leu Val Asp Glu Cys Asp Asp Asp Gln Ala
        595             600             605 aac tgc cac agt gga aca ggt gat gac ttc cag ctc aca ggt ggc acc    1872
Asn Cys His Ser Gly Thr Gly Asp Asp Phe Gln Leu Thr Gly Gly Thr
    610             615             620 act gtg ctg gcc aca gaa aag ccc acg gtc ata gac agc acc ata caa    1920
Thr Val Leu Ala Thr Glu Lys Pro Thr Val Ile Asp Ser Thr Ile Gln
625             630             635             640 tca gag ttt cca aca tat ggt ttt aac tgt gaa ttt ggc tgg ggc tct    1968
Ser Glu Phe Pro Thr Tyr Gly Phe Asn Cys Glu Phe Gly Trp Gly Ser
                645             650             655 cac aag acc ttc tgc cac tgg gaa cat gac aat cac gtg cag ctc aag    2016
His Lys Thr Phe Cys His Trp Glu His Asp Asn His Val Gln Leu Lys
            660             665             670 tgg agt gtg ttg acc agc aag acg gga ccc att cag gat cac aca gga    2064
Trp Ser Val Leu Thr Ser Lys Thr Gly Pro Ile Gln Asp His Thr Gly
        675             680             685 gat ggc aac ttc atc tat tcc caa gct gac gaa aat cag aag ggc aaa    2112
Asp Gly Asn Phe Ile Tyr Ser Gln Ala Asp Glu Asn Gln Lys Gly Lys
    690             695             700 gtg gct cgc ctg gtg agc cct gtg gtt tat tcc cag aac tct gcc cac    2160
Val Ala Arg Leu Val Ser Pro Val Val Tyr Ser Gln Asn Ser Ala His
705             710             715             720 tgc atg acc ttc tgg tat cac atg tct ggg tcc cac gtc ggc aca ctc    2208
Cys Met Thr Phe Trp Tyr His Met Ser Gly Ser His Val Gly Thr Leu
                725             730             735 agg gtc aaa ctg cgc tac cag aag cca gag gag tac gat cag ctg gtc    2256
Arg Val Lys Leu Arg Tyr Gln Lys Pro Glu Glu Tyr Asp Gln Leu Val
```

|  |  |  |  |  | 740 |  |  |  |  | 745 |  |  |  |  | 750 |  |  |
|---|---|---|---|---|---|---|---|---|---|---|---|---|---|---|---|---|---|

```
        740                     745                     750
tgg atg gcc att gga cac caa ggt gac cac tgg aag gaa ggg cgt gtc    2304
Trp Met Ala Ile Gly His Gln Gly Asp His Trp Lys Glu Gly Arg Val
        755                     760                     765 ttg ctc cac aag tct ctg aaa ctt tat cag gtg att ttc gag ggc gaa    2352
Leu Leu His Lys Ser Leu Lys Leu Tyr Gln Val Ile Phe Glu Gly Glu
        770                     775                     780 atc gga aaa gga aac ctt ggt ggg att gct gtg gat gac att agt att    2400
Ile Gly Lys Gly Asn Leu Gly Gly Ile Ala Val Asp Asp Ile Ser Ile
785                     790                     795                 800 aat aac cac att tca caa gaa gat tgt gca aaa cca gca gac ctg gat    2448
Asn Asn His Ile Ser Gln Glu Asp Cys Ala Lys Pro Ala Asp Leu Asp
                805                     810                     815 aaa aag aac cca gaa att aaa att gat gaa aca ggg agc acg cca gga    2496
Lys Lys Asn Pro Glu Ile Lys Ile Asp Glu Thr Gly Ser Thr Pro Gly
            820                     825                     830 tac gaa ggt gaa gga gaa ggt gac aag aac atc tcc agg aag cca ggc    2544
Tyr Glu Gly Glu Gly Glu Gly Asp Lys Asn Ile Ser Arg Lys Pro Gly
        835                     840                     845 aat gtg ttg aag acc tta gaa ccc atc ctc atc acc atc ata gcc atg    2592
Asn Val Leu Lys Thr Leu Glu Pro Ile Leu Ile Thr Ile Ile Ala Met
        850                     855                     860 agc gcc ctg ggg gtc ctc ctg ggg gct gtc tgt ggg gtc gtg ctg tac    2640
Ser Ala Leu Gly Val Leu Leu Gly Ala Val Cys Gly Val Val Leu Tyr
865                     870                     875                 880 tgt gcc tgt tgg cat aat ggg atg tca gaa aga aac ttg tct gcc ctg    2688
Cys Ala Cys Trp His Asn Gly Met Ser Glu Arg Asn Leu Ser Ala Leu
                885                     890                     895 gag aac tat aac ttt gaa ctt gtg gat ggt gtg aag ttg aaa aaa gac    2736
Glu Asn Tyr Asn Phe Glu Leu Val Asp Gly Val Lys Leu Lys Lys Asp
            900                     905                     910 aaa ctg aat aca cag agt act tat tcg gag gca tga                    2772
Lys Leu Asn Thr Gln Ser Thr Tyr Ser Glu Ala
        915                     920

<210> 2
<211> 923
<212> PRT
<213> human

<400> 2
Met Glu Arg Gly Leu Pro Leu Leu Cys Ala Val Leu Ala Leu Val Leu
```

```
  1                    5                      10                     15
Ala Pro Ala Gly Ala Phe Arg Asn Asp Glu Cys Gly Asp Thr Ile Lys
            20                  25                  30

Ile Glu Ser Pro Gly Tyr Leu Thr Ser Pro Gly Tyr Pro His Ser Tyr
            35                  40                  45

His Pro Ser Glu Lys Cys Glu Trp Leu Ile Gln Ala Pro Asp Pro Tyr
    50                  55                  60

Gln Arg Ile Met Ile Asn Phe Asn Pro His Phe Asp Leu Glu Asp Arg
65                  70                  75                  80

Asp Cys Lys Tyr Asp Tyr Val Glu Val Phe Asp Gly Glu Asn Glu Asn
                85                  90                  95

Gly His Phe Arg Gly Lys Phe Cys Gly Lys Ile Ala Pro Pro Pro Val
            100                 105                 110

Val Ser Ser Gly Pro Phe Leu Phe Ile Lys Phe Val Ser Asp Tyr Glu
        115                 120                 125

Thr His Gly Ala Gly Phe Ser Ile Arg Tyr Glu Ile Phe Lys Arg Gly
    130                 135                     140

Pro Glu Cys Ser Gln Asn Tyr Thr Thr Pro Ser Gly Val Ile Lys Ser
145                 150                 155                 160

Pro Gly Phe Pro Glu Lys Tyr Pro Asn Ser Leu Glu Cys Thr Tyr Ile
            165                 170                 175

Val Phe Ala Pro Lys Met Ser Glu Ile Ile Leu Glu Phe Glu Ser Phe
            180                 185                 190

Asp Leu Glu Pro Asp Ser Asn Pro Pro Gly Gly Met Phe Cys Arg Tyr
        195                 200                 205

Asp Arg Leu Glu Ile Trp Asp Gly Phe Pro Asp Val Gly Pro His Ile
    210                 215                 220

Gly Arg Tyr Cys Gly Gln Lys Thr Pro Gly Arg Ile Arg Ser Ser Ser
225                 230                 235                 240

Gly Ile Leu Ser Met Val Phe Tyr Thr Asp Ser Ala Ile Ala Lys Glu
                245                 250                 255

Gly Phe Ser Ala Asn Tyr Ser Val Leu Gln Ser Ser Val Ser Glu Asp
            260                 265                 270

Phe Lys Cys Met Glu Ala Leu Gly Met Glu Ser Gly Glu Ile His Ser
        275                 280                 285

Asp Gln Ile Thr Ala Ser Ser Gln Tyr Ser Thr Asn Trp Ser Ala Glu
```

```
         290                    295                    300
Arg Ser Arg Leu Asn Tyr Pro Glu Asn Gly Trp Thr Pro Gly Glu Asp
305                 310                 315                 320

Ser Tyr Arg Glu Trp Ile Gln Val Asp Leu Gly Leu Leu Arg Phe Val
                325                 330                 335

Thr Ala Val Gly Thr Gln Gly Ala Ile Ser Lys Glu Thr Lys Lys Lys
            340                 345                 350

Tyr Tyr Val Lys Thr Tyr Lys Ile Asp Val Ser Ser Asn Gly Glu Asp
        355                 360                 365

Trp Ile Thr Ile Lys Glu Gly Asn Lys Pro Val Leu Phe Gln Gly Asn
    370                 375                 380

Thr Asn Pro Thr Asp Val Val Val Ala Val Phe Pro Lys Pro Leu Ile
385                 390                 395                 400

Thr Arg Phe Val Arg Ile Lys Pro Ala Thr Trp Glu Thr Gly Ile Ser
                405                 410                 415

Met Arg Phe Glu Val Tyr Gly Cys Lys Ile Thr Asp Tyr Pro Cys Ser
            420                 425                 430

Gly Met Leu Gly Met Val Ser Gly Leu Ile Ser Asp Ser Gln Ile Thr
        435                 440                 445

Ser Ser Asn Gln Gly Asp Arg Asn Trp Met Pro Glu Asn Ile Arg Leu
        450                 455                 460

Val Thr Ser Arg Ser Gly Trp Ala Leu Pro Pro Ala Pro His Ser Tyr
465                 470                 475                 480

Ile Asn Glu Trp Leu Gln Ile Asp Leu Gly Glu Glu Lys Ile Val Arg
                485                 490                 495

Gly Ile Ile Ile Gln Gly Gly Lys His Arg Glu Asn Lys Val Phe Met
            500                 505                 510

Arg Lys Phe Lys Ile Gly Tyr Ser Asn Asn Gly Ser Asp Trp Lys Met
        515                 520                 525

Ile Met Asp Asp Ser Lys Arg Lys Ala Lys Ser Phe Glu Gly Asn Asn
    530                 535                 540

Asn Tyr Asp Thr Pro Glu Leu Arg Thr Phe Pro Ala Leu Ser Thr Arg
545                 550                 555                 560

Phe Ile Arg Ile Tyr Pro Glu Arg Ala Thr His Gly Gly Leu Gly Leu
                565                 570                 575

Arg Met Glu Leu Leu Gly Cys Glu Val Glu Ala Pro Thr Ala Gly Pro
```

```
                580                      585                       590

Thr Thr Pro Asn Gly Asn Leu Val Asp Glu Cys Asp Asp Gln Ala
        595                 600              605

Asn Cys His Ser Gly Thr Gly Asp Asp Phe Gln Leu Thr Gly Gly Thr
    610                 615                  620

Thr Val Leu Ala Thr Glu Lys Pro Thr Val Ile Asp Ser Thr Ile Gln
625                 630                 635                     640

Ser Glu Phe Pro Thr Tyr Gly Phe Asn Cys Glu Phe Gly Trp Gly Ser
                645                 650                 655

His Lys Thr Phe Cys His Trp Glu His Asp Asn His Val Gln Leu Lys
                660                 665                 670

Trp Ser Val Leu Thr Ser Lys Thr Gly Pro Ile Gln Asp His Thr Gly
        675                 680                 685

Asp Gly Asn Phe Ile Tyr Ser Gln Ala Asp Glu Asn Gln Lys Gly Lys
        690                 695                 700

Val Ala Arg Leu Val Ser Pro Val Tyr Ser Gln Asn Ser Ala His
705                 710                 715                     720

Cys Met Thr Phe Trp Tyr His Met Ser Gly Ser His Val Gly Thr Leu
                725                 730                 735

Arg Val Lys Leu Arg Tyr Gln Lys Pro Glu Glu Tyr Asp Gln Leu Val
                740                 745                 750

Trp Met Ala Ile Gly His Gln Gly Asp His Trp Lys Glu Gly Arg Val
            755                 760                 765

Leu Leu His Lys Ser Leu Lys Leu Tyr Gln Val Ile Phe Glu Gly Glu
    770                 775                 780

Ile Gly Lys Gly Asn Leu Gly Gly Ile Ala Val Asp Asp Ile Ser Ile
785                 790                 795                     800

Asn Asn His Ile Ser Gln Glu Asp Cys Ala Lys Pro Ala Asp Leu Asp
                805                 810                 815

Lys Lys Asn Pro Glu Ile Lys Ile Asp Glu Thr Gly Ser Thr Pro Gly
            820                 825                 830

Tyr Glu Gly Glu Gly Glu Gly Asp Lys Asn Ile Ser Arg Lys Pro Gly
            835                 840                 845

Asn Val Leu Lys Thr Leu Glu Pro Ile Leu Ile Thr Ile Ile Ala Met
    850                 855                 860

Ser Ala Leu Gly Val Leu Leu Gly Ala Val Cys Gly Val Val Leu Tyr
```

```
                    865                      870                      875                      880
Cys Ala Cys Trp His Asn Gly Met Ser Glu Arg Asn Leu Ser Ala Leu
                885                      890                      895
Glu Asn Tyr Asn Phe Glu Leu Val Asp Gly Val Lys Leu Lys Lys Asp
                900                      905                      910
Lys Leu Asn Thr Gln Ser Thr Tyr Ser Glu Ala
                915                      920
```

<210> 3
<211> 2766
<212> DNA
<213> rat

<220>
<221> CDS
<222> (1)..(2763)

<400> 3

```
atg gag agg ggg ctg ccg ttg ctg tgc gcc acg ctc gcc ctt gcc ctc     48
Met Glu Arg Gly Leu Pro Leu Leu Cys Ala Thr Leu Ala Leu Ala Leu
  1               5                  10                  15 gcc ctg ggg gct ttc cgc agc gat aaa tgt ggc ggg act ata aaa att     96
Ala Leu Gly Ala Phe Arg Ser Asp Lys Cys Gly Gly Thr Ile Lys Ile
                 20                  25                  30 gaa aac ccg ggg tac ctt aca tct ccc ggc tac cct cat tct tac cat    144
Glu Asn Pro Gly Tyr Leu Thr Ser Pro Gly Tyr Pro His Ser Tyr His
             35                  40                  45 cca agt gag aaa tgt gaa tgg cta atc caa gct ccg gag ccc tac cag    192
Pro Ser Glu Lys Cys Glu Trp Leu Ile Gln Ala Pro Glu Pro Tyr Gln
         50                  55                  60 aga atc atg atc aac ttc aac cca cat ttc gat ttg gag gac aga gac    240
Arg Ile Met Ile Asn Phe Asn Pro His Phe Asp Leu Glu Asp Arg Asp
 65                  70                  75                  80 tgc aag tat gac tat gtg gaa gtg atc gat gga gag aat gaa ggt ggc    288
Cys Lys Tyr Asp Tyr Val Glu Val Ile Asp Gly Glu Asn Glu Gly Gly
                 85                  90                  95 cgc ctg tgg ggg aag ttc tgt ggg aag atc gca cct tca cct gtg gtg    336
Arg Leu Trp Gly Lys Phe Cys Gly Lys Ile Ala Pro Ser Pro Val Val
                100                 105                 110 tct tca ggg cca ttt ctc ttc atc aaa ttt gtc tct gac tat gag acc    384
Ser Ser Gly Pro Phe Leu Phe Ile Lys Phe Val Ser Asp Tyr Glu Thr
            115                 120                 125
```

```
cac ggg gca gga ttt tcc atc cgc tat gaa atc ttc aag aga ggg ccc    432
His Gly Ala Gly Phe Ser Ile Arg Tyr Glu Ile Phe Lys Arg Gly Pro
    130                 135                 140 gaa tgt tct cag aac tat aca gca cct act gga gtg ata aag tcc cct    480
Glu Cys Ser Gln Asn Tyr Thr Ala Pro Thr Gly Val Ile Lys Ser Pro
145                 150                 155                 160 ggg ttc cct gaa aaa tac ccc aac agc ttg gag tgc acc tac atc atc    528
Gly Phe Pro Glu Lys Tyr Pro Asn Ser Leu Glu Cys Thr Tyr Ile Ile
                165                 170                 175 ttt gca cca aag atg tct gag ata atc cta gag ttt gaa agt ttt gac    576
Phe Ala Pro Lys Met Ser Glu Ile Ile Leu Glu Phe Glu Ser Phe Asp
            180                 185                 190 ctg gag caa gac tca aat cct ccc gga gga atg ttc tgt cgc tat gac    624
Leu Glu Gln Asp Ser Asn Pro Pro Gly Gly Met Phe Cys Arg Tyr Asp
        195                 200                 205 cgg ctg gag atc tgg gat gga ttc cct gaa gtt ggc cct cac att ggg    672
Arg Leu Glu Ile Trp Asp Gly Phe Pro Glu Val Gly Pro His Ile Gly
    210                 215                 220 cgt tac tgt ggg cag aaa act cct ggc cgg atc cgc tcc tct tca ggc    720
Arg Tyr Cys Gly Gln Lys Thr Pro Gly Arg Ile Arg Ser Ser Ser Gly
225                 230                 235                 240 att cta tcc atg gtc ttc tac act gac agc gca ata gca aag gaa ggt    768
Ile Leu Ser Met Val Phe Tyr Thr Asp Ser Ala Ile Ala Lys Glu Gly
                245                 250                 255 ttc tca gcc aac tac agc gtg ctg cag agc agc atc tct gaa gat ttc    816
Phe Ser Ala Asn Tyr Ser Val Leu Gln Ser Ser Ile Ser Glu Asp Phe
            260                 265                 270 aag tgt atg gag gct ctg ggc atg gaa tct gga gag atc cat tct gac    864
Lys Cys Met Glu Ala Leu Gly Met Glu Ser Gly Glu Ile His Ser Asp
        275                 280                 285 cag atc act gca tct tcc cag tat ggt acc aac tgg tct gtt gag cgc    912
Gln Ile Thr Ala Ser Ser Gln Tyr Gly Thr Asn Trp Ser Val Glu Arg
    290                 295                 300 tcc cgc ctg aac tac cct gaa aac ggg tgg aca cca gga gag gac tcc    960
Ser Arg Leu Asn Tyr Pro Glu Asn Gly Trp Thr Pro Gly Glu Asp Ser
305                 310                 315                 320 tac agg gag tgg atc cag gtg gac ttg ggc ctc ctg cga ttc gtt act   1008
Tyr Arg Glu Trp Ile Gln Val Asp Leu Gly Leu Leu Arg Phe Val Thr
                325                 330                 335 gct gtg ggg aca cag ggt gcc att tcc aag gaa acc aag aag aaa tat   1056
Ala Val Gly Thr Gln Gly Ala Ile Ser Lys Glu Thr Lys Lys Lys Tyr
```

```
                340                          345                          350
tat gtc aag act tac aga gta gac atc agc tcc aac gga gag gac tgg    1104
Tyr Val Lys Thr Tyr Arg Val Asp Ile Ser Ser Asn Gly Glu Asp Trp
        355                      360                      365 atc acc ctg aag gag gga aat aaa gcc att atc ttt cag gga aac acc    1152
Ile Thr Leu Lys Glu Gly Asn Lys Ala Ile Ile Phe Gln Gly Asn Thr
        370                      375                      380 aat ccc acg gat gtt gtc ttt gga gtt ttc ccc aaa cca ctg ata act    1200
Asn Pro Thr Asp Val Val Phe Gly Val Phe Pro Lys Pro Leu Ile Thr
385                      390                      395             400 cga ttt gtc cga atc aaa cct gca tcc tgg gaa act gga ata tct atg    1248
Arg Phe Val Arg Ile Lys Pro Ala Ser Trp Glu Thr Gly Ile Ser Met
                 405                      410                  415 aga ttt gaa gtt tat ggc tgc aag ata aca gat tac cct tgc tct gga    1296
Arg Phe Glu Val Tyr Gly Cys Lys Ile Thr Asp Tyr Pro Cys Ser Gly
                420                      425                  430 atg ttg ggc atg gtg tct gga ctt att tca gac tcc cag att aca gca    1344
Met Leu Gly Met Val Ser Gly Leu Ile Ser Asp Ser Gln Ile Thr Ala
        435                      440                      445 tcc aac caa gga gac agg aac tgg atg cca gaa aac atc cgc ctg gtg    1392
Ser Asn Gln Gly Asp Arg Asn Trp Met Pro Glu Asn Ile Arg Leu Val
        450                      455                      460 acc agt cga acc ggc tgg gcc ctg cca ccc tca ccc cac cca tac atc    1440
Thr Ser Arg Thr Gly Trp Ala Leu Pro Pro Ser Pro His Pro Tyr Ile
465                      470                      475             480 aat gaa tgg ctc caa gtg gac ctg gga gat gag aag ata gta aga ggt    1488
Asn Glu Trp Leu Gln Val Asp Leu Gly Asp Glu Lys Ile Val Arg Gly
                 485                      490                  495 gtc atc att caa ggt ggg aag cac cga gaa aac aaa gtg ttc atg agg    1536
Val Ile Ile Gln Gly Gly Lys His Arg Glu Asn Lys Val Phe Met Arg
                500                      505                  510 aag ttc aag atc gcc tac agt aac aat ggt tct gac tgg aaa atg atc    1584
Lys Phe Lys Ile Ala Tyr Ser Asn Asn Gly Ser Asp Trp Lys Met Ile
        515                      520                      525 atg gat gac agc aag cgc aag gct aag tct ttt gaa ggc aac aac aac    1632
Met Asp Asp Ser Lys Arg Lys Ala Lys Ser Phe Glu Gly Asn Asn Asn
        530                      535                      540 tat gac aca cct gag ctc cgg gcc ttt aca cct ctc tcc aca aga ttc    1680
Tyr Asp Thr Pro Glu Leu Arg Ala Phe Thr Pro Leu Ser Thr Arg Phe
545                      550                      555             560
```

```
atc agg atc tac ccc gag aga gcc aca cat agt ggg ctc gga ctg agg    1728
Ile Arg Ile Tyr Pro Glu Arg Ala Thr His Ser Gly Leu Gly Leu Arg
                565                 570                 575 atg gag cta ctg ggc tgt gaa gta gaa gtg cct aca gct gga ccc acg    1776
Met Glu Leu Leu Gly Cys Glu Val Glu Val Pro Thr Ala Gly Pro Thr
            580                 585                 590 aca ccc aat ggg aac ccc gtg gac gag tgt gac gat gac cag gcc aac    1824
Thr Pro Asn Gly Asn Pro Val Asp Glu Cys Asp Asp Asp Gln Ala Asn
            595                 600                 605 tgc cac agt ggc aca ggt gat gac ttc cag ctc aca gga ggc acc act    1872
Cys His Ser Gly Thr Gly Asp Asp Phe Gln Leu Thr Gly Gly Thr Thr
        610                 615                 620 gtc ctg gcc aca gag aag ccc acc att ata gac agc acc atc caa tca    1920
Val Leu Ala Thr Glu Lys Pro Thr Ile Ile Asp Ser Thr Ile Gln Ser
625                 630                 635                 640 gag ttc ccg aca tac ggt ttt aac tgc gag ttt ggc tgg ggc tct cac    1968
Glu Phe Pro Thr Tyr Gly Phe Asn Cys Glu Phe Gly Trp Gly Ser His
                645                 650                 655 aag aca ttc tgc cac tgg gaa cat gac agc cac gcg cag ctc agg tgg    2016
Lys Thr Phe Cys His Trp Glu His Asp Ser His Ala Gln Leu Arg Trp
            660                 665                 670 agg gtg ctg acc agc aag acg ggg ccc att cag gac cac aca gga gat    2064
Arg Val Leu Thr Ser Lys Thr Gly Pro Ile Gln Asp His Thr Gly Asp
        675                 680                 685 ggc aac ttc atc tat tcc caa gct gat gaa aat cag aaa ggc aaa gta    2112
Gly Asn Phe Ile Tyr Ser Gln Ala Asp Glu Asn Gln Lys Gly Lys Val
        690                 695                 700 gcc cgc ctg gtg agc cct gtg gtc tat tcc cag agt tct gcc cac tgc    2160
Ala Arg Leu Val Ser Pro Val Val Tyr Ser Gln Ser Ser Ala His Cys
705                 710                 715                 720 atg acc ttc tgg tat cac atg tcc ggc tct cat gtg ggt aca ctg agg    2208
Met Thr Phe Trp Tyr His Met Ser Gly Ser His Val Gly Thr Leu Arg
                725                 730                 735 gtc aaa ctg cac tac cag aag cca gag gaa tat gat caa ctg gtc tgg    2256
Val Lys Leu His Tyr Gln Lys Pro Glu Glu Tyr Asp Gln Leu Val Trp
            740                 745                 750 atg gtg gtc ggg cac caa gga gac cac tgg aag gaa ggg cgt gtc ttg    2304
Met Val Val Gly His Gln Gly Asp His Trp Lys Glu Gly Arg Val Leu
        755                 760                 765 ctg cac aaa tct ctg aaa ctg tat cag gtt att ttt gaa ggt gaa atc    2352
Leu His Lys Ser Leu Lys Leu Tyr Gln Val Ile Phe Glu Gly Glu Ile
```

```
                770                      775                       780
gga aaa gga aac ctc ggt ggg att gct gtg gat gat atc agt att aac    2400
Gly Lys Gly Asn Leu Gly Gly Ile Ala Val Asp Asp Ile Ser Ile Asn
785                 790                 795                 800 aac cac att cct cag gag gac tgt gca aaa cca aca gac cta gat aaa    2448
Asn His Ile Pro Gln Glu Asp Cys Ala Lys Pro Thr Asp Leu Asp Lys
                805                 810                 815 aag aac aca gaa att aaa ata gat gaa aca ggg agc acc cca gga tat    2496
Lys Asn Thr Glu Ile Lys Ile Asp Glu Thr Gly Ser Thr Pro Gly Tyr
            820                 825                 830 gaa gaa ggg aaa ggc gac aag aac atc tcc agg aag cca ggc aat gtg    2544
Glu Glu Gly Lys Gly Asp Lys Asn Ile Ser Arg Lys Pro Gly Asn Val
        835                 840                 845 ctt aag acc ctg gac ccc atc ctg atc acc atc ata gcc atg agt gcc    2592
Leu Lys Thr Leu Asp Pro Ile Leu Ile Thr Ile Ile Ala Met Ser Ala
    850                 855                 860 ctg ggg gtg ctc ctg ggt gca gtc tgt gga gtt gtg ctg tac tgt gcc    2640
Leu Gly Val Leu Leu Gly Ala Val Cys Gly Val Val Leu Tyr Cys Ala
865                 870                 875                 880 tgt tgg cac aat ggg atg tcg gaa agg aac cta tct gcc ctg gag aac    2688
Cys Trp His Asn Gly Met Ser Glu Arg Asn Leu Ser Ala Leu Glu Asn
                885                 890                 895 tat aac ttt gaa ctt gtg gat ggt gta aag ttg aaa aaa gat aaa ctg    2736
Tyr Asn Phe Glu Leu Val Asp Gly Val Lys Leu Lys Lys Asp Lys Leu
                900                 905                 910 aac cca cac agt aat tac tca gag gcg tga                            2766
Asn Pro His Ser Asn Tyr Ser Glu Ala
            915                 920

<210> 4
<211> 921
<212> PRT
<213> rat

<400> 4
Met Glu Arg Gly Leu Pro Leu Leu Cys Ala Thr Leu Ala Leu Ala Leu
 1               5                  10                  15

Ala Leu Gly Ala Phe Arg Ser Asp Lys Cys Gly Gly Thr Ile Lys Ile
                20                  25                  30

Glu Asn Pro Gly Tyr Leu Thr Ser Pro Gly Tyr Pro His Ser Tyr His
            35                  40                  45
```

Pro Ser Glu Lys Cys Glu Trp Leu Ile Gln Ala Pro Glu Pro Tyr Gln
    50                  55                  60
Arg Ile Met Ile Asn Phe Asn Pro His Phe Asp Leu Glu Asp Arg Asp
65              70                  75                  80
Cys Lys Tyr Asp Tyr Val Glu Val Ile Asp Gly Glu Asn Glu Gly Gly
            85                  90                  95
Arg Leu Trp Gly Lys Phe Cys Gly Lys Ile Ala Pro Ser Pro Val Val
            100                 105                 110
Ser Ser Gly Pro Phe Leu Phe Ile Lys Phe Val Ser Asp Tyr Glu Thr
        115                 120                 125
His Gly Ala Gly Phe Ser Ile Arg Tyr Glu Ile Phe Lys Arg Gly Pro
        130                 135                 140
Glu Cys Ser Gln Asn Tyr Thr Ala Pro Thr Gly Val Ile Lys Ser Pro
145                 150                 155                 160
Gly Phe Pro Glu Lys Tyr Pro Asn Ser Leu Glu Cys Thr Tyr Ile Ile
            165                 170                 175
Phe Ala Pro Lys Met Ser Glu Ile Ile Leu Glu Phe Glu Ser Phe Asp
            180                 185                 190
Leu Glu Gln Asp Ser Asn Pro Pro Gly Gly Met Phe Cys Arg Tyr Asp
        195                 200                 205
Arg Leu Glu Ile Trp Asp Gly Phe Pro Glu Val Gly Pro His Ile Gly
210                 215                 220
Arg Tyr Cys Gly Gln Lys Thr Pro Gly Arg Ile Arg Ser Ser Ser Gly
225                 230                 235                 240
Ile Leu Ser Met Val Phe Tyr Thr Asp Ser Ala Ile Ala Lys Glu Gly
            245                 250                 255
Phe Ser Ala Asn Tyr Ser Val Leu Gln Ser Ser Ile Ser Glu Asp Phe
            260                 265                 270
Lys Cys Met Glu Ala Leu Gly Met Glu Ser Gly Glu Ile His Ser Asp
        275                 280                 285
Gln Ile Thr Ala Ser Ser Gln Tyr Gly Thr Asn Trp Ser Val Glu Arg
    290                 295                 300
Ser Arg Leu Asn Tyr Pro Glu Asn Gly Trp Thr Pro Gly Glu Asp Ser
305                 310                 315                 320
Tyr Arg Glu Trp Ile Gln Val Asp Leu Gly Leu Leu Arg Phe Val Thr
            325                 330                 335

```
Ala Val Gly Thr Gln Gly Ala Ile Ser Lys Glu Thr Lys Lys Lys Tyr
            340                 345                 350
Tyr Val Lys Thr Tyr Arg Val Asp Ile Ser Ser Asn Gly Glu Asp Trp
            355                 360                 365
Ile Thr Leu Lys Glu Gly Asn Lys Ala Ile Ile Phe Gln Gly Asn Thr
    370                 375                 380
Asn Pro Thr Asp Val Val Phe Gly Val Phe Pro Lys Pro Leu Ile Thr
385                 390                 395                 400
Arg Phe Val Arg Ile Lys Pro Ala Ser Trp Glu Thr Gly Ile Ser Met
                405                 410                 415
Arg Phe Glu Val Tyr Gly Cys Lys Ile Thr Asp Tyr Pro Cys Ser Gly
            420                 425                 430
Met Leu Gly Met Val Ser Gly Leu Ile Ser Asp Ser Gln Ile Thr Ala
            435                 440                 445
Ser Asn Gln Gly Asp Arg Asn Trp Met Pro Glu Asn Ile Arg Leu Val
    450                 455                 460
Thr Ser Arg Thr Gly Trp Ala Leu Pro Pro Ser Pro His Pro Tyr Ile
465                 470                 475                 480
Asn Glu Trp Leu Gln Val Asp Leu Gly Asp Glu Lys Ile Val Arg Gly
                485                 490                 495
Val Ile Ile Gln Gly Gly Lys His Arg Glu Asn Lys Val Phe Met Arg
            500                 505                 510
Lys Phe Lys Ile Ala Tyr Ser Asn Asn Gly Ser Asp Trp Lys Met Ile
            515                 520                 525
Met Asp Asp Ser Lys Arg Lys Ala Lys Ser Phe Glu Gly Asn Asn Asn
    530                 535                 540
Tyr Asp Thr Pro Glu Leu Arg Ala Phe Thr Pro Leu Ser Thr Arg Phe
545                 550                 555                 560
Ile Arg Ile Tyr Pro Glu Arg Ala Thr His Ser Gly Leu Gly Leu Arg
                565                 570                 575
Met Glu Leu Leu Gly Cys Glu Val Glu Val Pro Thr Ala Gly Pro Thr
            580                 585                 590
Thr Pro Asn Gly Asn Pro Val Asp Glu Cys Asp Asp Gln Ala Asn
            595                 600                 605
Cys His Ser Gly Thr Gly Asp Asp Phe Gln Leu Thr Gly Gly Thr Thr
    610                 615                 620
```

Val Leu Ala Thr Glu Lys Pro Thr Ile Ile Asp Ser Thr Ile Gln Ser
625                 630                 635                 640

Glu Phe Pro Thr Tyr Gly Phe Asn Cys Glu Phe Gly Trp Gly Ser His
            645                 650                 655

Lys Thr Phe Cys His Trp Glu His Asp Ser His Ala Gln Leu Arg Trp
        660                 665                 670

Arg Val Leu Thr Ser Lys Thr Gly Pro Ile Gln Asp His Thr Gly Asp
            675                 680                 685

Gly Asn Phe Ile Tyr Ser Gln Ala Asp Glu Asn Gln Lys Gly Lys Val
        690                 695                 700

Ala Arg Leu Val Ser Pro Val Val Tyr Ser Gln Ser Ser Ala His Cys
705                 710                 715                 720

Met Thr Phe Trp Tyr His Met Ser Gly Ser His Val Gly Thr Leu Arg
            725                 730                 735

Val Lys Leu His Tyr Gln Lys Pro Glu Glu Tyr Asp Gln Leu Val Trp
            740                 745                 750

Met Val Val Gly His Gln Gly Asp His Trp Lys Glu Gly Arg Val Leu
            755                 760                 765

Leu His Lys Ser Leu Lys Leu Tyr Gln Val Ile Phe Glu Gly Glu Ile
        770                 775                 780

Gly Lys Gly Asn Leu Gly Gly Ile Ala Val Asp Asp Ile Ser Ile Asn
785                 790                 795                 800

Asn His Ile Pro Gln Glu Asp Cys Ala Lys Pro Thr Asp Leu Asp Lys
                805                 810                 815

Lys Asn Thr Glu Ile Lys Ile Asp Glu Thr Gly Ser Thr Pro Gly Tyr
            820                 825                 830

Glu Glu Gly Lys Gly Asp Lys Asn Ile Ser Arg Lys Pro Gly Asn Val
                835                 840                 845

Leu Lys Thr Leu Asp Pro Ile Leu Ile Thr Ile Ile Ala Met Ser Ala
        850                 855                 860

Leu Gly Val Leu Leu Gly Ala Val Cys Gly Val Val Leu Tyr Cys Ala
865                 870                 875                 880

Cys Trp His Asn Gly Met Ser Glu Arg Asn Leu Ser Ala Leu Glu Asn
                885                 890                 895

Tyr Asn Phe Glu Leu Val Asp Gly Val Lys Leu Lys Lys Asp Lys Leu

Asn Pro His Ser Asn Tyr Ser Glu Ala
        915                 920

<210> 5
<211> 3652
<212> DNA
<213> mouse

<220>
<221> CDS
<222> (348)..(3116)

t tttttttttt tttttttttt tttttcctcc ttcttcttct tcctgagaca  60
tggcccgggc agtggctcct ggaagaggaa caagtgtggg aaaagggaga ggaaatcgga 120
gctaaatgac aggatgcagg cgacttgaga cacaaaaaga gaagcgcttc tcgcgaattc 180
aggcattgcc tcgccgctag ccttccccgc caagacccgc tgaggatttt atggttctta 240
ggcggactta agagcgtttc ggattgttaa gattatcgtt tgctggtttt tcgtccgcgc 300
aatcgtgttc tcctgcggct gcctggggac tggcttggcg aaggagg atg gag agg    356
                                                  Met Glu Arg
                                                    1 ggg ctg ccg ttg ctg tgc gcc acg ctc gcc ctt gcc ctc gcc ctg gcg    404
Gly Leu Pro Leu Leu Cys Ala Thr Leu Ala Leu Ala Leu Ala Leu Ala
        5                   10                  15 ggc gct ttc cgc agc gac aaa tgt ggc ggg acc ata aaa atc gaa aac    452
Gly Ala Phe Arg Ser Asp Lys Cys Gly Gly Thr Ile Lys Ile Glu Asn
 20                  25                  30                  35 cca ggg tac ctc aca tct ccc ggt tac cct cat tct tac cat cca agt    500
Pro Gly Tyr Leu Thr Ser Pro Gly Tyr Pro His Ser Tyr His Pro Ser
                 40                  45                  50 gag aag tgt gaa tgg cta atc caa gct ccg gaa ccc tac cag aga atc    548
Glu Lys Cys Glu Trp Leu Ile Gln Ala Pro Glu Pro Tyr Gln Arg Ile
             55                  60                  65 ata atc aac ttc aac cca cat ttc gat ttg gag gac aga gac tgc aag    596
Ile Ile Asn Phe Asn Pro His Phe Asp Leu Glu Asp Arg Asp Cys Lys
         70                  75                  80 tat gac tac gtg gaa gta att gat ggg gag aat gaa ggc ggc cgc ctg    644
Tyr Asp Tyr Val Glu Val Ile Asp Gly Glu Asn Glu Gly Gly Arg Leu
     85                  90                  95 tgg ggg aag ttc tgt ggg aag att gca cct tct cct gtg gtg tct tca    692
Trp Gly Lys Phe Cys Gly Lys Ile Ala Pro Ser Pro Val Val Ser Ser

```
              100                 105                 110                 115
     ggg ccc ttt ctc ttc atc aaa ttt gtc tct gac tat gag aca cat ggg     740
     Gly Pro Phe Leu Phe Ile Lys Phe Val Ser Asp Tyr Glu Thr His Gly
                     120                 125                 130 gca ggg ttt tcc atc cgc tat gaa atc ttc aag aga ggg ccc gaa tgt     788
     Ala Gly Phe Ser Ile Arg Tyr Glu Ile Phe Lys Arg Gly Pro Glu Cys
                     135                 140                 145 tct cag aac tat aca gca cct act gga gtg ata aag tcc cct ggg ttc     836
     Ser Gln Asn Tyr Thr Ala Pro Thr Gly Val Ile Lys Ser Pro Gly Phe
             150                 155                 160 cct gaa aaa tac ccc aac tgc ttg gag tgc acc tac atc atc ttt gca     884
     Pro Glu Lys Tyr Pro Asn Cys Leu Glu Cys Thr Tyr Ile Ile Phe Ala
         165                 170                 175 cca aag atg tct gag ata atc ctg gag ttt gaa agt ttt gac ctg gag     932
     Pro Lys Met Ser Glu Ile Ile Leu Glu Phe Glu Ser Phe Asp Leu Glu
     180                 185                 190                 195 caa gac tcg aat cct ccc gga gga atg ttc tgt cgc tat gac cgg ctg     980
     Gln Asp Ser Asn Pro Pro Gly Gly Met Phe Cys Arg Tyr Asp Arg Leu
                     200                 205                 210 gag atc tgg gat gga ttc cct gaa gtt ggc cct cac att ggg cgt tat    1028
     Glu Ile Trp Asp Gly Phe Pro Glu Val Gly Pro His Ile Gly Arg Tyr
                 215                 220                 225 tgt ggg cag aaa act cct ggc cgg atc cgc tcc tct tca ggc gtt cta    1076
     Cys Gly Gln Lys Thr Pro Gly Arg Ile Arg Ser Ser Ser Gly Val Leu
                 230                 235                 240 tcc atg gtc ttt tac act gac agc gca ata gca aaa gaa ggt ttc tca    1124
     Ser Met Val Phe Tyr Thr Asp Ser Ala Ile Ala Lys Glu Gly Phe Ser
             245                 250                 255 gcc aac tac agt gtg cta cag agc agc atc tct gaa gat ttt aag tgt    1172
     Ala Asn Tyr Ser Val Leu Gln Ser Ser Ile Ser Glu Asp Phe Lys Cys
     260                 265                 270                 275 atg gag gct ctg ggc atg gaa tct gga gag atc cat tct gat cag atc    1220
     Met Glu Ala Leu Gly Met Glu Ser Gly Glu Ile His Ser Asp Gln Ile
                     280                 285                 290 act gca tct tca cag tat ggt acc aac tgg tct gta gag cgc tcc cgc    1268
     Thr Ala Ser Ser Gln Tyr Gly Thr Asn Trp Ser Val Glu Arg Ser Arg
                 295                 300                 305 ctg aac tac cct gaa aat ggg tgg act cca gga gaa gac tcc tac aag    1316
     Leu Asn Tyr Pro Glu Asn Gly Trp Thr Pro Gly Glu Asp Ser Tyr Lys
                 310                 315                 320
```

```
gag tgg atc cag gtg gac ttg ggc ctc ctg cga ttc gtt act gct gta    1364
Glu Trp Ile Gln Val Asp Leu Gly Leu Leu Arg Phe Val Thr Ala Val
    325             330                 335 ggg aca cag ggt gcc att tcc aag gaa acc aag aag aaa tat tat gtc    1412
Gly Thr Gln Gly Ala Ile Ser Lys Glu Thr Lys Lys Lys Tyr Tyr Val
340                 345                 350                 355 aag act tac aga gta gac atc agc tcc aac gga gag gac tgg atc tcc    1460
Lys Thr Tyr Arg Val Asp Ile Ser Ser Asn Gly Glu Asp Trp Ile Ser
                360                 365                 370 ctg aaa gag gga aat aaa gcc att atc ttt cag gga aac acc aac ccc    1508
Leu Lys Glu Gly Asn Lys Ala Ile Ile Phe Gln Gly Asn Thr Asn Pro
            375                 380                 385 aca gat gtt gtc tta gga gtt ttc tcc aaa cca ctg ata act cga ttt    1556
Thr Asp Val Val Leu Gly Val Phe Ser Lys Pro Leu Ile Thr Arg Phe
                390                 395                 400 gtc cga atc aaa cct gta tcc tgg gaa act ggt ata tct atg aga ttt    1604
Val Arg Ile Lys Pro Val Ser Trp Glu Thr Gly Ile Ser Met Arg Phe
        405                 410                 415 gaa gtt tat ggc tgc aag ata aca gat tat cct tgc tct gga atg ttg    1652
Glu Val Tyr Gly Cys Lys Ile Thr Asp Tyr Pro Cys Ser Gly Met Leu
420                 425                 430                 435 ggc atg gtg tct gga ctt att tca gac tcc cag att aca gca tcc aat    1700
Gly Met Val Ser Gly Leu Ile Ser Asp Ser Gln Ile Thr Ala Ser Asn
                440                 445                 450 caa gcc gac agg aat tgg atg cca gaa aac atc cgt ctg gtg acc agt    1748
Gln Ala Asp Arg Asn Trp Met Pro Glu Asn Ile Arg Leu Val Thr Ser
            455                 460                 465 cgt acc ggc tgg gca ctg cca ccc tca ccc cac cca tac acc aat gaa    1796
Arg Thr Gly Trp Ala Leu Pro Pro Ser Pro His Pro Tyr Thr Asn Glu
        470                 475                 480 tgg ctc caa gtg gac ctg gga gat gag aag ata gta aga ggt gtc atc    1844
Trp Leu Gln Val Asp Leu Gly Asp Glu Lys Ile Val Arg Gly Val Ile
    485                 490                 495 att cag ggt ggg aag cac cga gaa aac aag gtg ttc atg agg aag ttc    1892
Ile Gln Gly Gly Lys His Arg Glu Asn Lys Val Phe Met Arg Lys Phe
500                 505                 510                 515 aag atc gcc tat agt aac aat ggc tct gac tgg aaa act atc atg gat    1940
Lys Ile Ala Tyr Ser Asn Asn Gly Ser Asp Trp Lys Thr Ile Met Asp
                520                 525                 530 gac agc aag cgc aag gct aag tcg ttc gaa ggc aac aac aac tat gac    1988
Asp Ser Lys Arg Lys Ala Lys Ser Phe Glu Gly Asn Asn Asn Tyr Asp
```

```
                        535                      540                       545 aca cct gag ctt cgg acg ttt tca cct ctc tcc aca agg ttc atc agg      2036
        Thr Pro Glu Leu Arg Thr Phe Ser Pro Leu Ser Thr Arg Phe Ile Arg
                    550                 555                 560 atc tac cct gag aga gcc aca cac agt ggg ctt ggg ctg agg atg gag      2084
        Ile Tyr Pro Glu Arg Ala Thr His Ser Gly Leu Gly Leu Arg Met Glu
                565                 570                 575 cta ctg ggc tgt gaa gtg gaa gca cct aca gct gga cca acc aca ccc      2132
        Leu Leu Gly Cys Glu Val Glu Ala Pro Thr Ala Gly Pro Thr Thr Pro
        580                 585                 590                 595 aat ggg aac cca gtg cat gag tgt gac gac gac cag gcc aac tgc cac      2180
        Asn Gly Asn Pro Val His Glu Cys Asp Asp Asp Gln Ala Asn Cys His
                            600                 605                 610 agt ggc aca ggt gat gac ttc cag ctc aca gga ggc acc act gtc ctg      2228
        Ser Gly Thr Gly Asp Asp Phe Gln Leu Thr Gly Gly Thr Thr Val Leu
                        615                 620                 625 gcc aca gag aag cca acc att ata gac agc acc atc caa tca gag ttc      2276
        Ala Thr Glu Lys Pro Thr Ile Ile Asp Ser Thr Ile Gln Ser Glu Phe
                    630                 635                 640 ccg aca tac ggt ttt aac tgc gag ttt ggc tgg ggc tct cac aag aca      2324
        Pro Thr Tyr Gly Phe Asn Cys Glu Phe Gly Trp Gly Ser His Lys Thr
                645                 650                 655 ttc tgc cac tgg gag cat gac agc cat gca cag ctc agg tgg agt gtg      2372
        Phe Cys His Trp Glu His Asp Ser His Ala Gln Leu Arg Trp Ser Val
        660                 665                 670                 675 ctg acc agc aag aca ggg ccg att cag gac cat aca gga gat ggc aac      2420
        Leu Thr Ser Lys Thr Gly Pro Ile Gln Asp His Thr Gly Asp Gly Asn
                            680                 685                 690 ttc atc tat tcc caa gct gat gaa aat cag aaa ggc aaa gta gcc cgc      2468
        Phe Ile Tyr Ser Gln Ala Asp Glu Asn Gln Lys Gly Lys Val Ala Arg
                        695                 700                 705 ctg gtg agc cct gtg gtc tat tcc cag agc tct gcc cac tgt atg acc      2516
        Leu Val Ser Pro Val Val Tyr Ser Gln Ser Ser Ala His Cys Met Thr
                    710                 715                 720 ttc tgg tat cac atg tcc ggc tct cat gtg ggt aca ctg agg gtc aaa      2564
        Phe Trp Tyr His Met Ser Gly Ser His Val Gly Thr Leu Arg Val Lys
                725                 730                 735 cta cgc tac cag aag cca gag gaa tat gat caa ctg gtc tgg atg gtg      2612
        Leu Arg Tyr Gln Lys Pro Glu Glu Tyr Asp Gln Leu Val Trp Met Val
        740                 745                 750                 755
```

| | | | | | | | | | | | | | | | | |
|---|---|---|---|---|---|---|---|---|---|---|---|---|---|---|---|---|
|gtt|ggg|cac|caa|gga|gac|cac|tgg|aaa|gaa|gga|cgt|gtc|ttg|ctg|cac|2660|
|Val|Gly|His|Gln|Gly|Asp|His|Trp|Lys|Glu|Gly|Arg|Val|Leu|Leu|His| |
| | | |760| | | | |765| | | | |770| | | |
|aaa|tct|ctg|aaa|cta|tat|cag|gtt|att|ttt|gaa|ggt|gaa|atc|gga|aaa|2708|
|Lys|Ser|Leu|Lys|Leu|Tyr|Gln|Val|Ile|Phe|Glu|Gly|Glu|Ile|Gly|Lys| |
| | | |775| | | | |780| | | | |785| | | |
|gga|aac|ctt|ggt|gga|att|gct|gtg|gat|gat|atc|agt|att|aac|aac|cat|2756|
|Gly|Asn|Leu|Gly|Gly|Ile|Ala|Val|Asp|Asp|Ile|Ser|Ile|Asn|Asn|His| |
| | |790| | | | |795| | | | |800| | | | |
|att|tct|cag|gaa|gac|tgt|gca|aaa|cca|aca|gac|cta|gat|aaa|aag|aac|2804|
|Ile|Ser|Gln|Glu|Asp|Cys|Ala|Lys|Pro|Thr|Asp|Leu|Asp|Lys|Lys|Asn| |
| |805| | | | |810| | | | |815| | | | | |
|aca|gaa|att|aaa|att|gat|gaa|aca|ggg|agc|act|cca|gga|tat|gaa|gga|2852|
|Thr|Glu|Ile|Lys|Ile|Asp|Glu|Thr|Gly|Ser|Thr|Pro|Gly|Tyr|Glu|Gly| |
|820| | | | |825| | | | |830| | | | |835| |
|gaa|ggg|gaa|ggt|gac|aag|aac|atc|tcc|agg|aag|cca|ggc|aat|gtg|ctt|2900|
|Glu|Gly|Glu|Gly|Asp|Lys|Asn|Ile|Ser|Arg|Lys|Pro|Gly|Asn|Val|Leu| |
| | | |840| | | | |845| | | | |850| | | |
|aag|acc|ctg|gat|ccc|atc|ctg|atc|acc|atc|ata|gcc|atg|agt|gcc|ctg|2948|
|Lys|Thr|Leu|Asp|Pro|Ile|Leu|Ile|Thr|Ile|Ile|Ala|Met|Ser|Ala|Leu| |
| | | |855| | | | |860| | | | |865| | | |
|gga|gta|ctc|ctg|ggt|gca|gtc|tgt|gga|gtt|gtg|ctg|tac|tgt|gcc|tgt|2996|
|Gly|Val|Leu|Leu|Gly|Ala|Val|Cys|Gly|Val|Val|Leu|Tyr|Cys|Ala|Cys| |
| | |870| | | | |875| | | | |880| | | | |
|tgg|cac|aat|ggg|atg|tca|gaa|agg|aac|cta|tct|gcc|ctg|gag|aac|tat|3044|
|Trp|His|Asn|Gly|Met|Ser|Glu|Arg|Asn|Leu|Ser|Ala|Leu|Glu|Asn|Tyr| |
| |885| | | | |890| | | | |895| | | | | |
|aac|ttt|gaa|ctt|gtg|gat|ggt|gta|aag|ttg|aaa|aaa|gat|aaa|ctg|aac|3092|
|Asn|Phe|Glu|Leu|Val|Asp|Gly|Val|Lys|Leu|Lys|Lys|Asp|Lys|Leu|Asn| |
|900| | | | |905| | | | |910| | | | |915| |
|cca|cag|agt|aat|tac|tca|gag|gcg|tgaaggcacg|gagctggagg|gaacaaggga|3146|
|Pro|Gln|Ser|Asn|Tyr|Ser|Glu|Ala| | | | |
| | | | |920| | | | | | | | ggagcacggc aggagaacag gtggaggcat ggggactctg ttactctgct ttcactgtaa 3206 gctgggaagg gcggggactc tgttactccg ctttcactgt aagctcggaa gggcatccac 3266 gatgccatgc caggcttttc tcaggagctt caatgagcgt cacctacaga cacaagcagg 3326 tgactgcggt aacaacagga atcatgtaca agcctgcttt cttctcttgg tttcatttgg 3386 gtaatcagaa gccatttgag accaagtgtg actgacttca tggttcatcc tactagcccc 3446 cttttttcct ctctttctcc ttaccctgtg gtggattctt ctcggaaact gcaaaatcca 3506 agatgctggc actaggcgtt attcagtggg ccctttttgat ggacatgtga cctgtagccc 3566 agtgcccaga gcatattatc ataaccacat tcaggggac gccaacgtcc atccaccttt 3626 gcatcgctac ctgcagcgag cacagg 3652

<210> 6
<211> 923
<212> PRT
<213> mouse

<400> 6
Met Glu Arg Gly Leu Pro Leu Leu Cys Ala Thr Leu Ala Leu Ala Leu
1               5                   10                  15

Ala Leu Ala Gly Ala Phe Arg Ser Asp Lys Cys Gly Gly Thr Ile Lys
            20                  25                  30

Ile Glu Asn Pro Gly Tyr Leu Thr Ser Pro Gly Tyr Pro His Ser Tyr
        35                  40                  45

His Pro Ser Glu Lys Cys Glu Trp Leu Ile Gln Ala Pro Glu Pro Tyr
    50                  55                  60

Gln Arg Ile Ile Ile Asn Phe Asn Pro His Phe Asp Leu Glu Asp Arg
65                  70                  75                  80

Asp Cys Lys Tyr Asp Tyr Val Glu Val Ile Asp Gly Glu Asn Glu Gly
                85                  90                  95

Gly Arg Leu Trp Gly Lys Phe Cys Gly Lys Ile Ala Pro Ser Pro Val
            100                 105                 110

Val Ser Ser Gly Pro Phe Leu Phe Ile Lys Phe Val Ser Asp Tyr Glu
        115                 120                 125

Thr His Gly Ala Gly Phe Ser Ile Arg Tyr Glu Ile Phe Lys Arg Gly
    130                 135                 140

Pro Glu Cys Ser Gln Asn Tyr Thr Ala Pro Thr Gly Val Ile Lys Ser
145                 150                 155                 160

Pro Gly Phe Pro Glu Lys Tyr Pro Asn Cys Leu Glu Cys Thr Tyr Ile
                165                 170                 175

Ile Phe Ala Pro Lys Met Ser Glu Ile Ile Leu Glu Phe Glu Ser Phe
            180                 185                 190

Asp Leu Glu Gln Asp Ser Asn Pro Pro Gly Gly Met Phe Cys Arg Tyr
        195                 200                 205

```
Asp Arg Leu Glu Ile Trp Asp Gly Phe Pro Glu Val Gly Pro His Ile
    210             215                 220
Gly Arg Tyr Cys Gly Gln Lys Thr Pro Gly Arg Ile Arg Ser Ser Ser
225             230                 235                 240
Gly Val Leu Ser Met Val Phe Tyr Thr Asp Ser Ala Ile Ala Lys Glu
                245                 250                 255
Gly Phe Ser Ala Asn Tyr Ser Val Leu Gln Ser Ser Ile Ser Glu Asp
                260                 265                 270
Phe Lys Cys Met Glu Ala Leu Gly Met Glu Ser Gly Glu Ile His Ser
            275                 280                 285
Asp Gln Ile Thr Ala Ser Ser Gln Tyr Gly Thr Asn Trp Ser Val Glu
        290                 295                 300
Arg Ser Arg Leu Asn Tyr Pro Glu Asn Gly Trp Thr Pro Gly Glu Asp
305                 310                 315                 320
Ser Tyr Lys Glu Trp Ile Gln Val Asp Leu Gly Leu Leu Arg Phe Val
                325                 330                 335
Thr Ala Val Gly Thr Gln Gly Ala Ile Ser Lys Glu Thr Lys Lys Lys
            340                 345                 350
Tyr Tyr Val Lys Thr Tyr Arg Val Asp Ile Ser Ser Asn Gly Glu Asp
            355                 360                 365
Trp Ile Ser Leu Lys Glu Gly Asn Lys Ala Ile Ile Phe Gln Gly Asn
        370                 375                 380
Thr Asn Pro Thr Asp Val Val Leu Gly Val Phe Ser Lys Pro Leu Ile
385                 390                 395                 400
Thr Arg Phe Val Arg Ile Lys Pro Val Ser Trp Glu Thr Gly Ile Ser
                405                 410                 415
Met Arg Phe Glu Val Tyr Gly Cys Lys Ile Thr Asp Tyr Pro Cys Ser
                420                 425                 430
Gly Met Leu Gly Met Val Ser Gly Leu Ile Ser Asp Ser Gln Ile Thr
            435                 440                 445
Ala Ser Asn Gln Ala Asp Arg Asn Trp Met Pro Glu Asn Ile Arg Leu
        450                 455                 460
Val Thr Ser Arg Thr Gly Trp Ala Leu Pro Pro Ser Pro His Pro Tyr
465                 470                 475                 480
Thr Asn Glu Trp Leu Gln Val Asp Leu Gly Asp Glu Lys Ile Val Arg
                485                 490                 495
```

```
Gly Val Ile Ile Gln Gly Gly Lys His Arg Glu Asn Lys Val Phe Met
            500                 505                 510

Arg Lys Phe Lys Ile Ala Tyr Ser Asn Asn Gly Ser Asp Trp Lys Thr
        515                 520                 525

Ile Met Asp Asp Ser Lys Arg Lys Ala Lys Ser Phe Glu Gly Asn Asn
    530                 535                 540

Asn Tyr Asp Thr Pro Glu Leu Arg Thr Phe Ser Pro Leu Ser Thr Arg
545                 550                 555                 560

Phe Ile Arg Ile Tyr Pro Glu Arg Ala Thr His Ser Gly Leu Gly Leu
                565                 570                 575

Arg Met Glu Leu Leu Gly Cys Glu Val Glu Ala Pro Thr Ala Gly Pro
            580                 585                 590

Thr Thr Pro Asn Gly Asn Pro Val His Glu Cys Asp Asp Asp Gln Ala
            595                 600                 605

Asn Cys His Ser Gly Thr Gly Asp Asp Phe Gln Leu Thr Gly Gly Thr
    610                 615                 620

Thr Val Leu Ala Thr Glu Lys Pro Thr Ile Ile Asp Ser Thr Ile Gln
625                 630                 635                 640

Ser Glu Phe Pro Thr Tyr Gly Phe Asn Cys Glu Phe Gly Trp Gly Ser
                645                 650                 655

His Lys Thr Phe Cys His Trp Glu His Asp Ser His Ala Gln Leu Arg
            660                 665                 670

Trp Ser Val Leu Thr Ser Lys Thr Gly Pro Ile Gln Asp His Thr Gly
        675                 680                 685

Asp Gly Asn Phe Ile Tyr Ser Gln Ala Asp Glu Asn Gln Lys Gly Lys
    690                 695                 700

Val Ala Arg Leu Val Ser Pro Val Val Tyr Ser Gln Ser Ser Ala His
705                 710                 715                 720

Cys Met Thr Phe Trp Tyr His Met Ser Gly Ser His Val Gly Thr Leu
                725                 730                 735

Arg Val Lys Leu Arg Tyr Gln Lys Pro Glu Glu Tyr Asp Gln Leu Val
            740                 745                 750

Trp Met Val Val Gly His Gln Gly Asp His Trp Lys Glu Gly Arg Val
            755                 760                 765

Leu Leu His Lys Ser Leu Lys Leu Tyr Gln Val Ile Phe Glu Gly Glu
        770                 775                 780
```

```
Ile Gly Lys Gly Asn Leu Gly Gly Ile Ala Val Asp Asp Ile Ser Ile
785                 790                 795                 800

Asn Asn His Ile Ser Gln Glu Asp Cys Ala Lys Pro Thr Asp Leu Asp
                805                 810                 815

Lys Lys Asn Thr Glu Ile Lys Ile Asp Glu Thr Gly Ser Thr Pro Gly
            820                 825                 830

Tyr Glu Gly Glu Gly Glu Gly Asp Lys Asn Ile Ser Arg Lys Pro Gly
        835                 840                 845

Asn Val Leu Lys Thr Leu Asp Pro Ile Leu Ile Thr Ile Ile Ala Met
    850                 855                 860

Ser Ala Leu Gly Val Leu Leu Gly Ala Val Cys Gly Val Val Leu Tyr
865                 870                 875                 880

Cys Ala Cys Trp His Asn Gly Met Ser Glu Arg Asn Leu Ser Ala Leu
            885                 890                 895

Glu Asn Tyr Asn Phe Glu Leu Val Asp Gly Val Lys Leu Lys Lys Asp
            900                 905                 910

Lys Leu Asn Pro Gln Ser Asn Tyr Ser Glu Ala
        915                 920
```

<210> 7
<211> 3539
<212> DNA
<213> rat

<220>
<221> CDS
<222> (568)..(3294)

<400> 7
```
aaactggagc tccaccgcgg tggcggccgc ccgggcaggt ctagaattca gcggccgctg   60
aattctatcc agcggtcggt gcctctgccc gcgtgtgtgt cccgggtgcc ggggggacctg  120 tgtcagttag cgcttctgag atcacacagc tgcctagggg ccgtgtgatg cccagggcaa  180
ttcttggctt tgattttat tattattact attatttgc gttcagcttt cgggaaaccc    240
tcgtgatgtt gtaggataaa ggaaatgaca ctttgaggaa ctggagagaa catacacgcg   300
tttgggtttg aagaggaaac cggtctccgc ttccttagct tgctccctct ttgctgattt   360
caagagctat ctcctatgag gtggagatat tccagcaaga ataaaggtga agacagactg   420
actgccagga cccaggagga aaacgttgat cgttagagac ctttgcagaa gacaccacca   480
```

```
ggaggaaaat tagagaggaa aaacacaaag acataattat atggagatcc cacaaactta   540
gcccgggaga gagcttctct gtcaaaa atg gat atg ttt cct ctt acc tgg gtt   594
                              Met Asp Met Phe Pro Leu Thr Trp Val
                              1               5 ttc tta gct ctg tac ttt tca gga cac gaa gtg aga agc cag caa gat   642
Phe Leu Ala Leu Tyr Phe Ser Gly His Glu Val Arg Ser Gln Gln Asp
 10              15              20              25 cca cct tgc gga ggt cgg ccg aat tcc aag gat gct ggc tac atc act   690
Pro Pro Cys Gly Gly Arg Pro Asn Ser Lys Asp Ala Gly Tyr Ile Thr
             30              35              40 tcc cca ggc tac ccc cag gac tat ccc tcc cac cag aac tgt gag tgg   738
Ser Pro Gly Tyr Pro Gln Asp Tyr Pro Ser His Gln Asn Cys Glu Trp
         45              50              55 att gtc tac gcc ccc gaa ccc aac cag aag att gtt ctc aac ttc aac   786
Ile Val Tyr Ala Pro Glu Pro Asn Gln Lys Ile Val Leu Asn Phe Asn
         60              65              70 cct cac ttt gaa atc gag aaa cac gac tgc aag tat gac ttc att gag   834
Pro His Phe Glu Ile Glu Lys His Asp Cys Lys Tyr Asp Phe Ile Glu
 75              80              85 att cgg gat ggg gac agt gag tca gct gac ctc ctg ggc aag cac tgt   882
Ile Arg Asp Gly Asp Ser Glu Ser Ala Asp Leu Leu Gly Lys His Cys
 90              95              100             105 ggg aac atc gcc ccg ccc acc atc atc tcc tca ggc tcc gtg tta tac   930
Gly Asn Ile Ala Pro Pro Thr Ile Ile Ser Ser Gly Ser Val Leu Tyr
             110             115             120 atc aag ttc acc tca gac tac gcc cgg cag ggg gca ggt ttc tct cta   978
Ile Lys Phe Thr Ser Asp Tyr Ala Arg Gln Gly Ala Gly Phe Ser Leu
         125             130             135 cgc tat gag atc ttc aaa aca ggc tct gaa gat tgt tcc aag aac ttt  1026
Arg Tyr Glu Ile Phe Lys Thr Gly Ser Glu Asp Cys Ser Lys Asn Phe
         140             145             150 aca agc ccc aat ggg acc att gaa tct cca ggg ttt cca gag aag tat  1074
Thr Ser Pro Asn Gly Thr Ile Glu Ser Pro Gly Phe Pro Glu Lys Tyr
 155             160             165 cca cac aat ctg gac tgt acc ttc acc atc ctg gcc aaa ccc agg atg  1122
Pro His Asn Leu Asp Cys Thr Phe Thr Ile Leu Ala Lys Pro Arg Met
170             175             180             185 gag atc atc cta cag ttc ctg acc ttt gac ctg gag cat gac cct cta  1170
Glu Ile Ile Leu Gln Phe Leu Thr Phe Asp Leu Glu His Asp Pro Leu
             190             195             200
```

```
caa gtg ggg gaa gga gac tgt aaa tat gac tgg ctg gac atc tgg gat    1218
Gln Val Gly Glu Gly Asp Cys Lys Tyr Asp Trp Leu Asp Ile Trp Asp
            205                 210                 215 ggc att cca cat gtt gga cct ctg att ggc aag tac tgt ggg acg aaa    1266
Gly Ile Pro His Val Gly Pro Leu Ile Gly Lys Tyr Cys Gly Thr Lys
            220                 225                 230 aca ccc tcc aaa ctc cgc tcg tcc acg ggg atc ctc tcc ttg acc ttt    1314
Thr Pro Ser Lys Leu Arg Ser Ser Thr Gly Ile Leu Ser Leu Thr Phe
        235                 240                 245 cac acg gac atg gca gtg gcc aag gat ggc ttc tcc gca cgt tac tat    1362
His Thr Asp Met Ala Val Ala Lys Asp Gly Phe Ser Ala Arg Tyr Tyr
250                 255                 260                 265 ttg atc cac cag gag cca cct gag aat ttt cag tgc aat gtc cct ttg    1410
Leu Ile His Gln Glu Pro Pro Glu Asn Phe Gln Cys Asn Val Pro Leu
                    270                 275                 280 gga atg gag tct ggc cgg att gct aat gaa cag atc agt gcc tcc tcc    1458
Gly Met Glu Ser Gly Arg Ile Ala Asn Glu Gln Ile Ser Ala Ser Ser
                285                 290                 295 acc ttc tct gat ggg agg tgg act cct caa cag agc cgg ctc cat ggt    1506
Thr Phe Ser Asp Gly Arg Trp Thr Pro Gln Gln Ser Arg Leu His Gly
            300                 305                 310 gat gac aat ggc tgg aca ccc aat ttg gat tcc aac aag gag tat ctc    1554
Asp Asp Asn Gly Trp Thr Pro Asn Leu Asp Ser Asn Lys Glu Tyr Leu
        315                 320                 325 cag gtg gac ctg cgc ttc cta acc atg ctc aca gcc att gca aca cag    1602
Gln Val Asp Leu Arg Phe Leu Thr Met Leu Thr Ala Ile Ala Thr Gln
330                 335                 340                 345 gga gcc att tcc agg gaa acc cag aaa ggc tac tac gtc aaa tcg tac    1650
Gly Ala Ile Ser Arg Glu Thr Gln Lys Gly Tyr Tyr Val Lys Ser Tyr
                350                 355                 360 aag ctg gaa gtc agc aca aat ggt gaa gat tgg atg gtc tac cgg cat    1698
Lys Leu Glu Val Ser Thr Asn Gly Glu Asp Trp Met Val Tyr Arg His
            365                 370                 375 ggc aaa aac cac aag ata ttc caa gcg aac aat gat gcg acc gag gtg    1746
Gly Lys Asn His Lys Ile Phe Gln Ala Asn Asn Asp Ala Thr Glu Val
        380                 385                 390 gtg cta aac aag ctc cac atg cca ctg ctg act cgg ttc atc agg atc    1794
Val Leu Asn Lys Leu His Met Pro Leu Leu Thr Arg Phe Ile Arg Ile
    395                 400                 405 cgc ccg cag acg tgg cat ttg ggc att gcc ctt cgc ctg gag ctc ttt    1842
Arg Pro Gln Thr Trp His Leu Gly Ile Ala Leu Arg Leu Glu Leu Phe
```

```
              410                 415                 420                 425 ggc tgc cgg gtc aca gat gca ccc tgc tcc aac atg ctg ggg atg ctc     1890
Gly Cys Arg Val Thr Asp Ala Pro Cys Ser Asn Met Leu Gly Met Leu
                430                 435                 440 tcg ggc ctc att gct gat acc cag atc tct gcc tcc tcc acc cga gag     1938
Ser Gly Leu Ile Ala Asp Thr Gln Ile Ser Ala Ser Ser Thr Arg Glu
                445                 450                 455 tac ctc tgg agc ccc agt gct gcc cgc ctg gtt agt agc cgc tct ggc     1986
Tyr Leu Trp Ser Pro Ser Ala Ala Arg Leu Val Ser Ser Arg Ser Gly
                460                 465                 470 tgg ttt cct cgg aac cct caa gcc cag cca ggt gaa gaa tgg ctt cag     2034
Trp Phe Pro Arg Asn Pro Gln Ala Gln Pro Gly Glu Glu Trp Leu Gln
                475                 480                 485 gtt gac ctg ggg aca ccc aag aca gtg aaa ggg gtc atc atc cag gga     2082
Val Asp Leu Gly Thr Pro Lys Thr Val Lys Gly Val Ile Ile Gln Gly
490                 495                 500                 505 gcc cga gga gga gac agc atc act gcc gtg gaa gcc agg gcg ttt gta     2130
Ala Arg Gly Gly Asp Ser Ile Thr Ala Val Glu Ala Arg Ala Phe Val
                510                 515                 520 cgc aag ttc aaa gtc tcc tac agc cta aat ggc aag gac tgg gaa tat     2178
Arg Lys Phe Lys Val Ser Tyr Ser Leu Asn Gly Lys Asp Trp Glu Tyr
                525                 530                 535 atc cag gac ccc agg act cag cag aca aag ctg ttt gaa ggg aac atg     2226
Ile Gln Asp Pro Arg Thr Gln Gln Thr Lys Leu Phe Glu Gly Asn Met
                540                 545                 550 cac tat gac acc cct gac atc cga agg ttc gat cct gtt cca gcg cag     2274
His Tyr Asp Thr Pro Asp Ile Arg Arg Phe Asp Pro Val Pro Ala Gln
                555                 560                 565 tat gtg cgg gtg tac cca gag agg tgg tcg cca gca ggc atc ggg atg     2322
Tyr Val Arg Val Tyr Pro Glu Arg Trp Ser Pro Ala Gly Ile Gly Met
570                 575                 580                 585 agg ctg gag gtg ctg ggc tgt gac tgg aca gac tca aag ccc aca gtg     2370
Arg Leu Glu Val Leu Gly Cys Asp Trp Thr Asp Ser Lys Pro Thr Val
                590                 595                 600 gag acg ctg gga ccc acc gtg aag agt gaa gag act acc acc cca tat     2418
Glu Thr Leu Gly Pro Thr Val Lys Ser Glu Glu Thr Thr Thr Pro Tyr
                605                 610                 615 ccc atg gat gag gat gcc acc gag tgt ggg gaa aac tgc agc ttt gag     2466
Pro Met Asp Glu Asp Ala Thr Glu Cys Gly Glu Asn Cys Ser Phe Glu
                620                 625                 630
```

```
gat gac aaa gat ttg caa ctt cct tca gga ttc aac tgc aac ttt gat   2514
Asp Asp Lys Asp Leu Gln Leu Pro Ser Gly Phe Asn Cys Asn Phe Asp
        635                 640                 645 ttt ccg gaa gag acc tgt ggt tgg gtg tac gac cat gcc aag tgg ctc   2562
Phe Pro Glu Glu Thr Cys Gly Trp Val Tyr Asp His Ala Lys Trp Leu
650                 655                 660                 665 cgg agc acg tgg atc agc agc gct aac ccc aat gac aga aca ttt cca   2610
Arg Ser Thr Trp Ile Ser Ser Ala Asn Pro Asn Asp Arg Thr Phe Pro
                670                 675                 680 gat gac aag aac ttc ttg aaa ctg cag agt gat ggc cga cga gag ggc   2658
Asp Asp Lys Asn Phe Leu Lys Leu Gln Ser Asp Gly Arg Arg Glu Gly
        685                 690                 695 cag tac ggg cgg ctc atc agc cca ccg gtg cac ctg ccc cga agc cct   2706
Gln Tyr Gly Arg Leu Ile Ser Pro Pro Val His Leu Pro Arg Ser Pro
        700                 705                 710 gtg tgc atg gag ttc cag tac caa gcc atg ggc ggc cac ggg gtg gca   2754
Val Cys Met Glu Phe Gln Tyr Gln Ala Met Gly Gly His Gly Val Ala
        715                 720                 725 ctg cag gtg gtt cgg gaa gcc agc cag gaa agc aaa ctc ctt tgg gtc   2802
Leu Gln Val Val Arg Glu Ala Ser Gln Glu Ser Lys Leu Leu Trp Val
730                 735                 740                 745 atc cgt gag gac cag ggc agc gag tgg aag cac ggg cgc att atc ctg   2850
Ile Arg Glu Asp Gln Gly Ser Glu Trp Lys His Gly Arg Ile Ile Leu
                750                 755                 760 ccc agc tat gac atg gag tat cag atc gtg ttc gag gga gtg ata ggg   2898
Pro Ser Tyr Asp Met Glu Tyr Gln Ile Val Phe Glu Gly Val Ile Gly
        765                 770                 775 aag gga cga tcg gga gag att tcc atc gat gac att cgg ata agc act   2946
Lys Gly Arg Ser Gly Glu Ile Ser Ile Asp Asp Ile Arg Ile Ser Thr
        780                 785                 790 gat gtc cca ctg gag aac tgc atg gaa ccc ata tca gct ttt gca gat   2994
Asp Val Pro Leu Glu Asn Cys Met Glu Pro Ile Ser Ala Phe Ala Asp
        795                 800                 805 gaa tat gaa gga gat tgg agc aac tct tct tcc tct acc tca ggg gct   3042
Glu Tyr Glu Gly Asp Trp Ser Asn Ser Ser Ser Ser Thr Ser Gly Ala
810                 815                 820                 825 ggt gac ccc tca tct ggc aaa gaa aag agc tgg ctg tac acc cta gat   3090
Gly Asp Pro Ser Ser Gly Lys Glu Lys Ser Trp Leu Tyr Thr Leu Asp
                830                 835                 840 ccc att ctg atc acc atc atc gcc atg agc tcg ctg ggg gtc ctg ctg   3138
Pro Ile Leu Ile Thr Ile Ile Ala Met Ser Ser Leu Gly Val Leu Leu
```

```
                 845                    850                    855
ggg gcc acc tgt gcg ggc ctc ctc ctt tac tgc acc tgc tcc tat tcg      3186
Gly Ala Thr Cys Ala Gly Leu Leu Leu Tyr Cys Thr Cys Ser Tyr Ser
        860                    865                    870 ggt ctg agt tcg agg agc tgc acc aca ctg gag aac tac aac ttt gag      3234
Gly Leu Ser Ser Arg Ser Cys Thr Thr Leu Glu Asn Tyr Asn Phe Glu
    875                    880                    885 ctc tac gat ggc ctc aag cac aag gtc aag atc aat cat cag aag tgc      3282
Leu Tyr Asp Gly Leu Lys His Lys Val Lys Ile Asn His Gln Lys Cys
890                    895                    900                    905 tgc tcg gag gca tgaccgattg tgtctggatc gcttctggcg tttcattcca          3334
Cys Ser Glu Ala gtgagagggg ctagcgaaga ttacagtttt gttttgtttt gttttgtttt cccttttggaa  3394 actgaatgcc ataatctgga tcaaagtgtt ccagaatact gaaggtatgg acaggacaga   3454
caggccagtc tagggagaaa gggagatgca gctgtgaagg ggatcgttgc ccaccaggac   3514
tgtggtggcc aagtgaatgc aggaa                                          3539

<210> 8
<211> 909
<212> PRT
<213> rat

<400> 8
Met Asp Met Phe Pro Leu Thr Trp Val Phe Leu Ala Leu Tyr Phe Ser
  1               5                  10                  15

Gly His Glu Val Arg Ser Gln Gln Asp Pro Pro Cys Gly Gly Arg Pro
             20                  25                  30

Asn Ser Lys Asp Ala Gly Tyr Ile Thr Ser Pro Gly Tyr Pro Gln Asp
         35                  40                  45

Tyr Pro Ser His Gln Asn Cys Glu Trp Ile Val Tyr Ala Pro Glu Pro
     50                  55                  60

Asn Gln Lys Ile Val Leu Asn Phe Asn Pro His Phe Glu Ile Glu Lys
 65                  70                  75                  80

His Asp Cys Lys Tyr Asp Phe Ile Glu Ile Arg Asp Gly Asp Ser Glu
                 85                  90                  95

Ser Ala Asp Leu Leu Gly Lys His Cys Gly Asn Ile Ala Pro Pro Thr
            100                 105                 110

Ile Ile Ser Ser Gly Ser Val Leu Tyr Ile Lys Phe Thr Ser Asp Tyr
```

```
            115                 120                 125
Ala Arg Gln Gly Ala Gly Phe Ser Leu Arg Tyr Glu Ile Phe Lys Thr
    130             135                 140

Gly Ser Glu Asp Cys Ser Lys Asn Phe Thr Ser Pro Asn Gly Thr Ile
145             150                 155                 160

Glu Ser Pro Gly Phe Pro Glu Lys Tyr Pro His Asn Leu Asp Cys Thr
                165             170                 175

Phe Thr Ile Leu Ala Lys Pro Arg Met Glu Ile Leu Gln Phe Leu
            180             185                 190

Thr Phe Asp Leu Glu His Asp Pro Leu Gln Val Gly Glu Gly Asp Cys
        195                 200                 205

Lys Tyr Asp Trp Leu Asp Ile Trp Asp Gly Ile Pro His Val Gly Pro
    210                 215                 220

Leu Ile Gly Lys Tyr Cys Gly Thr Lys Thr Pro Ser Lys Leu Arg Ser
225                 230                 235                 240

Ser Thr Gly Ile Leu Ser Leu Thr Phe His Thr Asp Met Ala Val Ala
            245                 250                 255

Lys Asp Gly Phe Ser Ala Arg Tyr Tyr Leu Ile His Gln Glu Pro Pro
                260                 265                 270

Glu Asn Phe Gln Cys Asn Val Pro Leu Gly Met Glu Ser Gly Arg Ile
        275                 280                 285

Ala Asn Glu Gln Ile Ser Ala Ser Ser Thr Phe Ser Asp Gly Arg Trp
    290                 295                 300

Thr Pro Gln Gln Ser Arg Leu His Gly Asp Asp Asn Gly Trp Thr Pro
305                 310                 315                 320

Asn Leu Asp Ser Asn Lys Glu Tyr Leu Gln Val Asp Leu Arg Phe Leu
            325                 330                 335

Thr Met Leu Thr Ala Ile Ala Thr Gln Gly Ala Ile Ser Arg Glu Thr
            340                 345                 350

Gln Lys Gly Tyr Tyr Val Lys Ser Tyr Lys Leu Glu Val Ser Thr Asn
        355                 360                 365

Gly Glu Asp Trp Met Val Tyr Arg His Gly Lys Asn His Lys Ile Phe
    370                 375                 380

Gln Ala Asn Asn Asp Ala Thr Glu Val Val Leu Asn Lys Leu His Met
385                 390                 395                 400

Pro Leu Leu Thr Arg Phe Ile Arg Ile Arg Pro Gln Thr Trp His Leu
```

```
                    405                 410                 415
Gly Ile Ala Leu Arg Leu Glu Leu Phe Gly Cys Arg Val Thr Asp Ala
            420                 425                 430
Pro Cys Ser Asn Met Leu Gly Met Leu Ser Gly Leu Ile Ala Asp Thr
            435                 440                 445
Gln Ile Ser Ala Ser Ser Thr Arg Glu Tyr Leu Trp Ser Pro Ser Ala
            450                 455                 460
Ala Arg Leu Val Ser Ser Arg Ser Gly Trp Phe Pro Arg Asn Pro Gln
465                 470                 475                 480
Ala Gln Pro Gly Glu Glu Trp Leu Gln Val Asp Leu Gly Thr Pro Lys
            485                 490                 495
Thr Val Lys Gly Val Ile Ile Gln Gly Ala Arg Gly Gly Asp Ser Ile
            500                 505                 510
Thr Ala Val Glu Ala Arg Ala Phe Val Arg Lys Phe Lys Val Ser Tyr
            515                 520                 525
Ser Leu Asn Gly Lys Asp Trp Glu Tyr Ile Gln Asp Pro Arg Thr Gln
            530                 535                 540
Gln Thr Lys Leu Phe Glu Gly Asn Met His Tyr Asp Thr Pro Asp Ile
545                 550                 555                 560
Arg Arg Phe Asp Pro Val Pro Ala Gln Tyr Val Arg Val Tyr Pro Glu
            565                 570                 575
Arg Trp Ser Pro Ala Gly Ile Gly Met Arg Leu Glu Val Leu Gly Cys
            580                 585                 590
Asp Trp Thr Asp Ser Lys Pro Thr Val Glu Thr Leu Gly Pro Thr Val
            595                 600                 605
Lys Ser Glu Glu Thr Thr Thr Pro Tyr Pro Met Asp Glu Asp Ala Thr
            610                 615                 620
Glu Cys Gly Glu Asn Cys Ser Phe Glu Asp Asp Lys Asp Leu Gln Leu
625                 630                 635                 640
Pro Ser Gly Phe Asn Cys Asn Phe Asp Phe Pro Glu Glu Thr Cys Gly
            645                 650                 655
Trp Val Tyr Asp His Ala Lys Trp Leu Arg Ser Thr Trp Ile Ser Ser
            660                 665                 670
Ala Asn Pro Asn Asp Arg Thr Phe Pro Asp Asp Lys Asn Phe Leu Lys
            675                 680                 685
Leu Gln Ser Asp Gly Arg Arg Glu Gly Gln Tyr Gly Arg Leu Ile Ser
```

```
              690                 695                 700
   Pro Pro Val His Leu Pro Arg Ser Pro Val Cys Met Glu Phe Gln Tyr
   705             710                 715                 720

Gln Ala Met Gly Gly His Gly Val Ala Leu Gln Val Val Arg Glu Ala
                   725                 730                 735

Ser Gln Glu Ser Lys Leu Leu Trp Val Ile Arg Glu Asp Gln Gly Ser
                   740                 745                 750

Glu Trp Lys His Gly Arg Ile Ile Leu Pro Ser Tyr Asp Met Glu Tyr
           755                 760                 765

Gln Ile Val Phe Glu Gly Val Ile Gly Lys Gly Arg Ser Gly Glu Ile
           770                 775                 780

Ser Ile Asp Asp Ile Arg Ile Ser Thr Asp Val Pro Leu Glu Asn Cys
   785                 790                 795                 800

Met Glu Pro Ile Ser Ala Phe Ala Asp Glu Tyr Glu Gly Asp Trp Ser
                   805                 810                 815

Asn Ser Ser Ser Ser Thr Ser Gly Ala Gly Asp Pro Ser Ser Gly Lys
                   820                 825                 830

Glu Lys Ser Trp Leu Tyr Thr Leu Asp Pro Ile Leu Ile Thr Ile Ile
           835                 840                 845

Ala Met Ser Ser Leu Gly Val Leu Leu Gly Ala Thr Cys Ala Gly Leu
           850                 855                 860

Leu Leu Tyr Cys Thr Cys Ser Tyr Ser Gly Leu Ser Ser Arg Ser Cys
   865                 870                 875                 880

Thr Thr Leu Glu Asn Tyr Asn Phe Glu Leu Tyr Asp Gly Leu Lys His
                   885                 890                 895

Lys Val Lys Ile Asn His Gln Lys Cys Cys Ser Glu Ala
                   900                 905

<210> 9
<211> 4718
<212> DNA
<213> mouse

<220>
<221> CDS
<222> (567)..(3293)

<400> 9
aaactggagc tccaccgcgg tggcggccgc ccgggcaggt ctagaattca gcggccgctg  60
```

```
aattctatcc agcggtcggt gcctctgccc gcgtgtgtgt cccgggtgcc gggggacctg 120
tgtcagttag cgcttctgag atcacacagc tgcctagggg ccgtgtgatg cccagggcaa 180
ttcttggctt tgatttttat tattattact attattttgc gttcagcttt cgggaaaccc 240
tcgtgatgtt gtaggataaa ggaaatgaca ctttgaggaa ctggagagaa catacacgcg 300
tttgggtttg aagaggaaac cggtctccgc ttccttagct tgctccctct ttgctgattt 360
caagagctat ctcctatgag gtggagatat tccagcaaga ataaggtga agacagactg 420 actgccagga cccaggagga aaacgttgat cgttagagac ctttgcagaa gacaccacca 480
ggaggaaaat tagagaggaa aaacacaaag acataattat aggagatccc acaaacctag 540
cccgggagag agcctctctg tcaaaa
```

| | | | | | | |
|---|---|---|---|---|---|---|
| atg | gat | atg | ttt | cct | ctt | acc tgg gtt | 593 |
| Met | Asp | Met | Phe | Pro | Leu | Thr Trp Val |
| 1 | | | | 5 | | | ttc tta gct ctg tac ttt tca gga cac gaa gtg aga agc cag caa gat    641
Phe Leu Ala Leu Tyr Phe Ser Gly His Glu Val Arg Ser Gln Gln Asp
 10              15                  20                  25 cca ccc tgc gga ggt cgg ccg aat tcc aaa gat gct ggc tac atc act    689
Pro Pro Cys Gly Gly Arg Pro Asn Ser Lys Asp Ala Gly Tyr Ile Thr
                30                  35                  40 tcc cca ggc tac ccc cag gac tat ccc tcc cac cag aac tgt gag tgg    737
Ser Pro Gly Tyr Pro Gln Asp Tyr Pro Ser His Gln Asn Cys Glu Trp
            45                  50                  55 att gtc tac gcc ccc gaa ccc aac cag aag att gtt ctc aac ttc aac    785
Ile Val Tyr Ala Pro Glu Pro Asn Gln Lys Ile Val Leu Asn Phe Asn
        60                  65                  70 cct cac ttt gaa atc gag aaa cac gac tgc aag tat gac ttc att gag    833
Pro His Phe Glu Ile Glu Lys His Asp Cys Lys Tyr Asp Phe Ile Glu
    75                  80                  85 att cgg gat ggg gac agt gag tca gct gac ctc ctg ggc aag cac tgt    881
Ile Arg Asp Gly Asp Ser Glu Ser Ala Asp Leu Leu Gly Lys His Cys
 90                  95                 100                 105 ggg aac atc gcc ccg ccc acc atc atc tcc tca ggc tcc gtg tta tac    929
Gly Asn Ile Ala Pro Pro Thr Ile Ile Ser Ser Gly Ser Val Leu Tyr
                110                 115                 120 atc aag ttc acc tca gac tac gcc cgg cag ggg gca ggt ttc tct cta    977
Ile Lys Phe Thr Ser Asp Tyr Ala Arg Gln Gly Ala Gly Phe Ser Leu
            125                 130                 135 cgc tat gag atc ttc aaa aca ggc tct gaa gat tgt tcc aag aac ttt   1025
Arg Tyr Glu Ile Phe Lys Thr Gly Ser Glu Asp Cys Ser Lys Asn Phe

```
            140                    145                    150
aca agc ccc aat ggg acc att gaa tct cca ggg ttt cca gag aag tat    1073
Thr Ser Pro Asn Gly Thr Ile Glu Ser Pro Gly Phe Pro Glu Lys Tyr
    155                    160                    165 cca cac aat ctg gac tgt acc ttc acc atc ctg gcc aaa ccc agg atg    1121
Pro His Asn Leu Asp Cys Thr Phe Thr Ile Leu Ala Lys Pro Arg Met
170                     175                    180                185 gag atc atc cta cag ttc ctg acc ttt gac ctg gag cat gac cct cta    1169
Glu Ile Ile Leu Gln Phe Leu Thr Phe Asp Leu Glu His Asp Pro Leu
                190                    195                    200 caa gtg ggg gaa gga gac tgt aaa tat gac tgg ctg gac atc tgg gat    1217
Gln Val Gly Glu Gly Asp Cys Lys Tyr Asp Trp Leu Asp Ile Trp Asp
                    205                    210                    215 ggc att cca cat gtt gga cct ctg att ggc aag tac tgt ggg acg aaa    1265
Gly Ile Pro His Val Gly Pro Leu Ile Gly Lys Tyr Cys Gly Thr Lys
        220                    225                    230 aca ccc tcc aaa ctc cgc tcg tcc acg ggg atc ctc tcc ttg acc ttt    1313
Thr Pro Ser Lys Leu Arg Ser Ser Thr Gly Ile Leu Ser Leu Thr Phe
    235                    240                    245 cac acg gac atg gca gtg gcc aag gat ggc ttc tcc gca cgt tac tat    1361
His Thr Asp Met Ala Val Ala Lys Asp Gly Phe Ser Ala Arg Tyr Tyr
250                     255                    260                265 ttg atc cac cag gag cca cct gag aat ttt cag tgc aat gtc cct ttg    1409
Leu Ile His Gln Glu Pro Pro Glu Asn Phe Gln Cys Asn Val Pro Leu
                270                    275                    280 gga atg gag tct ggc cgg att gct aat gaa cag atc agt gcc tcc tcc    1457
Gly Met Glu Ser Gly Arg Ile Ala Asn Glu Gln Ile Ser Ala Ser Ser
                    285                    290                    295 acc ttc tct gat ggg agg tgg act cct caa cag agc cgg ctc cat ggt    1505
Thr Phe Ser Asp Gly Arg Trp Thr Pro Gln Gln Ser Arg Leu His Gly
        300                    305                    310 gat gac aat ggc tgg aca ccc aat ttg gat tcc aac aag gag tat ctc    1553
Asp Asp Asn Gly Trp Thr Pro Asn Leu Asp Ser Asn Lys Glu Tyr Leu
    315                    320                    325 cag gtg gac ctg cgc ttc cta acc atg ctc aca gcc att gca aca cag    1601
Gln Val Asp Leu Arg Phe Leu Thr Met Leu Thr Ala Ile Ala Thr Gln
330                     335                    340                345 gga gcc att tcc agg gaa acc cag aaa ggc tac tac gtc aaa tcg tac    1649
Gly Ala Ile Ser Arg Glu Thr Gln Lys Gly Tyr Tyr Val Lys Ser Tyr
                    350                    355                    360
```

```
aag ctg gaa gtc agc aca aat ggt gaa gat tgg atg gtc tac cgg cat    1697
Lys Leu Glu Val Ser Thr Asn Gly Glu Asp Trp Met Val Tyr Arg His
            365                 370                 375 ggc aaa aac cac aag ata ttc caa gcg aac aat gat gcg acc gag gtg    1745
Gly Lys Asn His Lys Ile Phe Gln Ala Asn Asn Asp Ala Thr Glu Val
            380                 385                 390 gtg cta aac aag ctc cac atg cca ctg ctg act cgg ttc atc agg atc    1793
Val Leu Asn Lys Leu His Met Pro Leu Leu Thr Arg Phe Ile Arg Ile
            395                 400                 405 cgc ccg cag acg tgg cat ttg ggc att gcc ctt cgc ctg gag ctc ttt    1841
Arg Pro Gln Thr Trp His Leu Gly Ile Ala Leu Arg Leu Glu Leu Phe
410                 415                 420                 425 ggc tgc cgg gtc aca gat gca ccc tgc tcc aac atg ctg ggg atg ctc    1889
Gly Cys Arg Val Thr Asp Ala Pro Cys Ser Asn Met Leu Gly Met Leu
                430                 435                 440 tcg ggc ctc att gct gat acc cag atc tct gcc tcc tcc acc cga gag    1937
Ser Gly Leu Ile Ala Asp Thr Gln Ile Ser Ala Ser Ser Thr Arg Glu
            445                 450                 455 tac ctc tgg agc ccc agt gct gcc cgc ctg gtt agt agc cgc tct ggc    1985
Tyr Leu Trp Ser Pro Ser Ala Ala Arg Leu Val Ser Ser Arg Ser Gly
            460                 465                 470 tgg ttt cct cgg aac cct caa gcc cag cca ggt gaa gaa tgg ctt cag    2033
Trp Phe Pro Arg Asn Pro Gln Ala Gln Pro Gly Glu Glu Trp Leu Gln
        475                 480                 485 gta gac ctg ggg aca ccc aag aca gtg aaa ggg gtc atc atc cag gga    2081
Val Asp Leu Gly Thr Pro Lys Thr Val Lys Gly Val Ile Ile Gln Gly
490                 495                 500                 505 gcc cga gga gga gac agc atc act gcc gtg gaa gcc agg gcg ttt gta    2129
Ala Arg Gly Gly Asp Ser Ile Thr Ala Val Glu Ala Arg Ala Phe Val
                510                 515                 520 cgc aag ttc aaa gtc tcc tac agc cta aat ggc aag gac tgg gaa tat    2177
Arg Lys Phe Lys Val Ser Tyr Ser Leu Asn Gly Lys Asp Trp Glu Tyr
            525                 530                 535 atc cag gac ccc agg act cag cag aca aag ctg ttt gaa ggg aac atg    2225
Ile Gln Asp Pro Arg Thr Gln Gln Thr Lys Leu Phe Glu Gly Asn Met
            540                 545                 550 cac tat gac acc cct gac atc cga agg ttc gat cct gtt cca gcg cag    2273
His Tyr Asp Thr Pro Asp Ile Arg Arg Phe Asp Pro Val Pro Ala Gln
            555                 560                 565 tat gtg cgg gtg tac cca gag agg tgg tcg cca gca ggc atc ggg atg    2321
Tyr Val Arg Val Tyr Pro Glu Arg Trp Ser Pro Ala Gly Ile Gly Met
```

```
              570                     575                     580                     585
       agg ctg gag gtg ctg ggc tgt gac tgg aca gac tca aag ccc aca gtg    2369
       Arg Leu Glu Val Leu Gly Cys Asp Trp Thr Asp Ser Lys Pro Thr Val
                       590                 595                 600 gag acg ctg gga ccc acc gtg aag agt gaa gag act acc acc cca tat    2417
       Glu Thr Leu Gly Pro Thr Val Lys Ser Glu Glu Thr Thr Thr Pro Tyr
                   605                 610                 615 ccc atg gat gag gat gcc acc gag tgt ggg gaa aac tgc agc ttt gag    2465
       Pro Met Asp Glu Asp Ala Thr Glu Cys Gly Glu Asn Cys Ser Phe Glu
                   620                 625                 630 gat gac aaa gat ttg caa ctt cct tca gga ttc aac tgc aac ttt gat    2513
       Asp Asp Lys Asp Leu Gln Leu Pro Ser Gly Phe Asn Cys Asn Phe Asp
                   635                 640                 645 ttt ccg gaa gag acc tgt ggt tgg gtg tac gac cat gcc aag tgg ctc    2561
       Phe Pro Glu Glu Thr Cys Gly Trp Val Tyr Asp His Ala Lys Trp Leu
       650                 655                 660                 665 cgg agc acg tgg atc agc agc gct aac ccc aat gac aga aca ttt cca    2609
       Arg Ser Thr Trp Ile Ser Ser Ala Asn Pro Asn Asp Arg Thr Phe Pro
                       670                 675                 680 gat gac aag aac ttc ttg aaa ctg cag agt gat ggc cga cga gag ggc    2657
       Asp Asp Lys Asn Phe Leu Lys Leu Gln Ser Asp Gly Arg Arg Glu Gly
                   685                 690                 695 cag tac ggg cgg ctc atc agc cca ccg gtg cac ctg ccc cga agc cct    2705
       Gln Tyr Gly Arg Leu Ile Ser Pro Pro Val His Leu Pro Arg Ser Pro
                   700                 705                 710 gtg tgc atg gag ttc cag tac caa gcc atg ggc ggc cac ggg gtg gca    2753
       Val Cys Met Glu Phe Gln Tyr Gln Ala Met Gly Gly His Gly Val Ala
                   715                 720                 725 ctg cag gtg gtt cgg gaa gcc agc cag gaa agc aaa ctc ctt tgg gtc    2801
       Leu Gln Val Val Arg Glu Ala Ser Gln Glu Ser Lys Leu Leu Trp Val
       730                 735                 740                 745 atc cgt gag gac cag ggc agc gag tgg aag cac ggg cgc att atc ctg    2849
       Ile Arg Glu Asp Gln Gly Ser Glu Trp Lys His Gly Arg Ile Ile Leu
                       750                 755                 760 ccc agc tat gac atg gag tat cag atc gtg ttc gag gga gtg ata ggg    2897
       Pro Ser Tyr Asp Met Glu Tyr Gln Ile Val Phe Glu Gly Val Ile Gly
                   765                 770                 775 aag gga cga tcg gga gag att tcc ggc gat gac att cgg ata agc act    2945
       Lys Gly Arg Ser Gly Glu Ile Ser Gly Asp Asp Ile Arg Ile Ser Thr
                   780                 785                 790
```

```
gat gtc cca ctg gag aac tgc atg gaa ccc ata tca gct ttt gca gat    2993
Asp Val Pro Leu Glu Asn Cys Met Glu Pro Ile Ser Ala Phe Ala Asp
    795                 800                 805 gaa tat gaa gga gat tgg agc aac tct tct tcc tct acc tca ggg gct    3041
Glu Tyr Glu Gly Asp Trp Ser Asn Ser Ser Ser Ser Thr Ser Gly Ala
810                 815                 820                 825 ggt gac ccc tca tct ggc aaa gaa aag agc tgg ctg tac acc cta gat    3089
Gly Asp Pro Ser Ser Gly Lys Glu Lys Ser Trp Leu Tyr Thr Leu Asp
                830                 835                 840 ccc att ctg atc acc atc atc gcc atg agc tcg ctg ggg gtc ctg ctg    3137
Pro Ile Leu Ile Thr Ile Ile Ala Met Ser Ser Leu Gly Val Leu Leu
            845                 850                 855 ggg gcc acc tgt gcg ggc ctc ctc ctt tac tgc acc tgc tcc tat tcg    3185
Gly Ala Thr Cys Ala Gly Leu Leu Leu Tyr Cys Thr Cys Ser Tyr Ser
            860                 865                 870 ggt ctg agt tcg agg agc tgc acc aca ctg gag aac tac aac ttt gag    3233
Gly Leu Ser Ser Arg Ser Cys Thr Thr Leu Glu Asn Tyr Asn Phe Glu
    875                 880                 885 ctc tac gat ggc ctc aag cac aag gtc aag atc aat cat cag aag tgc    3281
Leu Tyr Asp Gly Leu Lys His Lys Val Lys Ile Asn His Gln Lys Cys
890                 895                 900                 905 tgc tcg gag gca tgaccgattg tgtctggatc gcttctggcg tttcattcca        3333
Cys Ser Glu Ala gtgagagggg ctagcgaaga ttacagtttt gttttgtttt gttttgtttt ccctttggaa  3393
actgaatgcc ataatctgga tcaaagtgtt ccagaatact gaaggtatgg acaggacaga  3453
caggccagtc tagggagaaa gggagatgca gctgtgaagg ggatcgttgc ccaccaggac  3513
tgtggtggcc aagtgaatgc aggaaccggg cccggaattc cggctctcgg ctaaaatctc  3573
agctgcctct ggaaaggctc aaccatactc agtgccaact cagactctgt tgctgtggtg  3633
tcaacatgga tggatcatct gtaccttgta tttttagcag aattcatgct cagatttctt  3693
tgttctgaat ccttgctttg tgctagacac aaagcataca tgtccttcta aaattaatat  3753
gatcactata atctcctgtg tgcagaattc agaaatagac ctttgaaacc atttgcattg  3813
tgagtgcaga tccatgactg gggctagtgc agcaatgaaa cagaattcca gaaacagtgt  3873
gttcttttta ttatgggaaa atacagataa aaatggccac tgatgaacat gaaagttagc  3933
actttcccaa cacagtgtac acttgcaacc ttgttttgga tttctcatac accaagactg  3993
tgaaacacaa atttcaagaa tgtgttcaaa tgtgtgtgtg tgtgtgtgtg tgtgtgtgtg  4053
```

```
tgtgtgtgta tgtgtgtgtg tgtgtgtgtg cttgtgtgtt tctgtcagtg gtatgagtga 4113 tatgtatgca tgtgtgtatg tatatgtatg tatgtatgta tgtatgtacg tacatatgta 4173 tgtatgtatg tatgtatgta tgtatgtata tgtgtgtgtg tgtttgtgtg tgtgtgtgtt 4233 tgtgtgtgtg tgtgtggtaa gtgtggtatg tgtgtatgca tttgtctata tgtgtatctg 4293 tgtgtctatg tgtttctgtc agtggaatga gtggcatgtg tgcatgtgta tgtatgtgga 4353 tatgtgtgtt gtgtttatgt gcttgtgtat aagaggtaag tgtggtgtgt gtgcatgtgt 4413 ctctgtgtgt gtttgtctgt gtacctcttt gtataagtac ctgtgtttgt atgtgggaat 4473 atgtatattg aggcattgct gtgttagtat gtttatagaa aagaagacag tctgagatgt 4533 cttcctcaat acctctccac ttatatcttg gatagacaaa agtaatgaca aaaaattgct 4593 ggtgtgtata tggaaaaggg ggacacatat ccatggatgg tagaagtgta aactgtgcag 4653 tcactgtgga catcaatatg caggttcttc acaaatgtag atataaagct actatagtta 4713 taccc                                                              4718
```

<210> 10
<211> 909
<212> PRT
<213> mouse

<400> 10
```
Met Asp Met Phe Pro Leu Thr Trp Val Phe Leu Ala Leu Tyr Phe Ser
 1               5                  10                  15

Gly His Glu Val Arg Ser Gln Gln Asp Pro Pro Cys Gly Gly Arg Pro
             20                  25                  30

Asn Ser Lys Asp Ala Gly Tyr Ile Thr Ser Pro Gly Tyr Pro Gln Asp
         35                  40                  45

Tyr Pro Ser His Gln Asn Cys Glu Trp Ile Val Tyr Ala Pro Glu Pro
     50                  55                  60

Asn Gln Lys Ile Val Leu Asn Phe Asn Pro His Phe Glu Ile Glu Lys
 65                  70                  75                  80

His Asp Cys Lys Tyr Asp Phe Ile Glu Ile Arg Asp Gly Asp Ser Glu
                 85                  90                  95

Ser Ala Asp Leu Leu Gly Lys His Cys Gly Asn Ile Ala Pro Pro Thr
            100                 105                 110

Ile Ile Ser Ser Gly Ser Val Leu Tyr Ile Lys Phe Thr Ser Asp Tyr
```

```
              115                   120                   125
    Ala Arg Gln Gly Ala Gly Phe Ser Leu Arg Tyr Glu Ile Phe Lys Thr
        130                 135                 140

Gly Ser Glu Asp Cys Ser Lys Asn Phe Thr Ser Pro Asn Gly Thr Ile
145                 150                 155                 160

Glu Ser Pro Gly Phe Pro Glu Lys Tyr Pro His Asn Leu Asp Cys Thr
                    165                 170                 175

Phe Thr Ile Leu Ala Lys Pro Arg Met Glu Ile Ile Leu Gln Phe Leu
                180                 185                 190

Thr Phe Asp Leu Glu His Asp Pro Leu Gln Val Gly Glu Gly Asp Cys
            195                 200                 205

Lys Tyr Asp Trp Leu Asp Ile Trp Asp Gly Ile Pro His Val Gly Pro
            210                 215                 220

Leu Ile Gly Lys Tyr Cys Gly Thr Lys Thr Pro Ser Lys Leu Arg Ser
225                 230                 235                 240

Ser Thr Gly Ile Leu Ser Leu Thr Phe His Thr Asp Met Ala Val Ala
                    245                 250                 255

Lys Asp Gly Phe Ser Ala Arg Tyr Tyr Leu Ile His Gln Glu Pro Pro
                260                 265                 270

Glu Asn Phe Gln Cys Asn Val Pro Leu Gly Met Glu Ser Gly Arg Ile
                275                 280                 285

Ala Asn Glu Gln Ile Ser Ala Ser Ser Thr Phe Ser Asp Gly Arg Trp
            290                 295                 300

Thr Pro Gln Gln Ser Arg Leu His Gly Asp Asp Asn Gly Trp Thr Pro
305                 310                 315                 320

Asn Leu Asp Ser Asn Lys Glu Tyr Leu Gln Val Asp Leu Arg Phe Leu
                    325                 330                 335

Thr Met Leu Thr Ala Ile Ala Thr Gln Gly Ala Ile Ser Arg Glu Thr
                340                 345                 350

Gln Lys Gly Tyr Tyr Val Lys Ser Tyr Lys Leu Glu Val Ser Thr Asn
                355                 360                 365

Gly Glu Asp Trp Met Val Tyr Arg His Gly Lys Asn His Lys Ile Phe
            370                 375                 380

Gln Ala Asn Asn Asp Ala Thr Glu Val Val Leu Asn Lys Leu His Met
385                 390                 395                 400

Pro Leu Leu Thr Arg Phe Ile Arg Ile Arg Pro Gln Thr Trp His Leu
```

```
                    405                     410                    415

Gly Ile Ala Leu Arg Leu Glu Leu Phe Gly Cys Arg Val Thr Asp Ala
            420                     425                 430

Pro Cys Ser Asn Met Leu Gly Met Leu Ser Gly Leu Ile Ala Asp Thr
            435                     440                 445

Gln Ile Ser Ala Ser Ser Thr Arg Glu Tyr Leu Trp Ser Pro Ser Ala
        450                     455                 460

Ala Arg Leu Val Ser Ser Arg Ser Gly Trp Phe Pro Arg Asn Pro Gln
    465                 470                 475                     480

Ala Gln Pro Gly Glu Glu Trp Leu Gln Val Asp Leu Gly Thr Pro Lys
                    485                 490                     495

Thr Val Lys Gly Val Ile Ile Gln Gly Ala Arg Gly Gly Asp Ser Ile
                500                     505                 510

Thr Ala Val Glu Ala Arg Ala Phe Val Arg Lys Phe Lys Val Ser Tyr
                515                 520                     525

Ser Leu Asn Gly Lys Asp Trp Glu Tyr Ile Gln Asp Pro Arg Thr Gln
        530                     535                     540

Gln Thr Lys Leu Phe Glu Gly Asn Met His Tyr Asp Thr Pro Asp Ile
    545                     550                     555                 560

Arg Arg Phe Asp Pro Val Pro Ala Gln Tyr Val Arg Val Tyr Pro Glu
                    565                     570                     575

Arg Trp Ser Pro Ala Gly Ile Gly Met Arg Leu Glu Val Leu Gly Cys
                580                     585                 590

Asp Trp Thr Asp Ser Lys Pro Thr Val Glu Thr Leu Gly Pro Thr Val
                595                     600                 605

Lys Ser Glu Glu Thr Thr Thr Pro Tyr Pro Met Asp Glu Asp Ala Thr
        610                     615                 620

Glu Cys Gly Glu Asn Cys Ser Phe Glu Asp Asp Lys Asp Leu Gln Leu
    625                     630                     635                 640

Pro Ser Gly Phe Asn Cys Asn Phe Asp Phe Pro Glu Glu Thr Cys Gly
                    645                     650                 655

Trp Val Tyr Asp His Ala Lys Trp Leu Arg Ser Thr Trp Ile Ser Ser
                660                     665                 670

Ala Asn Pro Asn Asp Arg Thr Phe Pro Asp Asp Lys Asn Phe Leu Lys
            675                     680                 685

Leu Gln Ser Asp Gly Arg Arg Glu Gly Gln Tyr Gly Arg Leu Ile Ser
```

```
              690                 695                 700
Pro Pro Val His Leu Pro Arg Ser Pro Val Cys Met Glu Phe Gln Tyr
705                 710                 715                 720

Gln Ala Met Gly Gly His Gly Val Ala Leu Gln Val Val Arg Glu Ala
                725                 730                 735

Ser Gln Glu Ser Lys Leu Leu Trp Val Ile Arg Glu Asp Gln Gly Ser
                740                 745                 750

Glu Trp Lys His Gly Arg Ile Ile Leu Pro Ser Tyr Asp Met Glu Tyr
                755                 760                 765

Gln Ile Val Phe Glu Gly Val Ile Gly Lys Gly Arg Ser Gly Glu Ile
                770                 775                 780

Ser Gly Asp Asp Ile Arg Ile Ser Thr Asp Val Pro Leu Glu Asn Cys
785                 790                 795                 800

Met Glu Pro Ile Ser Ala Phe Ala Asp Glu Tyr Glu Gly Asp Trp Ser
                805                 810                 815

Asn Ser Ser Ser Ser Thr Ser Gly Ala Gly Asp Pro Ser Ser Gly Lys
                820                 825                 830

Glu Lys Ser Trp Leu Tyr Thr Leu Asp Pro Ile Leu Ile Thr Ile Ile
                835                 840                 845

Ala Met Ser Ser Leu Gly Val Leu Leu Gly Ala Thr Cys Ala Gly Leu
                850                 855                 860

Leu Leu Tyr Cys Thr Cys Ser Tyr Ser Gly Leu Ser Ser Arg Ser Cys
865                 870                 875                 880

Thr Thr Leu Glu Asn Tyr Asn Phe Glu Leu Tyr Asp Gly Leu Lys His
                885                 890                 895

Lys Val Lys Ile Asn His Gln Lys Cys Cys Ser Glu Ala
                900                 905

<210> 11
<211> 4733
<212> DNA
<213> mouse

<220>
<221> CDS
<222> (567)..(3308)

<400> 11
aaactggagc tccaccgcgg tggcggccgc ccgggcaggt ctagaattca gcggccgctg    60
```

```
aattctatcc agcggtcggt gcctctgccc gcgtgtgtgt cccgggtgcc gggggacctg   120
tgtcagttag cgcttctgag atcacacagc tgcctagggg ccgtgtgatg cccagggcaa   180
ttcttggctt tgatttttat tattattact attattttgc gttcagcttt cgggaaaccc   240
tcgtgatgtt gtaggataaa ggaaatgaca ctttgaggaa ctggagagaa catacacgcg   300
tttgggtttg aagaggaaac cggtctccgc ttccttagct tgctccctct ttgctgattt   360
caagagctat ctcctatgag gtggagatat tccagcaaga ataaaggtga agacagactg   420
actgccagga cccaggagga aaacgttgat cgttagagac ctttgcagaa gacaccacca   480
ggaggaaaat tagagaggaa aaacacaaag acataattat aggagatccc acaaacctag   540
cccgggagag agcctctctg tcaaaa atg gat atg ttt cct ctt acc tgg gtt    593
                               Met Asp Met Phe Pro Leu Thr Trp Val
                                1               5
```

| | | | | | | | | | | | | | | | | |
|---|---|---|---|---|---|---|---|---|---|---|---|---|---|---|---|---|
| ttc | tta | gct | ctg | tac | ttt | tca | gga | cac | gaa | gtg | aga | agc | cag | caa | gat | 641 |
| Phe | Leu | Ala | Leu | Tyr | Phe | Ser | Gly | His | Glu | Val | Arg | Ser | Gln | Gln | Asp | |
| | 10 | | | | 15 | | | | 20 | | | | | | 25 | |
| cca | ccc | tgc | gga | ggt | cgg | ccg | aat | tcc | aaa | gat | gct | ggc | tac | atc | act | 689 |
| Pro | Pro | Cys | Gly | Gly | Arg | Pro | Asn | Ser | Lys | Asp | Ala | Gly | Tyr | Ile | Thr | |
| | | | | 30 | | | | | 35 | | | | | 40 | | |
| tcc | cca | ggc | tac | ccc | cag | gac | tat | ccc | tcc | cac | cag | aac | tgt | gag | tgg | 737 |
| Ser | Pro | Gly | Tyr | Pro | Gln | Asp | Tyr | Pro | Ser | His | Gln | Asn | Cys | Glu | Trp | |
| | | | | 45 | | | | | 50 | | | | | 55 | | |
| att | gtc | tac | gcc | ccc | gaa | ccc | aac | cag | aag | att | gtt | ctc | aac | ttc | aac | 785 |
| Ile | Val | Tyr | Ala | Pro | Glu | Pro | Asn | Gln | Lys | Ile | Val | Leu | Asn | Phe | Asn | |
| | | | | 60 | | | | | 65 | | | | | 70 | | |
| cct | cac | ttt | gaa | atc | gag | aaa | cac | gac | tgc | aag | tat | gac | ttc | att | gag | 833 |
| Pro | His | Phe | Glu | Ile | Glu | Lys | His | Asp | Cys | Lys | Tyr | Asp | Phe | Ile | Glu | |
| | | 75 | | | | | 80 | | | | | 85 | | | | |
| att | cgg | gat | ggg | gac | agt | gag | tca | gct | gac | ctc | ctg | ggc | aag | cac | tgt | 881 |
| Ile | Arg | Asp | Gly | Asp | Ser | Glu | Ser | Ala | Asp | Leu | Leu | Gly | Lys | His | Cys | |
| | 90 | | | | | 95 | | | | | 100 | | | | 105 | |
| ggg | aac | atc | gcc | ccg | ccc | acc | atc | atc | tcc | tca | ggc | tcc | gtg | tta | tac | 929 |
| Gly | Asn | Ile | Ala | Pro | Pro | Thr | Ile | Ile | Ser | Ser | Gly | Ser | Val | Leu | Tyr | |
| | | | | | 110 | | | | | 115 | | | | | 120 | |
| atc | aag | ttc | acc | tca | gac | tac | gcc | cgg | cag | ggg | gca | ggt | ttc | tct | cta | 977 |
| Ile | Lys | Phe | Thr | Ser | Asp | Tyr | Ala | Arg | Gln | Gly | Ala | Gly | Phe | Ser | Leu | |
| | | | | 125 | | | | | 130 | | | | | 135 | | |
| cgc | tat | gag | atc | ttc | aaa | aca | ggc | tct | gaa | gat | tgt | tcc | aag | aac | ttt | 1025 |
| Arg | Tyr | Glu | Ile | Phe | Lys | Thr | Gly | Ser | Glu | Asp | Cys | Ser | Lys | Asn | Phe | |

```
            140                    145                      150
aca agc ccc aat ggg acc att gaa tct cca ggg ttt cca gag aag tat      1073
Thr Ser Pro Asn Gly Thr Ile Glu Ser Pro Gly Phe Pro Glu Lys Tyr
    155                     160                 165 cca cac aat ctg gac tgt acc ttc acc atc ctg gcc aaa ccc agg atg      1121
Pro His Asn Leu Asp Cys Thr Phe Thr Ile Leu Ala Lys Pro Arg Met
170                     175                 180                 185 gag atc atc cta cag ttc ctg acc ttt gac ctg gag cat gac cct cta      1169
Glu Ile Ile Leu Gln Phe Leu Thr Phe Asp Leu Glu His Asp Pro Leu
                190                 195                 200 caa gtg ggg gaa gga gac tgt aaa tat gac tgg ctg gac atc tgg gat      1217
Gln Val Gly Glu Gly Asp Cys Lys Tyr Asp Trp Leu Asp Ile Trp Asp
            205                 210                 215 ggc att cca cat gtt gga cct ctg att ggc aag tac tgt ggg acg aaa      1265
Gly Ile Pro His Val Gly Pro Leu Ile Gly Lys Tyr Cys Gly Thr Lys
        220                 225                 230 aca ccc tcc aaa ctc cgc tcg tcc acg ggg atc ctc tcc ttg acc ttt      1313
Thr Pro Ser Lys Leu Arg Ser Ser Thr Gly Ile Leu Ser Leu Thr Phe
    235                 240                 245 cac acg gac atg gca gtg gcc aag gat ggc ttc tcc gca cgt tac tat      1361
His Thr Asp Met Ala Val Ala Lys Asp Gly Phe Ser Ala Arg Tyr Tyr
250                 255                 260                 265 ttg atc cac cag gag cca cct gag aat ttt cag tgc aat gtc cct ttg      1409
Leu Ile His Gln Glu Pro Pro Glu Asn Phe Gln Cys Asn Val Pro Leu
                270                 275                 280 gga atg gag tct ggc cgg att gct aat gaa cag atc agt gcc tcc tcc      1457
Gly Met Glu Ser Gly Arg Ile Ala Asn Glu Gln Ile Ser Ala Ser Ser
            285                 290                 295 acc ttc tct gat ggg agg tgg act cct caa cag agc cgg ctc cat ggt      1505
Thr Phe Ser Asp Gly Arg Trp Thr Pro Gln Gln Ser Arg Leu His Gly
        300                 305                 310 gat gac aat ggc tgg aca ccc aat ttg gat tcc aac aag gag tat ctc      1553
Asp Asp Asn Gly Trp Thr Pro Asn Leu Asp Ser Asn Lys Glu Tyr Leu
    315                 320                 325 cag gtg gac ctg cgc ttc cta acc atg ctc aca gcc att gca aca cag      1601
Gln Val Asp Leu Arg Phe Leu Thr Met Leu Thr Ala Ile Ala Thr Gln
330                 335                 340                 345 gga gcc att tcc agg gaa acc cag aaa ggc tac tac gtc aaa tcg tac      1649
Gly Ala Ile Ser Arg Glu Thr Gln Lys Gly Tyr Tyr Val Lys Ser Tyr
                350                 355                 360
```

```
aag ctg gaa gtc agc aca aat ggt gaa gat tgg atg gtc tac cgg cat    1697
Lys Leu Glu Val Ser Thr Asn Gly Glu Asp Trp Met Val Tyr Arg His
            365                 370                 375 ggc aaa aac cac aag ata ttc caa gcg aac aat gat gcg acc gag gtg    1745
Gly Lys Asn His Lys Ile Phe Gln Ala Asn Asn Asp Ala Thr Glu Val
            380                 385                 390 gtg cta aac aag ctc cac atg cca ctg ctg act cgg ttc atc agg atc    1793
Val Leu Asn Lys Leu His Met Pro Leu Leu Thr Arg Phe Ile Arg Ile
            395                 400                 405 cgc ccg cag acg tgg cat ttg ggc att gcc ctt cgc ctg gag ctc ttt    1841
Arg Pro Gln Thr Trp His Leu Gly Ile Ala Leu Arg Leu Glu Leu Phe
410                 415                 420                 425 ggc tgc cgg gtc aca gat gca ccc tgc tcc aac atg ctg ggg atg ctc    1889
Gly Cys Arg Val Thr Asp Ala Pro Cys Ser Asn Met Leu Gly Met Leu
                430                 435                 440 tcg ggc ctc att gct gat acc cag atc tct gcc tcc tcc acc cga gag    1937
Ser Gly Leu Ile Ala Asp Thr Gln Ile Ser Ala Ser Ser Thr Arg Glu
            445                 450                 455 tac ctc tgg agc ccc agt gct gcc cgc ctg gtt agt agc cgc tct ggc    1985
Tyr Leu Trp Ser Pro Ser Ala Ala Arg Leu Val Ser Ser Arg Ser Gly
            460                 465                 470 tgg ttt cct cgg aac cct caa gcc cag cca ggt gaa gaa tgg ctt cag    2033
Trp Phe Pro Arg Asn Pro Gln Ala Gln Pro Gly Glu Glu Trp Leu Gln
            475                 480                 485 gta gac ctg ggg aca ccc aag aca gtg aaa ggg gtc atc atc cag gga    2081
Val Asp Leu Gly Thr Pro Lys Thr Val Lys Gly Val Ile Ile Gln Gly
490                 495                 500                 505 gcc cga gga gga gac agc atc act gcc gtg gaa gcc agg gcg ttt gta    2129
Ala Arg Gly Gly Asp Ser Ile Thr Ala Val Glu Ala Arg Ala Phe Val
                510                 515                 520 cgc aag ttc aaa gtc tcc tac agc cta aat ggc aag gac tgg gaa tat    2177
Arg Lys Phe Lys Val Ser Tyr Ser Leu Asn Gly Lys Asp Trp Glu Tyr
            525                 530                 535 atc cag gac ccc agg act cag cag aca aag ctg ttt gaa ggg aac atg    2225
Ile Gln Asp Pro Arg Thr Gln Gln Thr Lys Leu Phe Glu Gly Asn Met
            540                 545                 550 cac tat gac acc cct gac atc cga agg ttc gat cct gtt cca gcg cag    2273
His Tyr Asp Thr Pro Asp Ile Arg Arg Phe Asp Pro Val Pro Ala Gln
        555                 560                 565 tat gtg cgg gtg tac cca gag agg tgg tcg cca gca ggc atc ggg atg    2321
Tyr Val Arg Val Tyr Pro Glu Arg Trp Ser Pro Ala Gly Ile Gly Met
```

```
              570                 575                 580                 585
      agg ctg gag gtg ctg ggc tgt gac tgg aca gac tca aag ccc aca gtg      2369
      Arg Leu Glu Val Leu Gly Cys Asp Trp Thr Asp Ser Lys Pro Thr Val
                      590                 595                 600 gag acg ctg gga ccc acc gtg aag agt gaa gag act acc acc cca tat      2417
      Glu Thr Leu Gly Pro Thr Val Lys Ser Glu Glu Thr Thr Thr Pro Tyr
                      605                 610                 615 ccc atg gat gag gat gcc acc gag tgt ggg gaa aac tgc agc ttt gag      2465
      Pro Met Asp Glu Asp Ala Thr Glu Cys Gly Glu Asn Cys Ser Phe Glu
                      620                 625                 630 gat gac aaa gat ttg caa ctt cct tca gga ttc aac tgc aac ttt gat      2513
      Asp Asp Lys Asp Leu Gln Leu Pro Ser Gly Phe Asn Cys Asn Phe Asp
                      635                 640                 645 ttt ccg gaa gag acc tgt ggt tgg gtg tac gac cat gcc aag tgg ctc      2561
      Phe Pro Glu Glu Thr Cys Gly Trp Val Tyr Asp His Ala Lys Trp Leu
      650                 655                 660                 665 cgg agc acg tgg atc agc agc gct aac ccc aat gac aga aca ttt cca      2609
      Arg Ser Thr Trp Ile Ser Ser Ala Asn Pro Asn Asp Arg Thr Phe Pro
                      670                 675                 680 gat gac aag aac ttc ttg aaa ctg cag agt gat ggc cga cga gag ggc      2657
      Asp Asp Lys Asn Phe Leu Lys Leu Gln Ser Asp Gly Arg Arg Glu Gly
                      685                 690                 695 cag tac ggg cgg ctc atc agc cca ccg gtg cac ctg ccc cga agc cct      2705
      Gln Tyr Gly Arg Leu Ile Ser Pro Pro Val His Leu Pro Arg Ser Pro
                      700                 705                 710 gtg tgc atg gag ttc cag tac caa gcc atg ggc ggc cac ggg gtg gca      2753
      Val Cys Met Glu Phe Gln Tyr Gln Ala Met Gly Gly His Gly Val Ala
                      715                 720                 725 ctg cag gtg gtt cgg gaa gcc agc cag gaa agc aaa ctc ctt tgg gtc      2801
      Leu Gln Val Val Arg Glu Ala Ser Gln Glu Ser Lys Leu Leu Trp Val
      730                 735                 740                 745 atc cgt gag gac cag ggc agc gag tgg aag cac ggg cgc att atc ctg      2849
      Ile Arg Glu Asp Gln Gly Ser Glu Trp Lys His Gly Arg Ile Ile Leu
                      750                 755                 760 ccc agc tat gac atg gag tat cag atc gtg ttc gag gga gtg ata ggg      2897
      Pro Ser Tyr Asp Met Glu Tyr Gln Ile Val Phe Glu Gly Val Ile Gly
                      765                 770                 775 aag gga cga tcg gga gag att tcc ggc gat gac att cgg ata agc act      2945
      Lys Gly Arg Ser Gly Glu Ile Ser Gly Asp Asp Ile Arg Ile Ser Thr
                      780                 785                 790
```

```
gat gtc cca ctg gag aac tgc atg gaa ccc ata tca gct ttt gca ggt   2993
Asp Val Pro Leu Glu Asn Cys Met Glu Pro Ile Ser Ala Phe Ala Gly
    795                 800                 805 gag gat ttt aaa gat gaa tat gaa gga gat tgg agc aac tct tct tcc   3041
Glu Asp Phe Lys Asp Glu Tyr Glu Gly Asp Trp Ser Asn Ser Ser Ser
810             815                 820                     825 tct acc tca ggg gct ggt gac ccc tca tct ggc aaa gaa aag agc tgg   3089
Ser Thr Ser Gly Ala Gly Asp Pro Ser Ser Gly Lys Glu Lys Ser Trp
            830                 835                 840 ctg tac acc cta gat ccc att ctg atc acc atc atc gcc atg agc tcg   3137
Leu Tyr Thr Leu Asp Pro Ile Leu Ile Thr Ile Ile Ala Met Ser Ser
                845                 850                 855 ctg ggg gtc ctg ctg ggg gcc acc tgt gcg ggc ctc ctc ctt tac tgc   3185
Leu Gly Val Leu Leu Gly Ala Thr Cys Ala Gly Leu Leu Leu Tyr Cys
            860                 865                 870 acc tgc tcc tat tcg ggt ctg agt tcg agg agc tgc acc aca ctg gag   3233
Thr Cys Ser Tyr Ser Gly Leu Ser Ser Arg Ser Cys Thr Thr Leu Glu
    875                 880                 885 aac tac aac ttt gag ctc tac gat ggc ctc aag cac aag gtc aag atc   3281
Asn Tyr Asn Phe Glu Leu Tyr Asp Gly Leu Lys His Lys Val Lys Ile
890             895                 900                     905 aat cat cag aag tgc tgc tcg gag gca tgaccgattg tgtctggatc        3328
Asn His Gln Lys Cys Cys Ser Glu Ala
            910 gcttctggcg tttcattcca gtgagagggg ctagcgaaga ttacagtttt gttttgtttt 3388 gttttgtttt ccctttggaa actgaatgcc ataatctgga tcaaagtgtt ccagaatact 3448 gaaggtatgg acaggacaga caggccagtc tagggagaaa gggagatgca gctgtgaagg 3508 ggatcgttgc ccaccaggac tgtggtggcc aagtgaatgc aggaaccggg cccggaattc 3568 cggctctcgg ctaaaatctc agctgcctct ggaaaggctc aaccatactc agtgccaact 3628 cagactctgt tgctgtggtg tcaacatgga tggatcatct gtaccttgta tttttagcag 3688 aattcatgct cagatttctt tgttctgaat ccttgctttg tgctagacac aaagcataca 3748 tgtccttcta aaattaatat gatcactata atctcctgtg tgcagaattc agaaatagac 3808 ctttgaaacc atttgcattg tgagtgcaga tccatgactg gggctagtgc agcaatgaaa 3868 cagaattcca gaaacagtgt gttcttttta ttatgggaaa atacagataa aaatggccac 3928 tgatgaacat gaaagttagc actttcccaa cacagtgtac acttgcaacc ttgttttgga 3988
```

```
tttctcatac accaagactg tgaaacacaa atttcaagaa tgtgttcaaa tgtgtgtgtg    4048
tgtgtgtgtg tgtgtgtgtg tgtgtgtgta tgtgtgtgtg tgtgtgtgtg cttgtgtgtt    4108
tctgtcagtg gtatgagtga tatgtatgca tgtgtgtatg tatatgtatg tatgtatgta    4168
tgtatgtacg tacatatgta tgtatgtatg tatgtatgta tgtatgtata tgtgtgtgtg    4228
tgtttgtgtg tgtgtgtgtt tgtgtgtgtg tgtgtggtaa gtgtggtatg tgtgtatgca    4288
tttgtctata tgtgtatctg tgtgtctatg tgtttctgtc agtggaatga gtggcatgtg    4348
tgcatgtgta tgtatgtgga tatgtgtgtt gtgtttatgt gcttgtgtat aagaggtaag    4408
tgtggtgtgt gtgcatgtgt ctctgtgtgt gtttgtctgt gtacctcttt gtataagtac    4468
ctgtgtttgt atgtgggaat atgtatattg aggcattgct gtgttagtat gtttatagaa    4528
aagaagacag tctgagatgt cttcctcaat acctctccac ttatatcttg gatagacaaa    4588
agtaatgaca aaaaattgct ggtgtgtata tggaaaaggg ggacacatat ccatggatgg    4648
tagaagtgta aactgtgcag tcactgtgga catcaatatg caggttcttc acaaatgtag    4708
atataaagct actatagtta taccc                                         4733
```

<210> 12
<211> 914
<212> PRT
<213> mouse

<400> 12

```
Met Asp Met Phe Pro Leu Thr Trp Val Phe Leu Ala Leu Tyr Phe Ser
 1               5                  10                  15

Gly His Glu Val Arg Ser Gln Gln Asp Pro Pro Cys Gly Gly Arg Pro
                20                  25                  30

Asn Ser Lys Asp Ala Gly Tyr Ile Thr Ser Pro Gly Tyr Pro Gln Asp
            35                  40                  45

Tyr Pro Ser His Gln Asn Cys Glu Trp Ile Val Tyr Ala Pro Glu Pro
        50                  55                  60

Asn Gln Lys Ile Val Leu Asn Phe Asn Pro His Phe Glu Ile Glu Lys
 65                  70                  75                  80

His Asp Cys Lys Tyr Asp Phe Ile Glu Ile Arg Asp Gly Asp Ser Glu
                85                  90                  95

Ser Ala Asp Leu Leu Gly Lys His Cys Gly Asn Ile Ala Pro Pro Thr
                100                 105                 110
```

```
Ile Ile Ser Ser Gly Ser Val Leu Tyr Ile Lys Phe Thr Ser Asp Tyr
        115             120             125

Ala Arg Gln Gly Ala Gly Phe Ser Leu Arg Tyr Glu Ile Phe Lys Thr
    130             135             140

Gly Ser Glu Asp Cys Ser Lys Asn Phe Thr Ser Pro Asn Gly Thr Ile
145             150             155                         160

Glu Ser Pro Gly Phe Pro Glu Lys Tyr Pro His Asn Leu Asp Cys Thr
            165             170             175

Phe Thr Ile Leu Ala Lys Pro Arg Met Glu Ile Leu Gln Phe Leu
        180             185             190

Thr Phe Asp Leu Glu His Asp Pro Leu Gln Val Gly Glu Gly Asp Cys
        195             200             205

Lys Tyr Asp Trp Leu Asp Ile Trp Asp Gly Ile Pro His Val Gly Pro
    210             215             220

Leu Ile Gly Lys Tyr Cys Gly Thr Lys Thr Pro Ser Lys Leu Arg Ser
225             230             235                         240

Ser Thr Gly Ile Leu Ser Leu Thr Phe His Thr Asp Met Ala Val Ala
            245             250             255

Lys Asp Gly Phe Ser Ala Arg Tyr Tyr Leu Ile His Gln Glu Pro Pro
            260             265             270

Glu Asn Phe Gln Cys Asn Val Pro Leu Gly Met Glu Ser Gly Arg Ile
        275             280             285

Ala Asn Glu Gln Ile Ser Ala Ser Ser Thr Phe Ser Asp Gly Arg Trp
    290             295             300

Thr Pro Gln Gln Ser Arg Leu His Gly Asp Asp Asn Gly Trp Thr Pro
305             310             315             320

Asn Leu Asp Ser Asn Lys Glu Tyr Leu Gln Val Asp Leu Arg Phe Leu
            325             330             335

Thr Met Leu Thr Ala Ile Ala Thr Gln Gly Ala Ile Ser Arg Glu Thr
        340             345             350

Gln Lys Gly Tyr Tyr Val Lys Ser Tyr Lys Leu Glu Val Ser Thr Asn
    355             360             365

Gly Glu Asp Trp Met Val Tyr Arg His Gly Lys Asn His Lys Ile Phe
    370             375             380

Gln Ala Asn Asn Asp Ala Thr Glu Val Val Leu Asn Lys Leu His Met
385             390             395             400
```

```
Pro Leu Leu Thr Arg Phe Ile Arg Ile Arg Pro Gln Thr Trp His Leu
            405                 410                 415

Gly Ile Ala Leu Arg Leu Glu Leu Phe Gly Cys Arg Val Thr Asp Ala
            420                 425                 430

Pro Cys Ser Asn Met Leu Gly Met Leu Ser Gly Leu Ile Ala Asp Thr
            435                 440                 445

Gln Ile Ser Ala Ser Ser Thr Arg Glu Tyr Leu Trp Ser Pro Ser Ala
            450                 455                 460

Ala Arg Leu Val Ser Ser Arg Ser Gly Trp Phe Pro Arg Asn Pro Gln
465                 470                 475                 480

Ala Gln Pro Gly Glu Glu Trp Leu Gln Val Asp Leu Gly Thr Pro Lys
            485                 490                 495

Thr Val Lys Gly Val Ile Ile Gln Gly Ala Arg Gly Gly Asp Ser Ile
            500                 505                 510

Thr Ala Val Glu Ala Arg Ala Phe Val Arg Lys Phe Lys Val Ser Tyr
            515                 520                 525

Ser Leu Asn Gly Lys Asp Trp Glu Tyr Ile Gln Asp Pro Arg Thr Gln
            530                 535                 540

Gln Thr Lys Leu Phe Glu Gly Asn Met His Tyr Asp Thr Pro Asp Ile
545                 550                 555                 560

Arg Arg Phe Asp Pro Val Pro Ala Gln Tyr Val Arg Val Tyr Pro Glu
            565                 570                 575

Arg Trp Ser Pro Ala Gly Ile Gly Met Arg Leu Glu Val Leu Gly Cys
            580                 585                 590

Asp Trp Thr Asp Ser Lys Pro Thr Val Glu Thr Leu Gly Pro Thr Val
            595                 600                 605

Lys Ser Glu Glu Thr Thr Thr Pro Tyr Pro Met Asp Glu Asp Ala Thr
            610                 615                 620

Glu Cys Gly Glu Asn Cys Ser Phe Glu Asp Asp Lys Asp Leu Gln Leu
625                 630                 635                 640

Pro Ser Gly Phe Asn Cys Asn Phe Asp Phe Pro Glu Glu Thr Cys Gly
            645                 650                 655

Trp Val Tyr Asp His Ala Lys Trp Leu Arg Ser Thr Trp Ile Ser Ser
            660                 665                 670

Ala Asn Pro Asn Asp Arg Thr Phe Pro Asp Asp Lys Asn Phe Leu Lys
            675                 680                 685
```

```
Leu Gln Ser Asp Gly Arg Arg Glu Gly Gln Tyr Gly Arg Leu Ile Ser
    690                 695                 700
Pro Pro Val His Leu Pro Arg Ser Pro Val Cys Met Glu Phe Gln Tyr
705                 710                 715                 720
Gln Ala Met Gly Gly His Gly Val Ala Leu Gln Val Val Arg Glu Ala
            725                 730                 735
Ser Gln Glu Ser Lys Leu Leu Trp Val Ile Arg Glu Asp Gln Gly Ser
            740                 745                 750
Glu Trp Lys His Gly Arg Ile Ile Leu Pro Ser Tyr Asp Met Glu Tyr
            755                 760                 765
Gln Ile Val Phe Glu Gly Val Ile Gly Lys Gly Arg Ser Gly Glu Ile
            770                 775                 780
Ser Gly Asp Asp Ile Arg Ile Ser Thr Asp Val Pro Leu Glu Asn Cys
785                 790                 795                 800
Met Glu Pro Ile Ser Ala Phe Ala Gly Glu Asp Phe Lys Asp Glu Tyr
            805                 810                 815
Glu Gly Asp Trp Ser Asn Ser Ser Ser Thr Ser Gly Ala Gly Asp
            820                 825                 830
Pro Ser Ser Gly Lys Glu Lys Ser Trp Leu Tyr Thr Leu Asp Pro Ile
            835                 840                 845
Leu Ile Thr Ile Ile Ala Met Ser Ser Leu Gly Val Leu Leu Gly Ala
            850                 855                 860
Thr Cys Ala Gly Leu Leu Leu Tyr Cys Thr Cys Ser Tyr Ser Gly Leu
865                 870                 875                 880
Ser Ser Arg Ser Cys Thr Thr Leu Glu Asn Tyr Asn Phe Glu Leu Tyr
            885                 890                 895
Asp Gly Leu Lys His Lys Val Lys Ile Asn His Gln Lys Cys Cys Ser
            900                 905                 910
Glu Ala

<210> 13
<211> 4769
<212> DNA
<213> mouse

<220>
<221> CDS
<222> (567)..(3344)
```

<400> 13

```
aaactggagc tccaccgcgg tggcggccgc ccgggcaggt ctagaattca gcggccgctg    60
aattctatcc agcggtcggt gcctctgccc gcgtgtgtgt cccgggtgcc gggggaccctg   120 tgtcagttag cgcttctgag atcacacagc tgcctagggg ccgtgtgatg cccagggcaa   180
ttcttggctt tgatttttat tattattact attattttgc gttcagcttt cgggaaaccc   240
tcgtgatgtt gtaggataaa ggaaatgaca ctttgaggaa ctggagagaa catacacgcg   300
tttgggtttg aagaggaaac cggtctccgc ttccttagct tgctccctct ttgctgattt   360
caagagctat ctcctatgag gtggagatat tccagcaaga ataaggtga agacagactg    420 actgccagga cccaggagga aaacgttgat cgttagagac ctttgcagaa gacaccacca   480
ggaggaaaat tagagaggaa aaacacaaag acataattat aggagatccc acaaacctag   540
cccgggagag agcctctctg tcaaaa atg gat atg ttt cct ctt acc tgg gtt   593
                                 Met Asp Met Phe Pro Leu Thr Trp Val
                                  1               5 ttc tta gct ctg tac ttt tca gga cac gaa gtg aga agc cag caa gat   641
Phe Leu Ala Leu Tyr Phe Ser Gly His Glu Val Arg Ser Gln Gln Asp
 10              15                  20                  25 cca ccc tgc gga ggt cgg ccg aat tcc aaa gat gct ggc tac atc act   689
Pro Pro Cys Gly Gly Arg Pro Asn Ser Lys Asp Ala Gly Tyr Ile Thr
                 30                  35                  40 tcc cca ggc tac ccc cag gac tat ccc tcc cac cag aac tgt gag tgg   737
Ser Pro Gly Tyr Pro Gln Asp Tyr Pro Ser His Gln Asn Cys Glu Trp
                 45                  50                  55 att gtc tac gcc ccc gaa ccc aac cag aag att gtt ctc aac ttc aac   785
Ile Val Tyr Ala Pro Glu Pro Asn Gln Lys Ile Val Leu Asn Phe Asn
                 60                  65                  70 cct cac ttt gaa atc gag aaa cac gac tgc aag tat gac ttc att gag   833
Pro His Phe Glu Ile Glu Lys His Asp Cys Lys Tyr Asp Phe Ile Glu
         75                  80                  85 att cgg gat ggg gac agt gag tca gct gac ctc ctg ggc aag cac tgt   881
Ile Arg Asp Gly Asp Ser Glu Ser Ala Asp Leu Leu Gly Lys His Cys
 90                  95                 100                 105 ggg aac atc gcc ccg ccc acc atc atc tcc tca ggc tcc gtg tta tac   929
Gly Asn Ile Ala Pro Pro Thr Ile Ile Ser Ser Gly Ser Val Leu Tyr
                110                 115                 120 atc aag ttc acc tca gac tac gcc cgg cag ggg gca ggt ttc tct cta   977
Ile Lys Phe Thr Ser Asp Tyr Ala Arg Gln Gly Ala Gly Phe Ser Leu
```

```
                    125                     130                      135 cgc tat gag atc ttc aaa aca ggc tct gaa gat tgt tcc aag aac ttt    1025
Arg Tyr Glu Ile Phe Lys Thr Gly Ser Glu Asp Cys Ser Lys Asn Phe
        140                 145                 150 aca agc ccc aat ggg acc att gaa tct cca ggg ttt cca gag aag tat    1073
Thr Ser Pro Asn Gly Thr Ile Glu Ser Pro Gly Phe Pro Glu Lys Tyr
    155                 160                 165 cca cac aat ctg gac tgt acc ttc acc atc ctg gcc aaa ccc agg atg    1121
Pro His Asn Leu Asp Cys Thr Phe Thr Ile Leu Ala Lys Pro Arg Met
170                 175                 180                 185 gag atc atc cta cag ttc ctg acc ttt gac ctg gag cat gac cct cta    1169
Glu Ile Ile Leu Gln Phe Leu Thr Phe Asp Leu Glu His Asp Pro Leu
                190                 195                 200 caa gtg ggg gaa gga gac tgt aaa tat gac tgg ctg gac atc tgg gat    1217
Gln Val Gly Glu Gly Asp Cys Lys Tyr Asp Trp Leu Asp Ile Trp Asp
            205                 210                 215 ggc att cca cat gtt gga cct ctg att ggc aag tac tgt ggg acg aaa    1265
Gly Ile Pro His Val Gly Pro Leu Ile Gly Lys Tyr Cys Gly Thr Lys
        220                 225                 230 aca ccc tcc aaa ctc cgc tcg tcc acg ggg atc ctc tcc ttg acc ttt    1313
Thr Pro Ser Lys Leu Arg Ser Ser Thr Gly Ile Leu Ser Leu Thr Phe
    235                 240                 245 cac acg gac atg gca gtg gcc aag gat ggc ttc tcc gca cgt tac tat    1361
His Thr Asp Met Ala Val Ala Lys Asp Gly Phe Ser Ala Arg Tyr Tyr
250                 255                 260                 265 ttg atc cac cag gag cca cct gag aat ttt cag tgc aat gtc cct ttg    1409
Leu Ile His Gln Glu Pro Pro Glu Asn Phe Gln Cys Asn Val Pro Leu
                270                 275                 280 gga atg gag tct ggc cgg att gct aat gaa cag atc agt gcc tcc tcc    1457
Gly Met Glu Ser Gly Arg Ile Ala Asn Glu Gln Ile Ser Ala Ser Ser
            285                 290                 295 acc ttc tct gat ggg agg tgg act cct caa cag agc cgg ctc cat ggt    1505
Thr Phe Ser Asp Gly Arg Trp Thr Pro Gln Gln Ser Arg Leu His Gly
        300                 305                 310 gat gac aat ggc tgg aca ccc aat ttg gat tcc aac aag gag tat ctc    1553
Asp Asp Asn Gly Trp Thr Pro Asn Leu Asp Ser Asn Lys Glu Tyr Leu
    315                 320                 325 cag gtg gac ctg cgc ttc cta acc atg ctc aca gcc att gca aca cag    1601
Gln Val Asp Leu Arg Phe Leu Thr Met Leu Thr Ala Ile Ala Thr Gln
330                 335                 340                 345
```

```
gga gcc att tcc agg gaa acc cag aaa ggc tac tac gtc aaa tcg tac    1649
Gly Ala Ile Ser Arg Glu Thr Gln Lys Gly Tyr Tyr Val Lys Ser Tyr
                350                 355                 360 aag ctg gaa gtc agc aca aat ggt gaa gat tgg atg gtc tac cgg cat    1697
Lys Leu Glu Val Ser Thr Asn Gly Glu Asp Trp Met Val Tyr Arg His
                365                 370                 375 ggc aaa aac cac aag ata ttc caa gcg aac aat gat gcg acc gag gtg    1745
Gly Lys Asn His Lys Ile Phe Gln Ala Asn Asn Asp Ala Thr Glu Val
                380                 385                 390 gtg cta aac aag ctc cac atg cca ctg ctg act cgg ttc atc agg atc    1793
Val Leu Asn Lys Leu His Met Pro Leu Leu Thr Arg Phe Ile Arg Ile
        395                 400                 405 cgc ccg cag acg tgg cat ttg ggc att gcc ctt cgc ctg gag ctc ttt    1841
Arg Pro Gln Thr Trp His Leu Gly Ile Ala Leu Arg Leu Glu Leu Phe
410                 415                 420                 425 ggc tgc cgg gtc aca gat gca ccc tgc tcc aac atg ctg ggg atg ctc    1889
Gly Cys Arg Val Thr Asp Ala Pro Cys Ser Asn Met Leu Gly Met Leu
                430                 435                 440 tcg ggc ctc att gct gat acc cag atc tct gcc tcc tcc acc cga gag    1937
Ser Gly Leu Ile Ala Asp Thr Gln Ile Ser Ala Ser Ser Thr Arg Glu
                445                 450                 455 tac ctc tgg agc ccc agt gct gcc cgc ctg gtt agt agc cgc tct ggc    1985
Tyr Leu Trp Ser Pro Ser Ala Ala Arg Leu Val Ser Ser Arg Ser Gly
                460                 465                 470 tgg ttt cct cgg aac cct caa gcc cag cca ggt gaa gaa tgg ctt cag    2033
Trp Phe Pro Arg Asn Pro Gln Ala Gln Pro Gly Glu Glu Trp Leu Gln
        475                 480                 485 gta gac ctg ggg aca ccc aag aca gtg aaa ggg gtc atc atc cag gga    2081
Val Asp Leu Gly Thr Pro Lys Thr Val Lys Gly Val Ile Ile Gln Gly
490                 495                 500                 505 gcc cga gga gga gac agc atc act gcc gtg gaa gcc agg gcg ttt gta    2129
Ala Arg Gly Gly Asp Ser Ile Thr Ala Val Glu Ala Arg Ala Phe Val
                510                 515                 520 cgc aag ttc aaa gtc tcc tac agc cta aat ggc aag gac tgg gaa tat    2177
Arg Lys Phe Lys Val Ser Tyr Ser Leu Asn Gly Lys Asp Trp Glu Tyr
                525                 530                 535 atc cag gac ccc agg act cag cag aca aag ctg ttt gaa ggg aac atg    2225
Ile Gln Asp Pro Arg Thr Gln Gln Thr Lys Leu Phe Glu Gly Asn Met
        540                 545                 550 cac tat gac acc cct gac atc cga agg ttc gat cct gtt cca gcg cag    2273
His Tyr Asp Thr Pro Asp Ile Arg Arg Phe Asp Pro Val Pro Ala Gln
```

```
                555                    560                    565
tat gtg cgg gtg tac cca gag agg tgg tcg cca gca ggc atc ggg atg        2321
Tyr Val Arg Val Tyr Pro Glu Arg Trp Ser Pro Ala Gly Ile Gly Met
570                 575                 580                 585 agg ctg gag gtg ctg ggc tgt gac tgg aca gac tca aag ccc aca gtg        2369
Arg Leu Glu Val Leu Gly Cys Asp Trp Thr Asp Ser Lys Pro Thr Val
                590                 595                 600 gag acg ctg gga ccc acc gtg aag agt gaa gag act acc acc cca tat        2417
Glu Thr Leu Gly Pro Thr Val Lys Ser Glu Glu Thr Thr Thr Pro Tyr
                605                 610                 615 ccc atg gat gag gat gcc acc gag tgt ggg gaa aac tgc agc ttt gag        2465
Pro Met Asp Glu Asp Ala Thr Glu Cys Gly Glu Asn Cys Ser Phe Glu
            620                 625                 630 gat gac aaa gat ttg caa ctt cct tca gga ttc aac tgc aac ttt gat        2513
Asp Asp Lys Asp Leu Gln Leu Pro Ser Gly Phe Asn Cys Asn Phe Asp
        635                 640                 645 ttt ccg gaa gag acc tgt ggt tgg gtg tac gac cat gcc aag tgg ctc        2561
Phe Pro Glu Glu Thr Cys Gly Trp Val Tyr Asp His Ala Lys Trp Leu
650                 655                 660                 665 cgg agc acg tgg atc agc agc gct aac ccc aat gac aga aca ttt cca        2609
Arg Ser Thr Trp Ile Ser Ser Ala Asn Pro Asn Asp Arg Thr Phe Pro
                670                 675                 680 gat gac aag aac ttc ttg aaa ctg cag agt gat ggc cga cga gag ggc        2657
Asp Asp Lys Asn Phe Leu Lys Leu Gln Ser Asp Gly Arg Arg Glu Gly
                685                 690                 695 cag tac ggg cgg ctc atc agc cca ccg gtg cac ctg ccc cga agc cct        2705
Gln Tyr Gly Arg Leu Ile Ser Pro Pro Val His Leu Pro Arg Ser Pro
            700                 705                 710 gtg tgc atg gag ttc cag tac caa gcc atg ggc ggc cac ggg gtg gca        2753
Val Cys Met Glu Phe Gln Tyr Gln Ala Met Gly Gly His Gly Val Ala
        715                 720                 725 ctg cag gtg gtt cgg gaa gcc agc cag gaa agc aaa ctc ctt tgg gtc        2801
Leu Gln Val Val Arg Glu Ala Ser Gln Glu Ser Lys Leu Leu Trp Val
730                 735                 740                 745 atc cgt gag gac cag ggc agc gag tgg aag cac ggg cgc att atc ctg        2849
Ile Arg Glu Asp Gln Gly Ser Glu Trp Lys His Gly Arg Ile Ile Leu
                750                 755                 760 ccc agc tat gac atg gag tat cag atc gtg ttc gag gga gtg ata ggg        2897
Pro Ser Tyr Asp Met Glu Tyr Gln Ile Val Phe Glu Gly Val Ile Gly
            765                 770                 775
```

| | | |
|---|---|---|
| aag gga cga tcg gga gag att tcc ggc gat gac att cgg ata agc act<br>Lys Gly Arg Ser Gly Glu Ile Ser Gly Asp Asp Ile Arg Ile Ser Thr<br>    780                         785                    790 | 2945 |
| gat gtc cca ctg gag aac tgc atg gaa ccc ata tca gct ttt gca gtg<br>Asp Val Pro Leu Glu Asn Cys Met Glu Pro Ile Ser Ala Phe Ala Val<br>    795                         800                    805 | 2993 |
| gac atc cca gaa acc cat ggg gga gag ggc tat gaa gat gag att gat<br>Asp Ile Pro Glu Thr His Gly Gly Glu Gly Tyr Glu Asp Glu Ile Asp<br>810                        815                    820                825 | 3041 |
| gat gaa tat gaa gga gat tgg agc aac tct tct tcc tct acc tca ggg<br>Asp Glu Tyr Glu Gly Asp Trp Ser Asn Ser Ser Ser Ser Thr Ser Gly<br>                     830                    835                    840 | 3089 |
| gct ggt gac ccc tca tct ggc aaa gaa aag agc tgg ctg tac acc cta<br>Ala Gly Asp Pro Ser Ser Gly Lys Glu Lys Ser Trp Leu Tyr Thr Leu<br>                     845                    850                    855 | 3137 |
| gat ccc att ctg atc acc atc atc gcc atg agc tcg ctg ggg gtc ctg<br>Asp Pro Ile Leu Ile Thr Ile Ile Ala Met Ser Ser Leu Gly Val Leu<br>               860                    865                    870 | 3185 |
| ctg ggg gcc acc tgt gcg ggc ctc ctc ctt tac tgc acc tgc tcc tat<br>Leu Gly Ala Thr Cys Ala Gly Leu Leu Leu Tyr Cys Thr Cys Ser Tyr<br>    875                         880                        885 | 3233 |
| tcg ggt ctg agt tcg agg agc tgc acc aca ctg gag aac tac aac ttt<br>Ser Gly Leu Ser Ser Arg Ser Cys Thr Thr Leu Glu Asn Tyr Asn Phe<br>890                        895                    900                    905 | 3281 |
| gag ctc tac gat ggc ctc aag cac aag gtc aag atc aat cat cag aag<br>Glu Leu Tyr Asp Gly Leu Lys His Lys Val Lys Ile Asn His Gln Lys<br>                   910                    915                    920 | 3329 |
| tgc tgc tcg gag gca tgaccgattg tgtctggatc gcttctggcg tttcattcca<br>Cys Cys Ser Glu Ala<br>                 925 | 3384 | gtgagagggg ctagcgaaga ttacagtttt gttttgtttt gttttgtttt ccctttggaa 3444 actgaatgcc ataatctgga tcaaagtgtt ccagaatact gaaggtatgg acaggacaga 3504 caggccagtc tagggagaaa gggagatgca gctgtgaagg ggatcgttgc ccaccaggac 3564 tgtggtggcc aagtgaatgc aggaaccggg cccggaattc cggctctcgg ctaaaatctc 3624 agctgcctct ggaaaggctc aaccatactc agtgccaact cagactctgt tgctgtggtg 3684 tcaacatgga tggatcatct gtaccttgta ttttagcag aattcatgct cagatttctt 3744 tgttctgaat ccttgctttg tgctagacac aaagcataca tgtccttcta aattaatat 3804

```
gatcactata atctcctgtg tgcagaattc agaaatagac ctttgaaacc atttgcattg 3864 tgagtgcaga tccatgactg gggctagtgc agcaatgaaa cagaattcca gaaacagtgt 3924 gttctttta ttatgggaaa atacagataa aaatggccac tgatgaacat gaaagttagc 3984 actttcccaa cacagtgtac acttgcaacc ttgttttgga tttctcatac accaagactg 4044 tgaaacacaa atttcaagaa tgtgttcaaa tgtgtgtgtg tgtgtgtgtg tgtgtgtgtg 4104 tgtgtgtgta tgtgtgtgtg tgtgtgtgtg cttgtgtgtt tctgtcagtg gtatgagtga 4164 tatgtatgca tgtgtgtatg tatatgtatg tatgtatgta tgtatgtacg tacatatgta 4224 tgtatgtatg tatgtatgta tgtatgtata tgtgtgtgtg tgtttgtgtg tgtgtgtgtt 4284 tgtgtgtgtg tgtgtggtaa gtgtggtatg tgtgtatgca tttgtctata tgtgtatctg 4344 tgtgtctatg tgtttctgtc agtggaatga gtggcatgtg tgcatgtgta tgtatgtgga 4404 tatgtgtgtt gtgtttatgt gcttgtgtat aagaggtaag tgtggtgtgt gtgcatgtgt 4464 ctctgtgtgt gtttgtctgt gtacctcttt gtataagtac ctgtgtttgt atgtgggaat 4524 atgtatattg aggcattgct gtgttagtat gtttatagaa aagaagacag tctgagatgt 4584 cttcctcaat acctctccac ttatatcttg gatagacaaa agtaatgaca aaaaattgct 4644 ggtgtgtata tggaaaaggg ggacacatat ccatggatgg tagaagtgta aactgtgcag 4704 tcactgtgga catcaatatg caggttcttc acaaatgtag atataaagct actatagtta 4764 taccc                                                              4769
```

<210> 14
<211> 926
<212> PRT
<213> mouse

<400> 14
Met Asp Met Phe Pro Leu Thr Trp Val Phe Leu Ala Leu Tyr Phe Ser
 1               5                  10                  15

Gly His Glu Val Arg Ser Gln Gln Asp Pro Pro Cys Gly Gly Arg Pro
                20                  25                  30

Asn Ser Lys Asp Ala Gly Tyr Ile Thr Ser Pro Gly Tyr Pro Gln Asp
            35                  40                  45

Tyr Pro Ser His Gln Asn Cys Glu Trp Ile Val Tyr Ala Pro Glu Pro
        50                  55                  60

Asn Gln Lys Ile Val Leu Asn Phe Asn Pro His Phe Glu Ile Glu Lys

```
           65                      70                    75                     80

His Asp Cys Lys Tyr Asp Phe Ile Glu Ile Arg Asp Gly Asp Ser Glu
                       85                    90                 95

Ser Ala Asp Leu Leu Gly Lys His Cys Gly Asn Ile Ala Pro Pro Thr
                  100                   105                 110

Ile Ile Ser Ser Gly Ser Val Leu Tyr Ile Lys Phe Thr Ser Asp Tyr
               115                   120                125

Ala Arg Gln Gly Ala Gly Phe Ser Leu Arg Tyr Glu Ile Phe Lys Thr
           130                   135                 140

Gly Ser Glu Asp Cys Ser Lys Asn Phe Thr Ser Pro Asn Gly Thr Ile
   145                   150                   155                 160

Glu Ser Pro Gly Phe Pro Glu Lys Tyr Pro His Asn Leu Asp Cys Thr
                    165                   170                175

Phe Thr Ile Leu Ala Lys Pro Arg Met Glu Ile Ile Leu Gln Phe Leu
                180                   185                 190

Thr Phe Asp Leu Glu His Asp Pro Leu Gln Val Gly Glu Gly Asp Cys
            195                    200                  205

Lys Tyr Asp Trp Leu Asp Ile Trp Asp Gly Ile Pro His Val Gly Pro
            210                   215                   220

Leu Ile Gly Lys Tyr Cys Gly Thr Lys Thr Pro Ser Lys Leu Arg Ser
   225                   230                   235                 240

Ser Thr Gly Ile Leu Ser Leu Thr Phe His Thr Asp Met Ala Val Ala
                    245                   250                 255

Lys Asp Gly Phe Ser Ala Arg Tyr Tyr Leu Ile His Gln Glu Pro Pro
                260                    265                 270

Glu Asn Phe Gln Cys Asn Val Pro Leu Gly Met Glu Ser Gly Arg Ile
               275                   280                 285

Ala Asn Glu Gln Ile Ser Ala Ser Ser Thr Phe Ser Asp Gly Arg Trp
               290                   295                 300

Thr Pro Gln Gln Ser Arg Leu His Gly Asp Asp Asn Gly Trp Thr Pro
   305                    310                  315                  320

Asn Leu Asp Ser Asn Lys Glu Tyr Leu Gln Val Asp Leu Arg Phe Leu
                  325                   330                 335

Thr Met Leu Thr Ala Ile Ala Thr Gln Gly Ala Ile Ser Arg Glu Thr
               340                   345                 350

Gln Lys Gly Tyr Tyr Val Lys Ser Tyr Lys Leu Glu Val Ser Thr Asn
```

```
                355                      360                      365

Gly Glu Asp Trp Met Val Tyr Arg His Gly Lys Asn His Lys Ile Phe
        370                      375                  380

Gln Ala Asn Asn Asp Ala Thr Glu Val Val Leu Asn Lys Leu His Met
    385                  390                  395                  400

Pro Leu Leu Thr Arg Phe Ile Arg Ile Arg Pro Gln Thr Trp His Leu
                    405                      410                  415

Gly Ile Ala Leu Arg Leu Glu Leu Phe Gly Cys Arg Val Thr Asp Ala
                    420                  425                  430

Pro Cys Ser Asn Met Leu Gly Met Leu Ser Gly Leu Ile Ala Asp Thr
                435                      440                  445

Gln Ile Ser Ala Ser Ser Thr Arg Glu Tyr Leu Trp Ser Pro Ser Ala
                450                  455                      460

Ala Arg Leu Val Ser Ser Arg Ser Gly Trp Phe Pro Arg Asn Pro Gln
    465                      470                      475              480

Ala Gln Pro Gly Glu Glu Trp Leu Gln Val Asp Leu Gly Thr Pro Lys
                    485                      490                  495

Thr Val Lys Gly Val Ile Ile Gln Gly Ala Arg Gly Gly Asp Ser Ile
                500                      505                  510

Thr Ala Val Glu Ala Arg Ala Phe Val Arg Lys Phe Lys Val Ser Tyr
                515                  520                      525

Ser Leu Asn Gly Lys Asp Trp Glu Tyr Ile Gln Asp Pro Arg Thr Gln
                530                  535                  540

Gln Thr Lys Leu Phe Glu Gly Asn Met His Tyr Asp Thr Pro Asp Ile
    545                      550                  555                  560

Arg Arg Phe Asp Pro Val Pro Ala Gln Tyr Val Arg Val Tyr Pro Glu
                    565                      570                  575

Arg Trp Ser Pro Ala Gly Ile Gly Met Arg Leu Glu Val Leu Gly Cys
                580                  585                  590

Asp Trp Thr Asp Ser Lys Pro Thr Val Glu Thr Leu Gly Pro Thr Val
            595                      600                  605

Lys Ser Glu Glu Thr Thr Thr Pro Tyr Pro Met Asp Glu Asp Ala Thr
        610                      615                  620

Glu Cys Gly Glu Asn Cys Ser Phe Glu Asp Asp Lys Asp Leu Gln Leu
    625                      630                  635                  640

Pro Ser Gly Phe Asn Cys Asn Phe Asp Phe Pro Glu Glu Thr Cys Gly
```

```
              645                    650                    655
Trp Val Tyr Asp His Ala Lys Trp Leu Arg Ser Thr Trp Ile Ser Ser
            660                665                670
Ala Asn Pro Asn Asp Arg Thr Phe Pro Asp Asp Lys Asn Phe Leu Lys
        675                680                685
Leu Gln Ser Asp Gly Arg Arg Glu Gly Gln Tyr Gly Arg Leu Ile Ser
    690                695                700
Pro Pro Val His Leu Pro Arg Ser Pro Val Cys Met Glu Phe Gln Tyr
705                 710                715                720
Gln Ala Met Gly Gly His Gly Val Ala Leu Gln Val Val Arg Glu Ala
            725                730                735
Ser Gln Glu Ser Lys Leu Leu Trp Val Ile Arg Glu Asp Gln Gly Ser
        740                745                750
Glu Trp Lys His Gly Arg Ile Ile Leu Pro Ser Tyr Asp Met Glu Tyr
    755                760                765
Gln Ile Val Phe Glu Gly Val Ile Gly Lys Gly Arg Ser Gly Glu Ile
    770                775                780
Ser Gly Asp Asp Ile Arg Ile Ser Thr Asp Val Pro Leu Glu Asn Cys
785                 790                795                800
Met Glu Pro Ile Ser Ala Phe Ala Val Asp Ile Pro Glu Thr His Gly
            805                810                815
Gly Glu Gly Tyr Glu Asp Glu Ile Asp Asp Glu Tyr Glu Gly Asp Trp
            820                825                830
Ser Asn Ser Ser Ser Ser Thr Ser Gly Ala Gly Asp Pro Ser Ser Gly
        835                840                845
Lys Glu Lys Ser Trp Leu Tyr Thr Leu Asp Pro Ile Leu Ile Thr Ile
    850                855                860
Ile Ala Met Ser Ser Leu Gly Val Leu Leu Gly Ala Thr Cys Ala Gly
865                 870                875                880
Leu Leu Leu Tyr Cys Thr Cys Ser Tyr Ser Gly Leu Ser Ser Arg Ser
            885                890                895
Cys Thr Thr Leu Glu Asn Tyr Asn Phe Glu Leu Tyr Asp Gly Leu Lys
        900                905                910
His Lys Val Lys Ile Asn His Gln Lys Cys Cys Ser Glu Ala
    915                920                925
```

```
<210> 15
<211> 4784
<212> DNA
<213> mouse

<220>
<221> CDS
<222> (567)..(3359)

<400> 15
aaactggagc tccaccgcgg tggcggccgc ccgggcaggt ctagaattca gcggccgctg   60
aattctatcc agcggtcggt gcctctgccc gcgtgtgtgt cccgggtgcc gggggacctg  120
tgtcagttag cgcttctgag atcacacagc tgcctagggg ccgtgtgatg cccagggcaa  180
ttcttggctt tgattttat tattattact attattttgc gttcagcttt cgggaaaccc   240
tcgtgatgtt gtaggataaa ggaaatgaca ctttgaggaa ctggagagaa catacacgcg  300
tttgggtttg aagaggaaac cggtctccgc ttccttagct tgctccctct ttgctgattt  360
caagagctat ctcctatgag gtggagatat ccagcaaga ataaggtga agacagactg   420 actgccagga cccaggagga aaacgttgat cgttagagac ctttgcagaa gacaccacca  480
ggaggaaaat tagagaggaa aaacacaaag acataattat aggagatccc acaaacctag  540
cccgggagag agcctctctg tcaaaa atg gat atg ttt cct ctt acc tgg gtt   593
                                Met Asp Met Phe Pro Leu Thr Trp Val
                                 1               5 ttc tta gct ctg tac ttt tca gga cac gaa gtg aga agc cag caa gat    641
Phe Leu Ala Leu Tyr Phe Ser Gly His Glu Val Arg Ser Gln Gln Asp
 10              15                  20                  25 cca ccc tgc gga ggt cgg ccg aat tcc aaa gat gct ggc tac atc act    689
Pro Pro Cys Gly Gly Arg Pro Asn Ser Lys Asp Ala Gly Tyr Ile Thr
                 30                  35                  40 tcc cca ggc tac ccc cag gac tat ccc tcc cac cag aac tgt gag tgg    737
Ser Pro Gly Tyr Pro Gln Asp Tyr Pro Ser His Gln Asn Cys Glu Trp
             45                  50                  55 att gtc tac gcc ccc gaa ccc aac cag aag att gtt ctc aac ttc aac    785
Ile Val Tyr Ala Pro Glu Pro Asn Gln Lys Ile Val Leu Asn Phe Asn
         60                  65                  70 cct cac ttt gaa atc gag aaa cac gac tgc aag tat gac ttc att gag    833
Pro His Phe Glu Ile Glu Lys His Asp Cys Lys Tyr Asp Phe Ile Glu
     75                  80                  85 att cgg gat ggg gac agt gag tca gct gac ctc ctg ggc aag cac tgt    881
Ile Arg Asp Gly Asp Ser Glu Ser Ala Asp Leu Leu Gly Lys His Cys
```

```
       90                    95                    100                   105
ggg aac atc gcc ccg ccc acc atc atc tcc tca ggc tcc gtg tta tac    929
Gly Asn Ile Ala Pro Pro Thr Ile Ile Ser Ser Gly Ser Val Leu Tyr
                110                 115                 120 atc aag ttc acc tca gac tac gcc cgg cag ggg gca ggt ttc tct cta    977
Ile Lys Phe Thr Ser Asp Tyr Ala Arg Gln Gly Ala Gly Phe Ser Leu
                125                 130                 135 cgc tat gag atc ttc aaa aca ggc tct gaa gat tgt tcc aag aac ttt    1025
Arg Tyr Glu Ile Phe Lys Thr Gly Ser Glu Asp Cys Ser Lys Asn Phe
                140                 145                 150 aca agc ccc aat ggg acc att gaa tct cca ggg ttt cca gag aag tat    1073
Thr Ser Pro Asn Gly Thr Ile Glu Ser Pro Gly Phe Pro Glu Lys Tyr
        155                 160                 165 cca cac aat ctg gac tgt acc ttc acc atc ctg gcc aaa ccc agg atg    1121
Pro His Asn Leu Asp Cys Thr Phe Thr Ile Leu Ala Lys Pro Arg Met
170                 175                 180                 185 gag atc atc cta cag ttc ctg acc ttt gac ctg gag cat gac cct cta    1169
Glu Ile Ile Leu Gln Phe Leu Thr Phe Asp Leu Glu His Asp Pro Leu
                190                 195                 200 caa gtg ggg gaa gga gac tgt aaa tat gac tgg ctg gac atc tgg gat    1217
Gln Val Gly Glu Gly Asp Cys Lys Tyr Asp Trp Leu Asp Ile Trp Asp
            205                 210                 215 ggc att cca cat gtt gga cct ctg att ggc aag tac tgt ggg acg aaa    1265
Gly Ile Pro His Val Gly Pro Leu Ile Gly Lys Tyr Cys Gly Thr Lys
                220                 225                 230 aca ccc tcc aaa ctc cgc tcg tcc acg ggg atc ctc tcc ttg acc ttt    1313
Thr Pro Ser Lys Leu Arg Ser Ser Thr Gly Ile Leu Ser Leu Thr Phe
        235                 240                 245 cac acg gac atg gca gtg gcc aag gat ggc ttc tcc gca cgt tac tat    1361
His Thr Asp Met Ala Val Ala Lys Asp Gly Phe Ser Ala Arg Tyr Tyr
250                 255                 260                 265 ttg atc cac cag gag cca cct gag aat ttt cag tgc aat gtc cct ttg    1409
Leu Ile His Gln Glu Pro Pro Glu Asn Phe Gln Cys Asn Val Pro Leu
                270                 275                 280 gga atg gag tct ggc cgg att gct aat gaa cag atc agt gcc tcc tcc    1457
Gly Met Glu Ser Gly Arg Ile Ala Asn Glu Gln Ile Ser Ala Ser Ser
                285                 290                 295 acc ttc tct gat ggg agg tgg act cct caa cag agc cgg ctc cat ggt    1505
Thr Phe Ser Asp Gly Arg Trp Thr Pro Gln Gln Ser Arg Leu His Gly
        300                 305                 310
```

```
gat gac aat ggc tgg aca ccc aat ttg gat tcc aac aag gag tat ctc    1553
Asp Asp Asn Gly Trp Thr Pro Asn Leu Asp Ser Asn Lys Glu Tyr Leu
    315                 320                 325 cag gtg gac ctg cgc ttc cta acc atg ctc aca gcc att gca aca cag    1601
Gln Val Asp Leu Arg Phe Leu Thr Met Leu Thr Ala Ile Ala Thr Gln
330                 335                 340                 345 gga gcc att tcc agg gaa acc cag aaa ggc tac tac gtc aaa tcg tac    1649
Gly Ala Ile Ser Arg Glu Thr Gln Lys Gly Tyr Tyr Val Lys Ser Tyr
                350                 355                 360 aag ctg gaa gtc agc aca aat ggt gaa gat tgg atg gtc tac cgg cat    1697
Lys Leu Glu Val Ser Thr Asn Gly Glu Asp Trp Met Val Tyr Arg His
            365                 370                 375 ggc aaa aac cac aag ata ttc caa gcg aac aat gat gcg acc gag gtg    1745
Gly Lys Asn His Lys Ile Phe Gln Ala Asn Asn Asp Ala Thr Glu Val
        380                 385                 390 gtg cta aac aag ctc cac atg cca ctg ctg act cgg ttc atc agg atc    1793
Val Leu Asn Lys Leu His Met Pro Leu Leu Thr Arg Phe Ile Arg Ile
    395                 400                 405 cgc ccg cag acg tgg cat ttg ggc att gcc ctt cgc ctg gag ctc ttt    1841
Arg Pro Gln Thr Trp His Leu Gly Ile Ala Leu Arg Leu Glu Leu Phe
410                 415                 420                 425 ggc tgc cgg gtc aca gat gca ccc tgc tcc aac atg ctg ggg atg ctc    1889
Gly Cys Arg Val Thr Asp Ala Pro Cys Ser Asn Met Leu Gly Met Leu
                430                 435                 440 tcg ggc ctc att gct gat acc cag atc tct gcc tcc tcc acc cga gag    1937
Ser Gly Leu Ile Ala Asp Thr Gln Ile Ser Ala Ser Ser Thr Arg Glu
            445                 450                 455 tac ctc tgg agc ccc agt gct gcc cgc ctg gtt agt agc cgc tct ggc    1985
Tyr Leu Trp Ser Pro Ser Ala Ala Arg Leu Val Ser Ser Arg Ser Gly
        460                 465                 470 tgg ttt cct cgg aac cct caa gcc cag cca ggt gaa gaa tgg ctt cag    2033
Trp Phe Pro Arg Asn Pro Gln Ala Gln Pro Gly Glu Glu Trp Leu Gln
    475                 480                 485 gta gac ctg ggg aca ccc aag aca gtg aaa ggg gtc atc atc cag gga    2081
Val Asp Leu Gly Thr Pro Lys Thr Val Lys Gly Val Ile Ile Gln Gly
490                 495                 500                 505 gcc cga gga gga gac agc atc act gcc gtg gaa gcc agg gcg ttt gta    2129
Ala Arg Gly Gly Asp Ser Ile Thr Ala Val Glu Ala Arg Ala Phe Val
                510                 515                 520 cgc aag ttc aaa gtc tcc tac agc cta aat ggc aag gac tgg gaa tat    2177
Arg Lys Phe Lys Val Ser Tyr Ser Leu Asn Gly Lys Asp Trp Glu Tyr
```

```
                    525                     530                       535 atc cag gac ccc agg act cag cag aca aag ctg ttt gaa ggg aac atg      2225
Ile Gln Asp Pro Arg Thr Gln Gln Thr Lys Leu Phe Glu Gly Asn Met
            540                 545                 550 cac tat gac acc cct gac atc cga agg ttc gat cct gtt cca gcg cag      2273
His Tyr Asp Thr Pro Asp Ile Arg Arg Phe Asp Pro Val Pro Ala Gln
            555                 560                 565 tat gtg cgg gtg tac cca gag agg tgg tcg cca gca ggc atc ggg atg      2321
Tyr Val Arg Val Tyr Pro Glu Arg Trp Ser Pro Ala Gly Ile Gly Met
570                 575                 580                 585 agg ctg gag gtg ctg ggc tgt gac tgg aca gac tca aag ccc aca gtg      2369
Arg Leu Glu Val Leu Gly Cys Asp Trp Thr Asp Ser Lys Pro Thr Val
                590                 595                 600 gag acg ctg gga ccc acc gtg aag agt gaa gag act acc acc cca tat      2417
Glu Thr Leu Gly Pro Thr Val Lys Ser Glu Glu Thr Thr Thr Pro Tyr
            605                 610                 615 ccc atg gat gag gat gcc acc gag tgt ggg gaa aac tgc agc ttt gag      2465
Pro Met Asp Glu Asp Ala Thr Glu Cys Gly Glu Asn Cys Ser Phe Glu
            620                 625                 630 gat gac aaa gat ttg caa ctt cct tca gga ttc aac tgc aac ttt gat      2513
Asp Asp Lys Asp Leu Gln Leu Pro Ser Gly Phe Asn Cys Asn Phe Asp
            635                 640                 645 ttt ccg gaa gag acc tgt ggt tgg gtg tac gac cat gcc aag tgg ctc      2561
Phe Pro Glu Glu Thr Cys Gly Trp Val Tyr Asp His Ala Lys Trp Leu
650                 655                 660                 665 cgg agc acg tgg atc agc agc gct aac ccc aat gac aga aca ttt cca      2609
Arg Ser Thr Trp Ile Ser Ser Ala Asn Pro Asn Asp Arg Thr Phe Pro
                670                 675                 680 gat gac aag aac ttc ttg aaa ctg cag agt gat ggc cga cga gag ggc      2657
Asp Asp Lys Asn Phe Leu Lys Leu Gln Ser Asp Gly Arg Arg Glu Gly
            685                 690                 695 cag tac ggg cgg ctc atc agc cca ccg gtg cac ctg ccc cga agc cct      2705
Gln Tyr Gly Arg Leu Ile Ser Pro Pro Val His Leu Pro Arg Ser Pro
            700                 705                 710 gtg tgc atg gag ttc cag tac caa gcc atg ggc ggc cac ggg gtg gca      2753
Val Cys Met Glu Phe Gln Tyr Gln Ala Met Gly Gly His Gly Val Ala
            715                 720                 725 ctg cag gtg gtt cgg gaa gcc agc cag gaa agc aaa ctc ctt tgg gtc      2801
Leu Gln Val Val Arg Glu Ala Ser Gln Glu Ser Lys Leu Leu Trp Val
730                 735                 740                 745
```

```
atc cgt gag gac cag ggc agc gag tgg aag cac ggg cgc att atc ctg    2849
Ile Arg Glu Asp Gln Gly Ser Glu Trp Lys His Gly Arg Ile Ile Leu
            750                 755                 760 ccc agc tat gac atg gag tat cag atc gtg ttc gag gga gtg ata ggg    2897
Pro Ser Tyr Asp Met Glu Tyr Gln Ile Val Phe Glu Gly Val Ile Gly
            765                 770                 775 aag gga cga tcg gga gag att tcc ggc gat gac att cgg ata agc act    2945
Lys Gly Arg Ser Gly Glu Ile Ser Gly Asp Asp Ile Arg Ile Ser Thr
            780                 785                 790 gat gtc cca ctg gag aac tgc atg gaa ccc ata tca gct ttt gca ggt    2993
Asp Val Pro Leu Glu Asn Cys Met Glu Pro Ile Ser Ala Phe Ala Gly
    795                 800                 805 gag gat ttt aaa gtg gac atc cca gaa acc cat ggg gga gag ggc tat    3041
Glu Asp Phe Lys Val Asp Ile Pro Glu Thr His Gly Gly Glu Gly Tyr
810                 815                 820                 825 gaa gat gag att gat gat gaa tat gaa gga gat tgg agc aac tct tct    3089
Glu Asp Glu Ile Asp Asp Glu Tyr Glu Gly Asp Trp Ser Asn Ser Ser
            830                 835                 840 tcc tct acc tca ggg gct ggt gac ccc tca tct ggc aaa gaa aag agc    3137
Ser Ser Thr Ser Gly Ala Gly Asp Pro Ser Ser Gly Lys Glu Lys Ser
            845                 850                 855 tgg ctg tac acc cta gat ccc att ctg atc acc atc atc gcc atg agc    3185
Trp Leu Tyr Thr Leu Asp Pro Ile Leu Ile Thr Ile Ile Ala Met Ser
            860                 865                 870 tcg ctg ggg gtc ctg ctg ggg gcc acc tgt gcg ggc ctc ctc ctt tac    3233
Ser Leu Gly Val Leu Leu Gly Ala Thr Cys Ala Gly Leu Leu Leu Tyr
    875                 880                 885 tgc acc tgc tcc tat tcg ggt ctg agt tcg agg agc tgc acc aca ctg    3281
Cys Thr Cys Ser Tyr Ser Gly Leu Ser Ser Arg Ser Cys Thr Thr Leu
890                 895                 900                 905 gag aac tac aac ttt gag ctc tac gat ggc ctc aag cac aag gtc aag    3329
Glu Asn Tyr Asn Phe Glu Leu Tyr Asp Gly Leu Lys His Lys Val Lys
            910                 915                 920 atc aat cat cag aag tgc tgc tcg gag gca tgaccgattg tgtctggatc     3379
Ile Asn His Gln Lys Cys Cys Ser Glu Ala
            925                 930 gcttctggcg tttcattcca gtgagagggg ctagcgaaga ttacagtttt gttttgtttt  3439
gttttgtttt ccctttggaa actgaatgcc ataatctgga tcaaagtgtt ccagaatact  3499
gaaggtatgg acaggacaga caggccagtc tagggagaaa gggagatgca gctgtgaagg  3559
```

```
ggatcgttgc ccaccaggac tgtggtggcc aagtgaatgc aggaaccggg cccggaattc 3619 cggctctcgg ctaaaatctc agctgcctct ggaaaggctc aaccatactc agtgccaact 3679 cagactctgt tgctgtggtg tcaacatgga tggatcatct gtaccttgta tttttagcag 3739 aattcatgct cagatttctt tgttctgaat ccttgctttg tgctagacac aaagcataca 3799 tgtccttcta aaattaatat gatcactata atctcctgtg tgcagaattc agaaatagac 3859 ctttgaaacc atttgcattg tgagtgcaga tccatgactg gggctagtgc agcaatgaaa 3919 cagaattcca gaaacagtgt gttctttta ttatgggaaa atacagataa aaatggccac 3979 tgatgaacat gaaagttagc actttcccaa cacagtgtac acttgcaacc ttgttttgga 4039 tttctcatac accaagactg tgaaacacaa atttcaagaa tgtgttcaaa tgtgtgtgtg 4099 tgtgtgtgtg tgtgtgtgtg tgtgtgtgta tgtgtgtgtg tgtgtgtgtg cttgtgtgtt 4159 tctgtcagtg gtatgagtga tatgtatgca tgtgtgtatg tatatgtatg tatgtatgta 4219 tgtatgtacg tacatatgta tgtatgtatg tatgtatgta tgtatgtata tgtgtgtgtg 4279 tgtttgtgtg tgtgtgtgtt tgtgtgtgtg tgtgtggtaa gtgtggtatg tgtatgca 4339 tttgtctata tgtgtatctg tgtgtctatg tgtttctgtc agtggaatga gtggcatgtg 4399 tgcatgtgta tgtatgtgga tatgtgtgtt gtgtttatgt gcttgtgtat aagaggtaag 4459 tgtggtgtgt gtgcatgtgt ctctgtgtgt gtttgtctgt gtacctcttt gtataagtac 4519 ctgtgtttgt atgtgggaat atgtatattg aggcattgct gtgttagtat gtttatagaa 4579 aagaagacag tctgagatgt cttcctcaat acctctccac ttatatcttg gatagacaaa 4639 agtaatgaca aaaaattgct ggtgtgtata tggaaaaggg ggacacatat ccatggatgg 4699 tagaagtgta aactgtgcag tcactgtgga catcaatatg caggttcttc acaaatgtag 4759 atataaagct actatagtta taccc                                      4784
```

<210> 16
<211> 931
<212> PRT
<213> mouse

<400> 16
Met Asp Met Phe Pro Leu Thr Trp Val Phe Leu Ala Leu Tyr Phe Ser
1               5                   10                  15

Gly His Glu Val Arg Ser Gln Gln Asp Pro Cys Gly Gly Arg Pro
            20                  25                  30

```
Asn Ser Lys Asp Ala Gly Tyr Ile Thr Ser Pro Gly Tyr Pro Gln Asp
        35                  40                  45
Tyr Pro Ser His Gln Asn Cys Glu Trp Ile Val Tyr Ala Pro Glu Pro
        50                  55                  60
Asn Gln Lys Ile Val Leu Asn Phe Asn Pro His Phe Glu Ile Glu Lys
65                      70                  75                  80
His Asp Cys Lys Tyr Asp Phe Ile Glu Ile Arg Asp Gly Asp Ser Glu
                85                  90                  95
Ser Ala Asp Leu Leu Gly Lys His Cys Gly Asn Ile Ala Pro Pro Thr
                100                 105                 110
Ile Ile Ser Ser Gly Ser Val Leu Tyr Ile Lys Phe Thr Ser Asp Tyr
            115                 120                 125
Ala Arg Gln Gly Ala Gly Phe Ser Leu Arg Tyr Glu Ile Phe Lys Thr
            130                 135                 140
Gly Ser Glu Asp Cys Ser Lys Asn Phe Thr Ser Pro Asn Gly Thr Ile
145                 150                 155                 160
Glu Ser Pro Gly Phe Pro Glu Lys Tyr Pro His Asn Leu Asp Cys Thr
                165                 170                 175
Phe Thr Ile Leu Ala Lys Pro Arg Met Glu Ile Ile Leu Gln Phe Leu
            180                 185                 190
Thr Phe Asp Leu Glu His Asp Pro Leu Gln Val Gly Glu Gly Asp Cys
            195                 200                 205
Lys Tyr Asp Trp Leu Asp Ile Trp Asp Gly Ile Pro His Val Gly Pro
    210                 215                 220
Leu Ile Gly Lys Tyr Cys Gly Thr Lys Thr Pro Ser Lys Leu Arg Ser
225                 230                 235                 240
Ser Thr Gly Ile Leu Ser Leu Thr Phe His Thr Asp Met Ala Val Ala
            245                 250                 255
Lys Asp Gly Phe Ser Ala Arg Tyr Tyr Leu Ile His Gln Glu Pro Pro
            260                 265                 270
Glu Asn Phe Gln Cys Asn Val Pro Leu Gly Met Glu Ser Gly Arg Ile
            275                 280                 285
Ala Asn Glu Gln Ile Ser Ala Ser Ser Thr Phe Ser Asp Gly Arg Trp
    290                 295                 300
Thr Pro Gln Gln Ser Arg Leu His Gly Asp Asp Asn Gly Trp Thr Pro
305                 310                 315                 320
```

```
    Asn Leu Asp Ser Asn Lys Glu Tyr Leu Gln Val Asp Leu Arg Phe Leu
                    325                 330                 335

Thr Met Leu Thr Ala Ile Ala Thr Gln Gly Ala Ile Ser Arg Glu Thr
                    340                 345                 350

Gln Lys Gly Tyr Tyr Val Lys Ser Tyr Lys Leu Glu Val Ser Thr Asn
                    355                 360                 365

Gly Glu Asp Trp Met Val Tyr Arg His Gly Lys Asn His Lys Ile Phe
            370                 375                 380

Gln Ala Asn Asn Asp Ala Thr Glu Val Val Leu Asn Lys Leu His Met
    385                 390                 395                 400

Pro Leu Leu Thr Arg Phe Ile Arg Ile Arg Pro Gln Thr Trp His Leu
                    405                 410                 415

Gly Ile Ala Leu Arg Leu Glu Leu Phe Gly Cys Arg Val Thr Asp Ala
                    420                 425                 430

Pro Cys Ser Asn Met Leu Gly Met Leu Ser Gly Leu Ile Ala Asp Thr
                    435                 440                 445

Gln Ile Ser Ala Ser Ser Thr Arg Glu Tyr Leu Trp Ser Pro Ser Ala
            450                 455                 460

Ala Arg Leu Val Ser Ser Arg Ser Gly Trp Phe Pro Arg Asn Pro Gln
    465                 470                 475                 480

Ala Gln Pro Gly Glu Glu Trp Leu Gln Val Asp Leu Gly Thr Pro Lys
                    485                 490                 495

Thr Val Lys Gly Val Ile Ile Gln Gly Ala Arg Gly Gly Asp Ser Ile
                    500                 505                 510

Thr Ala Val Glu Ala Arg Ala Phe Val Arg Lys Phe Lys Val Ser Tyr
                    515                 520                 525

Ser Leu Asn Gly Lys Asp Trp Glu Tyr Ile Gln Asp Pro Arg Thr Gln
            530                 535                 540

Gln Thr Lys Leu Phe Glu Gly Asn Met His Tyr Asp Thr Pro Asp Ile
    545                 550                 555                 560

Arg Arg Phe Asp Pro Val Pro Ala Gln Tyr Val Arg Val Tyr Pro Glu
                    565                 570                 575

Arg Trp Ser Pro Ala Gly Ile Gly Met Arg Leu Glu Val Leu Gly Cys
                    580                 585                 590

Asp Trp Thr Asp Ser Lys Pro Thr Val Glu Thr Leu Gly Pro Thr Val
                    595                 600                 605
```

```
Lys Ser Glu Glu Thr Thr Thr Pro Tyr Pro Met Asp Glu Asp Ala Thr
    610             615             620
Glu Cys Gly Glu Asn Cys Ser Phe Glu Asp Asp Lys Asp Leu Gln Leu
625             630              635                         640
Pro Ser Gly Phe Asn Cys Asn Phe Asp Phe Pro Glu Glu Thr Cys Gly
                645             650              655
Trp Val Tyr Asp His Ala Lys Trp Leu Arg Ser Thr Trp Ile Ser Ser
            660              665              670
Ala Asn Pro Asn Asp Arg Thr Phe Pro Asp Asp Lys Asn Phe Leu Lys
        675             680              685
Leu Gln Ser Asp Gly Arg Arg Glu Gly Gln Tyr Gly Arg Leu Ile Ser
    690              695             700
Pro Pro Val His Leu Pro Arg Ser Pro Val Cys Met Glu Phe Gln Tyr
705              710             715                         720
Gln Ala Met Gly Gly His Gly Val Ala Leu Gln Val Val Arg Glu Ala
            725              730             735
Ser Gln Glu Ser Lys Leu Leu Trp Val Ile Arg Glu Asp Gln Gly Ser
            740             745              750
Glu Trp Lys His Gly Arg Ile Ile Leu Pro Ser Tyr Asp Met Glu Tyr
        755             760              765
Gln Ile Val Phe Glu Gly Val Ile Gly Lys Gly Arg Ser Gly Glu Ile
    770             775              780
Ser Gly Asp Asp Ile Arg Ile Ser Thr Asp Val Pro Leu Glu Asn Cys
785             790              795                         800
Met Glu Pro Ile Ser Ala Phe Ala Gly Glu Asp Phe Lys Val Asp Ile
                805             810              815
Pro Glu Thr His Gly Gly Glu Gly Tyr Glu Asp Glu Ile Asp Asp Glu
            820             825              830
Tyr Glu Gly Asp Trp Ser Asn Ser Ser Ser Thr Ser Gly Ala Gly
        835             840             845
Asp Pro Ser Ser Gly Lys Glu Lys Ser Trp Leu Tyr Thr Leu Asp Pro
    850             855             860
Ile Leu Ile Thr Ile Ile Ala Met Ser Ser Leu Gly Val Leu Leu Gly
865             870             875                         880
Ala Thr Cys Ala Gly Leu Leu Leu Tyr Cys Thr Cys Ser Tyr Ser Gly
                885             890             895
```

```
Leu Ser Ser Arg Ser Cys Thr Thr Leu Glu Asn Tyr Asn Phe Glu Leu
            900                 905                 910

Tyr Asp Gly Leu Lys His Lys Val Lys Ile Asn His Gln Lys Cys Cys
        915                 920                 925

Ser Glu Ala
    930

<210> 17
<211> 2730
<212> DNA
<213> human

<220>
<221> CDS
<222> (1)..(2727)

<400> 17
atg gat atg ttt cct ctc acc tgg gtt ttc tta gcc ctc tac ttt tca    48
Met Asp Met Phe Pro Leu Thr Trp Val Phe Leu Ala Leu Tyr Phe Ser
  1               5                  10                  15 aga cac caa gtg aga ggc caa cca gac cca ccg tgc gga ggt cgt ttg    96
Arg His Gln Val Arg Gly Gln Pro Asp Pro Pro Cys Gly Gly Arg Leu
             20                  25                  30 aat tcc aaa gat gct ggc tat atc acc tct ccc ggt tac ccc cag gac   144
Asn Ser Lys Asp Ala Gly Tyr Ile Thr Ser Pro Gly Tyr Pro Gln Asp
         35                  40                  45 tac ccc tcc cac cag aac tgc gag tgg att gtt tac gcc ccc gaa ccc   192
Tyr Pro Ser His Gln Asn Cys Glu Trp Ile Val Tyr Ala Pro Glu Pro
     50                  55                  60 aac cag aag att gtc ctc aac ttc aac cct cac ttt gaa atc gag aag   240
Asn Gln Lys Ile Val Leu Asn Phe Asn Pro His Phe Glu Ile Glu Lys
 65                  70                  75                  80 cac gac tgc aag tat gac ttt atc gag att cgg gat ggg gac agt gaa   288
His Asp Cys Lys Tyr Asp Phe Ile Glu Ile Arg Asp Gly Asp Ser Glu
                 85                  90                  95 tcc gca gac ctc ctg ggc aaa cac tgt ggg aac atc gcc ccg ccc acc   336
Ser Ala Asp Leu Leu Gly Lys His Cys Gly Asn Ile Ala Pro Pro Thr
            100                 105                 110 atc atc tcc tcg ggc tcc atg ctc tac atc aag ttc acc tcc gac tac   384
Ile Ile Ser Ser Gly Ser Met Leu Tyr Ile Lys Phe Thr Ser Asp Tyr
        115                 120                 125 gcc cgg cag ggg gca ggc ttc tct ctg cgc tac gag atc ttc aag aca   432
```

```
Ala Arg Gln Gly Ala Gly Phe Ser Leu Arg Tyr Glu Ile Phe Lys Thr
    130             135             140 ggc tct gaa gat tgc tca aaa aac ttc aca agc ccc aac ggg acc atc    480
Gly Ser Glu Asp Cys Ser Lys Asn Phe Thr Ser Pro Asn Gly Thr Ile
145             150             155             160 gaa tct cct ggg ttt cct gag aag tat cca cac aac ttg gac tgc acc    528
Glu Ser Pro Gly Phe Pro Glu Lys Tyr Pro His Asn Leu Asp Cys Thr
            165             170             175 ttt acc atc ctg gcc aaa ccc aag atg gag atc atc ctg cag ttc ctg    576
Phe Thr Ile Leu Ala Lys Pro Lys Met Glu Ile Ile Leu Gln Phe Leu
            180             185             190 atc ttt gac ctg gag cat gac cct ttg cag gtg gga gag ggg gac tgc    624
Ile Phe Asp Leu Glu His Asp Pro Leu Gln Val Gly Glu Gly Asp Cys
            195             200             205 aag tac gat tgg ctg gac atc tgg gat ggc att cca cat gtt ggc ccc    672
Lys Tyr Asp Trp Leu Asp Ile Trp Asp Gly Ile Pro His Val Gly Pro
    210             215             220 ctg att ggc aag tac tgt ggg acc aaa aca ccc tct gaa ctt cgt tca    720
Leu Ile Gly Lys Tyr Cys Gly Thr Lys Thr Pro Ser Glu Leu Arg Ser
225             230             235             240 tcg acg ggg atc ctc tcc ctg acc ttt cac acg gac atg gcg gtg gcc    768
Ser Thr Gly Ile Leu Ser Leu Thr Phe His Thr Asp Met Ala Val Ala
            245             250             255 aag gat ggc ttc tct gcg cgt tac tac ctg gtc cac caa gag cca cta    816
Lys Asp Gly Phe Ser Ala Arg Tyr Tyr Leu Val His Gln Glu Pro Leu
            260             265             270 gag aac ttt cag tgc aat gtt cct ctg ggc atg gag tct ggc cgg att    864
Glu Asn Phe Gln Cys Asn Val Pro Leu Gly Met Glu Ser Gly Arg Ile
            275             280             285 gct aat gaa cag atc agt gcc tca tct acc tac tct gat ggg agg tgg    912
Ala Asn Glu Gln Ile Ser Ala Ser Ser Thr Tyr Ser Asp Gly Arg Trp
    290             295             300 acc cct caa caa agc cgg ctc cat ggt gat gac aat ggc tgg acc ccc    960
Thr Pro Gln Gln Ser Arg Leu His Gly Asp Asp Asn Gly Trp Thr Pro
305             310             315             320 aac ttg gat tcc aac aag gag tat ctc cag gtg gac ctg cgc ttt tta    1008
Asn Leu Asp Ser Asn Lys Glu Tyr Leu Gln Val Asp Leu Arg Phe Leu
            325             330             335 acc atg ctc acg gcc atc gca aca cag gga gcg att tcc agg gaa aca    1056
Thr Met Leu Thr Ala Ile Ala Thr Gln Gly Ala Ile Ser Arg Glu Thr
            340             345             350
```

```
cag aat ggc tac tac gtc aaa tcc tac aag ctg gaa gtc agc act aat    1104
Gln Asn Gly Tyr Tyr Val Lys Ser Tyr Lys Leu Glu Val Ser Thr Asn
        355                 360                 365 gga gag gac tgg atg gtg tac cgg cat ggc aaa aac cac aag gta ttt    1152
Gly Glu Asp Trp Met Val Tyr Arg His Gly Lys Asn His Lys Val Phe
    370                 375                 380 caa gcc aac aac gat gca act gag gtg gtt ctg aac aag ctc cac gct    1200
Gln Ala Asn Asn Asp Ala Thr Glu Val Val Leu Asn Lys Leu His Ala
385                 390                 395                 400 cca ctg ctg aca agg ttt gtt aga atc cgc cct cag acc tgg cac tca    1248
Pro Leu Leu Thr Arg Phe Val Arg Ile Arg Pro Gln Thr Trp His Ser
                405                 410                 415 ggt atc gcc ctc cgg ctg gag ctc ttc ggc tgc cgg gtc aca gat gct    1296
Gly Ile Ala Leu Arg Leu Glu Leu Phe Gly Cys Arg Val Thr Asp Ala
            420                 425                 430 ccc tgc tcc aac atg ctg ggg atg ctc tca ggc ctc att gca gac tcc    1344
Pro Cys Ser Asn Met Leu Gly Met Leu Ser Gly Leu Ile Ala Asp Ser
        435                 440                 445 cag atc tcc gcc tct tcc acc cag gaa tac ctc tgg agc ccc agt gca    1392
Gln Ile Ser Ala Ser Ser Thr Gln Glu Tyr Leu Trp Ser Pro Ser Ala
    450                 455                 460 gcc cgc ctg gtc agc agc cgc tcg ggc tgg ttc cct cga atc cct cag    1440
Ala Arg Leu Val Ser Ser Arg Ser Gly Trp Phe Pro Arg Ile Pro Gln
465                 470                 475                 480 gcc cag ccc ggt gag gag tgg ctt cag gta gat ctg gga aca ccc aag    1488
Ala Gln Pro Gly Glu Glu Trp Leu Gln Val Asp Leu Gly Thr Pro Lys
                485                 490                 495 aca gtg aaa ggt gtc atc atc cag gga gcc cgc gga gga gac agt atc    1536
Thr Val Lys Gly Val Ile Ile Gln Gly Ala Arg Gly Gly Asp Ser Ile
            500                 505                 510 act gct gtg gaa gcc aga gca ttt gtg cgc aag ttc aaa gtc tcc tac    1584
Thr Ala Val Glu Ala Arg Ala Phe Val Arg Lys Phe Lys Val Ser Tyr
        515                 520                 525 agc cta aac ggc aag gac tgg gaa tac att cag gac ccc agg acc cag    1632
Ser Leu Asn Gly Lys Asp Trp Glu Tyr Ile Gln Asp Pro Arg Thr Gln
    530                 535                 540 cag cca aag ctg ttc gaa ggg aac atg cac tat gac acc cct gac atc    1680
Gln Pro Lys Leu Phe Glu Gly Asn Met His Tyr Asp Thr Pro Asp Ile
545                 550                 555                 560 cga agg ttt gac ccc att ccg gca cag tat gtg cgg gta tac ccg gag    1728
```

```
     Arg Arg Phe Asp Pro Ile Pro Ala Gln Tyr Val Arg Val Tyr Pro Glu
                     565                 570                 575 agg tgg tcg ccg gcg ggg att ggg atg cgg ctg gag gtg ctg ggc tgt    1776
     Arg Trp Ser Pro Ala Gly Ile Gly Met Arg Leu Glu Val Leu Gly Cys
                     580                 585                 590 gac tgg aca gac tcc aag ccc acg gta aaa acg ctg gga ccc act gtg    1824
     Asp Trp Thr Asp Ser Lys Pro Thr Val Lys Thr Leu Gly Pro Thr Val
                     595                 600                 605 aag agc gaa gag aca acc acc ccc tac ccc acc gaa gag gag gcc aca    1872
     Lys Ser Glu Glu Thr Thr Thr Pro Tyr Pro Thr Glu Glu Glu Ala Thr
                 610                 615                 620 gag tgt ggg gag aac tgc agc ttt gag gat gac aaa gat ttg cag ctc    1920
     Glu Cys Gly Glu Asn Cys Ser Phe Glu Asp Asp Lys Asp Leu Gln Leu
     625                 630                 635                 640 cct tcg gga ttc aat tgc aac ttc gat ttc ctc gag gag ccc tgt ggt    1968
     Pro Ser Gly Phe Asn Cys Asn Phe Asp Phe Leu Glu Glu Pro Cys Gly
                     645                 650                 655 tgg atg tat gac cat gcc aag tgg ctc cgg acc acc tgg gcc agc agc    2016
     Trp Met Tyr Asp His Ala Lys Trp Leu Arg Thr Thr Trp Ala Ser Ser
                     660                 665                 670 tcc agc cca aac gac cgg acg ttt cca gat gac agg aat ttc ttg cgg    2064
     Ser Ser Pro Asn Asp Arg Thr Phe Pro Asp Asp Arg Asn Phe Leu Arg
                     675                 680                 685 ctg cag agt gac agc cag aga gag ggc cag tat gcc cgg ctc atc agc    2112
     Leu Gln Ser Asp Ser Gln Arg Glu Gly Gln Tyr Ala Arg Leu Ile Ser
                 690                 695                 700 ccc cct gtc cac ctg ccc cga agc ccg gtg tgc atg gag ttc cag tac    2160
     Pro Pro Val His Leu Pro Arg Ser Pro Val Cys Met Glu Phe Gln Tyr
     705                 710                 715                 720 cag gcc acg ggc ggc cgc ggg gtg gcg ctg cag gtg gtg cgg gaa gcc    2208
     Gln Ala Thr Gly Gly Arg Gly Val Ala Leu Gln Val Val Arg Glu Ala
                     725                 730                 735 agc cag gag agc aag ttg ctg tgg gtc atc cgt gag gac cag ggc ggc    2256
     Ser Gln Glu Ser Lys Leu Leu Trp Val Ile Arg Glu Asp Gln Gly Gly
                 740                 745                 750 gag tgg aag cac ggg cgg atc atc ctg ccc agc tac gac atg gag tac    2304
     Glu Trp Lys His Gly Arg Ile Ile Leu Pro Ser Tyr Asp Met Glu Tyr
                 755                 760                 765 cag att gtg ttc gag gga gtg ata ggg aaa gga cgt tcc gga gag att    2352
     Gln Ile Val Phe Glu Gly Val Ile Gly Lys Gly Arg Ser Gly Glu Ile
             770                 775                 780
```

```
gcc att gat gac att cgg ata agc act gat gtc cca ctg gag aac tgc   2400
Ala Ile Asp Asp Ile Arg Ile Ser Thr Asp Val Pro Leu Glu Asn Cys
785             790                 795                 800 atg gaa ccc atc tcg gct ttt gca gat gaa tac gag gtg gac tgg agc   2448
Met Glu Pro Ile Ser Ala Phe Ala Asp Glu Tyr Glu Val Asp Trp Ser
                805                 810                 815 aat tct tct tct gca acc tca ggg tct ggc gcc ccc tcg acc gac aaa   2496
Asn Ser Ser Ser Ala Thr Ser Gly Ser Gly Ala Pro Ser Thr Asp Lys
            820                 825                 830 gaa aag agc tgg ctg tac acc ctg gat ccc atc ctc atc acc atc atc   2544
Glu Lys Ser Trp Leu Tyr Thr Leu Asp Pro Ile Leu Ile Thr Ile Ile
            835                 840                 845 gcc atg agc tca ctg ggc gtc ctc ctg ggg gcc acc tgt gca ggc ctc   2592
Ala Met Ser Ser Leu Gly Val Leu Leu Gly Ala Thr Cys Ala Gly Leu
        850                 855                 860 ctg ctc tac tgc acc tgt tcc tac tcg ggc ctg agc tcc cga agc tgc   2640
Leu Leu Tyr Cys Thr Cys Ser Tyr Ser Gly Leu Ser Ser Arg Ser Cys
865             870                 875                 880 acc aca ctg gag aac tac aac ttc gag ctc tac gat ggc ctt aag cac   2688
Thr Thr Leu Glu Asn Tyr Asn Phe Glu Leu Tyr Asp Gly Leu Lys His
                885                 890                 895 aag gtc aag atg aac cac caa aag tgc tgc tcc gag gca tga           2730
Lys Val Lys Met Asn His Gln Lys Cys Cys Ser Glu Ala
            900                 905

<210> 18
<211> 909
<212> PRT
<213> human

<400> 18
Met Asp Met Phe Pro Leu Thr Trp Val Phe Leu Ala Leu Tyr Phe Ser
1               5                   10                  15

Arg His Gln Val Arg Gly Gln Pro Asp Pro Pro Cys Gly Gly Arg Leu
                20                  25                  30

Asn Ser Lys Asp Ala Gly Tyr Ile Thr Ser Pro Gly Tyr Pro Gln Asp
            35                  40                  45

Tyr Pro Ser His Gln Asn Cys Glu Trp Ile Val Tyr Ala Pro Glu Pro
        50                  55                  60

Asn Gln Lys Ile Val Leu Asn Phe Asn Pro His Phe Glu Ile Glu Lys
65                  70                  75                  80
```

```
His Asp Cys Lys Tyr Asp Phe Ile Glu Ile Arg Asp Gly Asp Ser Glu
                85                  90                  95

Ser Ala Asp Leu Leu Gly Lys His Cys Gly Asn Ile Ala Pro Pro Thr
            100                 105                 110

Ile Ile Ser Ser Gly Ser Met Leu Tyr Ile Lys Phe Thr Ser Asp Tyr
        115                 120                 125

Ala Arg Gln Gly Ala Gly Phe Ser Leu Arg Tyr Glu Ile Phe Lys Thr
    130                 135                 140

Gly Ser Glu Asp Cys Ser Lys Asn Phe Thr Ser Pro Asn Gly Thr Ile
145                 150                 155                 160

Glu Ser Pro Gly Phe Pro Glu Lys Tyr Pro His Asn Leu Asp Cys Thr
                165                 170                 175

Phe Thr Ile Leu Ala Lys Pro Lys Met Glu Ile Ile Leu Gln Phe Leu
            180                 185                 190

Ile Phe Asp Leu Glu His Asp Pro Leu Gln Val Gly Glu Gly Asp Cys
        195                 200                 205

Lys Tyr Asp Trp Leu Asp Ile Trp Asp Gly Ile Pro His Val Gly Pro
    210                 215                 220

Leu Ile Gly Lys Tyr Cys Gly Thr Lys Thr Pro Ser Glu Leu Arg Ser
225                 230                 235                 240

Ser Thr Gly Ile Leu Ser Leu Thr Phe His Thr Asp Met Ala Val Ala
                245                 250                 255

Lys Asp Gly Phe Ser Ala Arg Tyr Tyr Leu Val His Gln Glu Pro Leu
            260                 265                 270

Glu Asn Phe Gln Cys Asn Val Pro Leu Gly Met Glu Ser Gly Arg Ile
        275                 280                 285

Ala Asn Glu Gln Ile Ser Ala Ser Ser Thr Tyr Ser Asp Gly Arg Trp
    290                 295                 300

Thr Pro Gln Gln Ser Arg Leu His Gly Asp Asp Asn Gly Trp Thr Pro
305                 310                 315                 320

Asn Leu Asp Ser Asn Lys Glu Tyr Leu Gln Val Asp Leu Arg Phe Leu
                325                 330                 335

Thr Met Leu Thr Ala Ile Ala Thr Gln Gly Ala Ile Ser Arg Glu Thr
            340                 345                 350

Gln Asn Gly Tyr Tyr Val Lys Ser Tyr Lys Leu Glu Val Ser Thr Asn
        355                 360                 365
```

Gly Glu Asp Trp Met Val Tyr Arg His Gly Lys Asn His Lys Val Phe
    370                 375             380
Gln Ala Asn Asn Asp Ala Thr Glu Val Val Leu Asn Lys Leu His Ala
385                 390             395                 400
Pro Leu Leu Thr Arg Phe Val Arg Ile Arg Pro Gln Thr Trp His Ser
            405             410             415
Gly Ile Ala Leu Arg Leu Glu Leu Phe Gly Cys Arg Val Thr Asp Ala
            420             425             430
Pro Cys Ser Asn Met Leu Gly Met Leu Ser Gly Leu Ile Ala Asp Ser
        435             440             445
Gln Ile Ser Ala Ser Ser Thr Gln Glu Tyr Leu Trp Ser Pro Ser Ala
    450             455             460
Ala Arg Leu Val Ser Ser Arg Ser Gly Trp Phe Pro Arg Ile Pro Gln
465             470             475                 480
Ala Gln Pro Gly Glu Glu Trp Leu Gln Val Asp Leu Gly Thr Pro Lys
            485             490             495
Thr Val Lys Gly Val Ile Ile Gln Gly Ala Arg Gly Gly Asp Ser Ile
            500             505             510
Thr Ala Val Glu Ala Arg Ala Phe Val Arg Lys Phe Lys Val Ser Tyr
        515             520             525
Ser Leu Asn Gly Lys Asp Trp Glu Tyr Ile Gln Asp Pro Arg Thr Gln
    530             535             540
Gln Pro Lys Leu Phe Glu Gly Asn Met His Tyr Asp Thr Pro Asp Ile
545             550             555                 560
Arg Arg Phe Asp Pro Ile Pro Ala Gln Tyr Val Arg Val Tyr Pro Glu
            565             570             575
Arg Trp Ser Pro Ala Gly Ile Gly Met Arg Leu Glu Val Leu Gly Cys
            580             585             590
Asp Trp Thr Asp Ser Lys Pro Thr Val Lys Thr Leu Gly Pro Thr Val
        595             600             605
Lys Ser Glu Glu Thr Thr Thr Pro Tyr Pro Thr Glu Glu Glu Ala Thr
    610             615             620
Glu Cys Gly Glu Asn Cys Ser Phe Glu Asp Asp Lys Asp Leu Gln Leu
625             630             635                 640
Pro Ser Gly Phe Asn Cys Asn Phe Asp Phe Leu Glu Glu Pro Cys Gly
            645             650             655

```
Trp Met Tyr Asp His Ala Lys Trp Leu Arg Thr Thr Trp Ala Ser Ser
        660                 665                 670

Ser Ser Pro Asn Asp Arg Thr Phe Pro Asp Asp Arg Asn Phe Leu Arg
        675                 680                 685

Leu Gln Ser Asp Ser Gln Arg Glu Gly Gln Tyr Ala Arg Leu Ile Ser
        690                 695                 700

Pro Pro Val His Leu Pro Arg Ser Pro Val Cys Met Glu Phe Gln Tyr
705                 710                 715                 720

Gln Ala Thr Gly Gly Arg Gly Val Ala Leu Gln Val Val Arg Glu Ala
                725                 730                 735

Ser Gln Glu Ser Lys Leu Leu Trp Val Ile Arg Glu Asp Gln Gly Gly
            740                 745                 750

Glu Trp Lys His Gly Arg Ile Ile Leu Pro Ser Tyr Asp Met Glu Tyr
        755                 760                 765

Gln Ile Val Phe Glu Gly Val Ile Gly Lys Gly Arg Ser Gly Glu Ile
        770                 775                 780

Ala Ile Asp Asp Ile Arg Ile Ser Thr Asp Val Pro Leu Glu Asn Cys
785                 790                 795                 800

Met Glu Pro Ile Ser Ala Phe Ala Asp Glu Tyr Glu Val Asp Trp Ser
                805                 810                 815

Asn Ser Ser Ser Ala Thr Ser Gly Ser Gly Ala Pro Ser Thr Asp Lys
            820                 825                 830

Glu Lys Ser Trp Leu Tyr Thr Leu Asp Pro Ile Leu Ile Thr Ile Ile
            835                 840                 845

Ala Met Ser Ser Leu Gly Val Leu Leu Gly Ala Thr Cys Ala Gly Leu
        850                 855                 860

Leu Leu Tyr Cys Thr Cys Ser Tyr Ser Gly Leu Ser Ser Arg Ser Cys
865                 870                 875                 880

Thr Thr Leu Glu Asn Tyr Asn Phe Glu Leu Tyr Asp Gly Leu Lys His
                885                 890                 895

Lys Val Lys Met Asn His Gln Lys Cys Cys Ser Glu Ala
                900                 905

<210> 19
<211> 2781
<212> DNA
<213> human
```

<220>
<221> CDS
<222> (1)..(2778)

<400> 19

| | | | | | | | | | | | | | | | | |
|---|---|---|---|---|---|---|---|---|---|---|---|---|---|---|---|---|
| atg | gat | atg | ttt | cct | ctc | acc | tgg | gtt | ttc | tta | gcc | ctc | tac | ttt | tca | 48 |
| Met | Asp | Met | Phe | Pro | Leu | Thr | Trp | Val | Phe | Leu | Ala | Leu | Tyr | Phe | Ser | |
| 1 | | | | 5 | | | | | 10 | | | | | 15 | | |

| aga | cac | caa | gtg | aga | ggc | caa | cca | gac | cca | ccg | tgc | gga | ggt | cgt | ttg | 96 |
|---|---|---|---|---|---|---|---|---|---|---|---|---|---|---|---|---|
| Arg | His | Gln | Val | Arg | Gly | Gln | Pro | Asp | Pro | Pro | Cys | Gly | Gly | Arg | Leu | |
| | | | 20 | | | | | 25 | | | | | 30 | | | |

| aat | tcc | aaa | gat | gct | ggc | tat | atc | acc | tct | ccc | ggt | tac | ccc | cag | gac | 144 |
|---|---|---|---|---|---|---|---|---|---|---|---|---|---|---|---|---|
| Asn | Ser | Lys | Asp | Ala | Gly | Tyr | Ile | Thr | Ser | Pro | Gly | Tyr | Pro | Gln | Asp | |
| | | 35 | | | | | 40 | | | | | 45 | | | | |

| tac | ccc | tcc | cac | cag | aac | tgc | gag | tgg | att | gtt | tac | gcc | ccc | gaa | ccc | 192 |
|---|---|---|---|---|---|---|---|---|---|---|---|---|---|---|---|---|
| Tyr | Pro | Ser | His | Gln | Asn | Cys | Glu | Trp | Ile | Val | Tyr | Ala | Pro | Glu | Pro | |
| 50 | | | | | 55 | | | | | 60 | | | | | | |

| aac | cag | aag | att | gtc | ctc | aac | ttc | aac | cct | cac | ttt | gaa | atc | gag | aag | 240 |
|---|---|---|---|---|---|---|---|---|---|---|---|---|---|---|---|---|
| Asn | Gln | Lys | Ile | Val | Leu | Asn | Phe | Asn | Pro | His | Phe | Glu | Ile | Glu | Lys | |
| 65 | | | | | 70 | | | | | 75 | | | | | 80 | |

| cac | gac | tgc | aag | tat | gac | ttt | atc | gag | att | cgg | gat | ggg | gac | agt | gaa | 288 |
|---|---|---|---|---|---|---|---|---|---|---|---|---|---|---|---|---|
| His | Asp | Cys | Lys | Tyr | Asp | Phe | Ile | Glu | Ile | Arg | Asp | Gly | Asp | Ser | Glu | |
| | | | | 85 | | | | | 90 | | | | | 95 | | |

| tcc | gca | gac | ctc | ctg | ggc | aaa | cac | tgt | ggg | aac | atc | gcc | ccg | ccc | acc | 336 |
|---|---|---|---|---|---|---|---|---|---|---|---|---|---|---|---|---|
| Ser | Ala | Asp | Leu | Leu | Gly | Lys | His | Cys | Gly | Asn | Ile | Ala | Pro | Pro | Thr | |
| | | | | 100 | | | | | 105 | | | | | 110 | | |

| atc | atc | tcc | tcg | ggc | tcc | atg | ctc | tac | atc | aag | ttc | acc | tcc | gac | tac | 384 |
|---|---|---|---|---|---|---|---|---|---|---|---|---|---|---|---|---|
| Ile | Ile | Ser | Ser | Gly | Ser | Met | Leu | Tyr | Ile | Lys | Phe | Thr | Ser | Asp | Tyr | |
| | | | 115 | | | | | 120 | | | | | 125 | | | |

| gcc | cgg | cag | ggg | gca | ggc | ttc | tct | ctg | cgc | tac | gag | atc | ttc | aag | aca | 432 |
|---|---|---|---|---|---|---|---|---|---|---|---|---|---|---|---|---|
| Ala | Arg | Gln | Gly | Ala | Gly | Phe | Ser | Leu | Arg | Tyr | Glu | Ile | Phe | Lys | Thr | |
| | | 130 | | | | | 135 | | | | | 140 | | | | |

| ggc | tct | gaa | gat | tgc | tca | aaa | aac | ttc | aca | agc | ccc | aac | ggg | acc | atc | 480 |
|---|---|---|---|---|---|---|---|---|---|---|---|---|---|---|---|---|
| Gly | Ser | Glu | Asp | Cys | Ser | Lys | Asn | Phe | Thr | Ser | Pro | Asn | Gly | Thr | Ile | |
| 145 | | | | | 150 | | | | | 155 | | | | | 160 | |

| gaa | tct | cct | ggg | ttt | cct | gag | aag | tat | cca | cac | aac | ttg | gac | tgc | acc | 528 |
|---|---|---|---|---|---|---|---|---|---|---|---|---|---|---|---|---|
| Glu | Ser | Pro | Gly | Phe | Pro | Glu | Lys | Tyr | Pro | His | Asn | Leu | Asp | Cys | Thr | |
| | | | | 165 | | | | | 170 | | | | | 175 | | |

| ttt | acc | atc | ctg | gcc | aaa | ccc | aag | atg | gag | atc | atc | ctg | cag | ttc | ctg | 576 |
|---|---|---|---|---|---|---|---|---|---|---|---|---|---|---|---|---|
| Phe | Thr | Ile | Leu | Ala | Lys | Pro | Lys | Met | Glu | Ile | Ile | Leu | Gln | Phe | Leu | |
| | | | 180 | | | | | 185 | | | | | 190 | | | |

```
atc ttt gac ctg gag cat gac cct ttg cag gtg gga gag ggg gac tgc    624
Ile Phe Asp Leu Glu His Asp Pro Leu Gln Val Gly Glu Gly Asp Cys
        195                 200                 205 aag tac gat tgg ctg gac atc tgg gat ggc att cca cat gtt ggc ccc    672
Lys Tyr Asp Trp Leu Asp Ile Trp Asp Gly Ile Pro His Val Gly Pro
        210                 215                 220 ctg att ggc aag tac tgt ggg acc aaa aca ccc tct gaa ctt cgt tca    720
Leu Ile Gly Lys Tyr Cys Gly Thr Lys Thr Pro Ser Glu Leu Arg Ser
225                 230                 235                 240 tcg acg ggg atc ctc tcc ctg acc ttt cac acg gac atg gcg gtg gcc    768
Ser Thr Gly Ile Leu Ser Leu Thr Phe His Thr Asp Met Ala Val Ala
                245                 250                 255 aag gat ggc ttc tct gcg cgt tac tac ctg gtc cac caa gag cca cta    816
Lys Asp Gly Phe Ser Ala Arg Tyr Tyr Leu Val His Gln Glu Pro Leu
        260                 265                 270 gag aac ttt cag tgc aat gtt cct ctg ggc atg gag tct ggc cgg att    864
Glu Asn Phe Gln Cys Asn Val Pro Leu Gly Met Glu Ser Gly Arg Ile
        275                 280                 285 gct aat gaa cag atc agt gcc tca tct acc tac tct gat ggg agg tgg    912
Ala Asn Glu Gln Ile Ser Ala Ser Ser Thr Tyr Ser Asp Gly Arg Trp
        290                 295                 300 acc cct caa caa agc cgg ctc cat ggt gat gac aat ggc tgg acc ccc    960
Thr Pro Gln Gln Ser Arg Leu His Gly Asp Asp Asn Gly Trp Thr Pro
305                 310                 315                 320 aac ttg gat tcc aac aag gag tat ctc cag gtg gac ctg cgc ttt tta   1008
Asn Leu Asp Ser Asn Lys Glu Tyr Leu Gln Val Asp Leu Arg Phe Leu
                325                 330                 335 acc atg ctc acg gcc atc gca aca cag gga gcg att tcc agg gaa aca   1056
Thr Met Leu Thr Ala Ile Ala Thr Gln Gly Ala Ile Ser Arg Glu Thr
                340                 345                 350 cag aat ggc tac tac gtc aaa tcc tac aag ctg gaa gtc agc act aat   1104
Gln Asn Gly Tyr Tyr Val Lys Ser Tyr Lys Leu Glu Val Ser Thr Asn
        355                 360                 365 gga gag gac tgg atg gtg tac cgg cat ggc aaa aac cac aag gta ttt   1152
Gly Glu Asp Trp Met Val Tyr Arg His Gly Lys Asn His Lys Val Phe
        370                 375                 380 caa gcc aac aac gat gca act gag gtg gtt ctg aac aag ctc cac gct   1200
Gln Ala Asn Asn Asp Ala Thr Glu Val Val Leu Asn Lys Leu His Ala
385                 390                 395                 400 cca ctg ctg aca agg ttt gtt aga atc cgc cct cag acc tgg cac tca   1248
Pro Leu Leu Thr Arg Phe Val Arg Ile Arg Pro Gln Thr Trp His Ser
```

```
                        405                         410                         415
ggt atc gcc ctc cgg ctg gag ctc ttc ggc tgc cgg gtc aca gat gct    1296
Gly Ile Ala Leu Arg Leu Glu Leu Phe Gly Cys Arg Val Thr Asp Ala
            420                 425                 430 ccc tgc tcc aac atg ctg ggg atg ctc tca ggc ctc att gca gac tcc    1344
Pro Cys Ser Asn Met Leu Gly Met Leu Ser Gly Leu Ile Ala Asp Ser
            435                 440                 445 cag atc tcc gcc tct tcc acc cag gaa tac ctc tgg agc ccc agt gca    1392
Gln Ile Ser Ala Ser Ser Thr Gln Glu Tyr Leu Trp Ser Pro Ser Ala
            450                 455                 460 gcc cgc ctg gtc agc agc cgc tcg ggc tgg ttc cct cga atc cct cag    1440
Ala Arg Leu Val Ser Ser Arg Ser Gly Trp Phe Pro Arg Ile Pro Gln
465                 470                 475                 480 gcc cag ccc ggt gag gag tgg ctt cag gta gat ctg gga aca ccc aag    1488
Ala Gln Pro Gly Glu Glu Trp Leu Gln Val Asp Leu Gly Thr Pro Lys
            485                 490                 495 aca gtg aaa ggt gtc atc atc cag gga gcc cgc gga gga gac agt atc    1536
Thr Val Lys Gly Val Ile Ile Gln Gly Ala Arg Gly Gly Asp Ser Ile
            500                 505                 510 act gct gtg gaa gcc aga gca ttt gtg cgc aag ttc aaa gtc tcc tac    1584
Thr Ala Val Glu Ala Arg Ala Phe Val Arg Lys Phe Lys Val Ser Tyr
            515                 520                 525 agc cta aac ggc aag gac tgg gaa tac att cag gac ccc agg acc cag    1632
Ser Leu Asn Gly Lys Asp Trp Glu Tyr Ile Gln Asp Pro Arg Thr Gln
            530                 535                 540 cag cca aag ctg ttc gaa ggg aac atg cac tat gac acc cct gac atc    1680
Gln Pro Lys Leu Phe Glu Gly Asn Met His Tyr Asp Thr Pro Asp Ile
545                 550                 555                 560 cga agg ttt gac ccc att ccg gca cag tat gtg cgg gta tac ccg gag    1728
Arg Arg Phe Asp Pro Ile Pro Ala Gln Tyr Val Arg Val Tyr Pro Glu
            565                 570                 575 agg tgg tcg ccg gcg ggg att ggg atg cgg ctg gag gtg ctg ggc tgt    1776
Arg Trp Ser Pro Ala Gly Ile Gly Met Arg Leu Glu Val Leu Gly Cys
            580                 585                 590 gac tgg aca gac tcc aag ccc acg gta aaa acg ctg gga ccc act gtg    1824
Asp Trp Thr Asp Ser Lys Pro Thr Val Lys Thr Leu Gly Pro Thr Val
            595                 600                 605 aag agc gaa gag aca acc acc ccc tac ccc acc gaa gag gag gcc aca    1872
Lys Ser Glu Glu Thr Thr Thr Pro Tyr Pro Thr Glu Glu Glu Ala Thr
            610                 615                 620
```

```
gag tgt ggg gag aac tgc agc ttt gag gat gac aaa gat ttg cag ctc    1920
Glu Cys Gly Glu Asn Cys Ser Phe Glu Asp Asp Lys Asp Leu Gln Leu
625                 630                 635                 640 cct tcg gga ttc aat tgc aac ttc gat ttc ctc gag gag ccc tgt ggt    1968
Pro Ser Gly Phe Asn Cys Asn Phe Asp Phe Leu Glu Glu Pro Cys Gly
                645                 650                 655 tgg atg tat gac cat gcc aag tgg ctc cgg acc acc tgg gcc agc agc    2016
Trp Met Tyr Asp His Ala Lys Trp Leu Arg Thr Thr Trp Ala Ser Ser
                660                 665                 670 tcc agc cca aac gac cgg acg ttt cca gat gac agg aat ttc ttg cgg    2064
Ser Ser Pro Asn Asp Arg Thr Phe Pro Asp Asp Arg Asn Phe Leu Arg
                675                 680                 685 ctg cag agt gac agc cag aga gag ggc cag tat gcc cgg ctc atc agc    2112
Leu Gln Ser Asp Ser Gln Arg Glu Gly Gln Tyr Ala Arg Leu Ile Ser
                690                 695                 700 ccc cct gtc cac ctg ccc cga agc ccg gtg tgc atg gag ttc cag tac    2160
Pro Pro Val His Leu Pro Arg Ser Pro Val Cys Met Glu Phe Gln Tyr
705                 710                 715                 720 cag gcc acg ggc ggc cgc ggg gtg gcg ctg cag gtg gtg cgg gaa gcc    2208
Gln Ala Thr Gly Gly Arg Gly Val Ala Leu Gln Val Val Arg Glu Ala
                725                 730                 735 agc cag gag agc aag ttg ctg tgg gtc atc cgt gag gac cag ggc ggc    2256
Ser Gln Glu Ser Lys Leu Leu Trp Val Ile Arg Glu Asp Gln Gly Gly
                740                 745                 750 gag tgg aag cac ggg cgg atc atc ctg ccc agc tac gac atg gag tac    2304
Glu Trp Lys His Gly Arg Ile Ile Leu Pro Ser Tyr Asp Met Glu Tyr
                755                 760                 765 cag att gtg ttc gag gga gtg ata ggg aaa gga cgt tcc gga gag att    2352
Gln Ile Val Phe Glu Gly Val Ile Gly Lys Gly Arg Ser Gly Glu Ile
                770                 775                 780 gcc att gat gac att cgg ata agc act gat gtc cca ctg gag aac tgc    2400
Ala Ile Asp Asp Ile Arg Ile Ser Thr Asp Val Pro Leu Glu Asn Cys
785                 790                 795                 800 atg gaa ccc atc tcg gct ttt gca gtg gac atc cca gaa ata cat gag    2448
Met Glu Pro Ile Ser Ala Phe Ala Val Asp Ile Pro Glu Ile His Glu
                805                 810                 815 aga gaa gga tat gaa gat gaa att gat gat gaa tac gag gtg gac tgg    2496
Arg Glu Gly Tyr Glu Asp Glu Ile Asp Asp Glu Tyr Glu Val Asp Trp
                820                 825                 830 agc aat tct tct tct gca acc tca ggg tct ggc gcc ccc tcg acc gac    2544
Ser Asn Ser Ser Ser Ala Thr Ser Gly Ser Gly Ala Pro Ser Thr Asp
```

```
                835                     840                     845
aaa gaa aag agc tgg ctg tac acc ctg gat ccc atc ctc atc acc atc    2592
Lys Glu Lys Ser Trp Leu Tyr Thr Leu Asp Pro Ile Leu Ile Thr Ile
        850                     855                     860 atc gcc atg agc tca ctg ggc gtc ctc ctg ggg gcc acc tgt gca ggc    2640
Ile Ala Met Ser Ser Leu Gly Val Leu Leu Gly Ala Thr Cys Ala Gly
865                     870                     875                 880 ctc ctg ctc tac tgc acc tgt tcc tac tcg ggc ctg agc tcc cga agc    2688
Leu Leu Leu Tyr Cys Thr Cys Ser Tyr Ser Gly Leu Ser Ser Arg Ser
                885                     890                     895 tgc acc aca ctg gag aac tac aac ttc gag ctc tac gat ggc ctt aag    2736
Cys Thr Thr Leu Glu Asn Tyr Asn Phe Glu Leu Tyr Asp Gly Leu Lys
            900                     905                     910 cac aag gtc aag atg aac cac caa aag tgc tgc tcc gag gca tga        2781
His Lys Val Lys Met Asn His Gln Lys Cys Cys Ser Glu Ala
            915                     920                     925

<210> 20
<211> 926
<212> PRT
<213> human

<400> 20
Met Asp Met Phe Pro Leu Thr Trp Val Phe Leu Ala Leu Tyr Phe Ser
 1               5                  10                  15

Arg His Gln Val Arg Gly Gln Pro Asp Pro Pro Cys Gly Gly Arg Leu
                20                  25                  30

Asn Ser Lys Asp Ala Gly Tyr Ile Thr Ser Pro Gly Tyr Pro Gln Asp
            35                  40                  45

Tyr Pro Ser His Gln Asn Cys Glu Trp Ile Val Tyr Ala Pro Glu Pro
        50                  55                  60

Asn Gln Lys Ile Val Leu Asn Phe Asn Pro His Phe Glu Ile Glu Lys
65                  70                  75                  80

His Asp Cys Lys Tyr Asp Phe Ile Glu Ile Arg Asp Gly Asp Ser Glu
                85                  90                  95

Ser Ala Asp Leu Leu Gly Lys His Cys Gly Asn Ile Ala Pro Pro Thr
            100                 105                 110

Ile Ile Ser Ser Gly Ser Met Leu Tyr Ile Lys Phe Thr Ser Asp Tyr
        115                 120                 125

Ala Arg Gln Gly Ala Gly Phe Ser Leu Arg Tyr Glu Ile Phe Lys Thr
```

```
            130                 135                  140
Gly Ser Glu Asp Cys Ser Lys Asn Phe Thr Ser Pro Asn Gly Thr Ile
145                 150                 155                 160

Glu Ser Pro Gly Phe Pro Glu Lys Tyr Pro His Asn Leu Asp Cys Thr
                165                 170                 175

Phe Thr Ile Leu Ala Lys Pro Lys Met Glu Ile Ile Leu Gln Phe Leu
                180                 185                 190

Ile Phe Asp Leu Glu His Asp Pro Leu Gln Val Gly Glu Gly Asp Cys
            195                 200                 205

Lys Tyr Asp Trp Leu Asp Ile Trp Asp Gly Ile Pro His Val Gly Pro
            210                 215                 220

Leu Ile Gly Lys Tyr Cys Gly Thr Lys Thr Pro Ser Glu Leu Arg Ser
225                 230                 235                 240

Ser Thr Gly Ile Leu Ser Leu Thr Phe His Thr Asp Met Ala Val Ala
                245                 250                 255

Lys Asp Gly Phe Ser Ala Arg Tyr Tyr Leu Val His Gln Glu Pro Leu
                260                 265                 270

Glu Asn Phe Gln Cys Asn Val Pro Leu Gly Met Glu Ser Gly Arg Ile
            275                 280                 285

Ala Asn Glu Gln Ile Ser Ala Ser Ser Thr Tyr Ser Asp Gly Arg Trp
            290                 295                 300

Thr Pro Gln Gln Ser Arg Leu His Gly Asp Asp Asn Gly Trp Thr Pro
305                 310                 315                 320

Asn Leu Asp Ser Asn Lys Glu Tyr Leu Gln Val Asp Leu Arg Phe Leu
                325                 330                 335

Thr Met Leu Thr Ala Ile Ala Thr Gln Gly Ala Ile Ser Arg Glu Thr
                340                 345                 350

Gln Asn Gly Tyr Tyr Val Lys Ser Tyr Lys Leu Glu Val Ser Thr Asn
                355                 360                 365

Gly Glu Asp Trp Met Val Tyr Arg His Gly Lys Asn His Lys Val Phe
            370                 375                 380

Gln Ala Asn Asn Asp Ala Thr Glu Val Val Leu Asn Lys Leu His Ala
385                 390                 395                 400

Pro Leu Leu Thr Arg Phe Val Arg Ile Arg Pro Gln Thr Trp His Ser
                405                 410                 415

Gly Ile Ala Leu Arg Leu Glu Leu Phe Gly Cys Arg Val Thr Asp Ala
```

```
                420              425              430
Pro Cys Ser Asn Met Leu Gly Met Leu Ser Gly Leu Ile Ala Asp Ser
        435                 440                 445
Gln Ile Ser Ala Ser Ser Thr Gln Glu Tyr Leu Trp Ser Pro Ser Ala
    450             455                 460
Ala Arg Leu Val Ser Ser Arg Ser Gly Trp Phe Pro Arg Ile Pro Gln
465                 470                 475                 480
Ala Gln Pro Gly Glu Glu Trp Leu Gln Val Asp Leu Gly Thr Pro Lys
                485                 490                 495
Thr Val Lys Gly Val Ile Ile Gln Gly Ala Arg Gly Gly Asp Ser Ile
            500                 505                 510
Thr Ala Val Glu Ala Arg Ala Phe Val Arg Lys Phe Lys Val Ser Tyr
        515                 520                 525
Ser Leu Asn Gly Lys Asp Trp Glu Tyr Ile Gln Asp Pro Arg Thr Gln
    530                 535                 540
Gln Pro Lys Leu Phe Glu Gly Asn Met His Tyr Asp Thr Pro Asp Ile
545                 550                 555                 560
Arg Arg Phe Asp Pro Ile Pro Ala Gln Tyr Val Arg Val Tyr Pro Glu
                565                 570                 575
Arg Trp Ser Pro Ala Gly Ile Gly Met Arg Leu Glu Val Leu Gly Cys
                580                 585                 590
Asp Trp Thr Asp Ser Lys Pro Thr Val Lys Thr Leu Gly Pro Thr Val
            595                 600                 605
Lys Ser Glu Glu Thr Thr Thr Pro Tyr Pro Thr Glu Glu Glu Ala Thr
    610                 615                 620
Glu Cys Gly Glu Asn Cys Ser Phe Glu Asp Asp Lys Asp Leu Gln Leu
625                 630                 635                 640
Pro Ser Gly Phe Asn Cys Asn Phe Asp Phe Leu Glu Glu Pro Cys Gly
                645                 650                 655
Trp Met Tyr Asp His Ala Lys Trp Leu Arg Thr Thr Trp Ala Ser Ser
                660                 665                 670
Ser Ser Pro Asn Asp Arg Thr Phe Pro Asp Asp Arg Asn Phe Leu Arg
        675                 680                 685
Leu Gln Ser Asp Ser Gln Arg Glu Gly Gln Tyr Ala Arg Leu Ile Ser
    690                 695                 700
Pro Pro Val His Leu Pro Arg Ser Pro Val Cys Met Glu Phe Gln Tyr
```

```
                705                  710                  715                  720
    Gln Ala Thr Gly Gly Arg Gly Val Ala Leu Gln Val Val Arg Glu Ala
                    725                  730                  735
    Ser Gln Glu Ser Lys Leu Leu Trp Val Ile Arg Glu Asp Gln Gly Gly
                    740                  745                  750
    Glu Trp Lys His Gly Arg Ile Ile Leu Pro Ser Tyr Asp Met Glu Tyr
                755                  760                  765
    Gln Ile Val Phe Glu Gly Val Ile Gly Lys Gly Arg Ser Gly Glu Ile
            770                  775                  780
    Ala Ile Asp Asp Ile Arg Ile Ser Thr Asp Val Pro Leu Glu Asn Cys
    785                  790                  795                  800
    Met Glu Pro Ile Ser Ala Phe Ala Val Asp Ile Pro Glu Ile His Glu
                         805                  810                  815
    Arg Glu Gly Tyr Glu Asp Glu Ile Asp Asp Glu Tyr Glu Val Asp Trp
                    820                  825                  830
    Ser Asn Ser Ser Ser Ala Thr Ser Gly Ser Gly Ala Pro Ser Thr Asp
                835                  840                  845
    Lys Glu Lys Ser Trp Leu Tyr Thr Leu Asp Pro Ile Leu Ile Thr Ile
        850                  855                  860
    Ile Ala Met Ser Ser Leu Gly Val Leu Leu Gly Ala Thr Cys Ala Gly
    865                  870                  875                  880
    Leu Leu Leu Tyr Cys Thr Cys Ser Tyr Ser Gly Leu Ser Ser Arg Ser
                    885                  890                  895
    Cys Thr Thr Leu Glu Asn Tyr Asn Phe Glu Leu Tyr Asp Gly Leu Lys
                900                  905                  910
    His Lys Val Lys Met Asn His Gln Lys Cys Cys Ser Glu Ala
            915                  920                  925

<210> 21
<211> 4765
<212> DNA
<213> mouse

<220>
<221> CDS
<222> (567)..(3269)

<400> 21
aaactggagc tccaccgcgg tggcggccgc ccgggcaggt ctagaattca gcggccgctg    60
```

```
aattctatcc agcggtcggt gcctctgccc gcgtgtgtgt cccgggtgcc gggggacctg    120
tgtcagttag cgcttctgag atcacacagc tgcctagggg ccgtgtgatg cccagggcaa    180
ttcttggctt tgatttttat tattattact attattttgc gttcagcttt cgggaaaccc    240
tcgtgatgtt gtaggataaa ggaaatgaca ctttgaggaa ctggagagaa catacacgcg    300
tttgggtttg aagaggaaac cggtctccgc ttccttagct tgctccctct ttgctgattt    360
caagagctat ctcctatgag gtggagatat tccagcaaga ataaggtga agacagactg      420 actgccagga cccaggagga aaacgttgat cgttagagac ctttgcagaa gacaccacca     480
ggaggaaaat tagagaggaa aaacacaaag acataattat aggagatccc acaaacctag    540
cccgggagag agcctctctg tcaaaa atg gat atg ttt cct ctt acc tgg gtt     593
                              Met Asp Met Phe Pro Leu Thr Trp Val
                               1               5
```

| | | | | | | | | | | | | | | | | |
|---|---|---|---|---|---|---|---|---|---|---|---|---|---|---|---|---|
| ttc | tta | gct | ctg | tac | ttt | tca | gga | cac | gaa | gtg | aga | agc | cag | caa | gat | 641 |
| Phe | Leu | Ala | Leu | Tyr | Phe | Ser | Gly | His | Glu | Val | Arg | Ser | Gln | Gln | Asp | |
| | 10 | | | | 15 | | | | | 20 | | | | | 25 | |
| cca | ccc | tgc | gga | ggt | cgg | ccg | aat | tcc | aaa | gat | gct | ggc | tac | atc | act | 689 |
| Pro | Pro | Cys | Gly | Gly | Arg | Pro | Asn | Ser | Lys | Asp | Ala | Gly | Tyr | Ile | Thr | |
| | | | | 30 | | | | | 35 | | | | | 40 | | |
| tcc | cca | ggc | tac | ccc | cag | gac | tat | ccc | tcc | cac | cag | aac | tgt | gag | tgg | 737 |
| Ser | Pro | Gly | Tyr | Pro | Gln | Asp | Tyr | Pro | Ser | His | Gln | Asn | Cys | Glu | Trp | |
| | | | | 45 | | | | | 50 | | | | | 55 | | |
| att | gtc | tac | gcc | ccc | gaa | ccc | aac | cag | aag | att | gtt | ctc | aac | ttc | aac | 785 |
| Ile | Val | Tyr | Ala | Pro | Glu | Pro | Asn | Gln | Lys | Ile | Val | Leu | Asn | Phe | Asn | |
| | | | | 60 | | | | | 65 | | | | | 70 | | |
| cct | cac | ttt | gaa | atc | gag | aaa | cac | gac | tgc | aag | tat | gac | ttc | att | gag | 833 |
| Pro | His | Phe | Glu | Ile | Glu | Lys | His | Asp | Cys | Lys | Tyr | Asp | Phe | Ile | Glu | |
| | 75 | | | | 80 | | | | | 85 | | | | | | |
| att | cgg | gat | ggg | gac | agt | gag | tca | gct | gac | ctc | ctg | ggc | aag | cac | tgt | 881 |
| Ile | Arg | Asp | Gly | Asp | Ser | Glu | Ser | Ala | Asp | Leu | Leu | Gly | Lys | His | Cys | |
| 90 | | | | 95 | | | | | 100 | | | | | 105 | | |
| ggg | aac | atc | gcc | ccg | ccc | acc | atc | atc | tcc | tca | ggc | tcc | gtg | tta | tac | 929 |
| Gly | Asn | Ile | Ala | Pro | Pro | Thr | Ile | Ile | Ser | Ser | Gly | Ser | Val | Leu | Tyr | |
| | | | | 110 | | | | | 115 | | | | | 120 | | |
| atc | aag | ttc | acc | tca | gac | tac | gcc | cgg | cag | ggg | gca | ggt | ttc | tct | cta | 977 |
| Ile | Lys | Phe | Thr | Ser | Asp | Tyr | Ala | Arg | Gln | Gly | Ala | Gly | Phe | Ser | Leu | |
| | | | 125 | | | | | 130 | | | | | 135 | | | |
| cgc | tat | gag | atc | ttc | aaa | aca | ggc | tct | gaa | gat | tgt | tcc | aag | aac | ttt | 1025 |
| Arg | Tyr | Glu | Ile | Phe | Lys | Thr | Gly | Ser | Glu | Asp | Cys | Ser | Lys | Asn | Phe | |

```
                    140                         145                         150
aca agc ccc aat ggg acc att gaa tct cca ggg ttt cca gag aag tat    1073
Thr Ser Pro Asn Gly Thr Ile Glu Ser Pro Gly Phe Pro Glu Lys Tyr
    155                     160                     165 cca cac aat ctg gac tgt acc ttc acc atc ctg gcc aaa ccc agg atg    1121
Pro His Asn Leu Asp Cys Thr Phe Thr Ile Leu Ala Lys Pro Arg Met
170                 175                     180                 185 gag atc atc cta cag ttc ctg acc ttt gac ctg gag cat gac cct cta    1169
Glu Ile Ile Leu Gln Phe Leu Thr Phe Asp Leu Glu His Asp Pro Leu
                190                     195                 200 caa gtg ggg gaa gga gac tgt aaa tat gac tgg ctg gac atc tgg gat    1217
Gln Val Gly Glu Gly Asp Cys Lys Tyr Asp Trp Leu Asp Ile Trp Asp
            205                     210                     215 ggc att cca cat gtt gga cct ctg att ggc aag tac tgt ggg acg aaa    1265
Gly Ile Pro His Val Gly Pro Leu Ile Gly Lys Tyr Cys Gly Thr Lys
        220                     225                     230 aca ccc tcc aaa ctc cgc tcg tcc acg ggg atc ctc tcc ttg acc ttt    1313
Thr Pro Ser Lys Leu Arg Ser Ser Thr Gly Ile Leu Ser Leu Thr Phe
    235                     240                     245 cac acg gac atg gca gtg gcc aag gat ggc ttc tcc gca cgt tac tat    1361
His Thr Asp Met Ala Val Ala Lys Asp Gly Phe Ser Ala Arg Tyr Tyr
250                 255                     260                 265 ttg atc cac cag gag cca cct gag aat ttt cag tgc aat gtc cct ttg    1409
Leu Ile His Gln Glu Pro Pro Glu Asn Phe Gln Cys Asn Val Pro Leu
                270                     275                 280 gga atg gag tct ggc cgg att gct aat gaa cag atc agt gcc tcc tcc    1457
Gly Met Glu Ser Gly Arg Ile Ala Asn Glu Gln Ile Ser Ala Ser Ser
            285                     290                     295 acc ttc tct gat ggg agg tgg act cct caa cag agc cgg ctc cat ggt    1505
Thr Phe Ser Asp Gly Arg Trp Thr Pro Gln Gln Ser Arg Leu His Gly
        300                     305                     310 gat gac aat ggc tgg aca ccc aat ttg gat tcc aac aag gag tat ctc    1553
Asp Asp Asn Gly Trp Thr Pro Asn Leu Asp Ser Asn Lys Glu Tyr Leu
    315                     320                     325 cag gtg gac ctg cgc ttc cta acc atg ctc aca gcc att gca aca cag    1601
Gln Val Asp Leu Arg Phe Leu Thr Met Leu Thr Ala Ile Ala Thr Gln
330                 335                     340                 345 gga gcc att tcc agg gaa acc cag aaa ggc tac tac gtc aaa tcg tac    1649
Gly Ala Ile Ser Arg Glu Thr Gln Lys Gly Tyr Tyr Val Lys Ser Tyr
                350                     355                     360
```

```
aag ctg gaa gtc agc aca aat ggt gaa gat tgg atg gtc tac cgg cat    1697
Lys Leu Glu Val Ser Thr Asn Gly Glu Asp Trp Met Val Tyr Arg His
            365                 370                 375 ggc aaa aac cac aag ata ttc caa gcg aac aat gat gcg acc gag gtg    1745
Gly Lys Asn His Lys Ile Phe Gln Ala Asn Asn Asp Ala Thr Glu Val
            380                 385                 390 gtg cta aac aag ctc cac atg cca ctg ctg act cgg ttc atc agg atc    1793
Val Leu Asn Lys Leu His Met Pro Leu Leu Thr Arg Phe Ile Arg Ile
    395                 400                 405 cgc ccg cag acg tgg cat ttg ggc att gcc ctt cgc ctg gag ctc ttt    1841
Arg Pro Gln Thr Trp His Leu Gly Ile Ala Leu Arg Leu Glu Leu Phe
410                 415                 420                 425 ggc tgc cgg gtc aca gat gca ccc tgc tcc aac atg ctg ggg atg ctc    1889
Gly Cys Arg Val Thr Asp Ala Pro Cys Ser Asn Met Leu Gly Met Leu
                430                 435                 440 tcg ggc ctc att gct gat acc cag atc tct gcc tcc tcc acc cga gag    1937
Ser Gly Leu Ile Ala Asp Thr Gln Ile Ser Ala Ser Ser Thr Arg Glu
            445                 450                 455 tac ctc tgg agc ccc agt gct gcc cgc ctg gtt agt agc cgc tct ggc    1985
Tyr Leu Trp Ser Pro Ser Ala Ala Arg Leu Val Ser Ser Arg Ser Gly
            460                 465                 470 tgg ttt cct cgg aac cct caa gcc cag cca ggt gaa gaa tgg ctt cag    2033
Trp Phe Pro Arg Asn Pro Gln Ala Gln Pro Gly Glu Glu Trp Leu Gln
            475                 480                 485 gta gac ctg ggg aca ccc aag aca gtg aaa ggg gtc atc atc cag gga    2081
Val Asp Leu Gly Thr Pro Lys Thr Val Lys Gly Val Ile Ile Gln Gly
490                 495                 500                 505 gcc cga gga gga gac agc atc act gcc gtg gaa gcc agg gcg ttt gta    2129
Ala Arg Gly Gly Asp Ser Ile Thr Ala Val Glu Ala Arg Ala Phe Val
                510                 515                 520 cgc aag ttc aaa gtc tcc tac agc cta aat ggc aag gac tgg gaa tat    2177
Arg Lys Phe Lys Val Ser Tyr Ser Leu Asn Gly Lys Asp Trp Glu Tyr
            525                 530                 535 atc cag gac ccc agg act cag cag aca aag ctg ttt gaa ggg aac atg    2225
Ile Gln Asp Pro Arg Thr Gln Gln Thr Lys Leu Phe Glu Gly Asn Met
            540                 545                 550 cac tat gac acc cct gac atc cga agg ttc gat cct gtt cca gcg cag    2273
His Tyr Asp Thr Pro Asp Ile Arg Arg Phe Asp Pro Val Pro Ala Gln
    555                 560                 565 tat gtg cgg gtg tac cca gag agg tgg tcg cca gca ggc atc ggg atg    2321
Tyr Val Arg Val Tyr Pro Glu Arg Trp Ser Pro Ala Gly Ile Gly Met
```

|  | 570 |  |  |  | 575 |  |  |  | 580 |  |  |  | 585 |  |  |
|---|---|---|---|---|---|---|---|---|---|---|---|---|---|---|---|
| agg | ctg | gag | gtg | ctg | ggc | tgt | gac | tgg | aca | gac | tca | aag | ccc | aca | gtg | 2369 |
| Arg | Leu | Glu | Val | Leu | Gly | Cys | Asp | Trp | Thr | Asp | Ser | Lys | Pro | Thr | Val |  |
|  |  |  |  | 590 |  |  |  |  | 595 |  |  |  |  | 600 |  |  |

| gag | acg | ctg | gga | ccc | acc | gtg | aag | agt | gaa | gag | act | acc | acc | cca | tat | 2417 |
|---|---|---|---|---|---|---|---|---|---|---|---|---|---|---|---|---|
| Glu | Thr | Leu | Gly | Pro | Thr | Val | Lys | Ser | Glu | Glu | Thr | Thr | Thr | Pro | Tyr |  |
|  |  |  | 605 |  |  |  |  |  | 610 |  |  |  | 615 |  |  |  |

| ccc | atg | gat | gag | gat | gcc | acc | gag | tgt | ggg | gaa | aac | tgc | agc | ttt | gag | 2465 |
|---|---|---|---|---|---|---|---|---|---|---|---|---|---|---|---|---|
| Pro | Met | Asp | Glu | Asp | Ala | Thr | Glu | Cys | Gly | Glu | Asn | Cys | Ser | Phe | Glu |  |
|  |  | 620 |  |  |  |  | 625 |  |  |  |  |  | 630 |  |  |  |

| gat | gac | aaa | gat | ttg | caa | ctt | cct | tca | gga | ttc | aac | tgc | aac | ttt | gat | 2513 |
|---|---|---|---|---|---|---|---|---|---|---|---|---|---|---|---|---|
| Asp | Asp | Lys | Asp | Leu | Gln | Leu | Pro | Ser | Gly | Phe | Asn | Cys | Asn | Phe | Asp |  |
|  | 635 |  |  |  |  | 640 |  |  |  |  | 645 |  |  |  |  |  |

| ttt | ccg | gaa | gag | acc | tgt | ggt | tgg | gtg | tac | gac | cat | gcc | aag | tgg | ctc | 2561 |
|---|---|---|---|---|---|---|---|---|---|---|---|---|---|---|---|---|
| Phe | Pro | Glu | Glu | Thr | Cys | Gly | Trp | Val | Tyr | Asp | His | Ala | Lys | Trp | Leu |  |
| 650 |  |  |  |  | 655 |  |  |  |  | 660 |  |  |  |  | 665 |  |

| cgg | agc | acg | tgg | atc | agc | agc | gct | aac | ccc | aat | gac | aga | aca | ttt | cca | 2609 |
|---|---|---|---|---|---|---|---|---|---|---|---|---|---|---|---|---|
| Arg | Ser | Thr | Trp | Ile | Ser | Ser | Ala | Asn | Pro | Asn | Asp | Arg | Thr | Phe | Pro |  |
|  |  |  |  | 670 |  |  |  |  | 675 |  |  |  |  | 680 |  |  |

| gat | gac | aag | aac | ttc | ttg | aaa | ctg | cag | agt | gat | ggc | cga | cga | gag | ggc | 2657 |
|---|---|---|---|---|---|---|---|---|---|---|---|---|---|---|---|---|
| Asp | Asp | Lys | Asn | Phe | Leu | Lys | Leu | Gln | Ser | Asp | Gly | Arg | Arg | Glu | Gly |  |
|  |  |  | 685 |  |  |  |  |  | 690 |  |  |  |  | 695 |  |  |

| cag | tac | ggg | cgg | ctc | atc | agc | cca | ccg | gtg | cac | ctg | ccc | cga | agc | cct | 2705 |
|---|---|---|---|---|---|---|---|---|---|---|---|---|---|---|---|---|
| Gln | Tyr | Gly | Arg | Leu | Ile | Ser | Pro | Pro | Val | His | Leu | Pro | Arg | Ser | Pro |  |
|  |  | 700 |  |  |  |  | 705 |  |  |  |  | 710 |  |  |  |  |

| gtg | tgc | atg | gag | ttc | cag | tac | caa | gcc | atg | ggc | ggc | cac | ggg | gtg | gca | 2753 |
|---|---|---|---|---|---|---|---|---|---|---|---|---|---|---|---|---|
| Val | Cys | Met | Glu | Phe | Gln | Tyr | Gln | Ala | Met | Gly | Gly | His | Gly | Val | Ala |  |
|  | 715 |  |  |  |  | 720 |  |  |  |  | 725 |  |  |  |  |  |

| ctg | cag | gtg | gtt | cgg | gaa | gcc | agc | cag | gaa | agc | aaa | ctc | ctt | tgg | gtc | 2801 |
|---|---|---|---|---|---|---|---|---|---|---|---|---|---|---|---|---|
| Leu | Gln | Val | Val | Arg | Glu | Ala | Ser | Gln | Glu | Ser | Lys | Leu | Leu | Trp | Val |  |
| 730 |  |  |  | 735 |  |  |  |  | 740 |  |  |  |  | 745 |  |  |

| atc | cgt | gag | gac | cag | ggc | agc | gag | tgg | aag | cac | ggg | cgc | att | atc | ctg | 2849 |
|---|---|---|---|---|---|---|---|---|---|---|---|---|---|---|---|---|
| Ile | Arg | Glu | Asp | Gln | Gly | Ser | Glu | Trp | Lys | His | Gly | Arg | Ile | Ile | Leu |  |
|  |  |  | 750 |  |  |  |  | 755 |  |  |  |  | 760 |  |  |  |

| ccc | agc | tat | gac | atg | gag | tat | cag | atc | gtg | ttc | gag | gga | gtg | ata | ggg | 2897 |
|---|---|---|---|---|---|---|---|---|---|---|---|---|---|---|---|---|
| Pro | Ser | Tyr | Asp | Met | Glu | Tyr | Gln | Ile | Val | Phe | Glu | Gly | Val | Ile | Gly |  |
|  |  | 765 |  |  |  |  | 770 |  |  |  |  | 775 |  |  |  |  |

| aag | gga | cga | tcg | gga | gag | att | tcc | atc | gat | gac | att | cgg | ata | agc | act | 2945 |
|---|---|---|---|---|---|---|---|---|---|---|---|---|---|---|---|---|
| Lys | Gly | Arg | Ser | Gly | Glu | Ile | Ser | Ile | Asp | Asp | Ile | Arg | Ile | Ser | Thr |  |
|  |  | 780 |  |  |  |  | 785 |  |  |  |  | 790 |  |  |  |  |

```
gat gtc cca ctg gag aac tgc atg gaa ccc ata tca gct ttt gca ggg   2993
Asp Val Pro Leu Glu Asn Cys Met Glu Pro Ile Ser Ala Phe Ala Gly
    795                 800                 805 ggc acc ctc ccg cca ggg acc gag ccc aca gtg gac acg gtg ccc gtg   3041
Gly Thr Leu Pro Pro Gly Thr Glu Pro Thr Val Asp Thr Val Pro Val
810                 815                 820                 825 cag ccc atc cca gcc tac tgg tat tac gtt atg gcg gcc ggg ggc gcc   3089
Gln Pro Ile Pro Ala Tyr Trp Tyr Tyr Val Met Ala Ala Gly Gly Ala
                830                 835                 840 gtg ctg gtg ctg gcc tcc gtc gtc ctg gcc ctg gtg ctc cac tac cac   3137
Val Leu Val Leu Ala Ser Val Val Leu Ala Leu Val Leu His Tyr His
                845                 850                 855 cgg ttc cgc tat gcg gcc aag aag acc gat cac tcc atc acc tac aaa   3185
Arg Phe Arg Tyr Ala Ala Lys Lys Thr Asp His Ser Ile Thr Tyr Lys
                860                 865                 870 acc tcc cac tac acc aac ggg gcc cct ctg gcg gtc gag ccc acc cta   3233
Thr Ser His Tyr Thr Asn Gly Ala Pro Leu Ala Val Glu Pro Thr Leu
    875                 880                 885 acc att aag cta gag caa gag cgg ggc tcg cac tgc tgagggcga          3279
Thr Ile Lys Leu Glu Gln Glu Arg Gly Ser His Cys
890                 895                 900 agcaggaaca gcgcccccc aaaaaaaacc caagaaagac tgcaaacacg ttgcctcgat   3339
tttgcacttt ttttctcctc gcctagtctc tgtgtgaacc ctcagacatc tctctccagg   3399
gtccccaacc ctgagcgctc tcatgtaccc cacaccattc tctgtggttc ttggttccgg   3459
tttctctttg ctctgatatt gtttgttttt aatcattatt ttttttcctt ttcttctttc   3519
cttttaatct tctctctttt attcctttct cccctccccg ccccgccttt ttctaatgat   3579
tttaaaccaa ctctaatgct gcatctggaa tcccagaaga gacccgcccc taagcacttc   3639
acaacccaag gctctgttgg ttttgttcca gagacaggcc ctgttgtttt ctcccccttgc   3699
cttatcccat ccctcctctc ctgggcaggc tgccaggtgt cttgagggga gcctggtcct   3759
gtatgtatgt acacagtaca ctcccatgtg aagaggtgtg tgtgtgtgtg tgtgtgtgtg   3819
tgtattttcg agggagagac tgattcactg tggaaggggg ggagtgtggg tgtgtgtaga   3879
gagggcccc ttccctctta tgttgcttct tctggggtac ttttcaagaa aataatatac   3939
tgtacacatt ttgtttactt ggagaagaga ttggagcttt tttgttgcct tatctagctc   3999
tggctgggtt tctgttggct gtcattgtca tctccaggta cctagacaaa tagagaccat   4059
```

```
tgggaatgca atgtggcttc acccatcctt atccccatcc caagccaccc aagactatgg  4119
ttcctccagt gcactcagac atgacccctt tgttatgtt tcctggtgtc tttgaagtca  4179
caagataaca gccattgggt gcatggagtc atttctactt ccagccctga agcaaatgtg  4239
tctcatgttg ccttataaaa aaaaccggaa ttcctgtagt tgaagagtaa gattttgtac  4299
ggtacatttt taatgacagc ttggatattg gaatactcaa cttttgttgt agccaatgag  4359
agggatatgc cactaatggt atctaaatca tacagtacgt actttaggat ggggacaaaa  4419
atcacaacga tttatttatt tatttactta gtgtatgtga gtgcactgtt ggtgtcttca  4479
gacacaccag aagatgactt cagatccgat tacatatggg ttgtgagcca ccatgtggtt  4539
gctgggattt gaactctgga cctctggaag agcagtcagt gcttgtaact ctgagccatc  4599
tttctagccc cccccccccc cccgctatct tttagaaatg taatttgcca tactttgagc  4659
aatgttcttg atgtcattag gatatttcac agataacttc acttaagata attagagcaa  4719
aaaaaaaaaa aaaaaaaaaa aaaaaaaaaa aaaaaaaaaa aaaaaa              4765
```

<210> 22
<211> 901
<212> PRT
<213> mouse

<400> 22
```
Met Asp Met Phe Pro Leu Thr Trp Val Phe Leu Ala Leu Tyr Phe Ser
 1               5                  10                  15

Gly His Glu Val Arg Ser Gln Gln Asp Pro Pro Cys Gly Gly Arg Pro
                20                  25                  30

Asn Ser Lys Asp Ala Gly Tyr Ile Thr Ser Pro Gly Tyr Pro Gln Asp
            35                  40                  45

Tyr Pro Ser His Gln Asn Cys Glu Trp Ile Val Tyr Ala Pro Glu Pro
        50                  55                  60

Asn Gln Lys Ile Val Leu Asn Phe Asn Pro His Phe Glu Ile Glu Lys
65                  70                  75                  80

His Asp Cys Lys Tyr Asp Phe Ile Glu Ile Arg Asp Gly Asp Ser Glu
                85                  90                  95

Ser Ala Asp Leu Leu Gly Lys His Cys Gly Asn Ile Ala Pro Pro Thr
            100                 105                 110

Ile Ile Ser Ser Gly Ser Val Leu Tyr Ile Lys Phe Thr Ser Asp Tyr
        115                 120                 125
```

```
Ala Arg Gln Gly Ala Gly Phe Ser Leu Arg Tyr Glu Ile Phe Lys Thr
    130             135                 140
Gly Ser Glu Asp Cys Ser Lys Asn Phe Thr Ser Pro Asn Gly Thr Ile
145             150                 155                 160
Glu Ser Pro Gly Phe Pro Glu Lys Tyr Pro His Asn Leu Asp Cys Thr
            165             170                 175
Phe Thr Ile Leu Ala Lys Pro Arg Met Glu Ile Leu Gln Phe Leu
            180             185                 190
Thr Phe Asp Leu Glu His Asp Pro Leu Gln Val Gly Glu Gly Asp Cys
        195             200                 205
Lys Tyr Asp Trp Leu Asp Ile Trp Asp Gly Ile Pro His Val Gly Pro
    210             215                 220
Leu Ile Gly Lys Tyr Cys Gly Thr Lys Thr Pro Ser Lys Leu Arg Ser
225             230             235                 240
Ser Thr Gly Ile Leu Ser Leu Thr Phe His Thr Asp Met Ala Val Ala
            245             250                 255
Lys Asp Gly Phe Ser Ala Arg Tyr Tyr Leu Ile His Gln Glu Pro Pro
            260             265                 270
Glu Asn Phe Gln Cys Asn Val Pro Leu Gly Met Glu Ser Gly Arg Ile
    275             280                 285
Ala Asn Glu Gln Ile Ser Ala Ser Ser Thr Phe Ser Asp Gly Arg Trp
    290             295                 300
Thr Pro Gln Gln Ser Arg Leu His Gly Asp Asp Asn Gly Trp Thr Pro
305             310             315                 320
Asn Leu Asp Ser Asn Lys Glu Tyr Leu Gln Val Asp Leu Arg Phe Leu
            325             330                 335
Thr Met Leu Thr Ala Ile Ala Thr Gln Gly Ala Ile Ser Arg Glu Thr
            340             345                 350
Gln Lys Gly Tyr Tyr Val Lys Ser Tyr Lys Leu Glu Val Ser Thr Asn
        355             360                 365
Gly Glu Asp Trp Met Val Tyr Arg His Gly Lys Asn His Lys Ile Phe
        370             375                 380
Gln Ala Asn Asn Asp Ala Thr Glu Val Val Leu Asn Lys Leu His Met
385             390                 395                 400
Pro Leu Leu Thr Arg Phe Ile Arg Ile Arg Pro Gln Thr Trp His Leu
            405             410                 415
```

```
Gly Ile Ala Leu Arg Leu Glu Leu Phe Gly Cys Arg Val Thr Asp Ala
            420                 425                 430

Pro Cys Ser Asn Met Leu Gly Met Leu Ser Gly Leu Ile Ala Asp Thr
            435                 440                 445

Gln Ile Ser Ala Ser Ser Thr Arg Glu Tyr Leu Trp Ser Pro Ser Ala
    450                 455                 460

Ala Arg Leu Val Ser Ser Arg Ser Gly Trp Phe Pro Arg Asn Pro Gln
465                 470                 475                 480

Ala Gln Pro Gly Glu Glu Trp Leu Gln Val Asp Leu Gly Thr Pro Lys
            485                 490                 495

Thr Val Lys Gly Val Ile Ile Gln Gly Ala Arg Gly Gly Asp Ser Ile
            500                 505                 510

Thr Ala Val Glu Ala Arg Ala Phe Val Arg Lys Phe Lys Val Ser Tyr
            515                 520                 525

Ser Leu Asn Gly Lys Asp Trp Glu Tyr Ile Gln Asp Pro Arg Thr Gln
    530                 535                 540

Gln Thr Lys Leu Phe Glu Gly Asn Met His Tyr Asp Thr Pro Asp Ile
545                 550                 555                 560

Arg Arg Phe Asp Pro Val Pro Ala Gln Tyr Val Arg Val Tyr Pro Glu
            565                 570                 575

Arg Trp Ser Pro Ala Gly Ile Gly Met Arg Leu Glu Val Leu Gly Cys
            580                 585                 590

Asp Trp Thr Asp Ser Lys Pro Thr Val Glu Thr Leu Gly Pro Thr Val
            595                 600                 605

Lys Ser Glu Glu Thr Thr Thr Pro Tyr Pro Met Asp Glu Asp Ala Thr
    610                 615                 620

Glu Cys Gly Glu Asn Cys Ser Phe Glu Asp Asp Lys Asp Leu Gln Leu
625                 630                 635                 640

Pro Ser Gly Phe Asn Cys Asn Phe Asp Phe Pro Glu Glu Thr Cys Gly
            645                 650                 655

Trp Val Tyr Asp His Ala Lys Trp Leu Arg Ser Thr Trp Ile Ser Ser
            660                 665                 670

Ala Asn Pro Asn Asp Arg Thr Phe Pro Asp Asp Lys Asn Phe Leu Lys
            675                 680                 685

Leu Gln Ser Asp Gly Arg Arg Glu Gly Gln Tyr Gly Arg Leu Ile Ser
    690                 695                 700
```

Pro Pro Val His Leu Pro Arg Ser Pro Val Cys Met Glu Phe Gln Tyr
705                 710                 715                 720

Gln Ala Met Gly Gly His Gly Val Ala Leu Gln Val Val Arg Glu Ala
            725                 730                 735

Ser Gln Glu Ser Lys Leu Leu Trp Val Ile Arg Glu Asp Gln Gly Ser
            740                 745                 750

Glu Trp Lys His Gly Arg Ile Ile Leu Pro Ser Tyr Asp Met Glu Tyr
            755                 760                 765

Gln Ile Val Phe Glu Gly Val Ile Gly Lys Gly Arg Ser Gly Glu Ile
    770                 775                 780

Ser Ile Asp Asp Ile Arg Ile Ser Thr Asp Val Pro Leu Glu Asn Cys
785                 790                 795                 800

Met Glu Pro Ile Ser Ala Phe Ala Gly Gly Thr Leu Pro Pro Gly Thr
                805                 810                 815

Glu Pro Thr Val Asp Thr Val Pro Val Gln Pro Ile Pro Ala Tyr Trp
            820                 825                 830

Tyr Tyr Val Met Ala Ala Gly Gly Ala Val Leu Val Leu Ala Ser Val
        835                 840                 845

Val Leu Ala Leu Val Leu His Tyr His Arg Phe Arg Tyr Ala Ala Lys
    850                 855                 860

Lys Thr Asp His Ser Ile Thr Tyr Lys Thr Ser His Tyr Thr Asn Gly
865                 870                 875                 880

Ala Pro Leu Ala Val Glu Pro Thr Leu Thr Ile Lys Leu Glu Gln Glu
                885                 890                 895

Arg Gly Ser His Cys
            900

<210> 23
<211> 4780
<212> DNA
<213> mouse

<220>
<221> CDS
<222> (567)..(3284)

<400> 23
aaactggagc tccaccgcgg tggcggccgc ccgggcaggt ctagaattca gcggccgctg 60
aattctatcc agcggtcggt gcctctgccc gcgtgtgtgt cccgggtgcc gggggacctg 120

```
tgtcagttag cgcttctgag atcacacagc tgcctagggg ccgtgtgatg cccagggcaa  180
ttcttggctt tgatttttat tattattact attattttgc gttcagcttt cgggaaaccc  240
tcgtgatgtt gtaggataaa ggaaatgaca ctttgaggaa ctggagagaa catacacgcg  300
tttgggtttg aagaggaaac cggtctccgc ttccttagct tgctccctct ttgctgattt  360
caagagctat ctcctatgag gtggagatat tccagcaaga ataaaggtga agacagactg  420
actgccagga cccaggagga aaacgttgat cgttagagac ctttgcagaa gacaccacca  480
ggaggaaaat tagagaggaa aaacacaaag acataattat aggagatccc acaaacctag  540
cccgggagag agcctctctg tcaaaa atg gat atg ttt cct ctt acc tgg gtt    593
                              Met Asp Met Phe Pro Leu Thr Trp Val
                               1               5 ttc tta gct ctg tac ttt tca gga cac gaa gtg aga agc cag caa gat    641
Phe Leu Ala Leu Tyr Phe Ser Gly His Glu Val Arg Ser Gln Gln Asp
 10              15                  20                  25 cca ccc tgc gga ggt cgg ccg aat tcc aaa gat gct ggc tac atc act    689
Pro Pro Cys Gly Gly Arg Pro Asn Ser Lys Asp Ala Gly Tyr Ile Thr
                30                  35                  40 tcc cca ggc tac ccc cag gac tat ccc tcc cac cag aac tgt gag tgg    737
Ser Pro Gly Tyr Pro Gln Asp Tyr Pro Ser His Gln Asn Cys Glu Trp
            45                  50                  55 att gtc tac gcc ccc gaa ccc aac cag aag att gtt ctc aac ttc aac    785
Ile Val Tyr Ala Pro Glu Pro Asn Gln Lys Ile Val Leu Asn Phe Asn
        60                  65                  70 cct cac ttt gaa atc gag aaa cac gac tgc aag tat gac ttc att gag    833
Pro His Phe Glu Ile Glu Lys His Asp Cys Lys Tyr Asp Phe Ile Glu
    75                  80                  85 att cgg gat ggg gac agt gag tca gct gac ctc ctg ggc aag cac tgt    881
Ile Arg Asp Gly Asp Ser Glu Ser Ala Asp Leu Leu Gly Lys His Cys
 90                  95                 100                 105 ggg aac atc gcc ccg ccc acc atc atc tcc tca ggc tcc gtg tta tac    929
Gly Asn Ile Ala Pro Pro Thr Ile Ile Ser Ser Gly Ser Val Leu Tyr
                110                 115                 120 atc aag ttc acc tca gac tac gcc cgg cag ggg gca ggt ttc tct cta    977
Ile Lys Phe Thr Ser Asp Tyr Ala Arg Gln Gly Ala Gly Phe Ser Leu
            125                 130                 135 cgc tat gag atc ttc aaa aca ggc tct gaa gat tgt tcc aag aac ttt   1025
Arg Tyr Glu Ile Phe Lys Thr Gly Ser Glu Asp Cys Ser Lys Asn Phe
        140                 145                 150
```

```
aca agc ccc aat ggg acc att gaa tct cca ggg ttt cca gag aag tat    1073
Thr Ser Pro Asn Gly Thr Ile Glu Ser Pro Gly Phe Pro Glu Lys Tyr
        155                 160                 165 cca cac aat ctg gac tgt acc ttc acc atc ctg gcc aaa ccc agg atg    1121
Pro His Asn Leu Asp Cys Thr Phe Thr Ile Leu Ala Lys Pro Arg Met
170                 175                 180                 185 gag atc atc cta cag ttc ctg acc ttt gac ctg gag cat gac cct cta    1169
Glu Ile Ile Leu Gln Phe Leu Thr Phe Asp Leu Glu His Asp Pro Leu
                190                 195                 200 caa gtg ggg gaa gga gac tgt aaa tat gac tgg ctg gac atc tgg gat    1217
Gln Val Gly Glu Gly Asp Cys Lys Tyr Asp Trp Leu Asp Ile Trp Asp
            205                 210                 215 ggc att cca cat gtt gga cct ctg att ggc aag tac tgt ggg acg aaa    1265
Gly Ile Pro His Val Gly Pro Leu Ile Gly Lys Tyr Cys Gly Thr Lys
        220                 225                 230 aca ccc tcc aaa ctc cgc tcg tcc acg ggg atc ctc tcc ttg acc ttt    1313
Thr Pro Ser Lys Leu Arg Ser Ser Thr Gly Ile Leu Ser Leu Thr Phe
    235                 240                 245 cac acg gac atg gca gtg gcc aag gat ggc ttc tcc gca cgt tac tat    1361
His Thr Asp Met Ala Val Ala Lys Asp Gly Phe Ser Ala Arg Tyr Tyr
250                 255                 260                 265 ttg atc cac cag gag cca cct gag aat ttt cag tgc aat gtc cct ttg    1409
Leu Ile His Gln Glu Pro Pro Glu Asn Phe Gln Cys Asn Val Pro Leu
                270                 275                 280 gga atg gag tct ggc cgg att gct aat gaa cag atc agt gcc tcc tcc    1457
Gly Met Glu Ser Gly Arg Ile Ala Asn Glu Gln Ile Ser Ala Ser Ser
            285                 290                 295 acc ttc tct gat ggg agg tgg act cct caa cag agc cgg ctc cat ggt    1505
Thr Phe Ser Asp Gly Arg Trp Thr Pro Gln Gln Ser Arg Leu His Gly
        300                 305                 310 gat gac aat ggc tgg aca ccc aat ttg gat tcc aac aag gag tat ctc    1553
Asp Asp Asn Gly Trp Thr Pro Asn Leu Asp Ser Asn Lys Glu Tyr Leu
    315                 320                 325 cag gtg gac ctg cgc ttc cta acc atg ctc aca gcc att gca aca cag    1601
Gln Val Asp Leu Arg Phe Leu Thr Met Leu Thr Ala Ile Ala Thr Gln
330                 335                 340                 345 gga gcc att tcc agg gaa acc cag aaa ggc tac tac gtc aaa tcg tac    1649
Gly Ala Ile Ser Arg Glu Thr Gln Lys Gly Tyr Tyr Val Lys Ser Tyr
                350                 355                 360 aag ctg gaa gtc agc aca aat ggt gaa gat tgg atg gtc tac cgg cat    1697
```

```
Lys Leu Glu Val Ser Thr Asn Gly Glu Asp Trp Met Val Tyr Arg His
            365                 370                 375 ggc aaa aac cac aag ata ttc caa gcg aac aat gat gcg acc gag gtg    1745
Gly Lys Asn His Lys Ile Phe Gln Ala Asn Asn Asp Ala Thr Glu Val
            380                 385                 390 gtg cta aac aag ctc cac atg cca ctg ctg act cgg ttc atc agg atc    1793
Val Leu Asn Lys Leu His Met Pro Leu Leu Thr Arg Phe Ile Arg Ile
        395                 400                 405 cgc ccg cag acg tgg cat ttg ggc att gcc ctt cgc ctg gag ctc ttt    1841
Arg Pro Gln Thr Trp His Leu Gly Ile Ala Leu Arg Leu Glu Leu Phe
410                 415                 420                 425 ggc tgc cgg gtc aca gat gca ccc tgc tcc aac atg ctg ggg atg ctc    1889
Gly Cys Arg Val Thr Asp Ala Pro Cys Ser Asn Met Leu Gly Met Leu
                430                 435                 440 tcg ggc ctc att gct gat acc cag atc tct gcc tcc tcc acc cga gag    1937
Ser Gly Leu Ile Ala Asp Thr Gln Ile Ser Ala Ser Ser Thr Arg Glu
            445                 450                 455 tac ctc tgg agc ccc agt gct gcc cgc ctg gtt agt agc cgc tct ggc    1985
Tyr Leu Trp Ser Pro Ser Ala Ala Arg Leu Val Ser Ser Arg Ser Gly
            460                 465                 470 tgg ttt cct cgg aac cct caa gcc cag cca ggt gaa gaa tgg ctt cag    2033
Trp Phe Pro Arg Asn Pro Gln Ala Gln Pro Gly Glu Glu Trp Leu Gln
        475                 480                 485 gta gac ctg ggg aca ccc aag aca gtg aaa ggg gtc atc atc cag gga    2081
Val Asp Leu Gly Thr Pro Lys Thr Val Lys Gly Val Ile Ile Gln Gly
490                 495                 500                 505 gcc cga gga gga gac agc atc act gcc gtg gaa gcc agg gcg ttt gta    2129
Ala Arg Gly Gly Asp Ser Ile Thr Ala Val Glu Ala Arg Ala Phe Val
                510                 515                 520 cgc aag ttc aaa gtc tcc tac agc cta aat ggc aag gac tgg gaa tat    2177
Arg Lys Phe Lys Val Ser Tyr Ser Leu Asn Gly Lys Asp Trp Glu Tyr
            525                 530                 535 atc cag gac ccc agg act cag cag aca aag ctg ttt gaa ggg aac atg    2225
Ile Gln Asp Pro Arg Thr Gln Gln Thr Lys Leu Phe Glu Gly Asn Met
            540                 545                 550 cac tat gac acc cct gac atc cga agg ttc gat cct gtt cca gcg cag    2273
His Tyr Asp Thr Pro Asp Ile Arg Arg Phe Asp Pro Val Pro Ala Gln
        555                 560                 565 tat gtg cgg gtg tac cca gag agg tgg tcg cca gca ggc atc ggg atg    2321
Tyr Val Arg Val Tyr Pro Glu Arg Trp Ser Pro Ala Gly Ile Gly Met
570                 575                 580                 585
```

```
agg ctg gag gtg ctg ggc tgt gac tgg aca gac tca aag ccc aca gtg    2369
Arg Leu Glu Val Leu Gly Cys Asp Trp Thr Asp Ser Lys Pro Thr Val
                590                 595                 600 gag acg ctg gga ccc acc gtg aag agt gaa gag act acc acc cca tat    2417
Glu Thr Leu Gly Pro Thr Val Lys Ser Glu Glu Thr Thr Thr Pro Tyr
            605                 610                 615 ccc atg gat gag gat gcc acc gag tgt ggg gaa aac tgc agc ttt gag    2465
Pro Met Asp Glu Asp Ala Thr Glu Cys Gly Glu Asn Cys Ser Phe Glu
                620                 625                 630 gat gac aaa gat ttg caa ctt cct tca gga ttc aac tgc aac ttt gat    2513
Asp Asp Lys Asp Leu Gln Leu Pro Ser Gly Phe Asn Cys Asn Phe Asp
            635                 640                 645 ttt ccg gaa gag acc tgt ggt tgg gtg tac gac cat gcc aag tgg ctc    2561
Phe Pro Glu Glu Thr Cys Gly Trp Val Tyr Asp His Ala Lys Trp Leu
650                 655                 660                 665 cgg agc acg tgg atc agc agc gct aac ccc aat gac aga aca ttt cca    2609
Arg Ser Thr Trp Ile Ser Ser Ala Asn Pro Asn Asp Arg Thr Phe Pro
                670                 675                 680 gat gac aag aac ttc ttg aaa ctg cag agt gat ggc cga cga gag ggc    2657
Asp Asp Lys Asn Phe Leu Lys Leu Gln Ser Asp Gly Arg Arg Glu Gly
            685                 690                 695 cag tac ggg cgg ctc atc agc cca ccg gtg cac ctg ccc cga agc cct    2705
Gln Tyr Gly Arg Leu Ile Ser Pro Pro Val His Leu Pro Arg Ser Pro
                700                 705                 710 gtg tgc atg gag ttc cag tac caa gcc atg ggc ggc cac ggg gtg gca    2753
Val Cys Met Glu Phe Gln Tyr Gln Ala Met Gly Gly His Gly Val Ala
            715                 720                 725 ctg cag gtg gtt cgg gaa gcc agc cag gaa agc aaa ctc ctt tgg gtc    2801
Leu Gln Val Val Arg Glu Ala Ser Gln Glu Ser Lys Leu Leu Trp Val
730                 735                 740                 745 atc cgt gag gac cag ggc agc gag tgg aag cac ggg cgc att atc ctg    2849
Ile Arg Glu Asp Gln Gly Ser Glu Trp Lys His Gly Arg Ile Ile Leu
                750                 755                 760 ccc agc tat gac atg gag tat cag atc gtg ttc gag gga gtg ata ggg    2897
Pro Ser Tyr Asp Met Glu Tyr Gln Ile Val Phe Glu Gly Val Ile Gly
            765                 770                 775 aag gga cga tcg gga gag att tcc atc gat gac att cgg ata agc act    2945
Lys Gly Arg Ser Gly Glu Ile Ser Ile Asp Asp Ile Arg Ile Ser Thr
                780                 785                 790 gat gtc cca ctg gag aac tgc atg gaa ccc ata tca gct ttt gca ggt    2993
```

```
                Asp Val Pro Leu Glu Asn Cys Met Glu Pro Ile Ser Ala Phe Ala Gly
                    795                 800                 805 gag gat ttt aaa ggg ggc acc ctc ccg cca ggg acc gag ccc aca gtg        3041
Glu Asp Phe Lys Gly Gly Thr Leu Pro Pro Gly Thr Glu Pro Thr Val
810                 815                 820                 825 gac acg gtg ccc gtg cag ccc atc cca gcc tac tgg tat tac gtt atg        3089
Asp Thr Val Pro Val Gln Pro Ile Pro Ala Tyr Trp Tyr Tyr Val Met
                    830                 835                 840 gcg gcc ggg ggc gcc gtg ctg gtg ctg gcc tcc gtc gtc ctg gcc ctg        3137
Ala Ala Gly Gly Ala Val Leu Val Leu Ala Ser Val Val Leu Ala Leu
                845                 850                 855 gtg ctc cac tac cac cgg ttc cgc tat gcg gcc aag aag acc gat cac        3185
Val Leu His Tyr His Arg Phe Arg Tyr Ala Ala Lys Lys Thr Asp His
                    860                 865                 870 tcc atc acc tac aaa acc tcc cac tac acc aac ggg gcc cct ctg gcg        3233
Ser Ile Thr Tyr Lys Thr Ser His Tyr Thr Asn Gly Ala Pro Leu Ala
                875                 880                 885 gtc gag ccc acc cta acc att aag cta gag caa gag cgg ggc tcg cac        3281
Val Glu Pro Thr Leu Thr Ile Lys Leu Glu Gln Glu Arg Gly Ser His
890                 895                 900                 905 tgc tgagggccga agcaggaaca gcgccccccc aaaaaaaacc caagaaagac             3334
Cys tgcaaacacg ttgcctcgat tttgcacttt ttttctcctc gcctagtctc tgtgtgaacc      3394
ctcagacatc tctctccagg gtccccaacc ctgagcgctc tcatgtaccc cacaccattc      3454
tctgtggttc ttggttccgg tttctctttg ctctgatatt gtttgttttt aatcattatt      3514
ttttttcctt ttcttctttc cttttaatct tctctctttt attcctttct cccctccccg      3574
ccccgccttt ttctaatgat tttaaaccaa ctctaatgct gcatctggaa tcccagaaga      3634
gacccgcccc taagcacttc acaacccaag gctctgttgg ttttgttcca gagacaggcc     3694
ctgttgtttt ctccccttgc cttatcccat ccctcctctc ctgggcaggc tgccaggtgt      3754
cttgagggga gcctggtcct gtatgtatgt acacagtaca ctcccatgtg aagaggtgtg     3814
tgtgtgtgtg tgtgtgtgtg tgtattttcg agggagagac tgattcactg tggaaggggg     3874
ggagtgtggg tgtgtgtaga gagggccccc ttccctctta tgttgcttct tctggggtac     3934
ttttcaagaa aataatatac tgtacacatt ttgtttactt ggagaagaga ttggagcttt      3994
tttgttgcct tatctagctc tggctgggtt tctgttggct gtcattgtca tctccaggta     4054
```

```
cctagacaaa tagagaccat tgggaatgca atgtggcttc acccatcctt atccccatcc 4114 caagccaccc aagactatgg ttcctccagt gcactcagac atgacccctt ttgttatgtt 4174 tcctggtgtc tttgaagtca caagataaca gccattgggt gcatggagtc atttctactt 4234 ccagccctga agcaaatgtg tctcatgttg ccttataaaa aaaaccggaa ttcctgtagt 4294 tgaagagtaa gattttgtac ggtacatttt taatgacagc ttggatattg gaatactcaa 4354 cttttgttgt agccaatgag agggatatgc cactaatggt atctaaatca tacagtacgt 4414 actttaggat ggggacaaaa atcacaacga tttatttatt tatttactta gtgtatgtga 4474 gtgcactgtt ggtgtcttca gacacaccag aagatgactt cagatccgat tacatatggg 4534 ttgtgagcca ccatgtggtt gctgggattt gaactctgga cctctggaag agcagtcagt 4594 gcttgtaact ctgagccatc tttctagccc cccccccccc cccgctatct tttagaaatg 4654 taatttgcca tactttgagc aatgttcttg atgtcattag gatatttcac agataacttc 4714 acttaagata attagagcaa aaaaaaaaaa aaaaaaaaaa aaaaaaaaaa aaaaaaaaaa 4774 aaaaaa                                                            4780
```

<210> 24
<211> 906
<212> PRT
<213> mouse

<400> 24
```
Met Asp Met Phe Pro Leu Thr Trp Val Phe Leu Ala Leu Tyr Phe Ser
 1               5                  10                  15

Gly His Glu Val Arg Ser Gln Gln Asp Pro Pro Cys Gly Gly Arg Pro
             20                  25                  30

Asn Ser Lys Asp Ala Gly Tyr Ile Thr Ser Pro Gly Tyr Pro Gln Asp
         35                  40                  45

Tyr Pro Ser His Gln Asn Cys Glu Trp Ile Val Tyr Ala Pro Glu Pro
     50                  55                  60

Asn Gln Lys Ile Val Leu Asn Phe Asn Pro His Phe Glu Ile Glu Lys
 65                  70                  75                  80

His Asp Cys Lys Tyr Asp Phe Ile Glu Ile Arg Asp Gly Asp Ser Glu
                 85                  90                  95

Ser Ala Asp Leu Leu Gly Lys His Cys Gly Asn Ile Ala Pro Pro Thr
            100                 105                 110
```

```
Ile Ile Ser Ser Gly Ser Val Leu Tyr Ile Lys Phe Thr Ser Asp Tyr
        115             120             125

Ala Arg Gln Gly Ala Gly Phe Ser Leu Arg Tyr Glu Ile Phe Lys Thr
        130             135             140

Gly Ser Glu Asp Cys Ser Lys Asn Phe Thr Ser Pro Asn Gly Thr Ile
145             150             155             160

Glu Ser Pro Gly Phe Pro Glu Lys Tyr Pro His Asn Leu Asp Cys Thr
                165             170             175

Phe Thr Ile Leu Ala Lys Pro Arg Met Glu Ile Ile Leu Gln Phe Leu
            180             185             190

Thr Phe Asp Leu Glu His Asp Pro Leu Gln Val Gly Glu Gly Asp Cys
        195             200             205

Lys Tyr Asp Trp Leu Asp Ile Trp Asp Gly Ile Pro His Val Gly Pro
    210             215             220

Leu Ile Gly Lys Tyr Cys Gly Thr Lys Thr Pro Ser Lys Leu Arg Ser
225             230             235             240

Ser Thr Gly Ile Leu Ser Leu Thr Phe His Thr Asp Met Ala Val Ala
            245             250             255

Lys Asp Gly Phe Ser Ala Arg Tyr Tyr Leu Ile His Gln Glu Pro Pro
            260             265             270

Glu Asn Phe Gln Cys Asn Val Pro Leu Gly Met Glu Ser Gly Arg Ile
        275             280             285

Ala Asn Glu Gln Ile Ser Ala Ser Ser Thr Phe Ser Asp Gly Arg Trp
        290             295             300

Thr Pro Gln Gln Ser Arg Leu His Gly Asp Asp Asn Gly Trp Thr Pro
305             310             315             320

Asn Leu Asp Ser Asn Lys Glu Tyr Leu Gln Val Asp Leu Arg Phe Leu
            325             330             335

Thr Met Leu Thr Ala Ile Ala Thr Gln Gly Ala Ile Ser Arg Glu Thr
            340             345             350

Gln Lys Gly Tyr Tyr Val Lys Ser Tyr Lys Leu Glu Val Ser Thr Asn
        355             360             365

Gly Glu Asp Trp Met Val Tyr Arg His Gly Lys Asn His Lys Ile Phe
        370             375             380

Gln Ala Asn Asn Asp Ala Thr Glu Val Val Leu Asn Lys Leu His Met
385             390             395             400
```

Pro Leu Leu Thr Arg Phe Ile Arg Ile Arg Pro Gln Thr Trp His Leu
            405                 410                 415

Gly Ile Ala Leu Arg Leu Glu Leu Phe Gly Cys Arg Val Thr Asp Ala
            420                 425                 430

Pro Cys Ser Asn Met Leu Gly Met Leu Ser Gly Leu Ile Ala Asp Thr
            435                 440                 445

Gln Ile Ser Ala Ser Ser Thr Arg Glu Tyr Leu Trp Ser Pro Ser Ala
    450                 455                 460

Ala Arg Leu Val Ser Ser Arg Ser Gly Trp Phe Pro Arg Asn Pro Gln
465                 470                 475                 480

Ala Gln Pro Gly Glu Glu Trp Leu Gln Val Asp Leu Gly Thr Pro Lys
            485                 490                 495

Thr Val Lys Gly Val Ile Ile Gln Gly Ala Arg Gly Gly Asp Ser Ile
            500                 505                 510

Thr Ala Val Glu Ala Arg Ala Phe Val Arg Lys Phe Lys Val Ser Tyr
            515                 520                 525

Ser Leu Asn Gly Lys Asp Trp Glu Tyr Ile Gln Asp Pro Arg Thr Gln
        530                 535                 540

Gln Thr Lys Leu Phe Glu Gly Asn Met His Tyr Asp Thr Pro Asp Ile
545                 550                 555                 560

Arg Arg Phe Asp Pro Val Pro Ala Gln Tyr Val Arg Val Tyr Pro Glu
            565                 570                 575

Arg Trp Ser Pro Ala Gly Ile Gly Met Arg Leu Glu Val Leu Gly Cys
            580                 585                 590

Asp Trp Thr Asp Ser Lys Pro Thr Val Glu Thr Leu Gly Pro Thr Val
        595                 600                 605

Lys Ser Glu Glu Thr Thr Thr Pro Tyr Pro Met Asp Glu Asp Ala Thr
    610                 615                 620

Glu Cys Gly Glu Asn Cys Ser Phe Glu Asp Asp Lys Asp Leu Gln Leu
625                 630                 635                 640

Pro Ser Gly Phe Asn Cys Asn Phe Asp Phe Pro Glu Glu Thr Cys Gly
            645                 650                 655

Trp Val Tyr Asp His Ala Lys Trp Leu Arg Ser Thr Trp Ile Ser Ser
            660                 665                 670

Ala Asn Pro Asn Asp Arg Thr Phe Pro Asp Asp Lys Asn Phe Leu Lys
            675                 680                 685

Leu Gln Ser Asp Gly Arg Arg Glu Gly Gln Tyr Gly Arg Leu Ile Ser
    690                 695                 700

Pro Pro Val His Leu Pro Arg Ser Pro Val Cys Met Glu Phe Gln Tyr
705                 710                 715                 720

Gln Ala Met Gly Gly His Gly Val Ala Leu Gln Val Val Arg Glu Ala
                725                 730                 735

Ser Gln Glu Ser Lys Leu Leu Trp Val Ile Arg Glu Asp Gln Gly Ser
            740                 745                 750

Glu Trp Lys His Gly Arg Ile Ile Leu Pro Ser Tyr Asp Met Glu Tyr
        755                 760                 765

Gln Ile Val Phe Glu Gly Val Ile Gly Lys Gly Arg Ser Gly Glu Ile
    770                 775                 780

Ser Ile Asp Asp Ile Arg Ile Ser Thr Asp Val Pro Leu Glu Asn Cys
785                 790                 795                 800

Met Glu Pro Ile Ser Ala Phe Ala Gly Glu Asp Phe Lys Gly Gly Thr
                805                 810                 815

Leu Pro Pro Gly Thr Glu Pro Thr Val Asp Thr Val Pro Val Gln Pro
            820                 825                 830

Ile Pro Ala Tyr Trp Tyr Tyr Val Met Ala Ala Gly Gly Ala Val Leu
        835                 840                 845

Val Leu Ala Ser Val Val Leu Ala Leu Val Leu His Tyr His Arg Phe
    850                 855                 860

Arg Tyr Ala Ala Lys Lys Thr Asp His Ser Ile Thr Tyr Lys Thr Ser
865                 870                 875                 880

His Tyr Thr Asn Gly Ala Pro Leu Ala Val Glu Pro Thr Leu Thr Ile
                885                 890                 895

Lys Leu Glu Gln Glu Arg Gly Ser His Cys
            900                 905

<210> 25
<211> 195
<212> DNA
<213> human

<220>
<221> CDS
<222> (1)..(195)

<400> 25
ttc gag gga gtg ata ggg aaa gga cgt tcc gga gag att gcc att gat    48

```
Phe Glu Gly Val Ile Gly Lys Gly Arg Ser Gly Glu Ile Ala Ile Asp
 1               5                  10                 15 gac att cgg ata agc act gat gtc cca ctg gag aac tgc atg gaa ccc      96
Asp Ile Arg Ile Ser Thr Asp Val Pro Leu Glu Asn Cys Met Glu Pro
             20                  25                  30 atc tcg gct ttt gca ggg ggc acc ctc ctg cca ggg acc gag ccc aca     144
Ile Ser Ala Phe Ala Gly Gly Thr Leu Leu Pro Gly Thr Glu Pro Thr
             35                  40                  45 gtg gac acg gtg ccc atg cag ccc atc cca gcc tac tgg tat tac gta     192
Val Asp Thr Val Pro Met Gln Pro Ile Pro Ala Tyr Trp Tyr Tyr Val
         50                  55                      60 atg                                                                  195
Met
 65
```

<210> 26
<211> 65
<212> PRT
<213> human

<400> 26
```
Phe Glu Gly Val Ile Gly Lys Gly Arg Ser Gly Glu Ile Ala Ile Asp
 1               5                  10                 15

Asp Ile Arg Ile Ser Thr Asp Val Pro Leu Glu Asn Cys Met Glu Pro
             20                  25                  30

Ile Ser Ala Phe Ala Gly Gly Thr Leu Leu Pro Gly Thr Glu Pro Thr
             35                  40                  45

Val Asp Thr Val Pro Met Gln Pro Ile Pro Ala Tyr Trp Tyr Tyr Val
         50                  55                      60

Met
 65
```